United States Patent
Yang et al.

(10) Patent No.: US 11,459,339 B2
(45) Date of Patent: Oct. 4, 2022

(54) BIARYL DERIVATIVE, PREPARATION METHOD THEREOF AND PHARMACEUTICAL APPLICATION THEREOF

(71) Applicant: Abbisko Therapeutics Co., Ltd., Shanghai (CN)

(72) Inventors: Fei Yang, Shanghai (CN); Yongxian Zhang, Shanghai (CN); Haiyan Ying, Shanghai (CN); Hongping Yu, Shanghai (CN); Zhui Chen, Shanghai (CN); Yaochang Xu, Shanghai (CN)

(73) Assignee: ABBISKO THERAPEUTICS CO., LTD., Shanghai (CN)

( * ) Notice: Subject to any disclaimer, the term of this patent is extended or adjusted under 35 U.S.C. 154(b) by 0 days.

(21) Appl. No.: 16/967,030

(22) PCT Filed: Jan. 29, 2019

(86) PCT No.: PCT/CN2019/073594
§ 371 (c)(1),
(2) Date: Aug. 3, 2020

(87) PCT Pub. No.: WO2019/149183
PCT Pub. Date: Aug. 8, 2019

(65) Prior Publication Data
US 2021/0032270 A1    Feb. 4, 2021

(30) Foreign Application Priority Data

Feb. 5, 2018 (CN) .......................... 201810111413.5
Jul. 13, 2018 (CN) .......................... 201810770644.7

(51) Int. Cl.
| C07D 519/00 | (2006.01) |
|---|---|
| C07D 401/12 | (2006.01) |
| C07D 401/14 | (2006.01) |
| C07D 405/14 | (2006.01) |
| C07D 413/14 | (2006.01) |

(52) U.S. Cl.
CPC ......... C07D 519/00 (2013.01); C07D 401/12 (2013.01); C07D 401/14 (2013.01); C07D 405/14 (2013.01); C07D 413/14 (2013.01)

(58) Field of Classification Search
None
See application file for complete search history.

(56) References Cited

FOREIGN PATENT DOCUMENTS

| CN | 105705489 A | 6/2016 |
|---|---|---|
| WO | 2017106634 A1 | 6/2017 |
| WO | 2017222976 A1 | 12/2017 |
| WO | 2018044783 A1 | 3/2018 |
| WO | 2018119221 A1 | 6/2018 |
| WO | 2018119224 A1 | 6/2018 |
| WO | 2019192506 A1 | 10/2019 |

OTHER PUBLICATIONS

Extended European Search Report dated Sep. 22, 2021 in EP Application No. 19748336.5.
Liu et al., "A comparative study of the recent most potent small-molecule PD-L1 inhibitors; what can we learn?" Medicinal Chemistry Research, vol. 30, pp. 1230-1239 (2021).
Int'l Search Report dated Apr. 2, 2019 in Int'l Application No. PCT/CN2019/073594.

*Primary Examiner* — Heidi Reese
(74) *Attorney, Agent, or Firm* — Panitch Schwarze Belisario & Nadel LLP

(57) ABSTRACT

Disclosed are a biaryl derivative having a structure represented by Formula (I) and inhibitory activity against PD-1/PD-L1 interaction, a preparation method thereof, and a pharmaceutical application thereof. The series of compounds of the can be widely applied to the preparation of a medicament for preventing and/or treating cancer or tumors, immune-related diseases and disorders, contagious diseases, infectious diseases or metabolic diseases that are mediated by a PD-1/PD-L1 signaling pathway, and shows promise for the development of a new generation of PD-1/PD-L1 inhibitors.

(I)

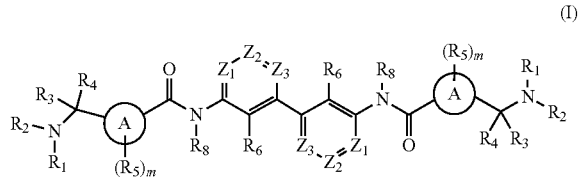

13 Claims, No Drawings

BIARYL DERIVATIVE, PREPARATION METHOD THEREOF AND PHARMACEUTICAL APPLICATION THEREOF

CROSS-REFERENCE TO RELATED APPLICATIONS

This application is a Section 371 of International Application No. PCT/CN2019/073594, filed Jan. 29, 2019, which was published in the Chinese language on Aug. 8, 2019 under International Publication No. WO 2019/149183 A1, which claims priority under 35 U.S.C. § 119(b) to Chinese Application No. 201810111413.5, filed on Feb. 5, 2018, and Chinese Application No. 201810770644.7, filed on Jul. 13, 2018, the disclosures of which are incorporated herein by reference in their entireties.

TECHNICAL FIELD

The present invention belongs to the field of pharmaceutical synthesis, and particularly relates to a biaryl derivative, a preparation method therefor and a pharmaceutical use thereof.

BACKGROUND

The immune system plays a very important role in controlling and eliminating diseases, such as cancer. However, tumor cells are often able to develop a strategy for escaping or suppressing the monitoring of the immune system to promote their malignant growth. One very important mechanism is to change the expression of co-stimulatory and co-inhibitory immune checkpoint molecules on immunocytes. Blocking the signal pathway of immune checkpoint molecules, such as PD1, has been proved to be an extremely promising and effective therapy.

Programmed cell death protein 1 (PD-1), also known as CD279, is a receptor expressed on the surfaces of activated T cells, natural killer T cells, B cells and macrophages. The structure of PD-1 contains an extracellular domain similar to an immunoglobulin variable region, a transmembrane domain and an intracellular domain, wherein the intracellular domain contains two phosphorylation sites located in an immunoreceptor tyrosine kinase-based inhibitory domain and an immunoreceptor tyrosine kinase-based transduction domain, suggesting that PD1 can down-regulate T cell receptor-mediated signal pathways.

PD1 has two ligands: PD-L1 and PDL2, and they are different in their expression profile. The expression of PDL1 will be up-regulated in macrophages and dendritic cells after treatment with lipopolysaccharide (LPS) and granulocyte-macrophage colony-stimulating factor (GM-CSF), and will also be up-regulated in T cells and B cells after stimulation of T cell receptor and B cell receptor signal pathways. PD-L1 is also highly expressed in almost all tumor cells, and the expression will be up-regulated after stimulation of interferon (IFN) gamma. As a matter of fact, the expression of PDL1 in a variety of tumors is considered to have prognostic relevance, but the expression of PD-L2 is relatively concentrated, and mainly on dendritic cells.

When T cells expressing PD-1 come into contact with cells expressing the ligands of PD-1, those antigen-stimulated functional activities, such as cell proliferation, cytokine release and cell lysis activity, are all inhibited. Therefore, the interaction between PD1 and its ligands thereof can function as an intrinsic negative feedback regulation mechanism to prevent T cell hyperactivation during infection, immune tolerance or tumorigenesis, thus reducing the occurrence of autoimmune diseases and promoting self tolerance. Long-term antigen stimulation, e.g., in tumor or long-term infection, will cause T cells to express high level of PD-1, gradually lose activities in response to these long-term antigens, and eventually become nonfunctional, namely, the so-called T cell exhaustion. B cells also have the inhibitory effect caused by PD1 and ligands thereof and corresponding functional exhaustion.

Some evidence from preclinical animal studies have indicated that PD-1 and its ligands thereof can down-regulate the immunoreaction. PD-1-deficient mice will develop lupus erythematosus-like acute proliferative glomerulonephritis and dilated cardiomyopathy. Utilizing the antibody of PDL1 to block the interaction between PD-1 and PDL1 has been proved to be able to restore and enhance T cell activation in many systems. The monoclonal antibody of PDL1 can also benefit patients with advanced cancers. In some preclinical animal tumor models, it was also shown that blocking the signal pathway of PD-1/PD-L1 with a monoclonal antibody can enhance the immunoreaction and lead to immunoreactions to a series of histologically different tumors. With the long-term infection LCMV model, the interaction between PD-1 and PD-L1 has been found to be able to inhibit the activation and proliferation of virus-specific CD8 T cells and the acquisition of effector cell functions. Besides being capable of enhancing the immunoreaction to long-term antigens, blocking the pathway of PD-1/PDL1 was also discovered to be able to enhance response to vaccines, including response to a therapeutic vaccine in long-term infection.

To sum up, if, besides the existing monoclonal antibody, a compound for blocking the interaction between PD1 and PDL1 can be developed, it can serve as an effective therapeutic means for blocking the PD-1/PDL1-mediated inhibitory signal pathway to enhance or restore the function of T cells. Therefore, the compound specifically blocking the interaction between PD-1 and PD-L1 will achieve a good therapeutic effect in immunotherapies for a variety of cancers and other immunity-associated diseases.

SUMMARY

The object of the present invention is to provide compounds for blocking the interaction between PD-1 and PD-L1, and thus to develop a new generation of PD-1/PD-L1 inhibitors.

The first aspect of the present invention provides a compound of formula (I), a stereoisomer, prodrug or pharmaceutically acceptable salt thereof:

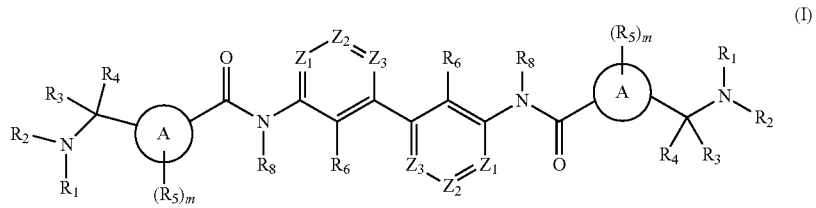

wherein ring A is 5-7 membered aromatic ring or 5-7 membered heteroaromatic ring;

$Z_1$, $Z_2$ and $Z_3$ are each independently $C(R_{11})$ or N;

$R_1$ and $R_2$ are each independently selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, $C_{3-10}$ cycloalkyl $C_{1-8}$ alkyl, 3-10 membered heterocyclyl, 3-10 membered heterocyclyl $C_{1-8}$ alkyl, $C_{5-10}$ aryl, $C_{5-10}$ aryl $C_{1-8}$ alkyl and 5-10 membered heteroaryl, or, $R_1$ and $R_2$, together with the nitrogen atom directly attached thereto, form 3-10 heterocyclyl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)(=N—$R_7$)$R_9$, —$C_{0-8}$—N=S(O)$R_9R_{10}$, —$C_{0-8}$—N=S$R_9R_{10}$, —$C_{0-8}$—P(O)(OH)$R_{12}$, —$C_{0-8}$—SF$_5$, —$C_{0-8}$—O—S(O)$_2R_{12}$, —$C_{0-8}$—S(O)$_rR_{12}$, —$C_{0-8}$—O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—N$R_{15}R_{16}$, —$C_{0-8}$—C(=N$R_{15}$)$R_{14}$, —$C_{0-8}$—N($R_{15}$)—C(=N$R_{16}$)$R_{14}$, —$C_{0-8}$—C(O)N$R_{15}R_{16}$ and —$C_{0-8}$—N($R_{15}$)—C(O)$R_{14}$;

$R_3$ and $R_4$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —$C_{0-8}$—S(O)$_rR_{12}$, —$C_{0-8}$—O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—N$R_{15}R_{16}$, —$C_{0-8}$—C(=N$R_{15}$)$R_{14}$, —$C_{0-8}$—N($R_{15}$)—C(=N$R_{16}$)$R_{14}$, —$C_{0-8}$—C(O)N$R_{15}R_{16}$ and —$C_{0-8}$—N($R_{15}$)—C(O)$R_{14}$, or, $R_3$ and $R_4$, together with the carbon atom directly attached thereto, form 3-10 membered cycloalkyl or 3-10 membered heterocyclyl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_rR_{12}$, —$C_{0-8}$—O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—N$R_{15}R_{16}$, —$C_{0-8}$—C(=N$R_{15}$)$R_{14}$, —$C_{0-8}$—N($R_{15}$)—C(=N$R_{16}$)$R_{14}$, —$C_{0-8}$—C(O)N$R_{15}R_{16}$ and —$C_{0-8}$—N($R_{15}$)—C(O)$R_{14}$;

$R_5$ is selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —$C_{0-8}$—S(O)(=N—$R_7$)$R_9$, —$C_{0-8}$—N=S(O)$R_9R_{10}$, —$C_{0-8}$—N=S$R_9R_{10}$, —$C_{0-8}$—P(O)(OH)$R_{12}$, —$C_{0-8}$—SF$_5$, —$C_{0-8}$—O—S(O)$_2R_{12}$, —$C_{0-8}$—S(O)$_rR_{12}$, —$C_{0-8}$—O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—N$R_{15}R_{16}$, —$C_{0-8}$—C(=N$R_{15}$)$R_{14}$, —$C_{0-8}$—N($R_{15}$)—C(=N$R_{16}$)$R_{14}$, —$C_{0-8}$—C(O)N$R_{15}R_{16}$ and —$C_{0-8}$—N($R_{15}$)—C(O)$R_{14}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_rR_{12}$, —$C_{0-8}$—O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—N$R_{15}R_{16}$, —$C_{0-8}$—C(=N$R_{15}$)$R_{14}$, —$C_{0-8}$—N($R_{15}$)—C(=N$R_{16}$)$R_{14}$, —$C_{0-8}$—C(O)N$R_{15}R_{16}$ and —$C_{0-8}$—N($R_{15}$)—C(O)$R_{14}$, above groups are optionally more further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_rR_{12}$, —$C_{0-8}$—O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—N$R_{15}R_{16}$, —$C_{0-8}$—C(=N$R_{15}$)$R_{14}$, —$C_{0-8}$—N($R_{15}$)—C(=N$R_{16}$)$R_{14}$, —$C_{0-8}$—C(O)N$R_{15}R_{16}$ and —$C_{0-8}$—N($R_{15}$)—C(O)$R_{14}$;

$R_6$ is selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —$C_{0-8}$—S(O)$_rR_{12}$, —$C_{0-8}$—O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—N$R_{15}R_{16}$, —$C_{0-8}$—C(=N$R_{15}$)$R_{14}$, —$C_{0-8}$—N($R_{15}$)—C(=N$R_{16}$)$R_{14}$, —$C_{0-8}$—C(O)N$R_{15}R_{16}$ and —$C_{0-8}$—N($R_{15}$)—C(O)$R_{14}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_rR_{12}$, —$C_{0-8}$—O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—N$R_{15}R_{16}$, —$C_{0-8}$—C(=N$R_{15}$)$R_{14}$, —$C_{0-8}$—N($R_{15}$)—C(=N$R_{16}$)$R_{14}$, —$C_{0-8}$—C(O)N$R_{15}R_{16}$ and —$C_{0-8}$—N($R_{15}$)—C(O)$R_{14}$;

$R_7$ is selected from the group consisting of hydrogen, deuterium, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —$C_{0-8}$—S(O)$_rR_2$, —$C_{0-8}$—C(O)O$R_{13}$, —$C_{0-8}$—C(O)$R_{14}$ and —$C_{0-8}$—C(O)N$R_{15}R_{16}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_rR_{12}$, —$C_{0-8}$—O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—N$R_{15}R_{16}$, —$C_{0-8}$—C(=N$R_{15}$)$R_{14}$, —$C_{0-8}$—N($R_{15}$)—C(=N$R_{16}$)$R_{14}$, —$C_{0-8}$—C(O)N$R_{15}R_{16}$ and —$C_{0-8}$—N($R_{15}$)—C(O)$R_{14}$;

each $R_8$ is independently selected from the group consisting of hydrogen, deuterium, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —$C_{0-8}$—S(O)$_rR_{12}$, —$C_{0-8}$—C(O)O$R_{13}$, —$C_{0-8}$—C(O)$R_{14}$ and —$C_{0-8}$—C(O)N$R_{15}R_{16}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_rR_{12}$, —$C_{0-8}$—C(O)O$R_{13}$, —$C_{0-8}$—C(O)$R_{14}$, —$C_{0-8}$—O—C(O)$R_{14}$, —$C_{0-8}$—N$R_{15}R_{16}$, —$C_{0-8}$—C(=N$R_{15}$)$R_{14}$, —$C_{0-8}$—N($R_{15}$)—C(=N$R_{16}$)$R_{14}$, —$C_{0-8}$—C(O)N$R_{15}R_{16}$ and —$C_{0-8}$—N($R_{15}$)—C(O)$R_{14}$;

$R_9$ and $R_{10}$ are each independently selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl and 5-10 membered heteroaryl, or, $R_9$ and $R_{10}$, together with the sulfur atom directly attached thereto, form 3-10 membered heterocyclyl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_rR_{12}$, —$C_{0-8}$—

O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—$NR_{15}R_{16}$, —$C_{0-8}$—C(=$NR_{15}$)$R_{14}$, —$C_{0-8}$—N($R_{15}$)—C(=$NR_{16}$)$R_{14}$, —$C_{0-8}$—C(O)$NR_{15}R_{16}$ and —$C_{0-8}$—N($R_{15}$)—C(O)$R_{14}$;

each $R_{11}$ is independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —$C_{0-8}$—S(O)$_r$$R_{12}$, —$C_{0-8}$—O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—$NR_{15}R_{16}$, —$C_{0-8}$—C(=$NR_{15}$)$R_{14}$, —$C_{0-8}$—N($R_{15}$)—C(=$NR_{16}$)$R_{14}$, —$C_{0-8}$—C(O)$NR_{15}R_{16}$ and —$C_{0-8}$—N($R_{15}$)—C(O)$R_{14}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_r$$R_{12}$, —$C_{0-8}$—O—$R_{13}$, —$C_{0-8}$—C(O)O$R_{13}$, —$C_{0-8}$—C(O)$R_{14}$, —$C_{0-8}$—O—C(O)$R_{14}$, —$C_{0-8}$—$NR_{15}R_{16}$, —$C_{0-8}$—C(=$NR_{15}$)$R_{14}$, —$C_{0-8}$—N($R_{15}$)—C(=$NR_{16}$)$R_{14}$, —$C_{0-8}$—C(O)$NR_{15}R_{16}$ and —$C_{0-8}$—N($R_{15}$)—C(O)$R_{14}$;

each $R_{12}$ is independently selected from the group consisting of hydrogen, deuterium, hydroxy, halogen, $C_{1-10}$ alkyl, $C_{1-10}$ alkoxy, $C_{2-10}$ alkenyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{15}R_{16}$, above groups are optionally further substituted by one or more substituents selected from the group consisting of deuterium, halogen, hydroxy, carbonyl, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{15}R_{16}$;

each $R_{13}$ is independently selected from the group consisting of hydrogen, deuterium, $C_{1-10}$ alkyl, $C_{2-10}$ alkenyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, hydroxy, carbonyl, cyano, $C_{1-10}$ alkyl, $C_{2-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{3-10}$ aryloxy, 5-10 membered heteroaryl, 5-10 membered heteroaryloxy and —$NR_{15}R_{16}$;

each $R_{14}$ is independently selected from the group consisting of hydrogen, deuterium, hydroxy, $C_{1-10}$ alkyl, $C_{1-10}$ alkoxy, $C_{2-10}$ alkenyl, $C_{2-10}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{15}R_{16}$, above groups are optionally further substituted by one or more substituents selected from the group consisting of deuterium, halogen, hydroxy, cyano, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{15}R_{16}$;

$R_{15}$ and $R_{16}$ are each independently selected from the group consisting of hydrogen, deuterium, hydroxy, $C_{1-10}$ alkoxy, $C_{1-10}$ alkyl, $C_{2-10}$ alkenyl, $C_{2-10}$ alkynyl, $C_{2-10}$ cycloalkyl, 3-10 membered heterocyclyl, $C_{5-10}$ aryl, 5-10 membered heteroaryl, sulfinyl, sulfonyl, methanesulfonyl, isopropylsulfonyl, cyclopropylsulfonyl, p-toluenesulfonyl, aminosulfonyl, dimethylaminosulfonyl, amino, monoalkylamino, dialkylamino and $C_{1-10}$ alkanoyl, above groups are optionally further substituted by one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-10}$ alkanoyl; or, $R_{15}$ and $R_{16}$, together with the nitrogen atom directly attached thereto, form 4-10 membered heterocyclyl or 4-10 membered heteroaryl, above groups are optionally further substituted by one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{2-10}$ deuterioalkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-10}$ alkanoyl;

each m is 0, 1, 2 or 3; and each r is 0, 1 or 2.

As a preferred embodiment, in the compound of formula (I), the stereoisomer, prodrug or pharmaceutically acceptable salt thereof, $Z_1$, $Z_2$ and $Z_3$ are each independently C($R_{11}$) or N;

each $R_{11}$ is independently selected from the group consisting of hydrogen, deuterium, halogen, cyano, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—O—$R_{13}$, —$C_{0-8}$—C(O)O$R_{13}$, —$C_{0-8}$—C(O)$R_{14}$, —$C_{0-4}$—O—C(O)$R_{14}$, —$C_{0-4}$—$NR_{15}R_{16}$, —$C_{0-4}$—C(=$NR_{15}$)$R_{14}$, —$C_{0-4}$—N($R_{15}$)—C(=$NR_{16}$)$R_{14}$, —$C_{0-4}$—C(O)$NR_{15}R_{16}$ and —$C_{0-4}$—N($R_{15}$)—C(O)$R_{14}$, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, —$C_{0-4}$—S(O)$_r$$R_{12}$, —$C_{0-4}$—O—$R_{13}$, —$C_{0-4}$—C(O)O$R_{13}$, —$C_{0-8}$—C(O)$R_{14}$, —$C_{0-4}$—O—C(O)$R_{14}$, —$C_{0-4}$—$NR_{15}R_{16}$, —$C_{0-4}$—C(=$NR_{15}$)$R_{14}$, —$C_{0-8}$—N($R_{15}$)—C(=$NR_{16}$)$R_{14}$, —$C_{0-8}$—C(O)$NR_{15}R_{16}$ and —$C_{0-4}$—N($R_{15}$)—C(O)$R_{14}$, and $R_{12}$, $R_{13}$, $R_{14}$, $R_{15}$, $R_{16}$ and r are defined as those in the compound of formula (I).

As a further preferred embodiment, in the compound of formula (I), the stereoisomer, prodrug or pharmaceutically acceptable salt thereof, $Z_1$, $Z_2$ and $Z_3$ are each C($R_{11}$) or N; each $R_{11}$ is independently selected from the group consisting of hydrogen, deuterium, fluorine, chlorine, cyano, methyl, isopropyl, vinyl, allyl, ethynyl, cyclopropyl, 3-oxacyclobutyl, 3-azacyclobutyl, phenyl, pyridyl, diazole, triazole, methanesulfonyl, aminosulfonyl, methoxy, methoxyacyl, acetyl, acetoxy, amino, dimethylamino, aminoacyl and acetylamino, above groups are optionally further substituted by one or more substituents selected from the group consisting of deuterium, fluorine, chlorine, cyano, methyl, trifluoromethyl, cyclopropyl, phenyl, pyridyl, methanesulfonyl, methoxy and amino.

As a more further preferred embodiment, in the compound of formula (I), the stereoisomer, prodrug or pharmaceutically acceptable salt thereof, $Z_1$, $Z_2$ and $Z_3$ are each C($R_{11}$) or N; each $R_{11}$ is independently selected from the group consisting of hydrogen, deuterium, fluorine, chlorine, cyano, methyl, cyclopropyl, phenyl, pyridyl, diazole, triazole and methoxy, above groups are optionally further substituted by one or more substituents selected from the group consisting of deuterium, fluorine, chlorine, cyano, methyl, trifluoromethyl, cyclopropyl, phenyl, pyridyl, methanesulfonyl, methoxy and amino.

As a preferred embodiment, in the compound of formula (I), the stereoisomer, prodrug or pharmaceutically acceptable salt thereof, $R_6$ is selected from the group consisting of hydrogen, deuterium, halogen, cyano, $C_{1-4}$ alkyl, $C_{2-4}$ alkenyl, $C_{2-4}$ alkynyl, $C_{3-4}$ cycloalkyl, 3-8 membered heterocyclyl, $C_{5-8}$ aryl, 5-8 membered heteroaryl, —$C_{0-4}$—S(O)$_r$$R_{12}$, —$C_{0-4}$—O—$R_{13}$, —$C_{0-4}$—C(O)O$R_{13}$, —$C_{0-4}$—C(O)$R_{14}$, —$C_{0-4}$—O—C(O)$R_{14}$, —$C_{0-4}$—N$R_{15}R_{16}$, —$C_{0-4}$—C(=N$R_{15}$)$R_{14}$, —$C_{0-4}$—N($R_{15}$)—C(=N$R_{16}$)$R_{14}$, —$C_{0-4}$—C(O)N$R_{15}R_{16}$ and —$C_{0-4}$—N($R_{15}$)—C(O)$R_{14}$, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, —$C_{0-4}$—S(O)$_r$$R_{12}$, —$C_{0-4}$—O—$R_{13}$, —$C_{0-4}$—C(O)O$R_{13}$, —$C_{0-4}$—C(O)$R_{14}$, —$C_{0-4}$—O—C(O)$R_{14}$, —$C_{0-4}$—N$R_{15}R_{16}$, —$C_{0-4}$—C(=N$R_{15}$)$R_{14}$, —$C_{0-4}$—N($R_{13}$)—C(=N$R_{16}$)$R_{14}$, —$C_{0-4}$—C(O)N$R_{15}R_{16}$ and —$C_{0-4}$—N($R_{15}$)—C(O)$R_{14}$, wherein $R_{12}$, $R_{13}$, $R_{14}$, $R_{15}$, $R_{16}$ and r are defined as those in the compound of formula (I).

As a further preferred embodiment, in the compound of formula (I), the stereoisomer, prodrug or pharmaceutically acceptable salt thereof, $R_6$ is selected from the group consisting of hydrogen, deuterium, fluorine, chlorine, cyano, methyl, isopropyl, vinyl, allyl, ethynyl, cyclopropyl, cyclobutyl, 3-oxacyclobutyl, 3-azacyclobutyl, phenyl, pyridyl, diazole, triazole, methanesulfonyl, aminosulfonyl, methoxy, methoxyacyl, acetyl, acetoxy, amino, dimethylamino, aminoacyl and acetylamino, above groups are optionally further substituted by one or more substituents selected from the group consisting of deuterium, fluorine, chlorine, cyano, methyl, trifluoromethyl, cyclopropyl, phenyl, pyridyl, methanesulfonyl, methoxy and amino.

As a more further preferred embodiment, in the compound of formula (I), the stereoisomer, prodrug or pharmaceutically acceptable salt thereof, $R_6$ is selected from the group consisting of hydrogen, deuterium, fluorine, chlorine, cyano, methyl, ethyl, isopropyl, trideuteriomethyl, trifluoromethyl, difluoromethyl, cyanomethyl, aminomethyl, cyclopropylmethyl, methoxymethyl, vinyl, ethynyl, cyclopropyl, cyclobutyl, 3-oxacyclobutyl, 3-azacyclobutyl, methoxy, trideuteriomethoxy, difluoromethoxy and trifluoromethoxy.

As a preferred embodiment, in the compound of formula (I), the stereoisomer, prodrug or pharmaceutically acceptable salt thereof, $R_3$ and $R_4$ are each independently selected from the group consisting of hydrogen, deuterium, halogen, cyano, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)$_r$$R_{12}$, —$C_{0-4}$—O—$R_{13}$, —$C_{0-4}$—C(O)O$R_{13}$, —$C_{0-4}$—C(O)$R_{14}$, —$C_{0-4}$—O—C(O)$R_{14}$, —$C_{0-4}$—N$R_{15}R_{16}$, —$C_{0-4}$—C(=N$R_{15}$)$R_{14}$, —$C_{0-4}$—N($R_{15}$)—C(=N$R_{16}$)$R_{14}$, —$C_{0-4}$—C(O)N$R_{15}R_{16}$ and —$C_{0-4}$—N($R_{15}$)—C(O)$R_{14}$, or, $R_3$ and $R_4$, together with the carbon atom directly attached thereto, form 3-8 membered cycloalkyl or 3-8 membered heterocyclyl, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, —$C_{0-4}$—S(O)$_r$$R_{12}$, —$C_{0-4}$—O—$R_{13}$, —$C_{0-4}$—C(O)O$R_{13}$, —$C_{0-4}$—C(O)$R_{14}$, —$C_{0-4}$—O—C(O)$R_{14}$, —$C_{0-4}$—N$R_{15}R_{16}$, —$C_{0-4}$—C(=N$R_{15}$)$R_{14}$, —$C_{0-4}$—N($R_{15}$)—C(=N$R_{16}$)$R_{14}$, —$C_{0-4}$—C(O)N$R_{15}R_{16}$ and —$C_{0-4}$—N($R_{15}$)—C(O)$R_{14}$, wherein $R_{12}$, $R_{13}$, $R_{14}$, $R_{15}$, $R_{16}$ and r are defined as those in the compound of formula (I).

As a further preferred embodiment, in the compound of formula (I), the stereoisomer, prodrug or pharmaceutically acceptable salt thereof, $R_3$ and $R_4$ are each independently selected from the group consisting of hydrogen, deuterium, fluorine, chlorine, cyano, methyl, isopropyl, vinyl, allyl, ethynyl, cyclopropyl, 3-oxacyclobutyl, 3-azacyclobutyl, phenyl, pyridyl, diazole, triazole, methanesulfonyl, aminosulfonyl, methoxy, methoxyacyl, acetyl, acetoxy, amino, dimethylamino, aminoacyl and acetylamino, or, $R_3$ and $R_4$, together with the carbon atom directly attached thereto, form 3-6 membered cycloalkyl or 3-6 membered heterocyclyl, above groups are optionally further substituted by one or more substituents selected from the group consisting of deuterium, fluorine, chlorine, cyano, methyl, trifluoromethyl, cyclopropyl, phenyl, pyridyl, methanesulfonyl, methoxy and amino.

As a more further preferred embodiment, in the compound of formula (I), the stereoisomer, prodrug or pharmaceutically acceptable salt thereof, $R_3$ and $R_4$ are each independently selected from the group consisting of hydrogen, deuterium, fluorine, chlorine, cyano, methyl, cyclopropyl, phenyl, pyridyl, diazole, triazole and methoxy, or, $R_3$ and $R_4$, together with the carbon atom directly attached thereto, form cyclopropyl, cyclobutyl, 3-oxacyclobutyl or 3-azacyclobutyl, above groups are optionally further substituted by one or more substituents selected from the group consisting of deuterium, fluorine, chlorine, cyano, methyl, trifluoromethyl, cyclopropyl, phenyl, pyridyl, methanesulfonyl, methoxy and amino.

As a preferred embodiment, in the compound of formula (I), the stereoisomer, prodrug or pharmaceutically acceptable salt thereof, $R_5$ is selected from the group consisting of hydrogen, deuterium, halogen, cyano, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)(=N—$R_7$)$R_9$, —$C_{0-4}$—N=S(O)$R_9R_{10}$, —$C_{0-4}$—N=S$R_9R_{10}$, —$C_{0-4}$—P(O)(OH)$R_{12}$, —$C_{0-4}$—S$F_5$, —$C_{0-4}$—O—S(O)$_2R_{12}$, —$C_{0-4}$—S(O)$_r$$R_{12}$, —$C_{0-4}$—O—$R_{13}$, —$C_{0-4}$—C(O)O$R_{13}$, —$C_{0-4}$—C(O)$R_{14}$, —$C_{0-4}$—O—C(O)$R_{14}$, —$C_{0-4}$—N$R_{15}R_{16}$, —$C_{0-4}$—C(=N$R_{15}$)$R_{14}$, —$C_{0-4}$—N($R_{15}$)—C(=N$R_{16}$)$R_{14}$, —$C_{0-4}$—C(O)N$R_{15}R_{16}$ and —$C_{0-4}$—N($R_{15}$)—C(O)$R_{14}$, above groups are optionally further substituted by one or more substituents selected from the group consisting of deuterium, halogen, cyan, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, —$C_{0-4}$—S(O)$_r$$R_{12}$, —$C_{0-4}$—O—$R_{13}$, —$C_{0-4}$—C(O)O$R_{13}$, —$C_{0-4}$—C(O)$R_{14}$, —$C_{0-4}$—O—C(O)$R_{14}$, —$C_{0-4}$—N$R_{15}R_{16}$, —$C_{0-4}$—C(=N$R_{15}$)$R_{14}$, —$C_{0-4}$—N($R_{15}$)—C(=N$R_{16}$)$R_{14}$, —$C_{0-4}$—C(O)N$R_{15}R_{16}$ and —$C_{0-4}$—N($R_{15}$)—C(O)$R_{14}$, above groups are optionally more further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{12}$, —$C_{0-4}$—O—$R_{13}$, —$C_{0-4}$—C(O)O$R_{13}$, —$C_{0-4}$—C(O)$R_{14}$, —$C_{0-4}$—O—C(O)$R_{14}$, —$C_{0-4}$—N$R_{15}R_{16}$, —$C_{0-4}$—C(=N$R_{15}$)$R_{14}$, —$C_{0-4}$—N($R_{15}$)—C(=N$R_{16}$)$R_{14}$, —$C_{0-4}$—C(O)N$R_{15}R_{16}$ and —$C_{0-4}$—N($R_{15}$)—C(O)$R_{14}$, wherein $R_7$, $R_9$, $R_{10}$, $R_{12}$, $R_{13}$, $R_{14}$, $R_{15}$, $R_{16}$ and r are defined as those in the compound of formula (I).

As a further preferred embodiment, in the compound of formula (I), the stereoisomer, prodrug or pharmaceutically acceptable salt thereof, $R_5$ is selected from the group consisting of hydrogen, deuterium, fluorine, chlorine, cyano, methyl, ethyl, isopropyl, vinyl, allyl, ethynyl, cyclopropyl, cyclobutyl, 3-oxacyclobutyl, 3-azacyclobutyl, phenyl, pyridyl, diazole, triazole, —$SF_5$, —S(O)(=NH)$CH_3$, —N=S(O)$(CH_3)_2$, —N=S$(CH_3)_2$, —$C_{0-4}$—P(O)(OH)F, —O—S(O)$_2$F, fluorosulfonyl, methanesulfonyl, aminosulfonyl, methoxy, methoxyacyl, acetyl, acetoxy, amino, dimethylamino, aminoacyl, acetylamino and the following structure:

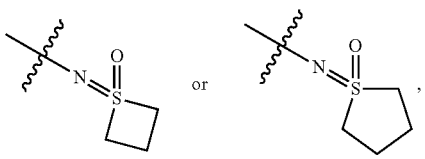 [SMILES: *N=S1(=O)CCC1 ; *N=S1(=O)CCCC1]

above groups are optionally further substituted by one or more substituents selected from the group consisting of deuterium, fluorine, chlorine, cyano, methyl, trifluoromethyl, cyclopropyl, phenyl, pyridyl, diazole, triazole, methanesulfonyl, aminosulfonyl, methoxy and amino, above groups are optionally more further substituted by one or more substituents selected from the group consisting of deuterium, fluorine, chlorine, cyano, methyl, trifluoromethyl, cyclopropyl, phenyl, pyridyl, methanesulfonyl, aminosulfonyl, methoxy and amino.

As a further preferred embodiment, in the compound of formula (I), the stereoisomer, prodrug or pharmaceutically acceptable salt thereof, ring A is 5-6 membered aromatic ring or 5-6 membered heteroaromatic ring.

As a more further preferred embodiment, in the compound of formula (I), the stereoisomer, prodrug or pharmaceutically acceptable salt thereof, ring A is selected from the following group consisting of:

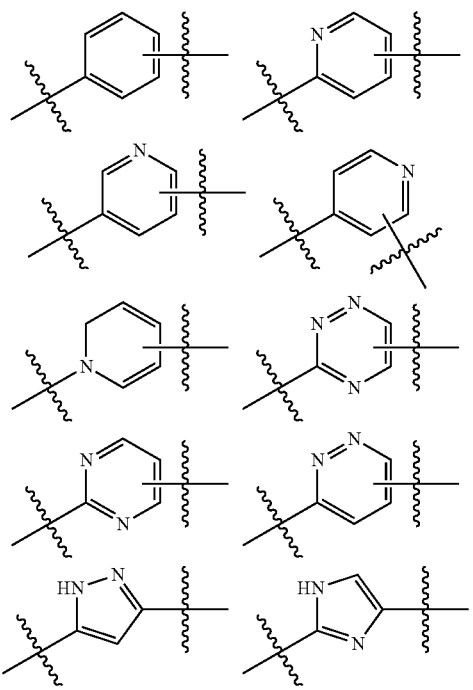

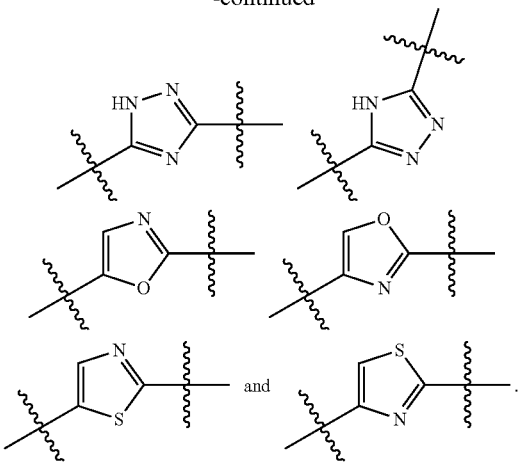

As a more further preferred embodiment, in the compound of formula (I), the stereoisomer, prodrug or pharmaceutically acceptable salt thereof, the compound of formula (I) is a compound with the structure shown as formula (II):

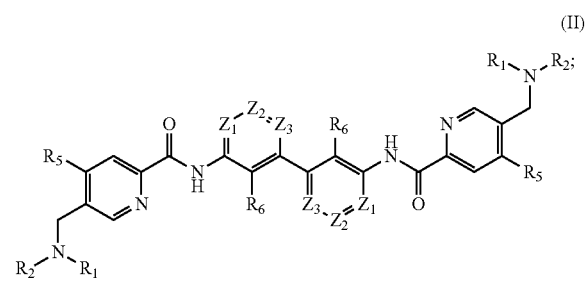

wherein, $Z_1$, $Z_2$ and $Z_3$ are each independently $C(R_{11})$;

$R_5$ is selected from the group consisting of hydrogen, deuterium, fluorine, chlorine, cyano, methyl, ethyl, isopropyl, vinyl, allyl, ethynyl, cyclopropyl, cyclobutyl, 3-oxacyclobutyl, 3 azacyclobutyl, phenyl, pyridyl, diazole, triazole, —$SF_5$, —S(O)(=NH)$CH_3$, —N=S(O)$(CH_3)_2$, —N=S$(CH_3)_2$, —$C_{0-4}$—P(O)(OH)F, —O—S(O)$_2$F, fluorosulfonyl, methanesulfonyl, aminosulfonyl, methoxy, methoxyacyl, acetyl, acetoxy, amino, dimethylamino, aminoacyl, acetylamino and the following structure:

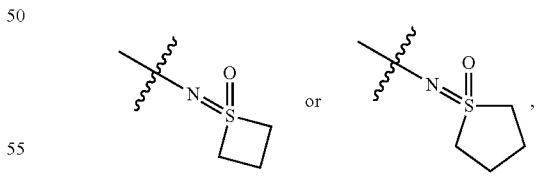

above groups are optionally further substituted by one or more substituents selected from the group consisting of deuterium, fluorine, chlorine, cyano, methyl, trifluoromethyl, cyclopropyl, phenyl, pyridyl, diazole, triazole, methanesulfonyl, aminosulfonyl, methoxy and amino, above groups are optionally more further substituted by one or more substituents selected from the group consisting of deuterium, fluorine, chlorine, cyano, methyl, trifluoromethyl, cyclopropyl, phenyl, pyridyl, methanesulfonyl, aminosulfonyl, methoxy and amino;

$R_6$ is selected from the group consisting of hydrogen, deuterium, fluorine, chlorine, cyano, methyl, ethyl, isopropyl, vinyl, allyl, ethynyl, cyclopropyl, cyclobutyl, 3-oxacyclobutyl, 3-azacyclobutyl, phenyl, pyridyl, diazole, triazole, methanesulfonyl, aminosulfonyl, methoxy, methoxyacyl, acetyl, acetoxy, amino, dimethylamino, aminoacyl and acetylamino, above groups are optionally further substituted by one or more substituents selected from the group consisting of deuterium, fluorine, chlorine, cyano, methyl, trifluoromethyl, cyclopropyl, phenyl, pyridyl, methanesulfonyl, methoxy and amino;

each $R_{11}$ is independently selected from the group consisting of hydrogen, deuterium, fluorine, chlorine, cyano, methyl, isopropyl, vinyl, allyl, ethynyl, cyclopropyl, 3-oxacyclobutyl, 3-azacyclobutyl, phenyl, pyridyl, diazole, triazole, methanesulfonyl, aminosulfonyl, methoxy, methoxyacyl, acetyl, acetoxy, amino, dimethylamino, aminoacyl and acetylamino, above groups are optionally further substituted by one or more substituents selected from the group consisting of deuterium, fluorine, chlorine, cyano, methyl, trifluoromethyl, cyclopropyl, phenyl, pyridyl, methanesulfonyl, methoxy and amino; and $R_1$ and $R_2$ are as defined as those in the compound of formula (I).

As a more further preferred embodiment, in the compound of formula (I), the stereoisomer, prodrug or pharmaceutically acceptable salt thereof, $R_6$ is selected from the group consisting of hydrogen, deuterium, fluorine, chlorine, cyano, methyl, ethyl, isopropyl, trideuteriomethyl, trifluoromethyl, difluoromethyl, cyanomethyl, aminomethyl, cyclopropylmethyl, methoxymethyl, vinyl, ethynyl, cyclopropyl, cyclobutyl, 3-oxacyclobutyl, 3-azacyclobutyl, methoxy, trideuteriomethoxy, difluoromethoxy and trifluoromethoxy; and each $R_{11}$ is independently selected from the group consisting of hydrogen, deuterium, fluorine, chlorine, cyano, methyl, cyclopropyl, phenyl, pyridyl, diazole, triazole and methoxy, above groups are optionally further substituted by one or more substituents selected from the group consisting of deuterium, fluorine, chlorine, cyano, methyl, trifluoromethyl, cyclopropyl, phenyl, pyridyl, methanesulfonyl, methoxy and amino.

As a more further preferred embodiment, in the compound of formula (I), the stereoisomer, prodrug or pharmaceutically acceptable salt thereof, the compound of formula (I) is a compound with the structure shown as formula (III):

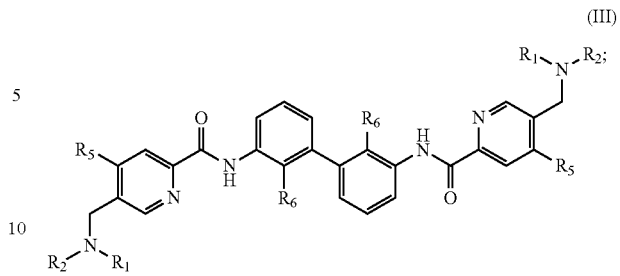

(III)

wherein, $R_6$ is selected from the group consisting of deuterium, chlorine, fluorine, methyl, cyano, trideuteriomethyl, cyanomethyl, aminomethyl, cyclopropylmethyl, methoxymethyl and cyclopropyl; $R_5$ is selected from the group consisting of hydrogen, deuterium, fluorine, chlorine, cyano, methyl, ethyl, isopropyl, vinyl, allyl, ethynyl, cyclopropyl, cyclobutyl, 3-oxacyclobutyl, 3-azacyclobutyl, phenyl, pyridyl, diazole, triazole, —SF$_5$, —S(O)(=NH)CH$_3$, —N=S(O)(CH$_3$)$_2$, —P(O)(OH)F, —O—S(O)$_2$F, —N=S(CH$_3$)$_2$, fluorosulfonyl, methanesulfonyl, aminosulfonyl, methoxy, methoxyacyl, acetyl, acetoxy, amino, dimethylamino, aminoacyl, acetylamino and the following structure:

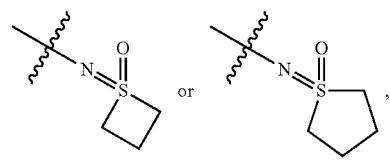 [SMILES: *N=S1(=O)CCC1 ; *N=S1(=O)CCCC1]

above groups are optionally further substituted by one or more substituents selected from the group consisting of deuterium, fluorine, chlorine, cyano, methyl, trifluoromethyl, cyclopropyl, phenyl, pyridyl, diazole, triazole, methanesulfonyl, aminosulfonyl, methoxy or amino, above groups are optionally more further substituted by one or more substituents selected from the group consisting of deuterium, fluorine, chlorine, cyano, methyl, trifluoromethyl, cyclopropyl, phenyl, pyridyl, methanesulfonyl, aminosulfonyl, methoxy and amino; and $R_1$ and $R_2$ are defined as those in the compound of formula (I).

As a more further preferred embodiment, in the compound of formula (I), the stereoisomer, prodrug or pharmaceutically acceptable salt thereof, the compound of formula (I) is a compound with the structure shown as formula (IVa), formula (IVb), formula (IVc) or formula (IVd):

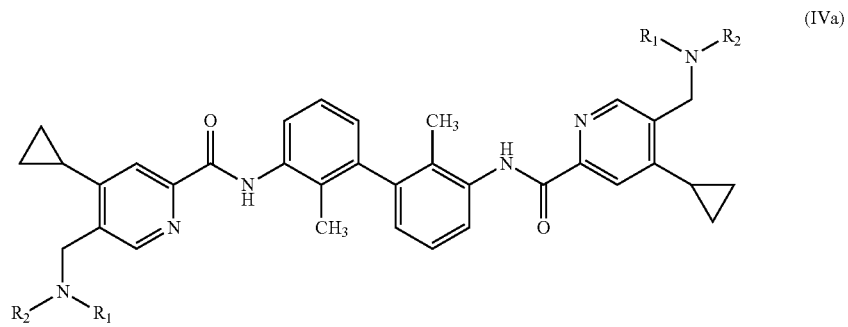

(IVa)

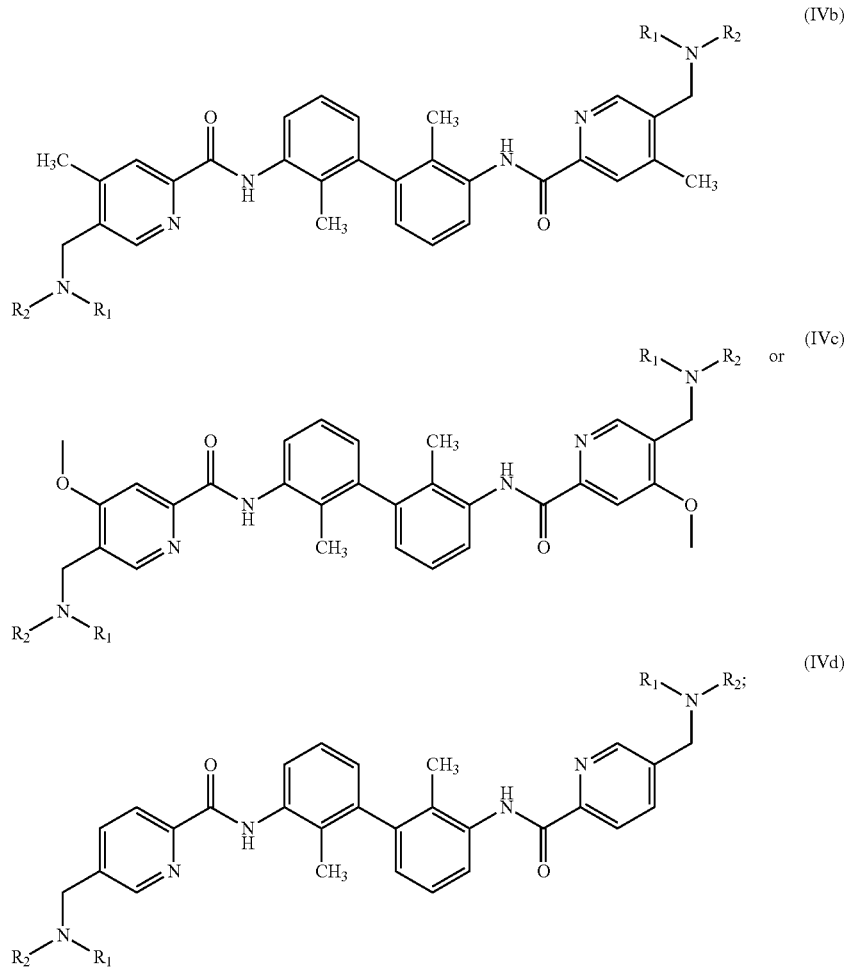

wherein, $R_1$ and $R_2$ are each independently defined as those in the compound of formula (I).

As a more further preferred embodiment, in the compound of formula (I), the stereoisomer, prodrug or pharmaceutically acceptable salt thereof, $R_1$ and $R_2$ are each independently selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, $C_{3-8}$ cycloalkyl $C_{1-4}$ alkyl, 3-8 membered heterocyclyl, $C_{5-8}$ aryl and 5-8 membered heteroaryl, or, $R_1$ and $R_2$, together with the nitrogen atom directly attached thereto, form 3-8 membered heterocyclyl, the heteroatom in the heterocyclyl is selected from the group consisting of N, O, S and/or Si, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —S(O)(=N—$R_7$)$R_9$, —N=S(O)$R_9R_{10}$, —N=S$R_9R_{10}$, —P(O)(OH)$R_{12}$, —SF$_5$, —O—S(O)$_2$ $R_{12}$, —S(O)$_rR_{12}$, —O—$R_{13}$, —C(O)O$R_{13}$, —C(O)$R_{14}$, —O—C(O)$R_{14}$, —N$R_{15}R_{16}$, —C(=N$R_{15}$)$R_{14}$, —N($R_{16}$)—C(=N$R_{16}$)$R_{14}$, —C(O)N$R_{15}R_{16}$ and —N($R_{15}$)—C(O)$R_{14}$; and $R_7$, $R_9$, $R_{10}$, $R_{12}$, $R_{13}$, $R_{14}$, $R_{15}$, $R_{16}$ and r are defined as those in the compound of formula (I).

As a more further preferred embodiment, in the compound of formula (I), the stereoisomer, prodrug or pharmaceutically acceptable salt thereof, $R_1$ is hydrogen, deuterium or methyl; $R_2$ is selected from the group consisting of hydrogen, deuterium, hydroxy, $C_{1-4}$ alkyl, $C_{3-8}$ cycloalkyl, $C_{3-8}$ cycloalkyl $C_{1-4}$ alkyl, 3-8 membered heterocyclyl, $C_{5-8}$ aryl and 5-8 membered heteroaryl, or, $R_1$ and $R_2$, together with the nitrogen atom directly attached thereto, form 3-8 membered heterocyclyl, the heteroatom in the heterocyclyl is selected from the group consisting of N, O, S and/or Si, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, —S(O)(=N—$R_7$)$R_9$, —N=S(O)$R_9R_{10}$, —N=S$R_9R_{10}$, —P(O)(OH)$R_{12}$, —SF$_5$, —O—S(O)$_2$ $R_{12}$, —S(O)$_rR_{12}$, —O—$R_{13}$, —C(O)O$R_{13}$, —C(O)$R_{14}$, —O—C(O)$R_{14}$, —N$R_{15}R_{16}$, —C(=N$R_{15}$)$R_{14}$, —N($R_{15}$)—C(=N$R_{16}$)$R_{14}$, —C(O)N$R_{15}R_{16}$ and —N($R_{15}$)—C(O)$R_{14}$;

$R_7$ is selected from the group consisting of hydrogen, deuterium, $C_{1-4}$ alkyl, $C_{2-4}$ alkenyl, $C_{3-6}$ cycloalkyl, 3-6 membered heterocyclyl, phenyl, 5-8 membered heteroaryl, methanesulfonyl and acetyl, above groups are optionally further substituted by one or more substituents selected from the group consisting of deuterium, fluorine, chlorine, cyano, hydroxy, methyl, ethyl, trifluoromethyl, difluoromethyl, trideuteriomethyl, dideuteriomethyl, cyclopropyl, phenyl, diazole, triazole, methoxy, ethoxy, carboxyl, methoxycarbonyl, ethoxycarbonyl, acetyl, acetoxy, amino and dimethylamino;

$R_9$ and $R_{10}$ are each independently selected from the group consisting of hydrogen, deuterium, hydroxy, $C_{1-4}$ alkyl, $C_{2-4}$ alkenyl, $C_{3-6}$ cycloalkyl, 3-6 membered heterocyclyl, phenyl and 5-8 membered heteroaryl, or, $R_9$ and $R_{10}$, together with the sulfur atom directly attached thereto, form 3-6 membered heterocyclyl, above groups are optionally further substituted by one or more substituents selected from the group consisting of deuterium, fluorine, chlorine, cyano, hydroxy, methyl, ethyl, trifluoromethyl, difluoromethyl, trideuteriomethyl, dideuteriomethyl, cyclopropyl, phenyl, diazole, triazole, methoxy, ethoxy, carboxyl, methoxycarbonyl, ethoxycarbonyl, acetyl, acetoxy, amino and dimethylamino;

each $R_{12}$ is independently selected from the group consisting of hydrogen, deuterium, hydroxy, halogen, $C_{1-4}$ alkyl, $C_{3-6}$ cycloalkyl, 3-6 membered heterocyclyl, phenyl, 5-8 membered heteroaryl and —$NR_{15}R_{16}$, above groups are optionally further substituted by one or more substituents selected from the group consisting of deuterium, fluorine, chlorine, hydroxy, carbonyl, $C_{1-4}$ alkyl, $C_{1-4}$ alkoxy, $C_{3-6}$ cycloalkyl, $C_{3-6}$ cycloalkyloxy, 3-6 membered heterocyclyl, phenyl, 5-8 membered heteroaryl, amino and dimethylamino;

each $R_{13}$ is independently selected from the group consisting of hydrogen, deuterium, $C_{1-4}$ alkyl, $C_{2-4}$ alkenyl, $C_{3-6}$ cycloalkyl, 3-6 membered heterocyclyl, phenyl and 5-8 membered heteroaryl, above groups are optionally further substituted by one or more substituents selected from the group consisting of deuterium, halogen, hydroxy, carbonyl, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, phenyl, phenoxy, 5-8 membered heteroaryl, 5-8 membered heteroaryloxy and —$NR_{15}R_{16}$;

each $R_{14}$ is independently selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-6}$ cycloalkyl, $C_{3-6}$ cycloalkyloxy, 3-6 membered heterocyclyl, 3-6 membered heterocyclyloxy, phenyl, phenoxy, 5-8 membered heteroaryl, 5-8 membered heteroaryloxy and —$NR_{15}R_{16}$, above groups are optionally further substituted by one or more substituents selected from the group consisting of deuterium, halogen, hydroxy, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, phenyl, phenoxy, 5-8 membered heteroaryl, 5-8 membered heteroaryloxy and —$NR_{15}R_{16}$;

each of $R_{15}$ and $R_{16}$ is independently selected from the group consisting of hydrogen, deuterium, hydroxy, $C_{1-4}$ alkoxy, $C_{1-4}$ alkyl, $C_{2-4}$ alkenyl, $C_{2-4}$ alkynyl, $C_{3-6}$ cycloalkyl, 3-6 membered heterocyclyl, phenyl, 5-8 membered heteroaryl, sulfinyl, sulfonyl, methanesulfonyl, isopropylsulfonyl, cyclopropylsulfonyl, p-toluenesulfonyl, aminosulfonyl, dimethylaminosulfonyl, amino, monoalkylamino, dialkylamino and $C_{1-4}$ alkanoyl, above groups are optionally further substituted by one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, phenyl, phenoxy, 5-8 membered heteroaryl, 5-8 membered heteroaryloxy, amino, monoalkylamino, dialkylamino and $C_{1-4}$ alkanoyl; or, $R_{15}$ and $R_{16}$, together with the nitrogen atom directly attached thereto, form 4-6 membered heterocyclyl or 4-6 membered heteroaryl, above groups are optionally further substituted by one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, phenyl, phenoxy, 5-8 membered heteroaryl, 5-8 membered heteroaryloxy, amino, monoalkylamino, dialkylamino and $C_{1-4}$ alkanoyl; and r is independently 0, 1 or 2.

As the most preferred embodiment, the compound of formula (I), the stereoisomer, prodrug or pharmaceutically acceptable salt thereof include, but are not limited to, the following compounds:

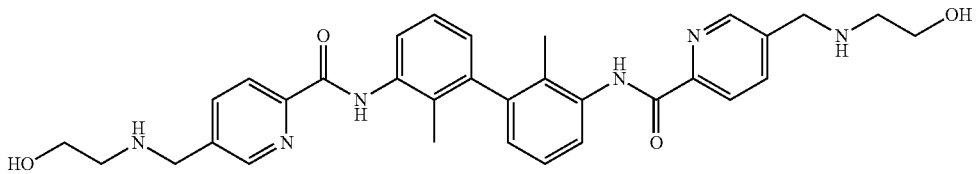

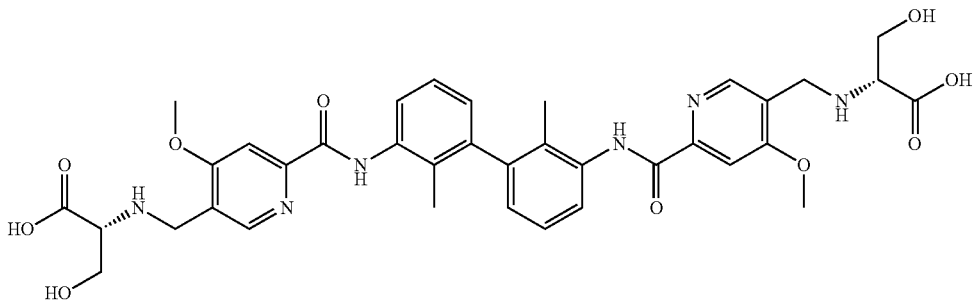

-continued
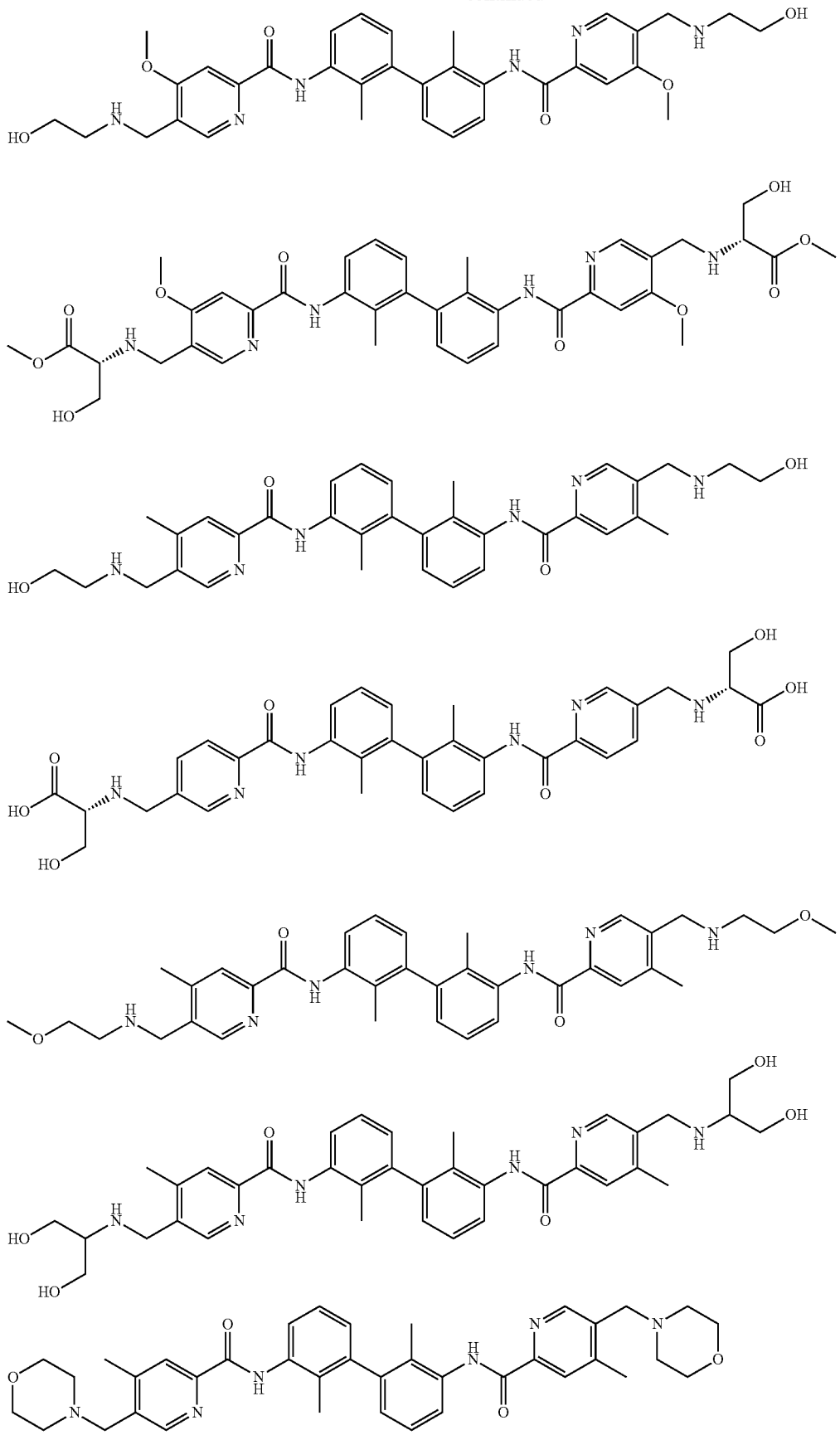

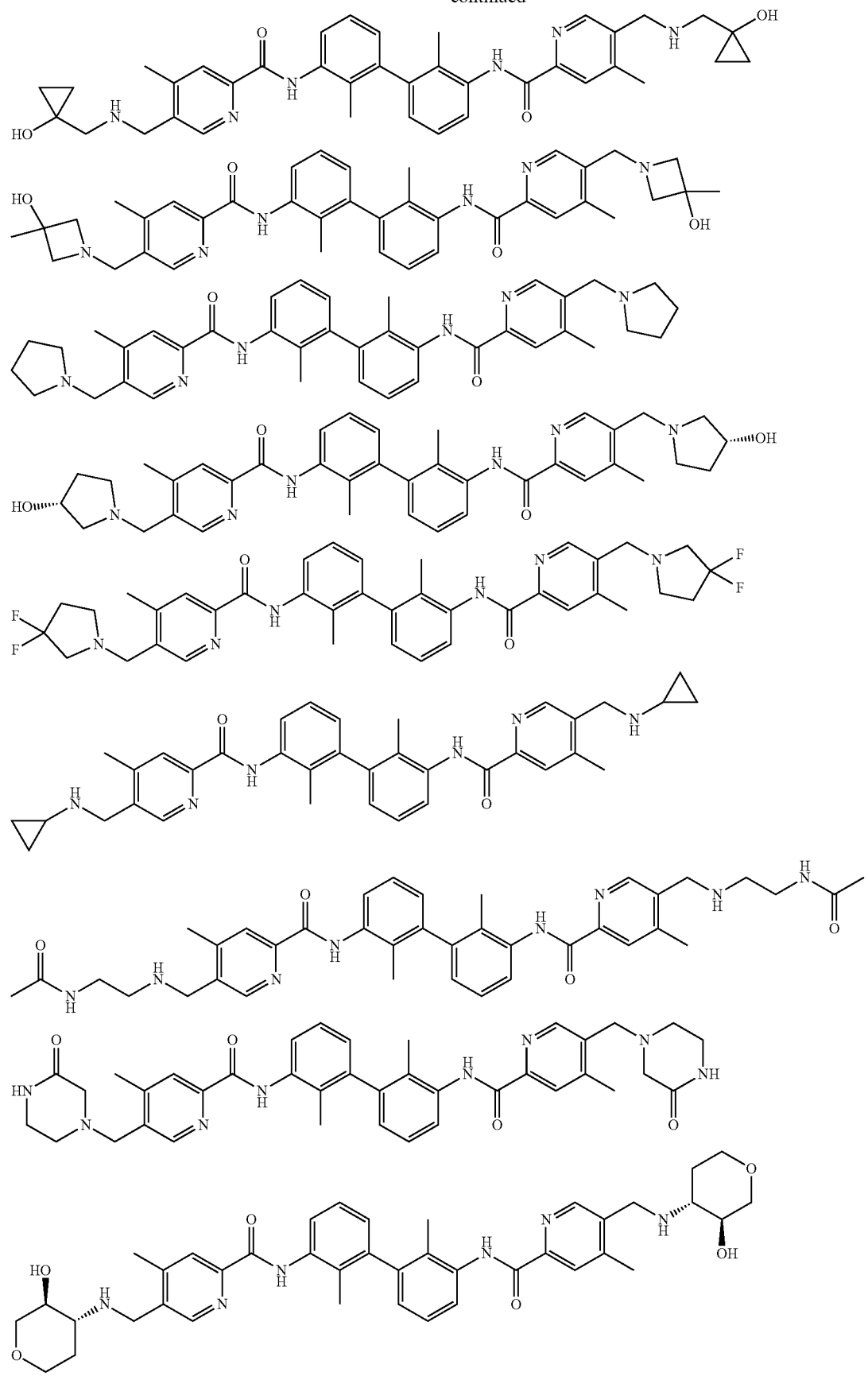

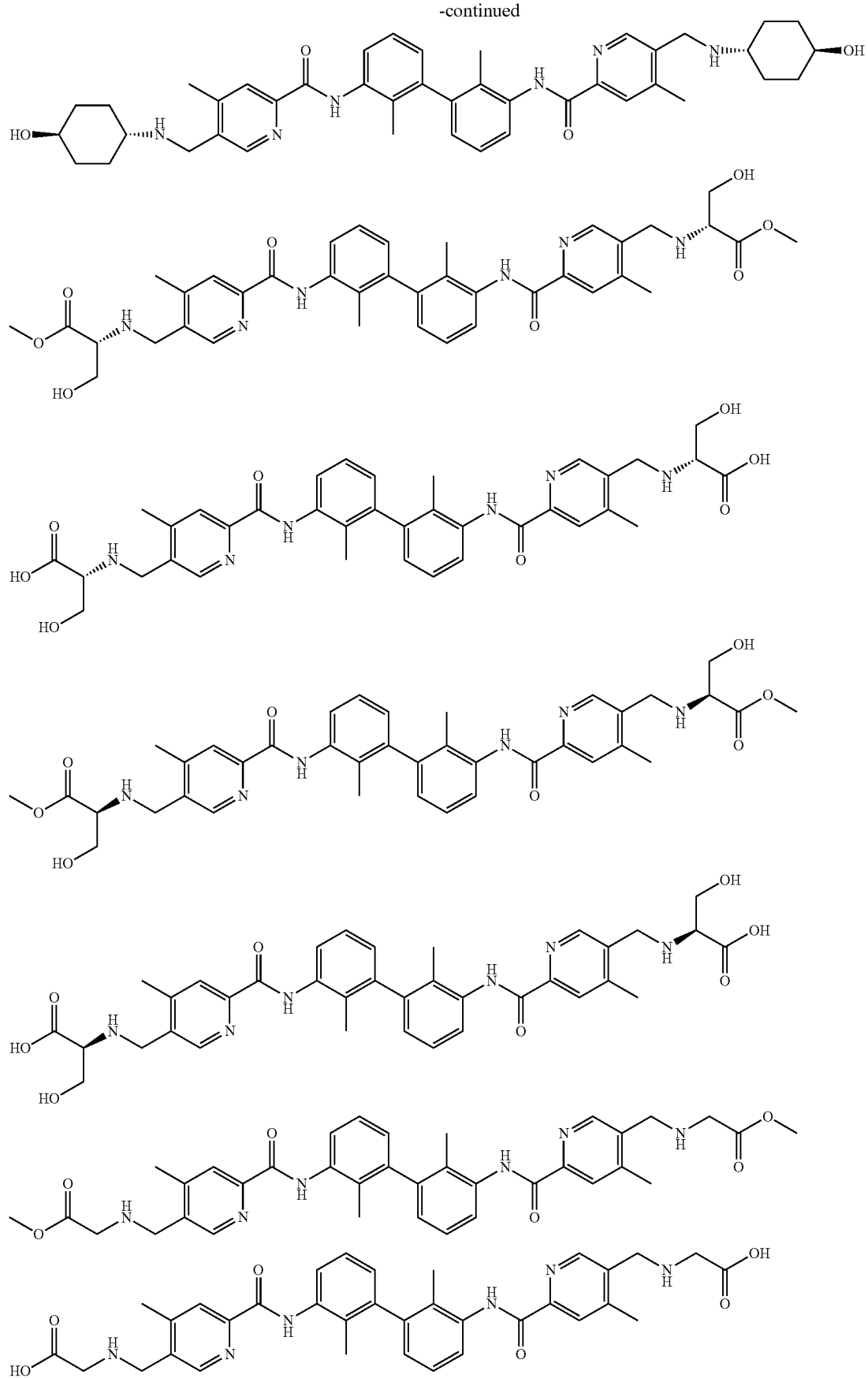

-continued
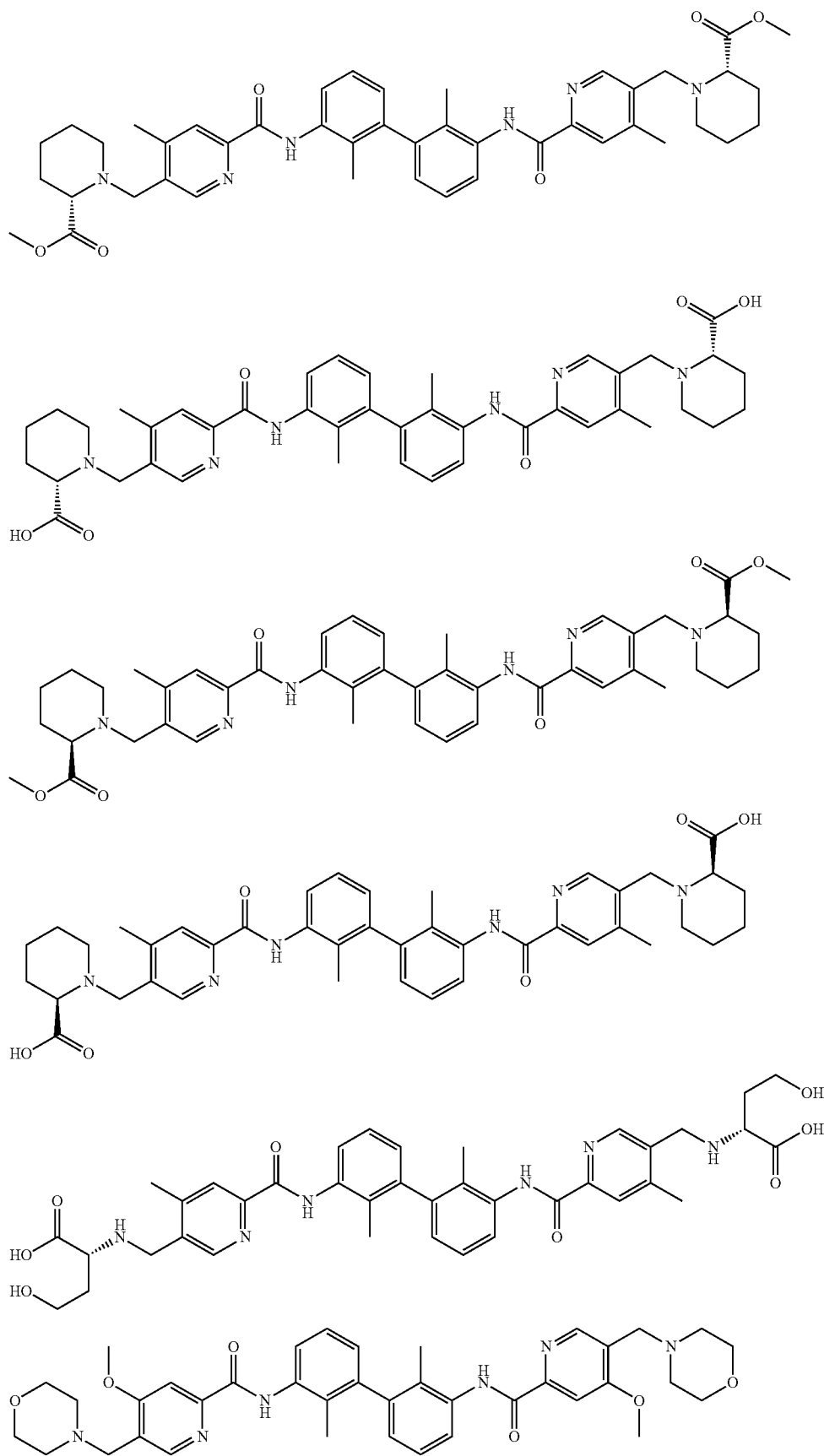

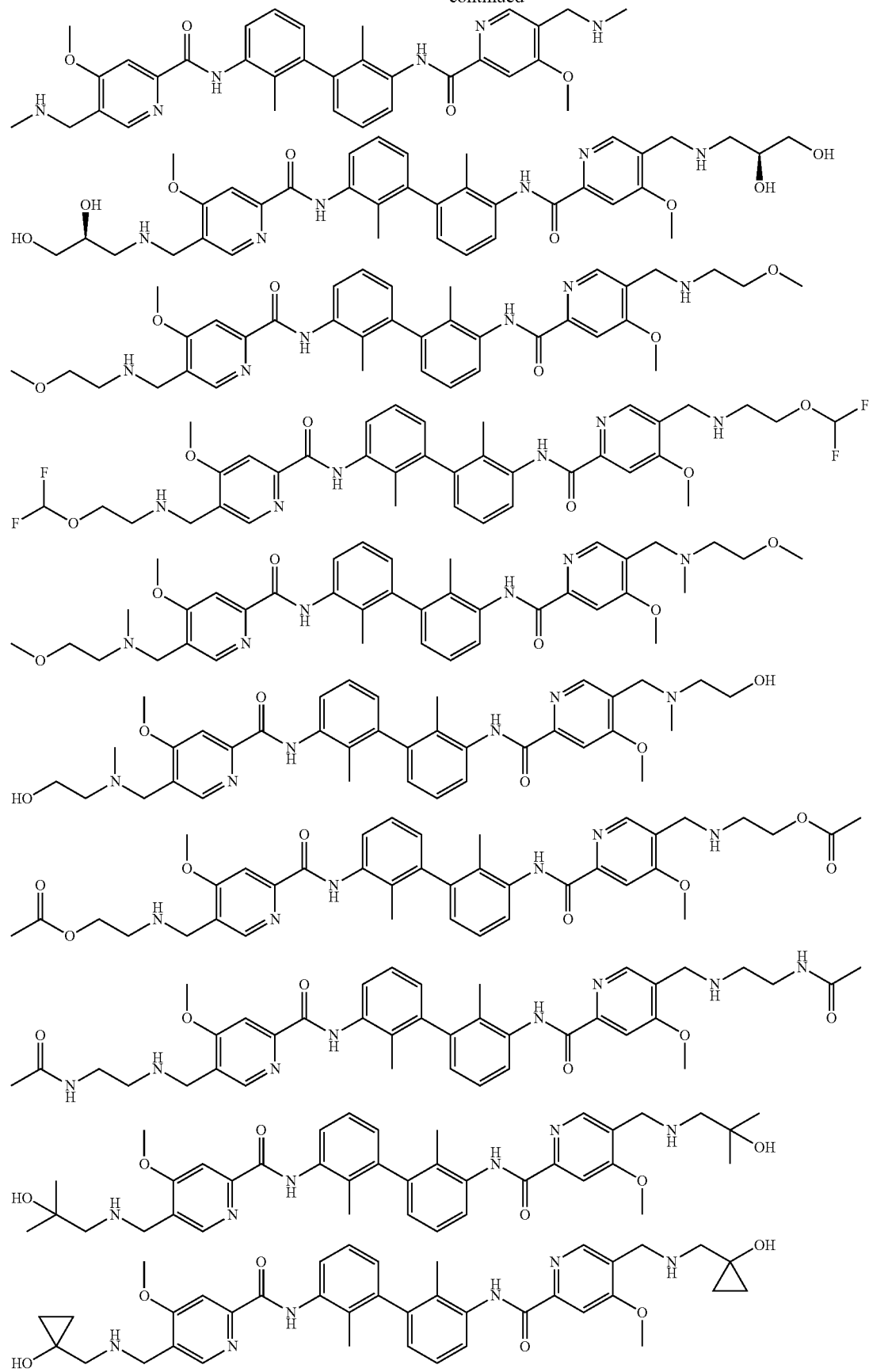

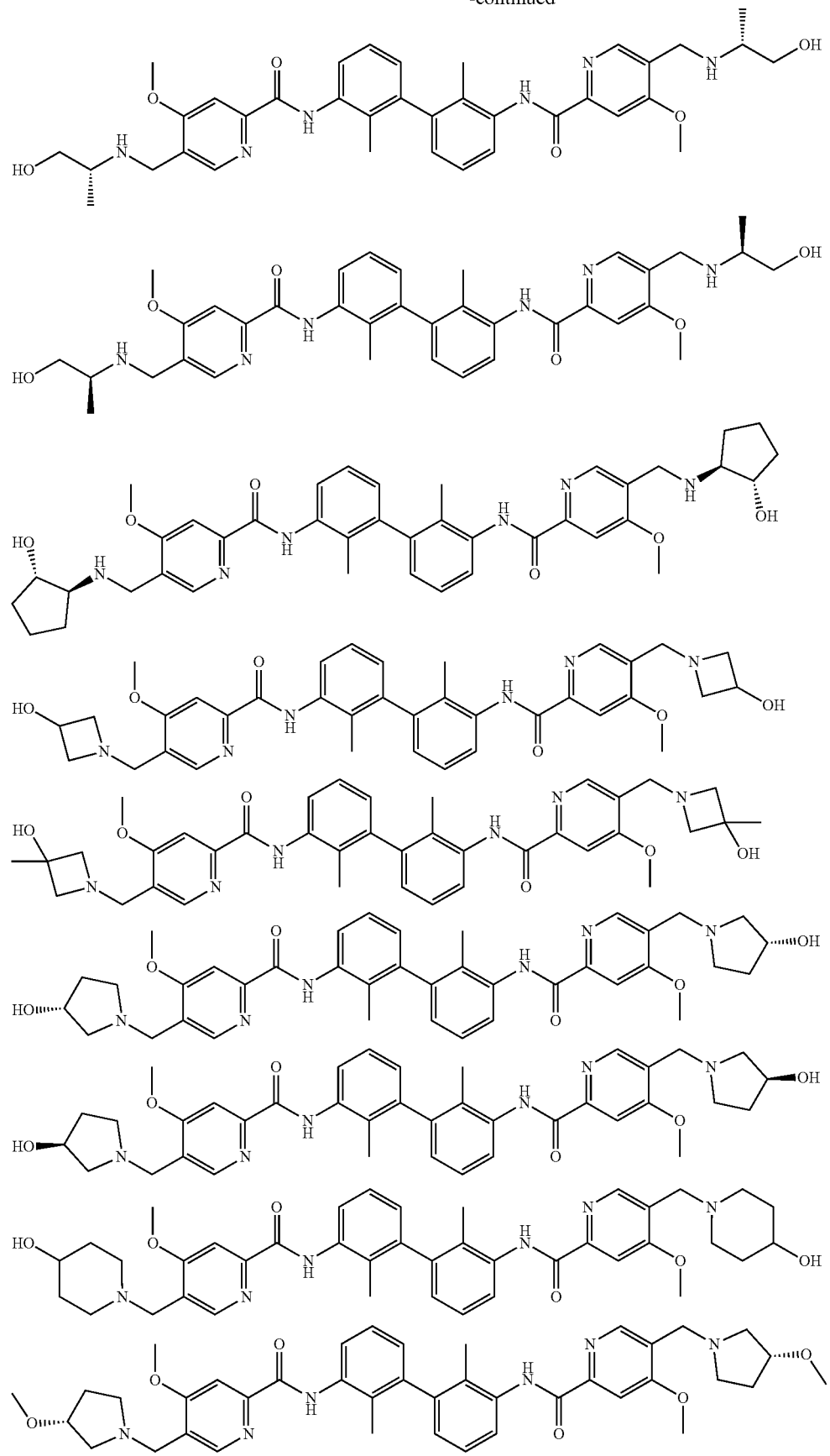

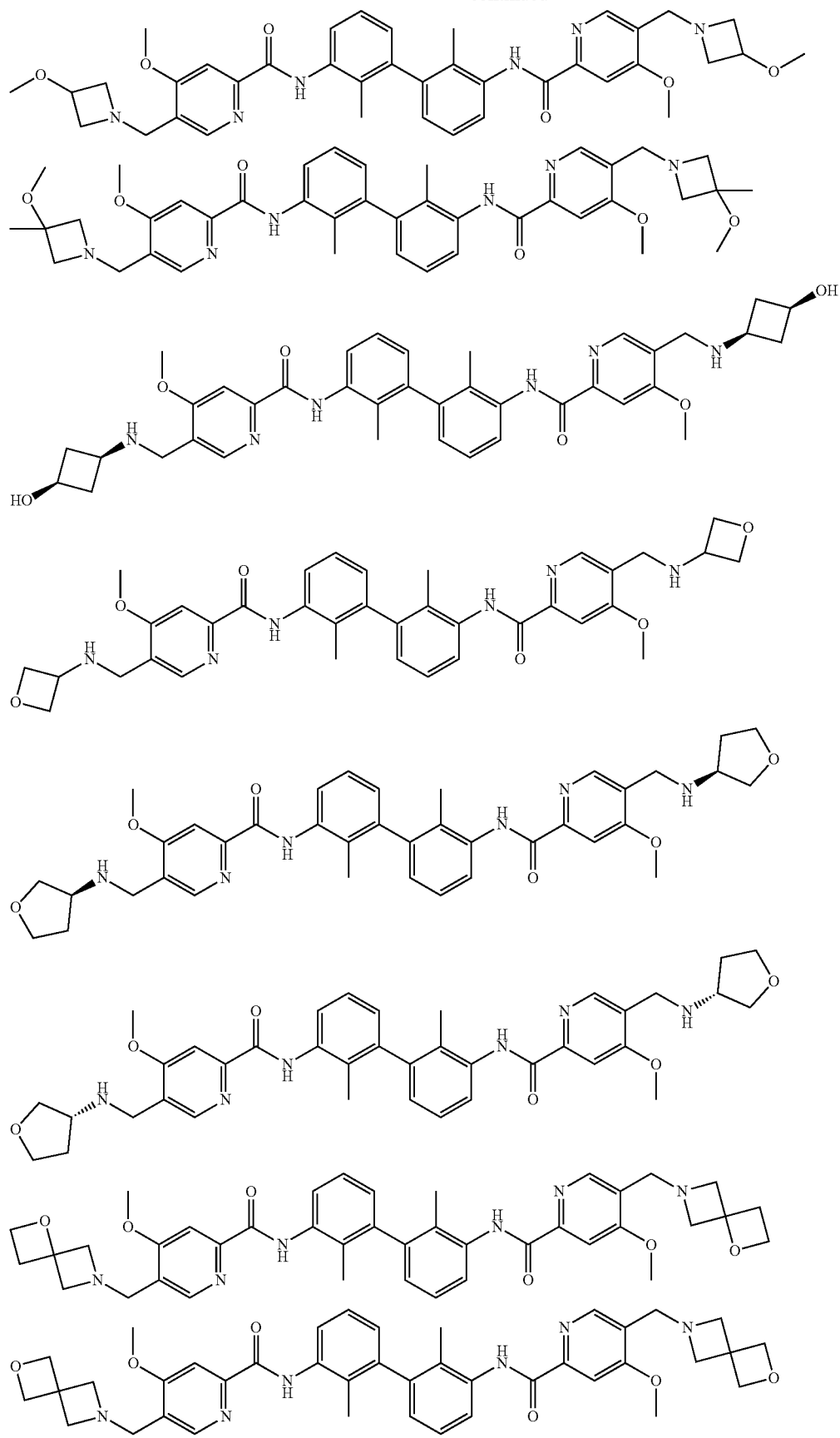

31 32
-continued
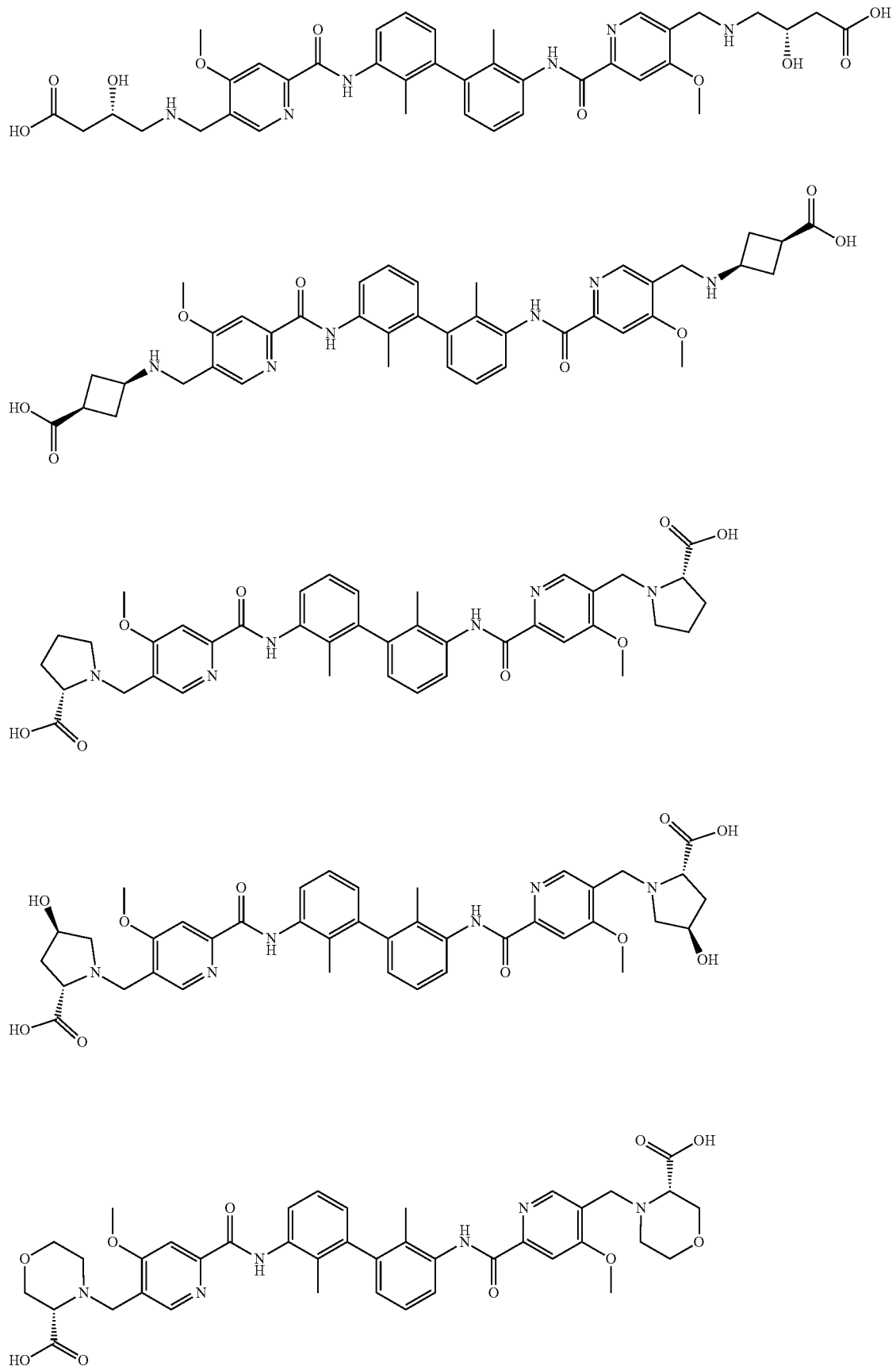

-continued
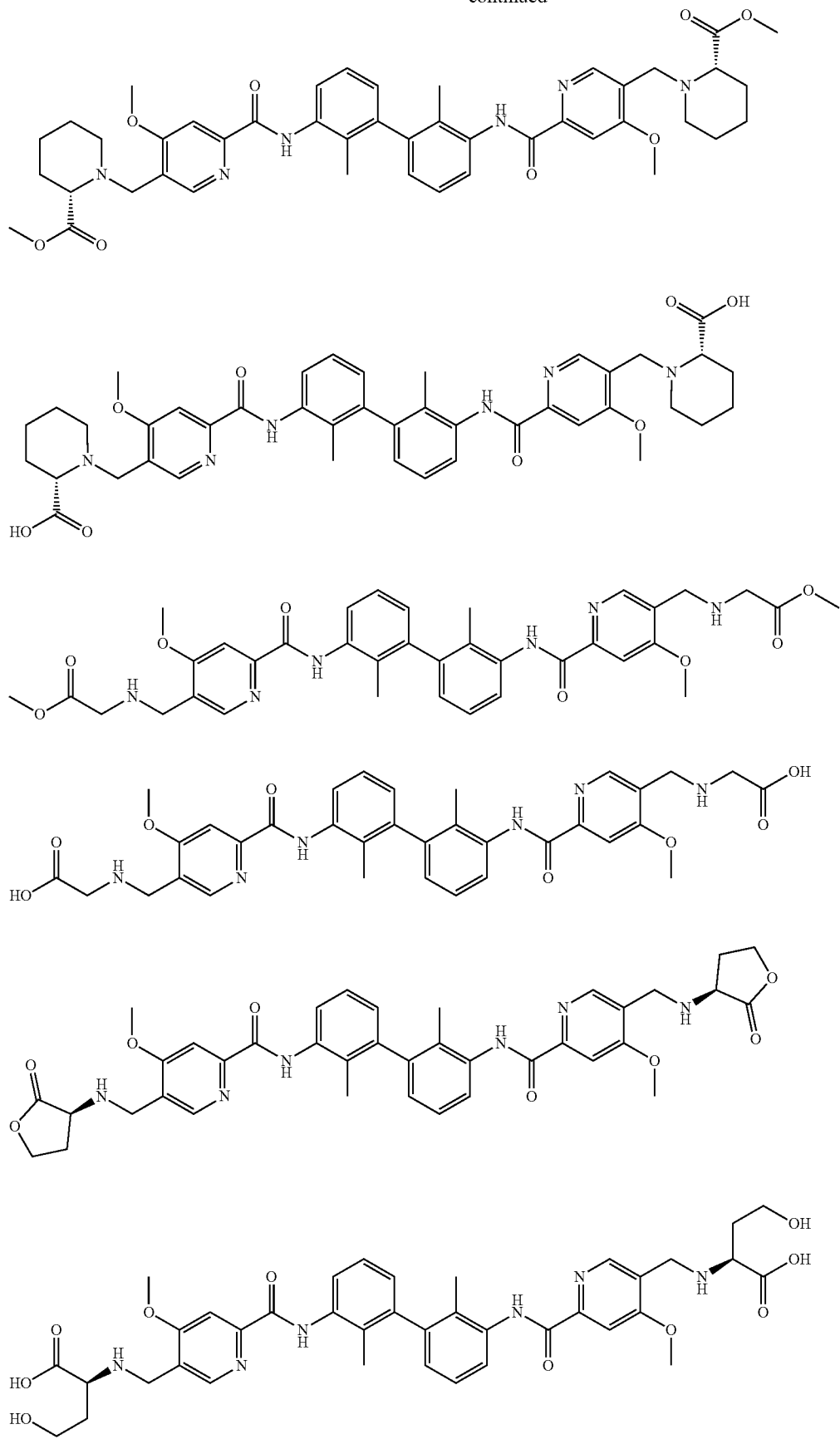

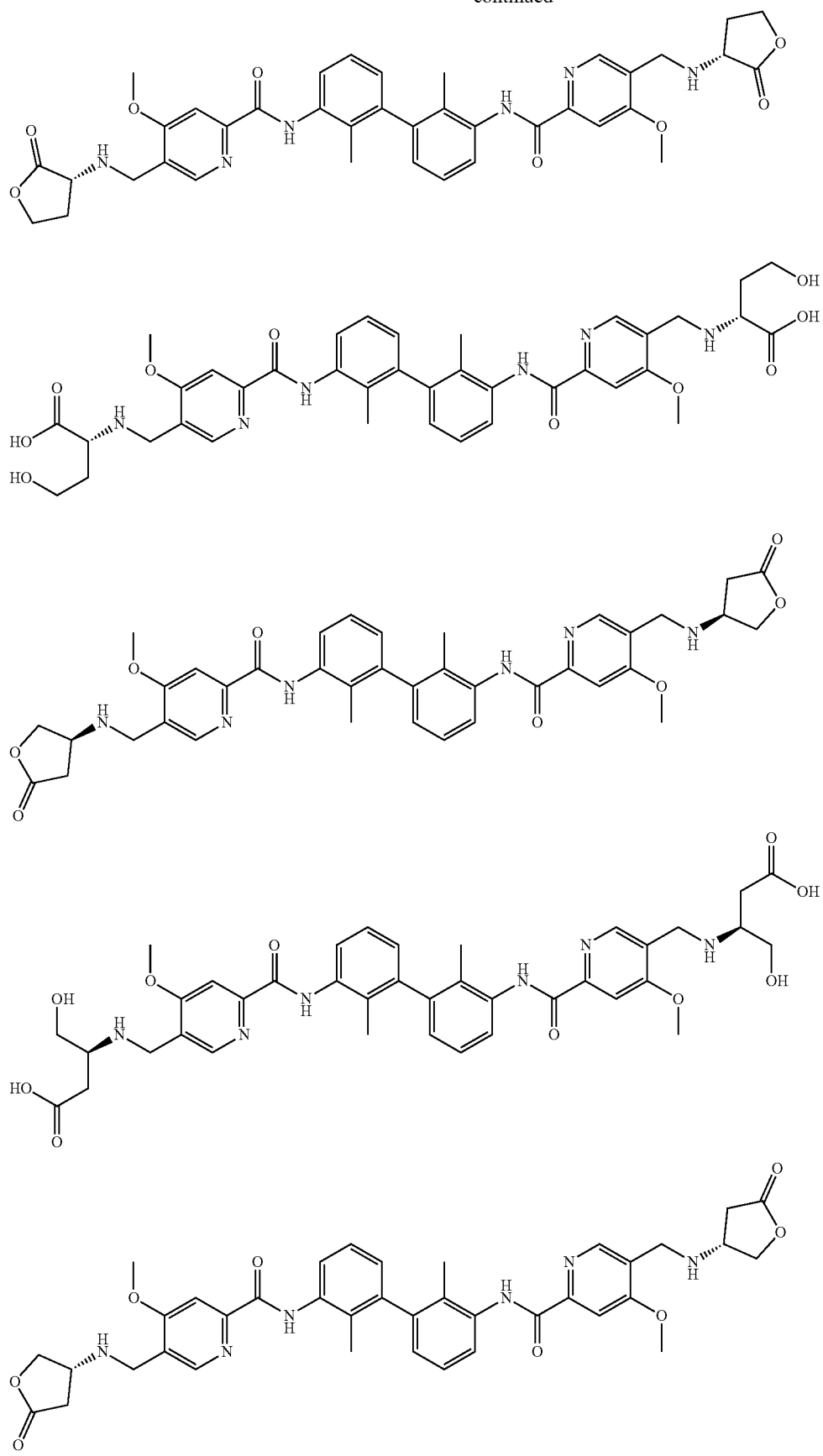

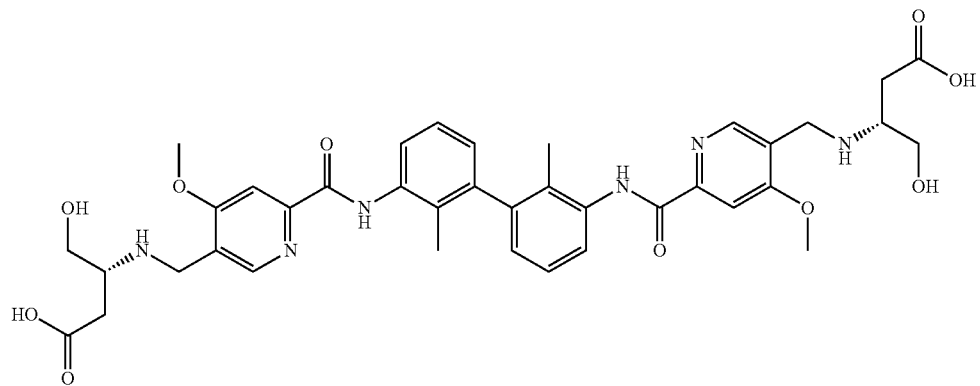
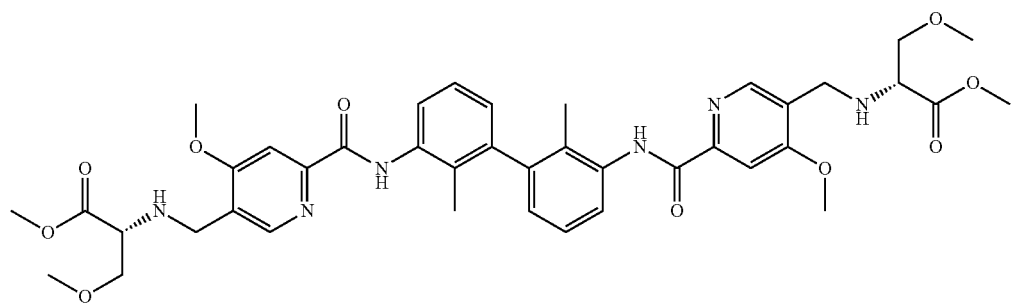
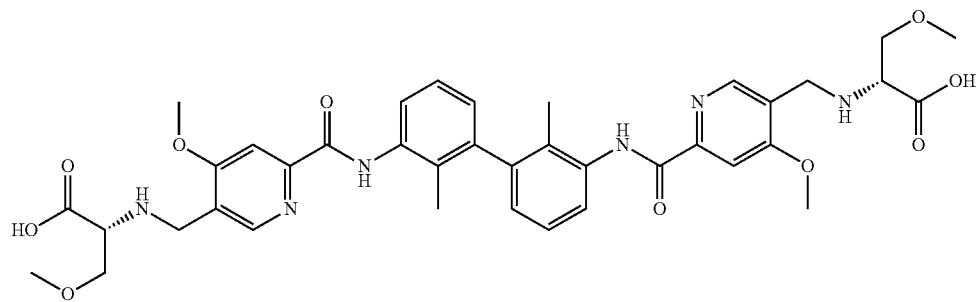
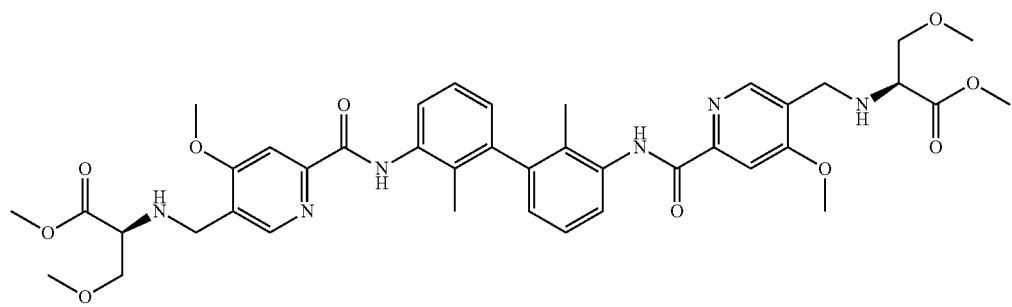
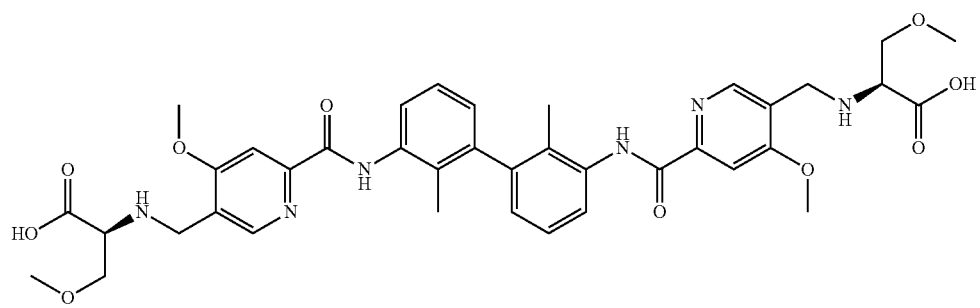

-continued
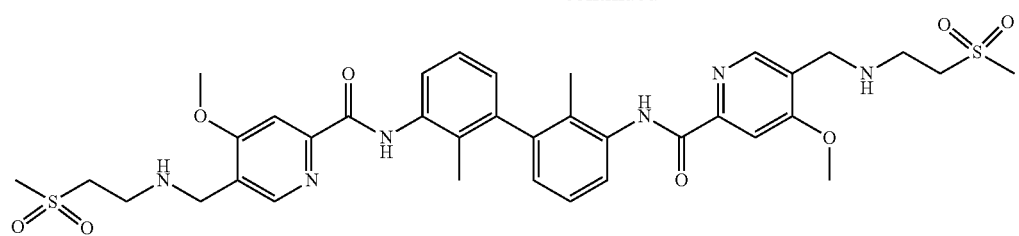
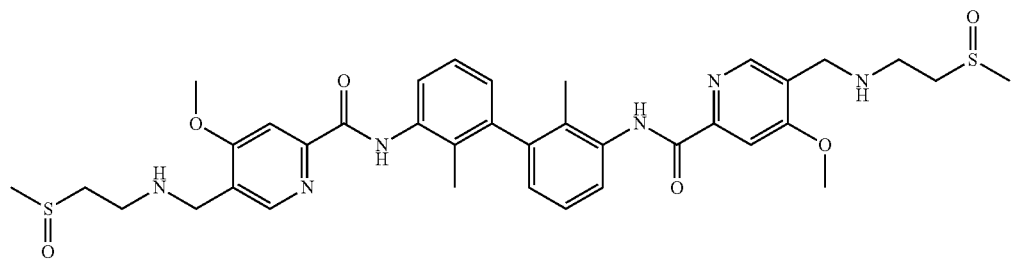
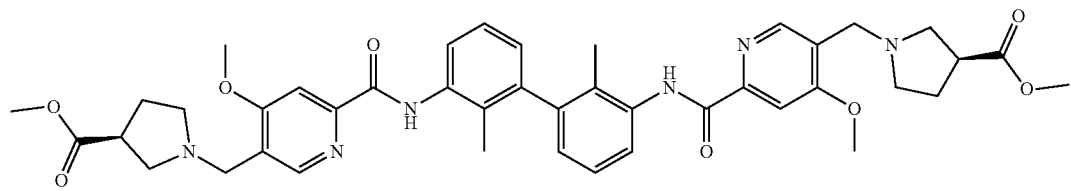
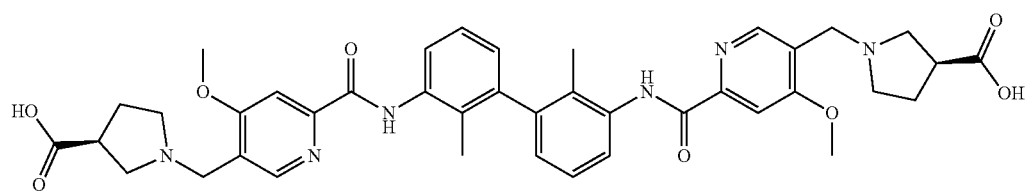
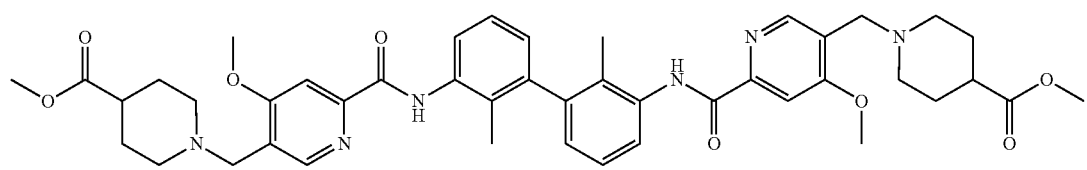
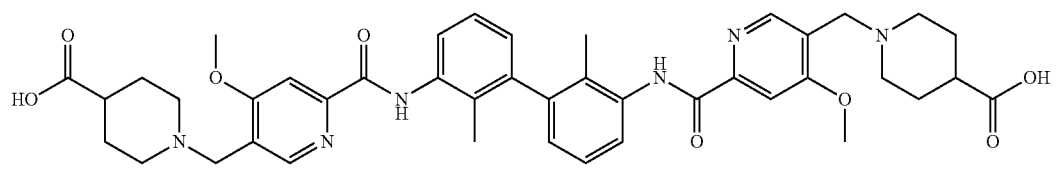
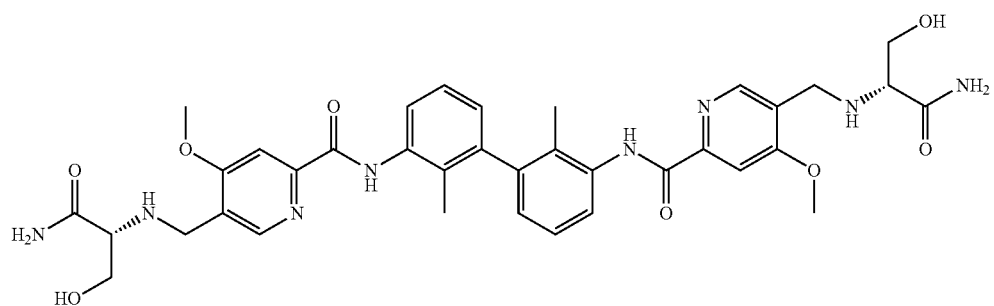

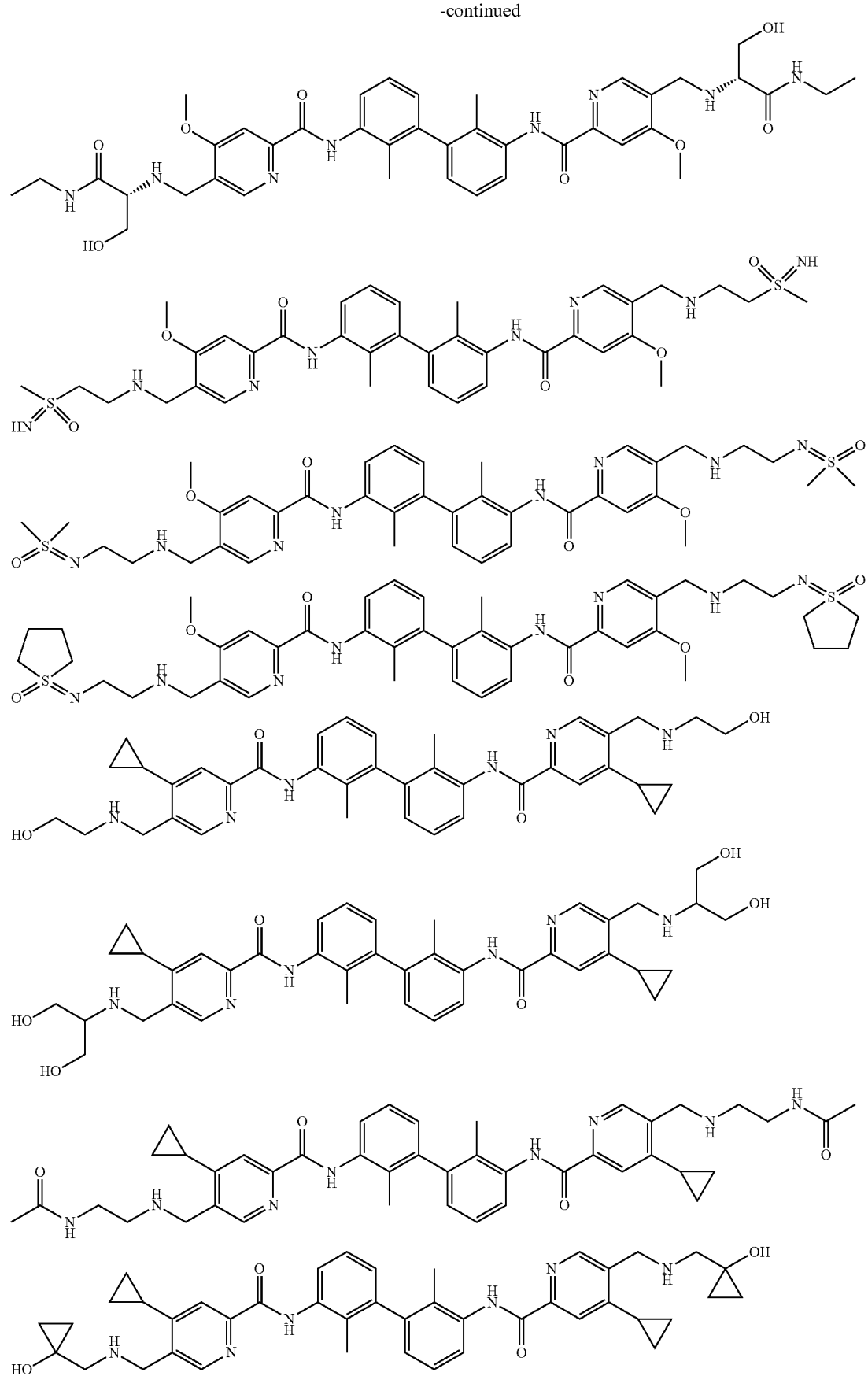

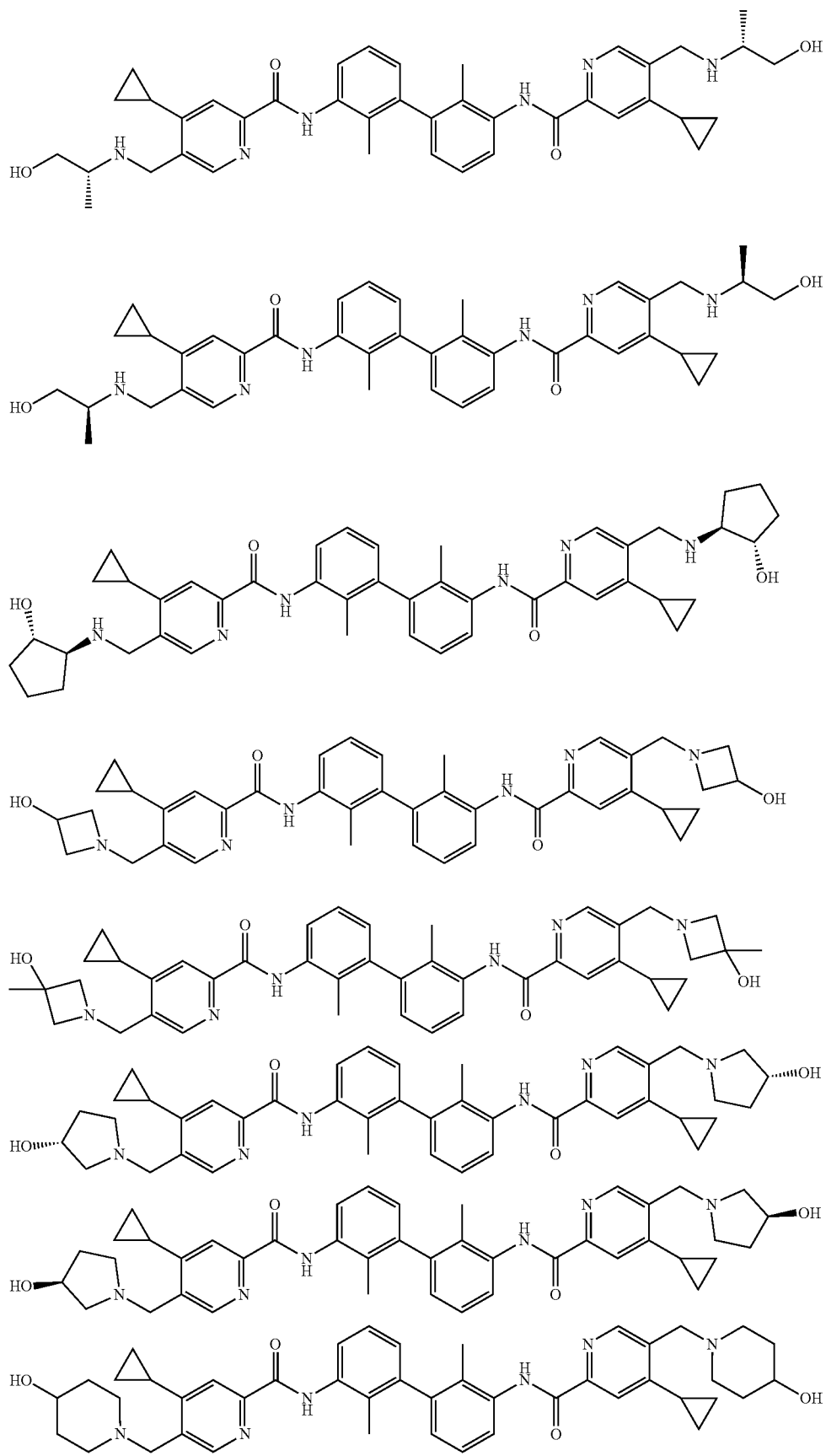

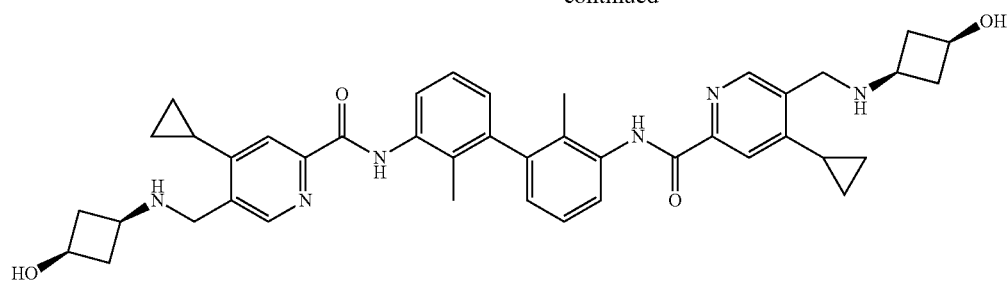
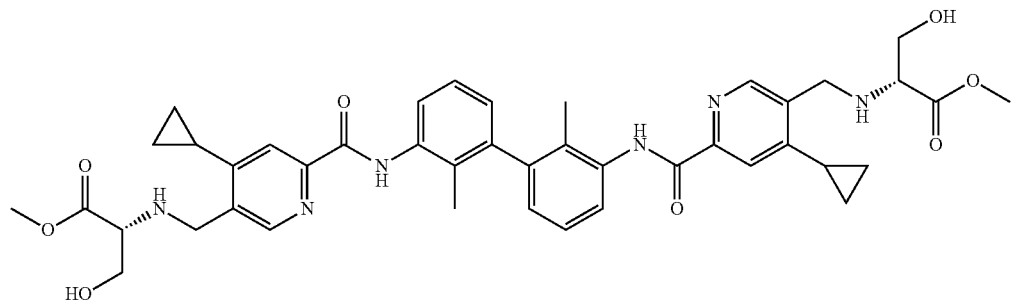
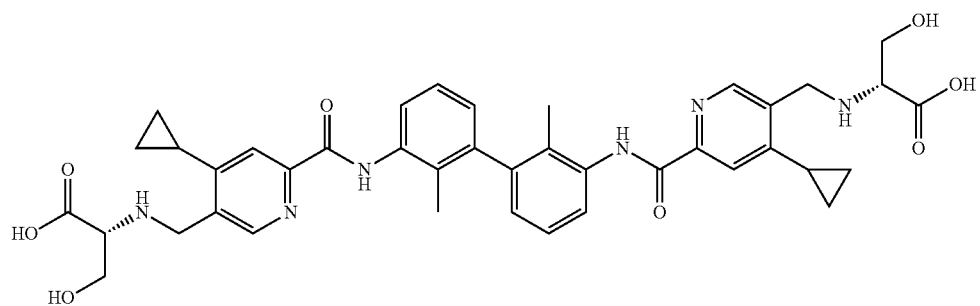
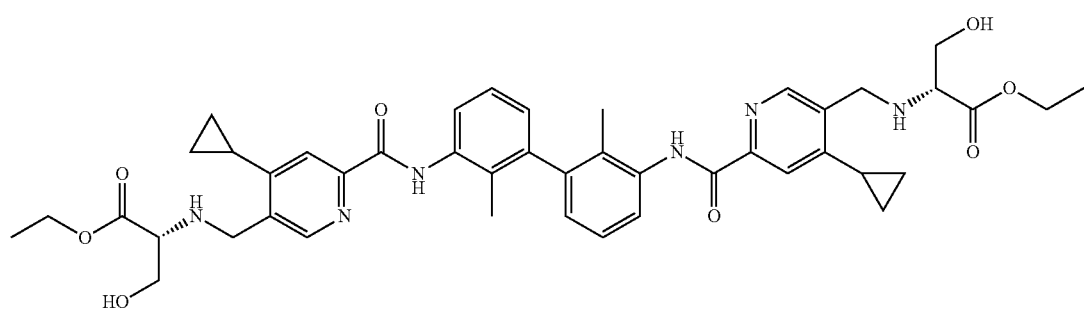
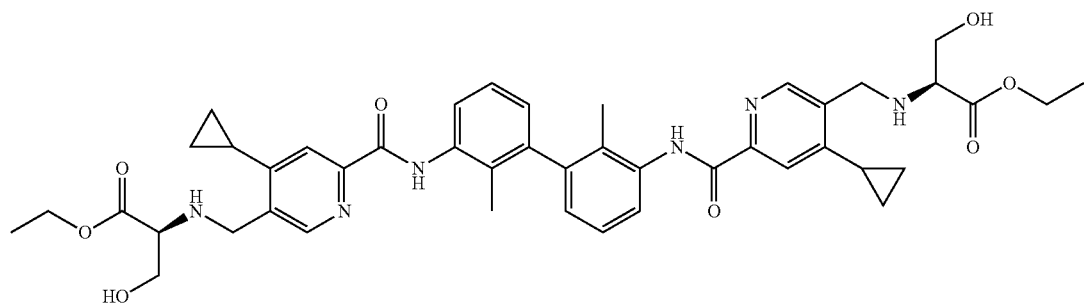

-continued
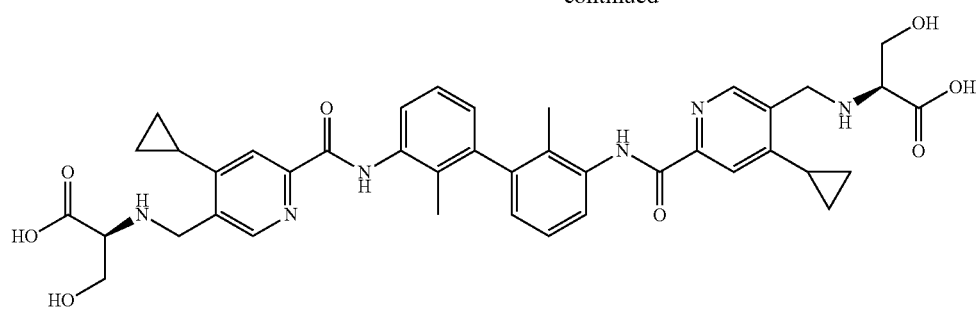
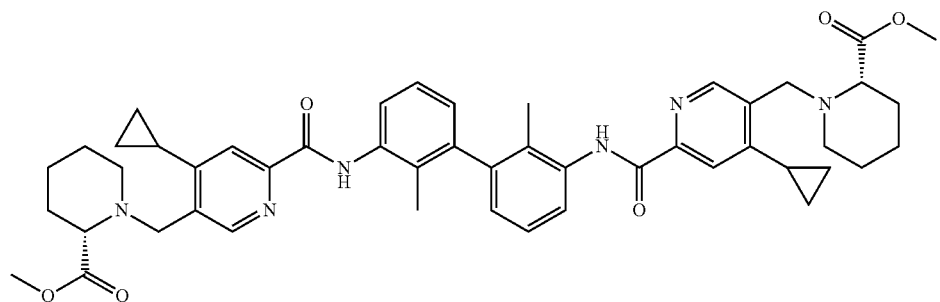
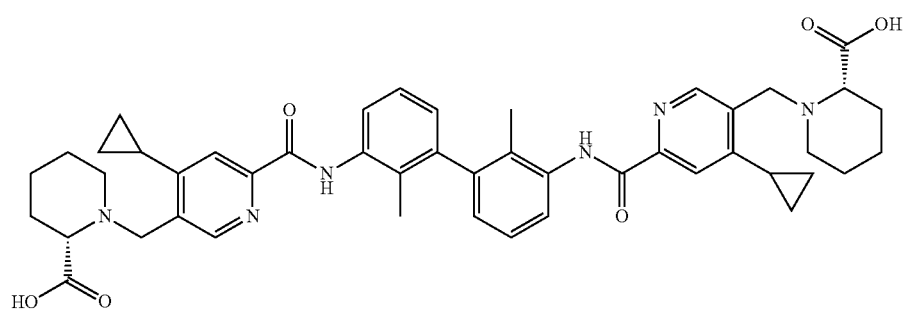
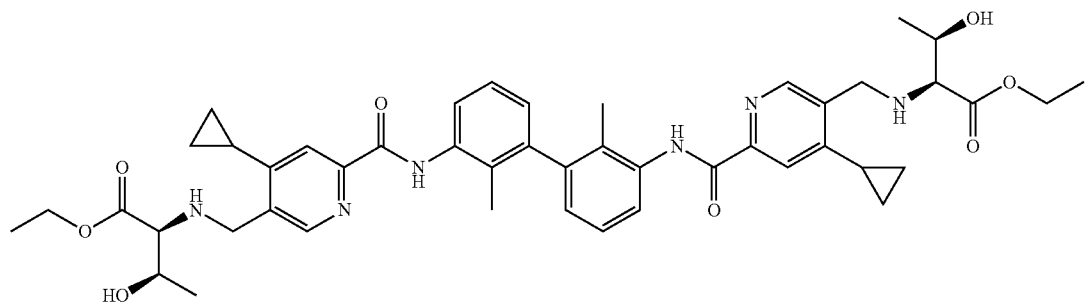
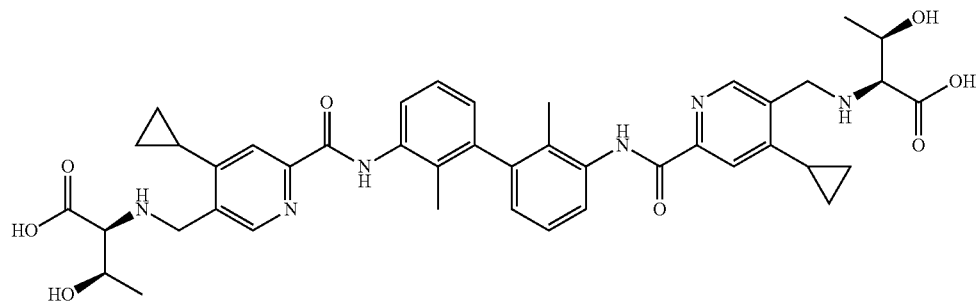

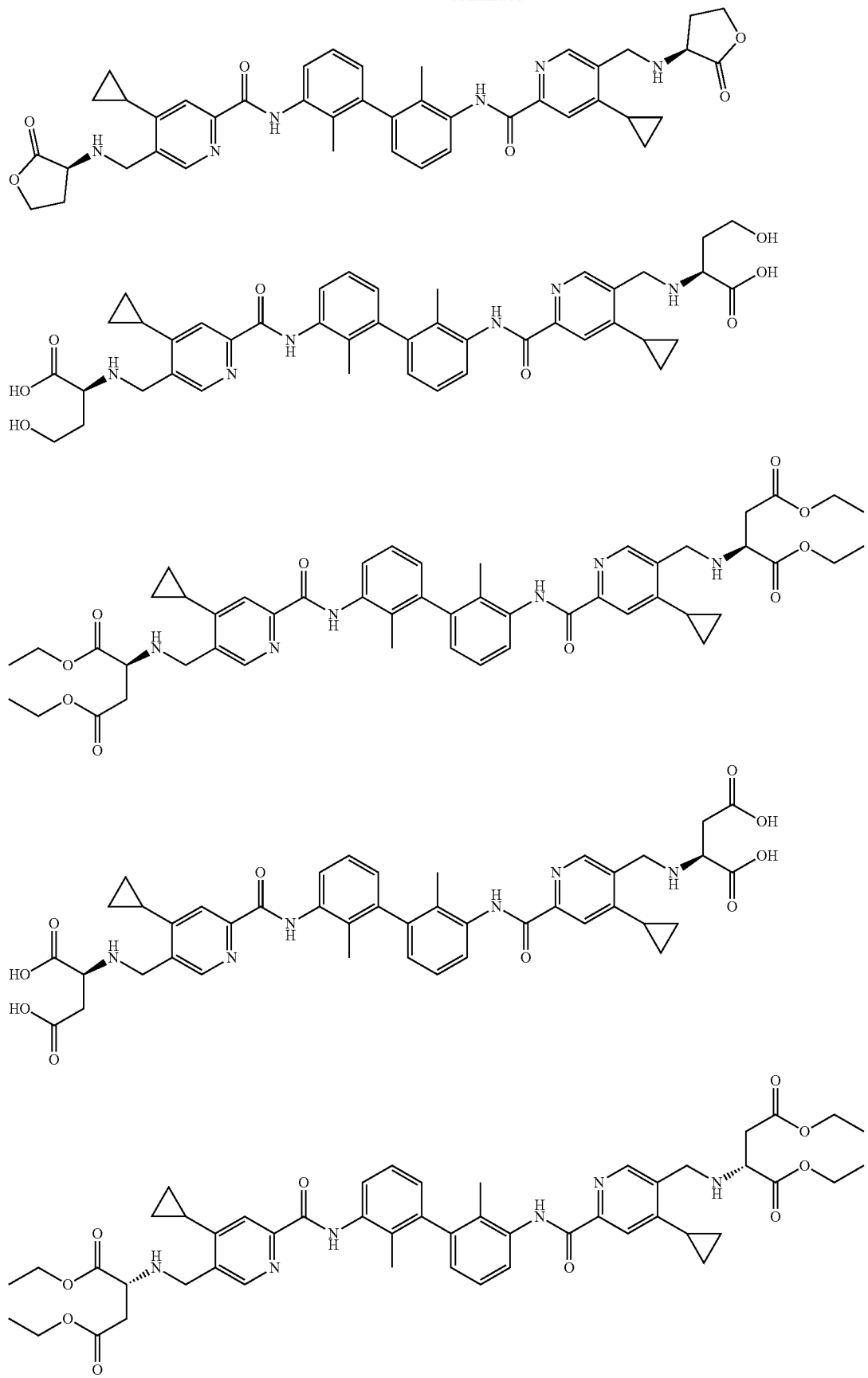

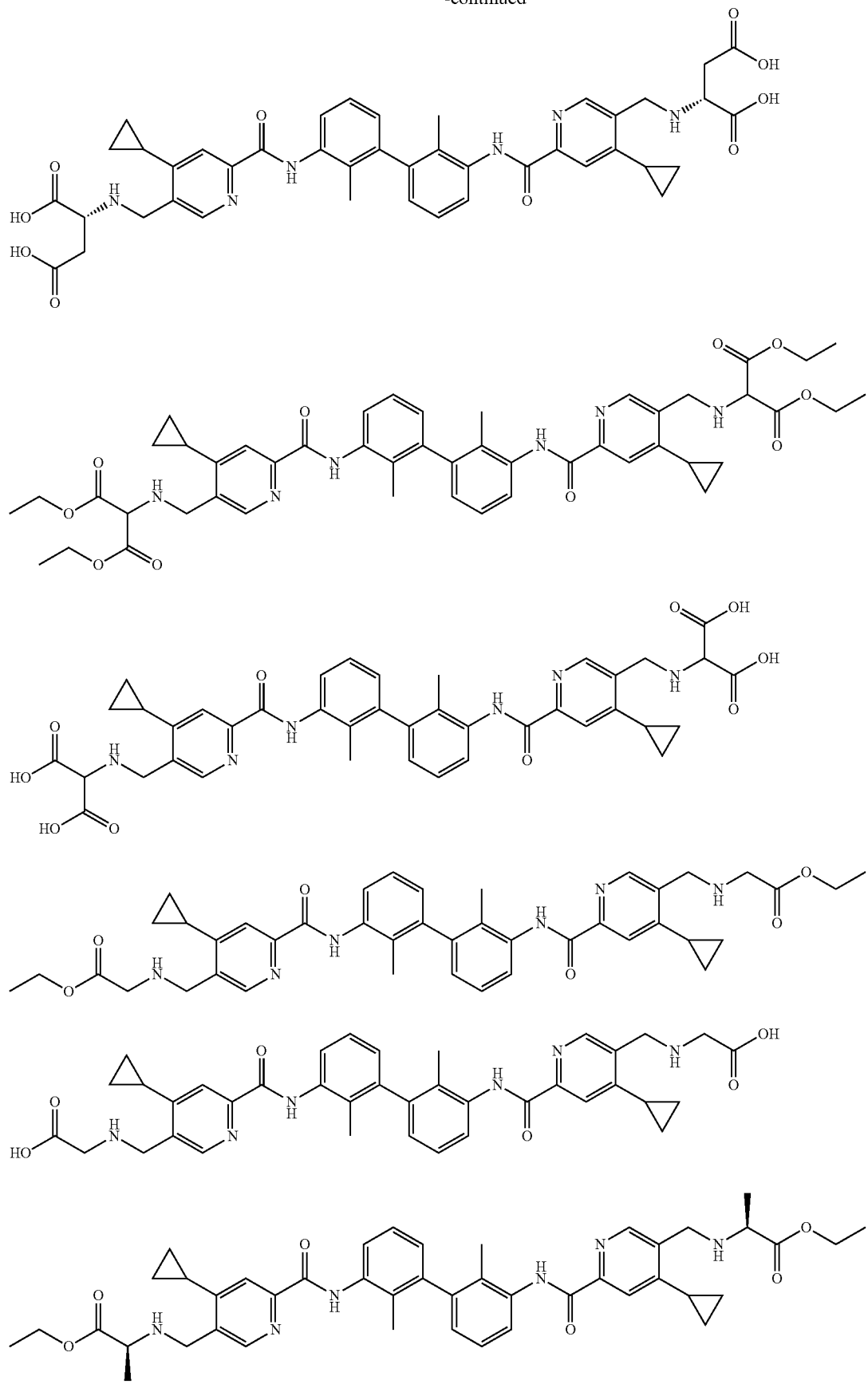

-continued
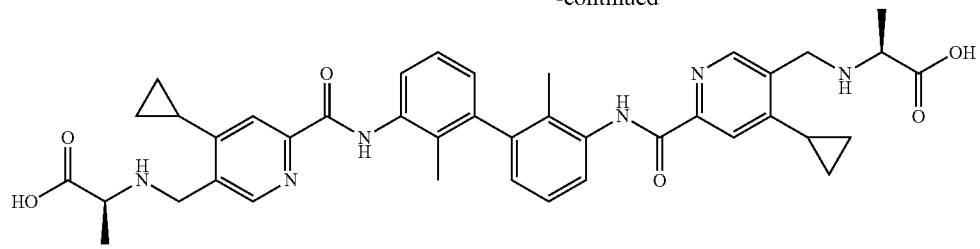
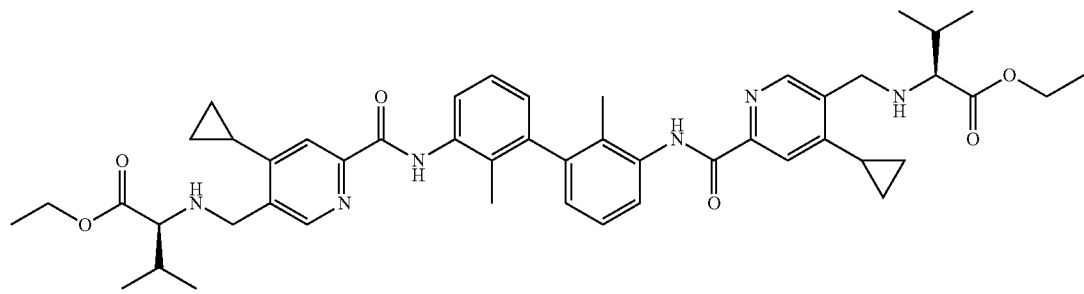
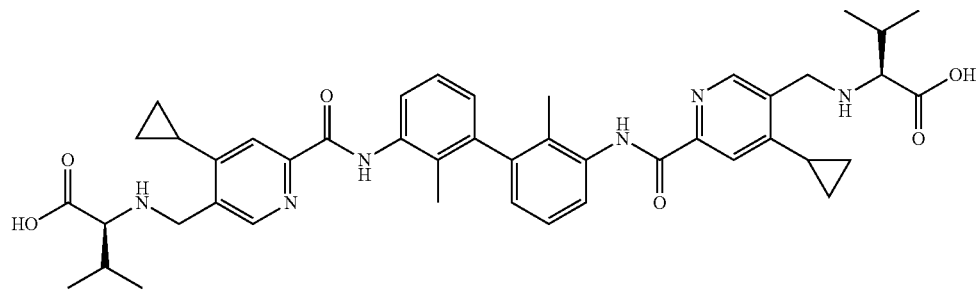
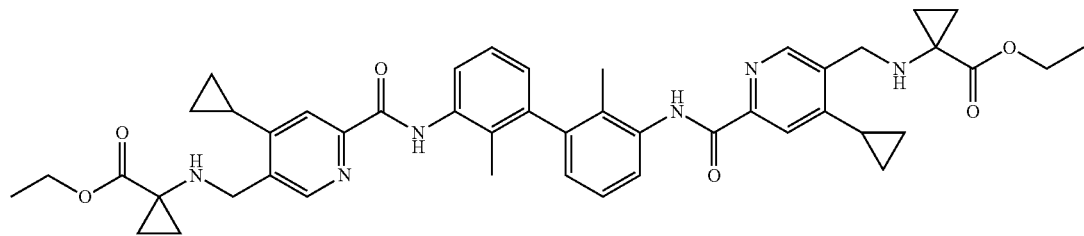
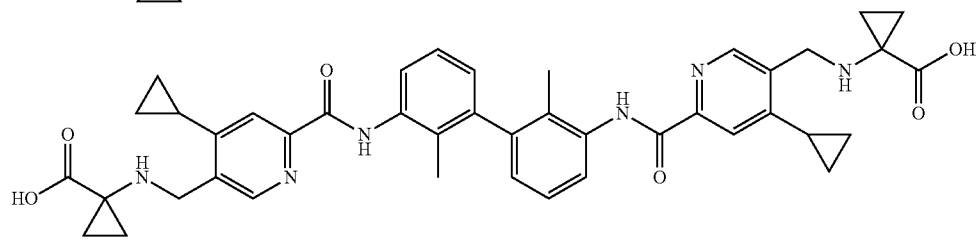
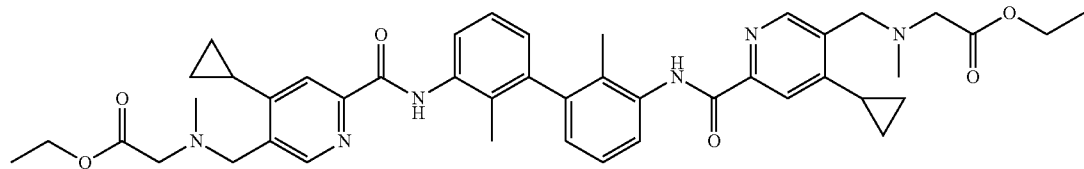
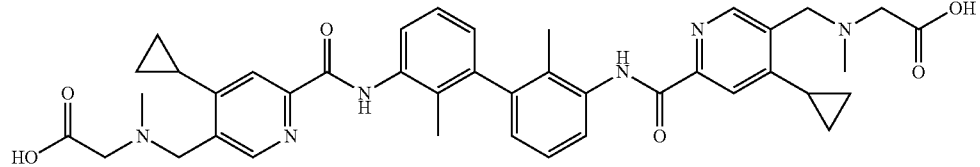

-continued
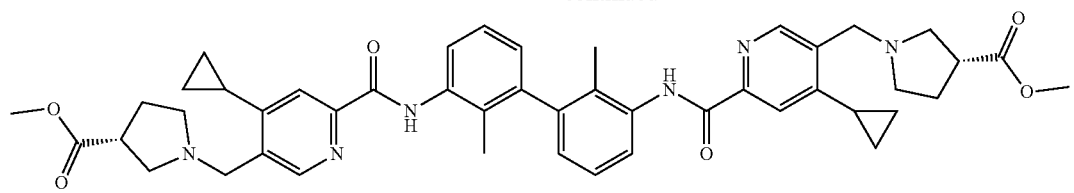
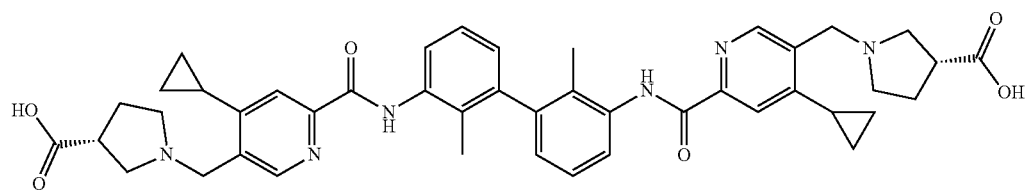
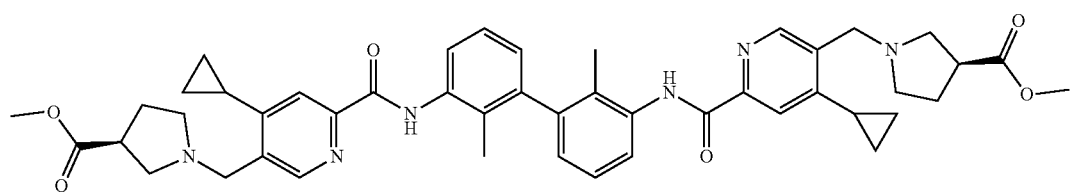
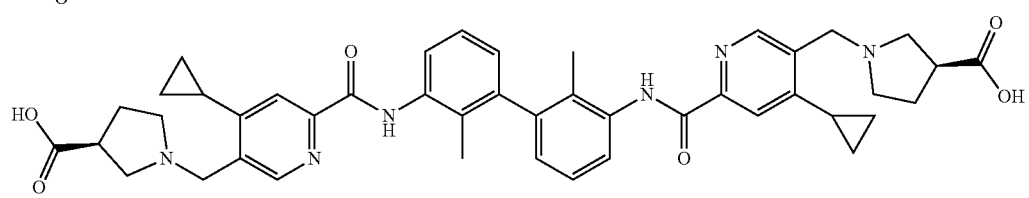
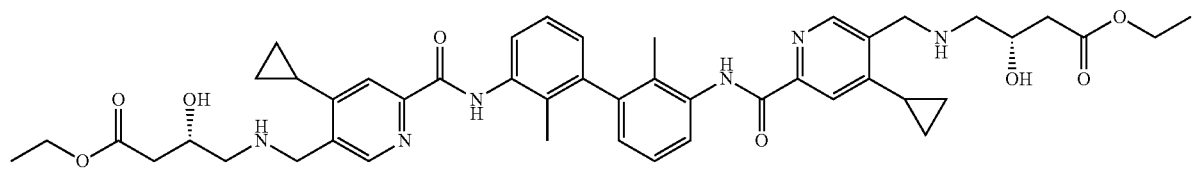
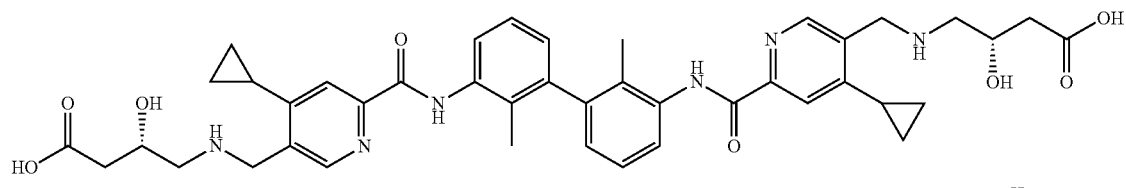
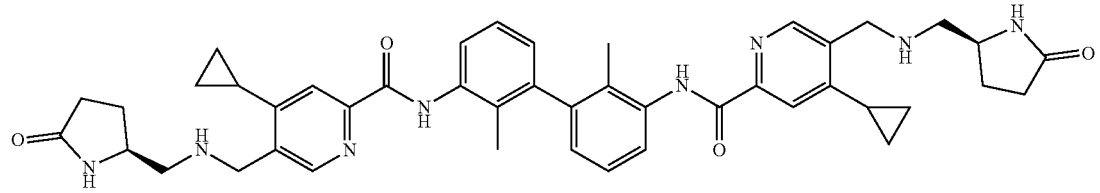
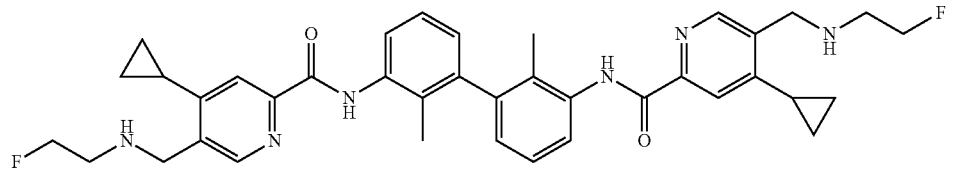
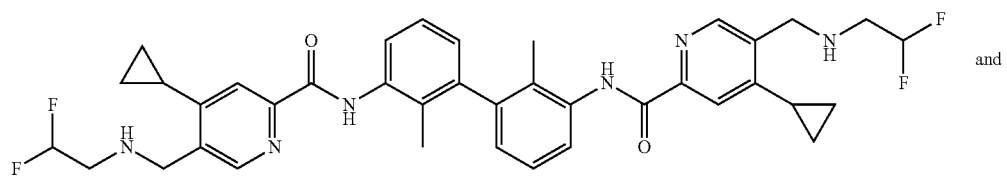
and -continued

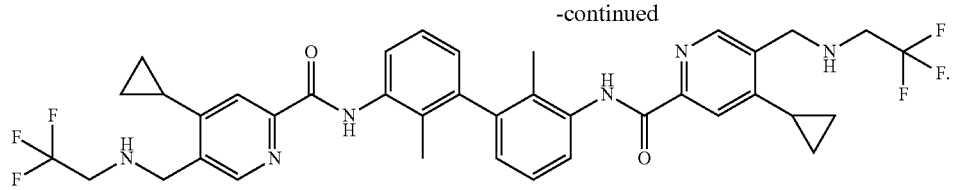

The second aspect of the present invention provides a process for preparing the compound of formula (I), the stereoisomer, prodrug or pharmaceutically acceptable salt thereof, comprising the following steps:

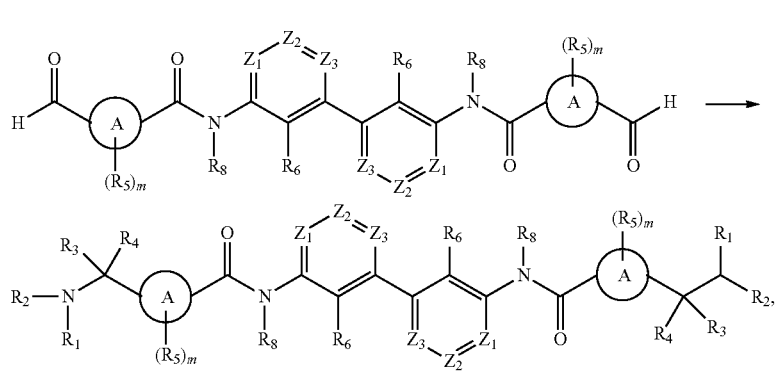

wherein ring A, $Z_1$, $Z_2$, $Z_3$, $R_1$, $R_2$, $R_3$, $R_4$, $R_5$, $R_6$, $R_8$ and m are defined as those in the compound of formula (I).

The third aspect of the present invention provides a pharmaceutical composition, comprising the aforementioned compound of formula (I), the stereoisomer, prodrug or pharmaceutically acceptable salt thereof, and a pharmaceutically acceptable carrier.

The fourth aspect of the present invention provides a use of the aforementioned compound of formula (I), the stereoisomer, prodrug or pharmaceutically acceptable salt thereof or the aforementioned pharmaceutical composition in the preparation of a medicament for preventing and/or treating PD-1/PD-L1 signal pathway-mediated disease.

As a preferred embodiment, the aforementioned PD-1/PD-L1 signal pathway-mediated disease is cancer or tumor, immune-related disease and disorder, communicable disease, infectious disease and metabolic disease.

As a further preferred embodiment, the aforementioned infectious disease is bacterial infectious disease, viral infectious disease or fungal infectious disease.

As a further preferred embodiment, the aforementioned cancer or tumor is selected from lymphoma (including but not limited to lymphocytic lymphoma, primary central nervous system lymphoma, T cell lymphoma, diffuse large B cell lymphoma, follicle center lymphoma, Hodgkin lymphoma, non-Hodgkin lymphoma or primary mediastinal large B cell lymphoma), sarcoma (including but not limited to Kaposi's sarcoma, fibrosarcoma, liposarcoma, chondrosarcoma, osteosarcoma, leiomyosarcoma, rhabdomyosarcoma, soft tissue sarcoma, angiosarcoma or lymphangiosarcoma), melanoma, glioblastoma, synovioma, meningioma, biliary tract tumor, thymic tumor, neuroma, seminoma, nephroblastoma, pleomorphic adenoma, hepatocellular papilloma, renal tubule adenoma, cystadenoma, papilloma, adenoma, leiomyoma, rhabdomyoma, hemangioma, lymphangioma, osteoma, chondroma, lipoma, fibroma, central nervous system tumor, rhachiophyma, brain stem glioma, pituitary adenoma, multiple myeloma, ovarian tumor, myelodysplastic syndrome or mesothelioma, prostate cancer, recurrent prostate cancer or prostate cancer having developed resistance to existing medicaments, thyroid cancer, parathyroid cancer, anal cancer, testicular cancer, urethral carcinoma, penile cancer, bladder cancer, ureteral cancer, uterine cancer, ovarian cancer, fallopian tube cancer, endometrial cancer, cervical cancer, vaginal cancer, vulvar cancer, adrenal cancer, Merkel cell carcinoma, embryonal carcinoma, chronic or acute leukemia (including but not limited to acute myeloid leukemia, chronic myeloid leukemia, acute lymphoblastic leukemia, chronic granulocytic leukemia and chronic lymphoblastic leukemia), bronchial carcinoma, esophageal cancer, nasopharyngeal carcinoma, hepatocellular carcinoma, renal cell carcinoma, small cell lung cancer, basal cell carcinoma, lung cancer, breast cancer, adenocarcinoma, papillary carcinoma, cystadenocarcinoma, squamous non-small cell lung cancer, non-squamous non-small cell lung cancer, rectal cancer, colon cancer, colorectal cancer, gastric cancer, pancreatic cancer, head and neck squamous cell carcinoma, head and neck cancer, gastrointestinal cancer, bone cancer, skin cancer, small intestine cancer, endocrine cancer, renal pelvic carcinoma, epidermoid carcinoma, abdominal wall carcinoma, renal cell carcinoma, transitional cell carcinoma, choriocarcinoma, or metastatic tumor, especially metastatic tumor expressing PD-L1.

As a further preferred embodiment, the aforementioned immune-related disease and disorder is selected from rheumatic arthritis, renal failure, lupus erythematosus, asthma, psoriasis, ulcerative colitis, pancreatitis, allergy, fibrosis, anemia, fibromyalgia, Alzheimer's disease, congestive heart failure, stroke, aortic valve stenosis, arteriosclerosis, osteoporosis, Parkinson's disease, infection, Crohn's disease, ulcerative colitis, allergic contact dermatitis and eczema, systemic sclerosis or multiple sclerosis.

As a further preferred embodiment, the aforementioned communicable disease or infectious disease is selected from sepsis, liver infection, HIV, hepatitis A, hepatitis B, hepatitis C, hepatitis D, herpes virus, papillomavirus or influenza.

As a further preferred embodiment, the aforementioned metabolic disease is selected from diabetes, diabetic ketoacidosis, hyperglycemic hyperosmolar syndrome, hypoglycemia, gout, malnutrition, vitamin A deficiency, scurvy, vitamin D deficiency or osteoporosis.

The fifth aspect of the present invention provides the aforementioned compound of formula (I), the stereoisomer, prodrug or pharmaceutically acceptable salt thereof or the aforementioned pharmaceutical composition for use as a medicament for preventing and/or treating PD-1/PD-L1 signal pathway-mediated cancer or tumor, immune-related disease and disorder, communicable disease, infectious disease or metabolic disease.

The sixth aspect of the present invention provides a method for preventing and/or treating PD-1/PD-L1 signal pathway-mediated cancer or tumor, immune-related disease and disorder, communicable disease, infectious disease or metabolic disease, comprising administering the aforementioned compound of formula (I), the stereoisomer, prodrug or pharmaceutically acceptable salt thereof or the aforementioned pharmaceutical composition to a patient.

The seventh aspect of the present invention provides a method for enhancing, stimulating, regulating and/or increasing the immune response mediated by the PD-1/PD-L1 signal pathway in a subject in need, comprising administering the aforementioned compound of formula (I), the stereoisomer, prodrug or pharmaceutically acceptable salt thereof or the aforementioned pharmaceutical composition to a patient.

The eighth aspect of the present invention provides a method for inhibiting the growth, proliferation or metastasis of tumor cells, comprising administering the aforementioned compound of formula (I), the stereoisomer, prodrug or pharmaceutically acceptable salt thereof or the aforementioned pharmaceutical composition to a patient.

The ninth aspect of the present invention provides a method for treating PD-1/PD-L1 signal pathway-mediated communicable disease, infectious disease, metabolic disease or disorder, comprising administering the aforementioned compound of formula (I), the stereoisomer, prodrug or pharmaceutically acceptable salt thereof or the aforementioned pharmaceutical composition to a patient.

DETAILED DESCRIPTION OF THE INVENTION

After an extensive and intensive research, the inventors of the present invention, for the first time, developed a series of compounds of general formula (I) that are globally symmetrical but have some differences locally in structure, and in particular the compounds of a fully symmetrical structure, and the series of compounds are biaryl derivatives for inhibiting the interaction between PD-1 and PD-L1. With a strong inhibitory effect on the interaction between PD-1 and PD-L1, the series of compounds of the present invention can be widely applied in the preparation of medicaments for preventing and/or treating cancer or tumor, immune-related disease and disorder, communicable disease, infectious disease or metabolic disease that is mediated by the PD-1/PD-L1 signal pathway, and are expected to be developed into a new generation of PD-1/PD-L1 inhibitors. The present invention is achieved on this basis.

Detailed description: Unless otherwise stated, the following terms used in the specification and claims have the following meanings.

"Alkyl" refers to linear or branched saturated aliphatic alkyl groups, for example, "CHO alkyl" means a linear or branched alkyl containing 1 to 10 carbon atoms, which includes, but is not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or various branched isomers thereof, etc.

Alkyl may be optionally substituted or unsubstituted, and when it is substituted, the substituent is preferably one or more of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_r$R$_{12}$, —$C_{0-8}$—O—R$_{13}$, —$C_{0-8}$—C(O)OR$_{13}$, —$C_{0-8}$—C(O)R$_{13}$, —$C_{0-8}$—O—C(O)R$_{14}$, —$C_{0-8}$—NR$_{15}$R$_{16}$, —$C_{0-8}$—C(=NR$_{15}$)R$_{14}$, —$C_{0-8}$—N(R$_{15}$)—C(=NR$_{16}$)R$_{14}$, —$C_{0-8}$—C(O)NR$_{15}$R$_{16}$ and —$C_{0-8}$—N(R$_{15}$)—C(O)R$_{14}$.

"Cycloalkyl" or "carbocycle" refers to a monocyclic or polycyclic hydrocarbon substituent that is saturated or partially unsaturated, for example, "$C_{3-10}$ cycloalkyl" means a cycloalkyl containing 3 to 10 carbon atoms, which may be monocyclic cycloalkyl and polycyclic cycloalkyl, wherein, monocyclic cycloalkyl includes, but is not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc.

Polycyclic cycloalkyl includes spirocycloalkyl, fused cycloalkyl and bridged cycloalkyl. "Spirocycloalkyl" refers to a polycyclic group in which a carbon atom (called spiro-atom) is shared among monocyclic rings, wherein those rings may contain one or more double bonds, but none of them has a fully conjugated π-electron system. According to the number of the spiro-atoms shared among the rings, the spirocycloalkyl may be monospirocycloalkyl, bispirocycloalkyl or polyspirocycloalkyl, including but not limited to:

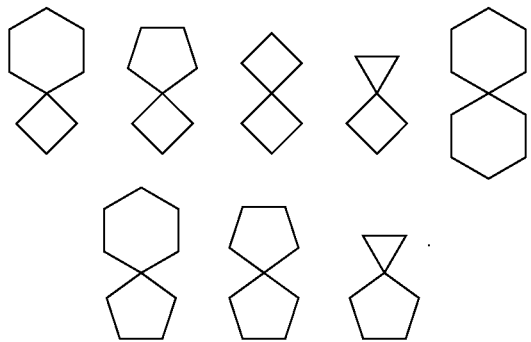

"Fused cycloalkyl" refers to an all-carbon polycyclic group in which each ring shares a pair of adjacent carbon atoms with the other rings in the system, wherein one or more of the rings may contain one or more double bonds, but none of them has a fully conjugated π-electron system. According to the number of formed rings, the fused cycloalkyl may be bicyclic, tricyclic, tetracyclic or polycyclic, including but not limited to:

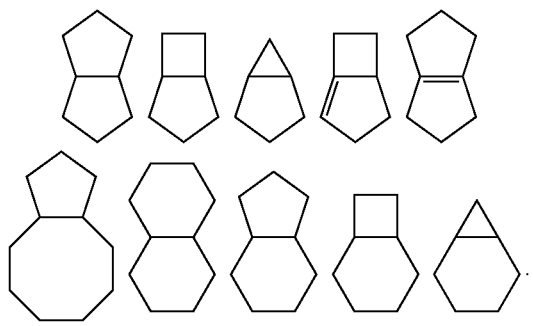

"Bridged cycloalkyl" refers to an all-carbon polycyclic group in which any two rings share two carbon atoms that are not directly connected to each other, wherein these rings may contain one or more double bonds, but none of them has a fully conjugated π-electron system. According to the number of formed rings, the bridged cycloalkyl may be bicyclic, tricyclic, tetracyclic or polycyclic, including but not limited to:

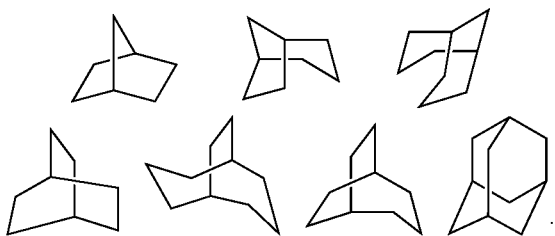

The cycloalkyl ring can be fused to an aryl, heteroaryl or heterocycloalkyl ring, wherein the ring attached to the parent structure is cycloalkyl, which includes, but is not limited to, indanyl, tetrahydronaphthyl, benzocycloheptyl, etc.

Cycloalkyl may be optionally substituted or unsubstituted, and when it is substituted, the substituent is preferably one or more of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_r$R$_{12}$, —$C_{0-8}$—O—R$_{13}$, —$C_{0-8}$—C(O)OR$_{13}$, —$C_{0-8}$—C(O)R$_{13}$, —$C_{0-8}$—O—C(O)R$_{14}$, —$C_{0-4}$—NR$_{15}$R$_{16}$, —$C_{0-8}$—C(=NR$_{15}$)R$_{14}$, —$C_{0-8}$—N(R$_{15}$)—C(=NR$_{16}$)R$_{14}$, —$C_{0-4}$—C(O)NR$_{15}$R$_{16}$ and —$C_{0-8}$—N(R$_{15}$)—C(O)R$_{14}$.

"Heterocyclyl" or "heterocyclic ring" refers to a monocyclic or polycyclic hydrocarbon substituent that is saturated or partially unsaturated, wherein one or more of the ring atoms are heteroatoms selected from nitrogen, oxygen, silicon or S(O)$_r$ (wherein r is an integer of 0, 1 or 2), excluding ring portions of —O—O—, —O—S— or —S—S—, and the remaining ring atoms are carbon atoms. For example, "4-10 membered heterocyclyl" refers to a cyclic group containing 4 to 10 ring atoms, and "3-6 membered heterocyclyl" means a cyclic group containing 3 to 6 ring atoms.

Monocyclic heterocyclyl includes, but is not limited to, pyrrolidinyl, piperidinyl, piperazinyl, morpholinyl, thiomorpholinyl, homopiperazinyl, etc.

Polycyclic heterocyclyl includes spiroheterocyclyl, fused heterocyclyl, and bridged heterocyclyl. "Spiroheterocyclyl" refers to a polycyclic heterocyclyl group in which an atom (called spiro-atom) is shared among monocyclic rings, wherein one or more ring atoms are heteroatoms selected from nitrogen, oxygen, silicon or S(O)$_r$ (wherein r is an integer of 0, 1 or 2), and the remaining ring atoms are carbon atoms. These rings may contain one or more double bonds, but none of them has a fully conjugated π-electron system. According to the number of spiro-atoms shared among the rings, spiroheterocyclyl may be monospiroheterocyclyl, bispiroheterocyclyl or polyspiroheterocyclyl. Spiroheterocyclyl includes, but is not limited to:

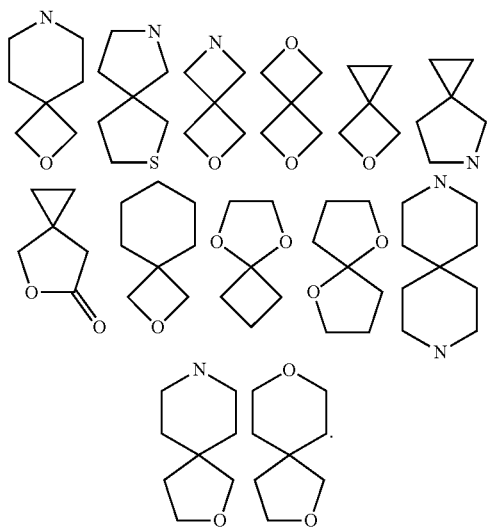

"Fused heterocyclyl" refers to a polycyclic heterocyclyl in which each ring shares a pair of adjacent atoms with the other rings in the system, wherein one or more of the rings may contain one or more double bonds, but none of them has a fully conjugated π-electron system, wherein one or more of the ring atoms are heteroatoms selected from nitrogen, oxygen, silicon or S(O)$_r$ (wherein r is an integer of 0, 1 or 2), and the remaining ring atoms are carbon atoms. According to the number of formed rings, the fused heterocyclyl may be bicyclic, tricyclic, tetracyclic or polycyclic, including, but not limited to:

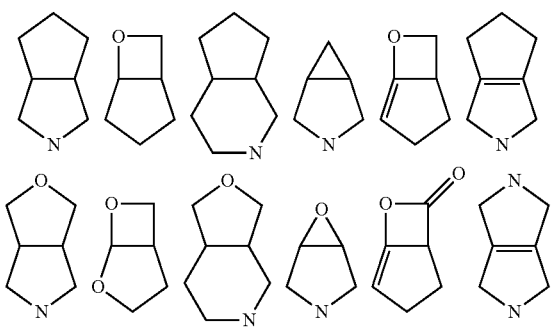

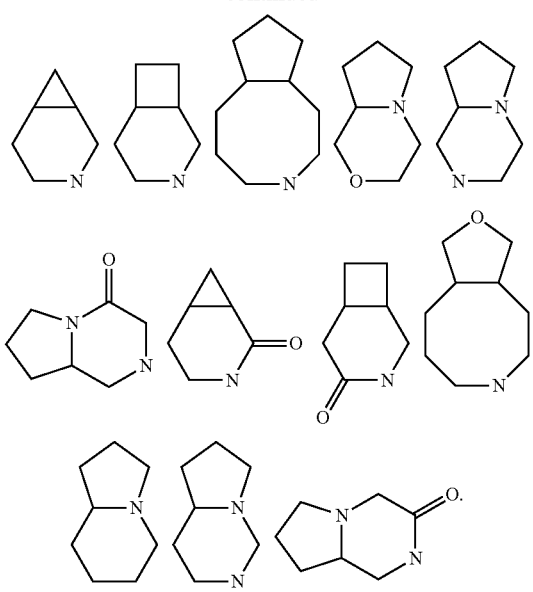

"Bridged heterocyclyl" refers to a polycyclic heterocyclyl in which any two rings share two carbon atoms that are not directly attached to each other, wherein these rings may contain one or more double bonds, but none of them has a fully conjugated π-electron system, wherein one or more of the ring atoms are heteroatoms selected from nitrogen, oxygen, silicon or $S(O)_r$ (wherein r is an integer of 0, 1 or 2), and the remaining ring atoms are carbon atoms. According to the number of formed rings, the bridged heterocyclyl may be bicyclic, tricyclic, tetracyclic or polycyclic, including, but not limited to:

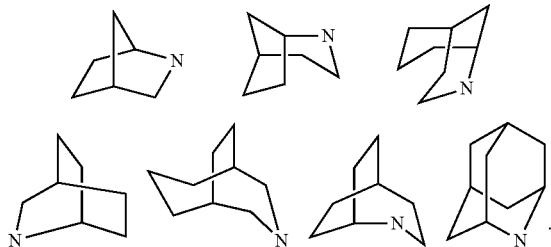

The heterocyclyl ring may be fused to an aryl, heteroaryl or cycloalkyl ring, wherein the ring attached to the parent structure is heterocyclyl, including, but not limited to:

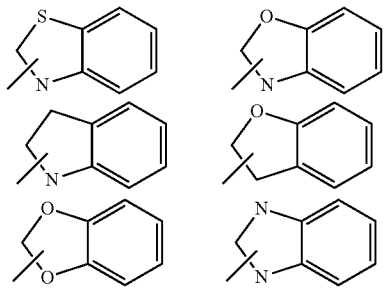

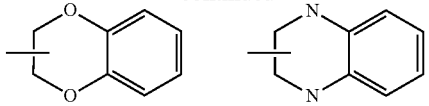

Heterocyclyl may be optionally substituted or unsubstituted, and when it is substituted, the substituent is preferably one or more of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, $-C_{0-8}-S(O)_rR_{12}$, $-C_{0-8}-O-R_{13}$, $-C_{0-8}-C(O)OR_{13}$, $-C_{0-8}-C(O)R_{13}$, $-C_{0-8}-O-C(O)R_{14}$, $-C_{0-8}-NR_{15}R_{16}$, $-C_{0-8}-C(=NR_{15})R_{14}$, $-C_{0-8}-N(R_{15})-C(=NR_{16})R_{14}$, $-C_{0-4}-C(O)NR_{15}R_{16}$ and $-C_{0-8}-N(R_{15})-C(O)R_{14}$.

"Aryl" or "aromatic ring" means an all-carbon monocyclic or fused-polycyclic group (i.e., rings that share a pair of adjacent carbon atoms) and a polycyclic group having a conjugated π-electron system (i.e., rings with adjacent pairs of carbon atoms), for example, "$C_{5-10}$ aryl" means an all-carbon aryl group containing 5 to 10 carbon atoms, and "5-10 membered aryl" means an all-carbon aryl group containing 5 to 10 carbon atoms, including, but not limited to, phenyl and naphthyl. The aryl ring can be fused to a heteroaryl, heterocyclyl or cycloalkyl ring, wherein the ring attached to the parent structure is the aryl ring, including, but not limited to:

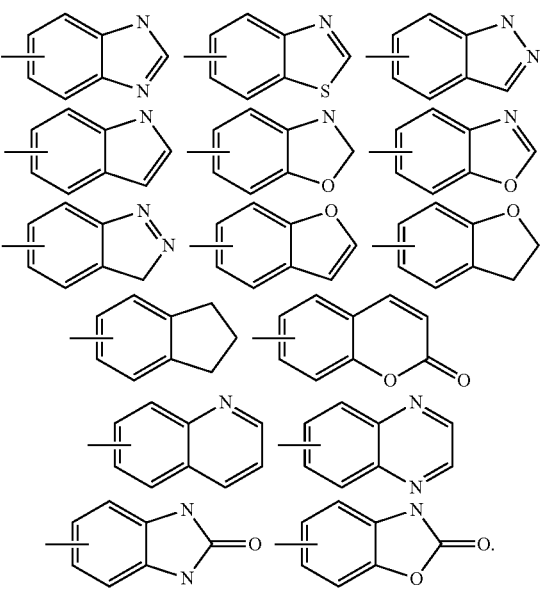

Aryl may be substituted or unsubstituted, and when it is substituted, the substituent is preferably one or more of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, $-C_{0-8}-S(O)_rR_{12}$, $-C_{0-8}-O-R_{13}$, $-C_{0-8}-C(O)OR_{13}$, $-C_{0-8}-C(O)R_{13}$, $-C_{0-8}-O-C(O)R_{13}$, $-C_{0-8}-NR_{15}R_{16}$, $-C_{0-8}-C(=NR_{15})R_{14}$, $-C_{0-8}-N(R_{15})-C(=NR_{16})R_{14}$, $-C_{0-8}-C(O)NR_{15}R_{16}$ and $-C_{0-8}-N(R_{15})-C(O)R_{14}$.

"Heteroaryl" or "heteroaromatic ring" refers to a heteroaromatic system containing 1 to 4 heteroatoms, and the heteroatoms include heteroatoms selected from nitrogen, oxygen or S(O)r (wherein r is an integer of 0, 1 or 2), for example, 5-10 membered heteroaryl means a heteroaromatic system containing 5 to 10 ring atoms, and 5-8 membered heteroaryl means a heteroaromatic system containing 5 to 8 ring atoms, including, but not limited to, furyl, thiophenyl, pyridyl, pyrrolyl, N-alkylpyrrolyl, pyrimidinyl, pyrazinyl, imidazolyl, tetrazolyl, etc. The heteroaryl ring can be fused to an aryl, heterocyclyl or cycloalkyl ring, wherein the ring attached to the parent structure is the heteroaryl ring, including, but not limited to:

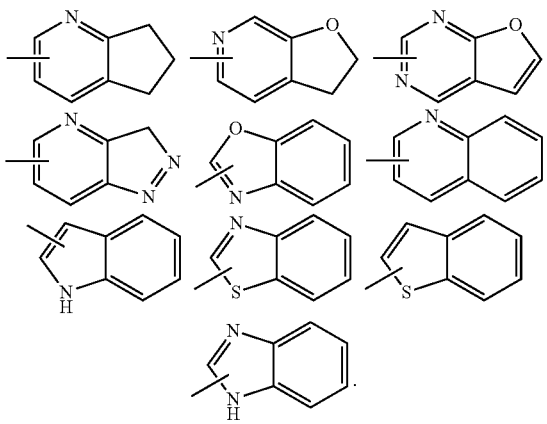

Heteroaryl may be optionally substituted or unsubstituted, and when it is substituted, the substituent is preferably one or more of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_r$R$_{12}$, —$C_{0-8}$—O—R$_{13}$, —$C_{0-8}$—C(O)OR$_{13}$, —$C_{0-8}$—C(O)R$_{13}$, —$C_{0-8}$—O—C(O)R$_{14}$, —$C_{0-8}$—NR$_{15}$R$_{16}$, —$C_{0-8}$—C(=NR$_{15}$)R$_{14}$, —$C_{0-8}$—N(R$_{15}$)—C(=NR$_{16}$)R$_{14}$, —$C_{0-8}$—C(O)NR$_{15}$R$_{16}$ and —$C_{0-8}$—N(R$_{15}$)—C(O)R$_{14}$.

"Alkenyl" refers to an alkyl defined as above consisting of at least two carbon atoms and at least one carbon-carbon double bond, for example, $C_{2-10}$ alkenyl means a linear or branched alkenyl group containing 2 to 10 carbon atoms. The alkenyl includes, but is not limited to, vinyl, l-propenyl, 2-propenyl, 1-, 2- or 3-butenyl, etc.

Alkenyl may be substituted or unsubstituted, and when it is substituted, the substituent is preferably one or more of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_r$R$_{12}$, —$C_{0-8}$—O—R$_{13}$, —$C_{0-8}$—C(O)OR$_{13}$, —$C_{0-8}$—C(O)R$_{13}$, —$C_{0-8}$—O—C(O)R$_{14}$, —$C_{0-8}$—NR$_{15}$R$_{16}$, —$C_{0-8}$—C(=NR$_{15}$)R$_{14}$, —$C_{0-8}$—N(R$_{15}$)—C(=NR$_{16}$)R$_{14}$, —$C_{0-8}$—C(O)NR$_{15}$R$_{16}$ and —$C_{0-8}$—N(R$_{15}$)—C(O)R$_{14}$.

"Alkynyl" refers to an alkyl defined as above consisting of at least two carbon atoms and at least one carbon-carbon triple bond, for example, $C_{2-10}$ alkynyl means a linear or branched alkynyl group containing 2 to 10 carbon atoms. The alkynyl includes, but is not limited to, ethynyl, 1-propynyl, 2-propynyl, 1-, 2- or 3-butynyl, etc.

Alkynyl may be substituted or unsubstituted, and when it is substituted, the substituent is preferably one or more of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_r$R$_{12}$, —$C_{0-8}$—O—R$_{13}$, —$C_{0-8}$—C(O)OR$_{13}$, —$C_{0-8}$—C(O)R$_{13}$, —$C_{0-8}$—O—C(O)R$_{14}$, —$C_{0-8}$—NR$_{15}$R$_{16}$, —$C_{0-8}$—C(=NR$_{15}$)R$_{14}$, —$C_{0-8}$—N(R$_{15}$)—C(=NR$_{16}$)R$_{14}$, —$C_{0-8}$—C(O)NR$_{15}$R$_{16}$ and —$C_{0-8}$—N(R$_{15}$)—C(O)R$_{14}$.

"Alkoxy" refers to —O-(alkyl), wherein the alkyl is defined as above, for example, "$C_{1-10}$ alkoxy" means an alkoxy group containing 1 to 10 carbon atoms, including, but not limited to, methoxy, ethoxy, propoxy, butoxy, etc.

Alkoxy may be optionally substituted or unsubstituted, and when it is substituted, the substituent is preferably one or more of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_r$R$_{12}$, —$C_{0-8}$—O—R$_{13}$, —$C_{0-8}$—C(O)OR$_{13}$, —$C_{0-8}$—C(O)R$_{13}$, —$C_{0-8}$—O—C(O)R$_{14}$, —$C_{0-8}$—NR$_{15}$R$_{16}$, —$C_{0-8}$—C(=NR$_{15}$)R$_{14}$, —$C_{0-8}$—N(R$_{15}$)—C(=NR$_{16}$)R$_{14}$, —$C_{0-8}$—C(O)NR$_{15}$R$_{16}$ and —$C_{0-8}$—N(R$_{15}$)—C(O)R$_{14}$.

"Cycloalkyloxy" refers to —O-cycloalkyl, wherein the cycloalkyl is defined as above, for example, "$C_{3-10}$ cycloalkyloxy" means a cycloalkyloxy group containing 3 to 10 carbon atoms, including, but not limited to, cyclopropyloxy, cyclobutyloxy, cyclopentyloxy, cyclohexyloxy, etc.

Cycloalkyloxy may be optionally substituted or unsubstituted, and when it is substituted, the substituent is preferably one or more of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_r$R$_{12}$, —$C_{0-8}$—O—R$_{13}$, —$C_{0-8}$—C(O)OR$_{13}$, —$C_{0-8}$—C(O)R$_{13}$, —$C_{0-8}$—O—C(O)R$_{14}$, —$C_{0-8}$—NR$_{15}$R$_{16}$, —$C_{0-8}$—C(=NR$_{15}$)R$_{14}$, —$C_{0-8}$—N(R$_{15}$)—C(=NR$_{16}$)R$_{14}$, —$C_{0-8}$—C(O)NR$_{15}$R$_{16}$ and —$C_{0-8}$—N(R$_{15}$)—C(O)R$_{14}$.

"Heterocyclyloxy" refers to —O-heterocyclyl, wherein heterocyclyl is defined as above, for example, "$C_{3-10}$ heterocyclyloxy" means a heterocyclyloxy group containing 3 to 10 carbon atoms, including, but not limited to, azacyclobutyloxy, oxacyclobutyloxy, azacyclopentyloxy, nitrogen, oxacyclohexyloxy, etc.

Heterocyclyloxy may be optionally substituted or unsubstituted, and when it is substituted, the substituent is preferably one or more of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$—S(O)$_r$R$_{12}$, —$C_{0-8}$—O—R$_{13}$, —$C_{0-8}$—C(O)OR$_{13}$, —$C_{0-8}$—C(O)R$_{13}$, —$C_{0-8}$—O—C(O)R$_{14}$, —$C_{0-8}$—NR$_{15}$R$_{16}$, —$C_{0-8}$—C(=NR$_{15}$)R$_{14}$, —$C_{0-8}$—N(R$_{15}$)—C(=NR$_{16}$)R$_{14}$, —$C_{0-8}$—C(O)NR$_{15}$R$_{16}$ and —$C_{0-8}$—N(R$_{15}$)—C(O)R$_{14}$.

"$C_{1-10}$ alkanoyl" refers to a monovalent atomic group which is obtained after a hydroxy group is removed from the $C_{1-10}$ alkyl acid, and is also generally referred to as "$C_{0-9}$—C(O)—", for example, "$C_1$—C(O)—" refers to an acetyl; "$C_2$—C(O)—" refers to a propionyl; and "$C_3$—C(O)—" refers to a butyryl or isobutyryl.

"—$C_{0-8}$—$S(O)_rR_{12}$" means that the sulfur atom in —$S(O)_rR_{12}$ is attached to $C_{0-8}$ alkyl, wherein $C_0$ alkyl refers to a bond, and $C_{1-8}$ alkyl is defined as above.

"—$C_{0-8}$—O—$R_{13}$" means that the oxygen atom in —O—$R_{13}$ is attached to $C_{0-8}$ alkyl, wherein $C_0$ alkyl refers to a bond, and $C_{1-8}$ alkyl is defined as above.

"—$C_{0-8}$—$C(O)OR_{13}$" means that carbonyl in —C(O)$OR_{13}$ is attached to $C_{0-8}$ alkyl, wherein $C_0$ alkyl refers to a bond, and $C_{1-8}$ alkyl is defined as above.

"—$C_{0-8}$—$C(O)R_{14}$" means that carbonyl in —$C(O)R_{14}$ is attached to $C_{0-8}$ alkyl, wherein $C_0$ alkyl refers to a bond, and $C_{1-8}$ alkyl is defined as above.

"—$C_{0-8}$—O—$C(O)R_{14}$" means that the oxygen atom in —O—$C(O)R_{14}$ is attached to $C_{0-8}$ alkyl, wherein $C_0$ alkyl refers to a bond, and $C_{1-8}$ alkyl is defined as above.

"—$C_{0-8}$—$NR_{15}R_{16}$" means that the nitrogen atom in —$NR_{15}R_{16}$ is attached to $C_{0-8}$ alkyl, wherein $C_0$ alkyl refers to a bond, and $C_{1-8}$ alkyl is defined as above.

"—$C_{0-8}$—C(=$NR_{15}$)$R_{14}$" means that the nitrogen atom in —C(=$NR_{15}$)$R_{14}$ is attached to $C_{0-8}$ alkyl, wherein $C_0$ alkyl refers to a bond, and $C_{1-8}$ alkyl is defined as above.

"—$C_{0-8}$—N($R_{15}$)—C(=$NR_{16}$)$R_{14}$" means that the nitrogen atom in —N($R_{15}$)—C(=$NR_{16}$)$R_{14}$ is attached to $C_{0-8}$ alkyl, wherein $C_0$ alkyl means a bond, and $C_{1-8}$ alkyl is defined as above.

"—$C_{0-8}$—$C(O)NR_{15}R_{16}$" means that carbonyl in —$C(O)NR_{15}R_{16}$ is attached to $C_{0-8}$ alkyl, wherein $C_0$ alkyl refers to a bond, and $C_{1-8}$ alkyl is defined as above.

"—$C_{0-8}$—N($R_{15}$)—$C(O)R_{14}$" means that the nitrogen atom in —N($R_{15}$)—$C(O)R_{14}$ is attached to $C_{0-8}$ alkyl, wherein $C_0$ alkyl means a bond, and $C_{1-8}$ alkyl is defined as above.

"$C_{1-10}$ haloalkyl" refers to an alkyl group having 1 to 10 carbon atoms in which hydrogens on the alkyl are optionally substituted by a fluorine, chlorine, bromine or iodine atom, including, but not limited to, difluoromethyl, dichloromethyl, dibromomethyl, trifluoromethyl, trichloromethyl, tribromomethyl, etc.

"$C_{1-10}$ haloalkoxy" refers to an alkoxy group having 1 to 10 carbon atoms in which hydrogens on the alkyl are optionally substituted by a fluorine, chlorine, bromine or iodine atom, including, but not limited to, difluoromethoxy, dichloromethoxy, dibromomethoxy, trifluoromethoxy, trichloromethoxy, tribromomethoxy, etc.

"$C_{1-10}$ deuterioalkyl" refers to an alkyl group having 1 to 10 carbon atoms in which hydrogens on the alkyl are optionally substituted by a deuterium atom, including, but not limited to, monodeuteriomethyl, dideuteriomethyl, trideuteriomethyl, etc.

"Halogen" refers to fluorine, chlorine, bromine or iodine.

"DCM" refers to dichloromethane, "PE" refers to petroleum ether, "EtOAc"/"EA" refers to ethyl acetate, "MeOH" refers to methanol, "DMF" refers to N,N-dimethylformamide, "THF" refers to tetrahydrofuran, "DIPEA" refers to N,N-diisopropylethylamine, "DM P" refers to Dess-Martin Periodinane, with a chemical name as (1,1,1-triacetoxy)-1,1-dihydro-1,2-benziodoxol-3(1H)-one, "HATU" refers to 2-(7-azabenzotriazol-1-yl)-N,N,N',N'-tetramethyluronium hexafluorophosphate, "LiAlH$_4$" refers to lithium aluminum hydride, "NaBH$_4$" refers to sodium borohydride, "K$_2$CO$_3$" refers to potassium carbonate, "Na$_2$CO$_3$" refers to sodium carbonate, "NaHCO$_3$" refers to sodium bicarbonate, "NaOH" refers to sodium hydroxide, "KOAc" refers to potassium acetate, "K$_3$PO$_4$" refers to potassium phosphate, "HOAc" refers to acetic acid, "CaCl$_2$" refers to calcium chloride, "NBS" refers to N-bromosuccinimide, "PhI(OAc)$_2$" refers to iodobenzene diacetate, "Raney-Ni" refers to raney nickel, "NaIO$_4$" refers to sodium periodate, "KMnO$_4$" refers to potassium permanganate, "NaBH$_3$CN" refers to sodium cyanoborohydride, "Pd(dppf)Cl$_2$" refers to [1,1'-bis(diphenylphosphine)ferrocene]palladium dichloride dichloromethane, and "SPhos-Pd-G2" refers to chloro(2-dicyclohexylphosphino-2',6'-dimethoxy-1,1'-biphenyl)[2-(2'-amino-1,1'-biphenyl)]palladium(II).

The term "optional" or "optionally" means that the event or circumstance subsequently described may, but not necessarily, occur, and that the description includes instances where the event or circumstance occurs or does not occur. For example, "heterocyclyl group optionally substituted by alkyl" means that alkyl may be, but not necessarily, present, and that the description includes instances where the heterocyclyl group is or is not substituted by alkyl.

The term "substituted" means that one or more hydrogen atoms in the group are each independently substituted by a corresponding number of substituents. It goes without saying that a substituent is only in its possible chemical position, and those skilled in the art will be able to determine (by experiments or theories) possible or impossible substitution without undue efforts. For example, it may be unstable when an amino or hydroxy having a free hydrogen is bound to a carbon atom having an unsaturated bond (such as olefin).

"Pharmaceutical composition" refers to a mixture containing one or more of the compounds described herein or a physiologically/pharmaceutically acceptable salt or prodrug thereof, and other chemical components, for example physiologically/pharmaceutically acceptable carriers and excipients. The purpose of the pharmaceutical composition is to promote the administration to an organism, which facilitates the absorption of the active ingredient, thereby exerting biological activities.

The present invention is further explained in detail below with reference to examples, which are not intended to limit the present invention, and the present invention is not merely limited to the contents of the examples.

The compound structure of the present invention is determined by nuclear magnetic resonance (NMR) and/or liquid chromatography-mass spectrometry (LC-MS). The NMR chemical shift (δ) is given in parts per million (ppm). The NMR determination is conducted by using a Bruker AVANCE-400 or AVANCE-500 nuclear magnetic resonance apparatus, with hexadeuterodimethyl sulfoxide (DMSO-d$_6$), tetradeuteromethanol (CD$_3$OD), deuterium oxide (D$_2$O) and deuterated chloroform (CDCl$_3$) as determination solvents, and tetramethylsilane (TMS) as an internal standard.

The LC-MS determination is conducted by using an Agilent 6120 mass spectrometer. The HPLC determination is conducted by using an Agilent 1200 DAD high pressure liquid chromatograph (Sunfire C18 150×4.6 mm chromatographic column) and a Waters 2695-2996 high pressure liquid chromatograph (Gimini C18 150×4.6 mm chromatographic column).

Yantai Yellow Sea HSGF254 or Qingdao GF254 silica gel plate is adopted as a thin layer chromatography (TLC) silica gel plate. The specification adopted by TLC is 0.15-0.20 mm, and the specification adopted by thin layer chromatography for the separation of products is 0.4-0.5 mm. The Yantai Yellow Sea silica gel with 200 to 300 meshes is generally utilized as a carrier in column chromatography.

Starting materials in the examples of the present invention are known and commercially available, or may be synthesized by using or according to methods known in the art.

Unless otherwise stated, all reactions of the present invention are carried out under a dry nitrogen or argon atmosphere with continuous magnetic stirring, wherein the solvent is a dry solvent, and the reaction temperature is in degree centigrade (° C.).

Preparation of Intermediates

1. Preparation of N,N'-(2,2'-dimethyl-[1,1'-biphenyl]-3,3'-diyl)bis(5-formylpicolinamide)

Step 1: Synthesis of 2-methyl-3-(4,4,5,5-tetramethyl-1,3,2-dioxaborolan-2-yl)aniline

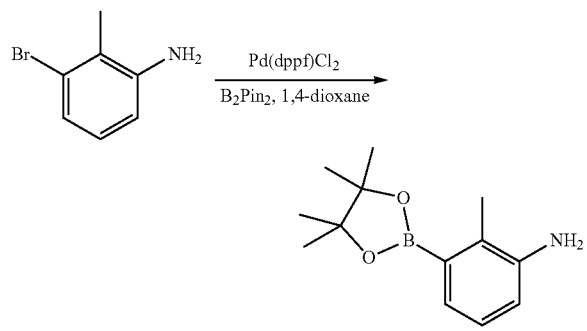

3-bromo-2-methylaniline (2.0 g, 10.75 mmol) and bis(pinacolato)diboron (4.097 g, 16.13 mmol) were dissolved in 1,4-dioxane (30 mL), and then KOAc (3.161 g, 32.26 mmol) and Pd(dppf)Cl₂ (0.786 g, 1.08 mmol) were added. The nitrogen was charged to replace by evacuation for protection. The solution was heated to 80° C. and reacted for 16 hrs until the reaction was completed. The reaction solution was directly used in the next step without being further purified. MS m/z (ESI): 234 [M+H]⁺.

Step 2: Synthesis of 2,2'-dimethyl-[1,1'-biphenyl]-3,3'-diamine

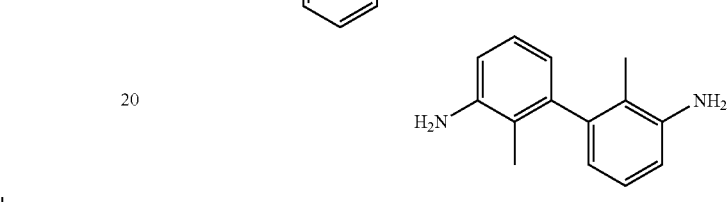

3-bromo-2-methylaniline (1.667 g, 8.96 mmol) was added to the above reaction solution, 1,4-dioxane (10 mL) and water (8 mL) were added. K₂CO₃ (3.71 g, 26.89 mmol) and Pd(dppf)Cl₂ (0.655 g, 0.90 mmol) were then added, and the nitrogen was charged to replace by evacuation for protection. The solution was heated to 95° C. and reacted for 2 hrs. After the reaction was completed, the reaction solution was concentrated under reduced pressure. The obtained crude product was separated by rapid silica gel column chromatography (PE/EA 2:1) to obtain 2,2'-dimethyl-[1,1'-biphenyl]-3,3'-diamine (1.8 g, yield: 95%). MS m/z (ESI): 213 [M+H]⁺.

Step 3: Synthesis of dimethyl 6,6'-(((2,2'-dimethyl-[1,1'-biphenyl]-3,3'-diyl)bis(azanediyl))bis(carbonyl))dinicotinate

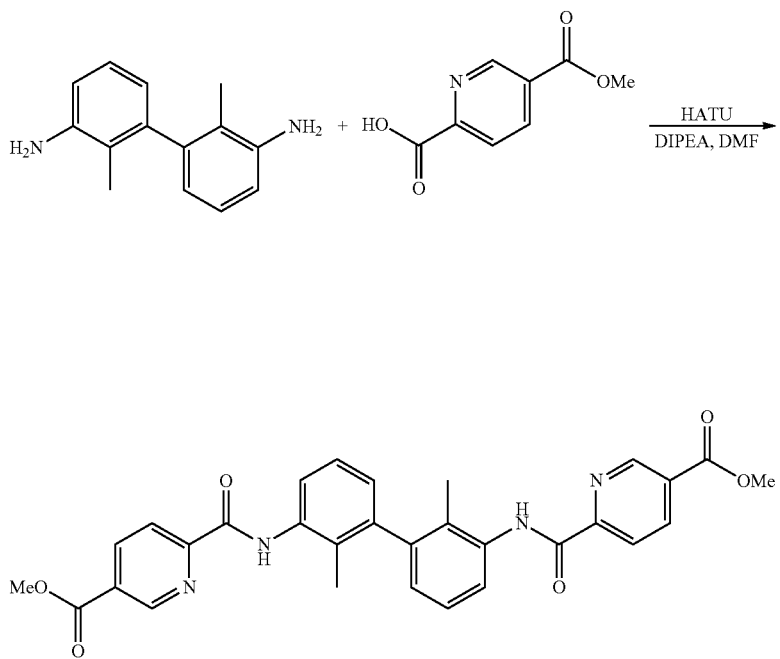

2,2'-dimethyl-[1,1'-biphenyl]-3,3'-diamine (2.0 g, 9.42 mmol) and 5-(methoxycarbonyl)picolinic acid (4.268 g, 23.55 mmol) were dissolved in DMF (20 mL), and DIPEA (6.076 g, 47.10 mmol) and HATU (10.74 g, 28.26 mmol) were then added. The reaction solution was stirred at room temperature for 0.5 hr. After the reaction was completed, the reaction mixture was filtered, and the filter cake was dried to obtain dimethyl 6,6'-(((2,2'-dimethyl-[1,1'-biphenyl]-3,3'-diyl)bis(azanediyl))bis(carbonyl))dinicotinate (1.0 g, yield: 20%). MS m/z (ESI): 539 [M+H]⁺.

Step 4: Synthesis of N,N'-(2,2'-dimethyl-[1,1'-biphenyl]-3,3'-diyl)bis(5-(hydroxymethyl) picolinamide)

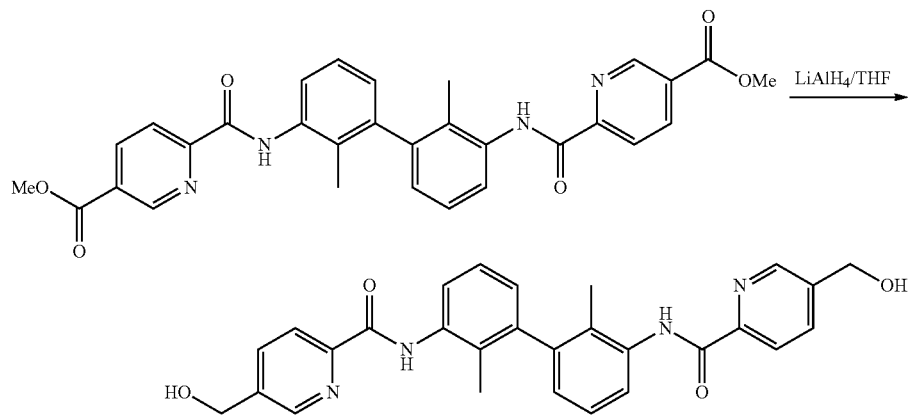

Dimethyl 6,6'-(((2,2'-dimethyl-[1,1'-biphenyl]-3,3'-diyl)bis(azanediyl))bis(carbonyl)) dinicotinate (1.0 g, 1.86 mmol) was dissolved in tetrahydrofuran (20 mL), and LiAlH₄ (0.353 g, 9.28 mmol) was added in batches. After the addition, the reaction solution was stirred at room temperature for 2 hrs. After the reaction was completed, sodium sulfate decahydrate was added for quenching. The reaction solution was filtered, and the filtrate was concentrated. The crude product was separated by rapid silica gel column chromatography (PE/EA 1:1) to obtain N,N'-(2,2'-dimethyl-[1,1'-biphenyl]-3,3'-diyl)bis(5-(hydroxymethyl)picolinamide) (0.35 g, yield: 42%). MS m/z (ESI): 483 [M+H]⁺.

Step 5: Synthesis of N,N'-(2,2'-dimethyl-[1,1'-biphenyl]-3,3'-diyl)bis(5-formylpicolinamide)

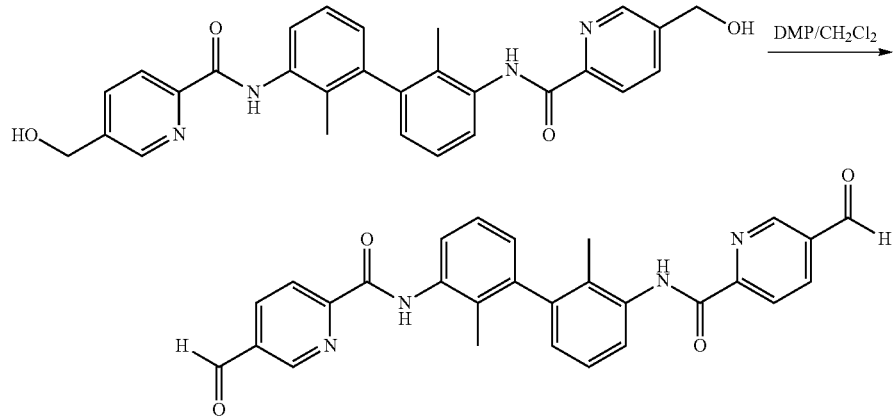

N,N'-(2,2'-dimethyl-[1,1'-biphenyl]-3,3'-diyl)bis(5-(hydroxymethyl)picolinamide) (350 mg, 0.73 mmol) was dissolved in dichloromethane (10 mL), and NaHCO₃ (366 mg, 4.3 mmol) and DMP (769 mg, 1.81 mmol) were then added. The reaction solution was stirred at room temperature for 1 hr. After the reaction was completed, the reaction solution was filtered, and the filtrate was concentrated. The crude product was separated by rapid silica gel column chromatography (PE/EA 1:1) to obtain N,N'-(2,2'-dimethyl-[1,1'-biphenyl]-3,3'-diyl)bis(5-formylpicolinamide) (280 mg, yield: 81%). MS m/z (ESI): 479 [M+H]⁺.

2. Preparation of N,N'-(2,2'-dimethyl-[1,1'-biphenyl]-3,3'-diyl)bis(5-formyl-4-methoxypicolinamide)

Step 1: Synthesis of N,N'-(2,2'-dimethyl-[1,1'-biphenyl]-3,3'-diyl)bis(5-bromo-4-methyl picolinamide)

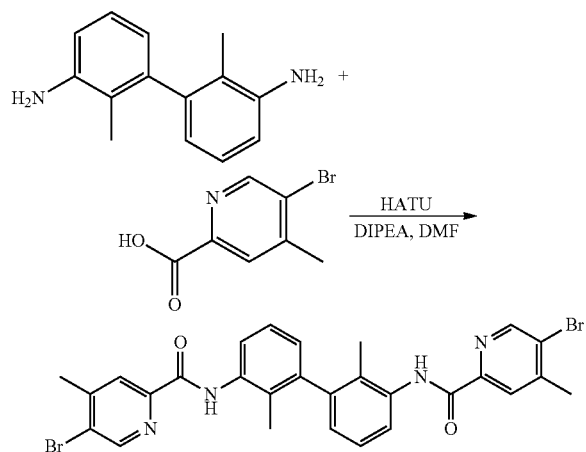

2,2'-dimethyl-[1,1'-biphenyl]-3,3'-diamine (491 mg, 2.32 mmol) was dissolved in DMF (15 mL), 5-bromo-4-methylpicolinic acid (1000 mg, 4.63 mmol), DIPEA (1492 mg, 11.56 mmol) and HATU (2637 mg, 6.94 mmol) were then added, and the reaction solution was stirred at room temperature for 1 hr. The reaction solution was filtered, the filter cake was washed with ethyl acetate, and then dried to obtain N,N'-(2,2'-dimethyl-[1,1'-biphenyl]-3,3'-diyl)bis(5-bromo-4-methylpicolinamide) (366 mg, yield: 26%). MS m/z (ESI): 609 [M+H]⁺.

Step 2: Synthesis of N,N'-(2,2'-dimethyl-[1,1'-biphenyl]-3,3'-diyl)bis(4-methyl-5-vinylpicolinamide)

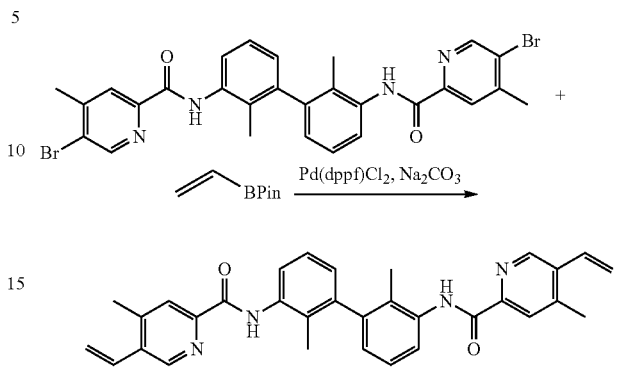

N,N'-(2,2'-dimethyl-[1,1'-biphenyl]-3,3'-diyl)bis(5-bromo-4-methylpicolinamide) (336 mg, 0.60 mmol) was dissolved in the mixture of 1,4-dioxane (10 mL) and water (2 mL), 4,4,5,5-tetramethyl-2-vinyl-1,3,2-dioxaborolane (927 mg, 6.02 mmol), Na₂CO₃ (191 mg, 1.81 mmol) and Pd(dppf)Cl₂ (44 mg, 0.06 mmol) were then added, and the nitrogen was charged for protection. The solution was heated to 95° C. and reacted for 2 hrs. After the reaction was completed, the reaction solution was concentrated under reduced pressure. The crude product was separated by silica gel column chromatography (PE/EA 2:1) to obtain N,N'-(2,2'-dimethyl-[1,1'-biphenyl]-3,3'-diyl)bis(4-methyl-5-vinylpicolinamide) (260 mg, yield: 86%). MS m/z (ESI): 503 [M+H]⁺.

Step 3: Synthesis of N,N'-(2,2'-dimethyl-[1,1'-biphenyl]-3,3'-diyl)bis(5-formyl-4-methyl picolinamide)

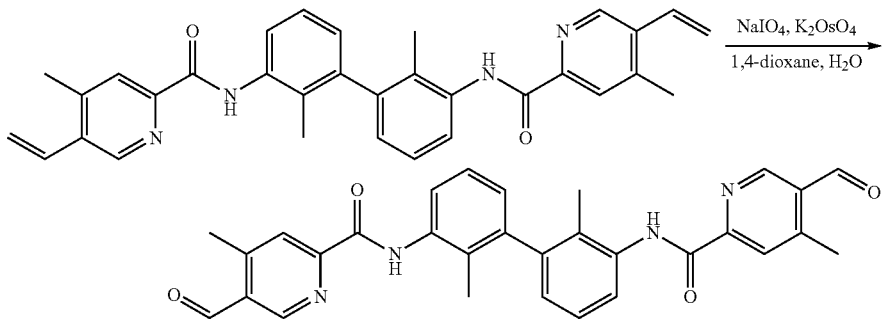

N,N'-(2,2'-dimethyl-[1,1'-biphenyl]-3,3'-diyl)bis(4-methyl-5-vinylpicolinamide) (310 mg, 0.62 mmol) was dissolved in the mixture of 1,4-dioxane (10 mL) and water (3 mL), sodium periodate (396 mg, 1.85 mmol) and potassium osmate dihydrate (23 mg, 0.062 mmol) were then added, and the reaction solution was stirred at room temperature for 2 hrs. After the reaction was completed, the reaction solution was diluted with water, and extracted three times with dichloromethane. The organic phases were combined, successively washed with water and a saturated brine, and dried over anhydrous sodium sulfate. The solution was filtrated and concentrated, and the crude product was separated by rapid silica gel column chromatography to obtain N,N'-(2,2'-dimethyl-[1,1'-biphenyl]-3,3'-diyl)bis(5-formyl-4-methylpicolinamide)(46 mg, yield: 15%). MS m/z (ESI): 507 [M+H]$^+$.

3. Preparation of N,N'-(2,2'-dimethyl-[1,1'-biphenyl]-3,3'-diyl)bis(5-formyl-4-methoxypicolinamide)

Step 1: Synthesis of methyl 4-methoxypicolinate

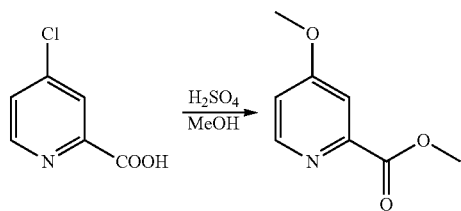

4-chloropicolinic acid (100 g, 0.64 mol) was added to methanol (500 mL), and concentrated sulfuric acid (4 mL) was then added, and the reaction solution was heated to 80° C., and then stirred for 60 hrs. After the reaction was completed, the reaction solution was concentrated, added with a saturated sodium bicarbonate aqueous solution, and then extracted with ethyl acetate. The organic phase was successively washed with water and a saturated brine, and then dried over sodium sulfate. The obtained organic phase was filtered and concentrated. The crude product was separated by silica gel column chromatography [eluent:petroleum ether:ethyl acetate] to obtain methyl 4-methoxypicolinate (55.6 g, yield: 52%). MS m/z (ESI): 168 [M+H]$^+$.

Step 2: Synthesis of methyl 5-bromo-4-methoxypicolinate

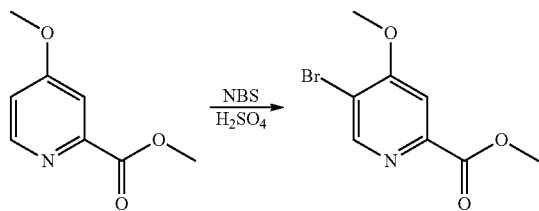

Methyl 4-methoxypicolinate (20 g, 0.12 mol) was added to concentrated sulfuric acid (150 mL), NBS (38.3 g, 0.22 mol) was added, and the reaction solution was stirred at room temperature for 16 hrs. After the reaction was completed, water, a sodium bicarbonate aqueous solution were successively added and then extracted with ethyl acetate. The organic phases were combined, successively washed with water and a saturated brine, and then dried over anhydrous sodium sulfate. The obtained organic phase was filtered and concentrated. The crude product was separated by silica gel column chromatography to obtain methyl 5-bromo-4-methoxypicolinate (22.5 g, yield: 77%). MS m/z (ESI): 246/248 [M+H]$^+$.

Step 3: Synthesis of 5-bromo-4-methoxypicolinic Acid

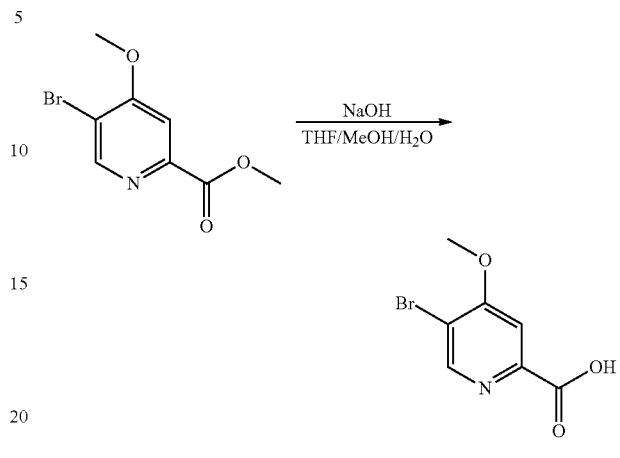

Methyl 5-bromo-4-methoxypicoinate (22.5 g, 91.4 mmol) was dissolved in a mixture solvent of tetrahydrofuran (80 mL), methanol (80 mL) and water (32 mL), NaOH (9.1 g, 0.23 mol) was then added, and the reaction solution was stirred at room temperature for 0.5 hr. After the reaction was completed, the reaction solution was concentrated, neutralized with a 1N HCl solution, and then extracted with a mixture solvent of dichloromethane and methanol (12:1). The organic phases were combined, washed with a saturated brine, and then dried over anhydrous sodium sulfate. The obtained organic phase was filtered, and concentrated to obtain 5-bromo-4-methoxypicolinic acid (19.1 g, yield: 90%). MS m/z (ESI): 232.2/234.2 [M+H]$^+$.

Step 4: Synthesis of N,N'-(2,2'-dimethyl-[1,1'-biphenyl]-3,3'-diyl)bis(5-bromo-4-methoxypicolinamide)

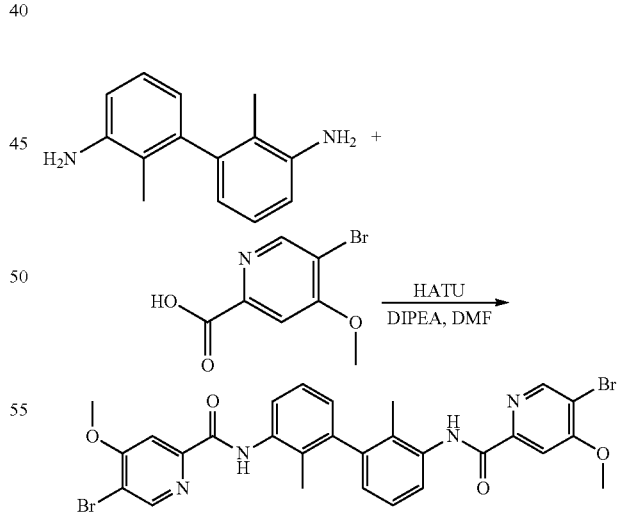

2,2'-dimethyl-[1,1'-biphenyl]-3,3'-diamine (1.73 g, 8.2 mmol) and 5-bromo-4-methoxy picolinic acid (3.98 g, 17.2 mmol) were dissolved in DMF (30 mL), and N,N-diisopropylethylamine (5.27 g, 40.7 mmol) and 2-(azole benzotrinitrogen 7-oxide)-N,N,N',N'-tetramethylureahexafluorinephosphoric acid (9.30 g, 24.5 mmol) were then added, and the reaction solution was stirred at room temperature for 12 hrs.

After the reaction was completed, the solid appeared in the solution was collected by filtering, and the filter cake was washed with ethyl acetate, and dried to obtain N,N'-(2,2'-dimethyl-[1,1'-biphenyl]-3,3∝-diyl)bis(5-bromo-4-methoxypicolinamide) (4.35 g, yield: 83%). MS m/z (ESI): 641.2 [M+H]⁺.

Step 5: Synthesis of N,N'-(2,2'-dimethyl-[1,1'-biphenyl]-3,3'-diyl)bis(4-methoxy-5-vinylpicolinamide

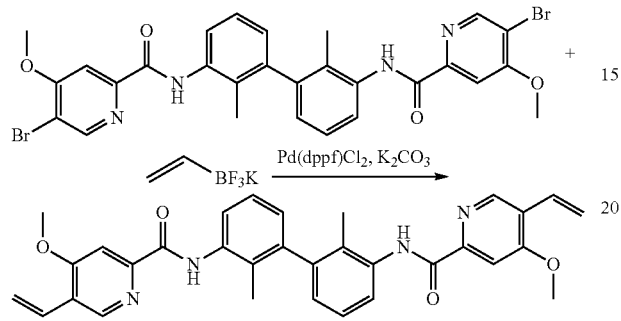

N,N'-(2,2'-dimethyl-[1,1'-biphenyl]-3,3'-diyl)bis(5-bromo-4-methoxypicolinamide) (4.35 g, 6.8 mmol) was added to the mixture of 1,4-dioxane (50 mL) and water (10 mL), and potassium carbonate (2.82 g, 20.4 mmol), potassium vinyltrifluoroborate (9.1 g, 68.0 mmol) and [1,1'-bis(diphenylphosphino)ferrocene]palladium dichloride (500 mg, 0.68 mmol) were successively added. Under a nitrogen atmosphere, the reaction solution was heated to 100° C., and stirred for 5 hrs. After the reaction was completed, water and ethyl acetate was successively added to extract the reaction solution. The organic phases were combined, successively washed with water and a saturated brine, and then dried over anhydrous sodium sulfate. The obtained organic phase was filtered and concentrated. The crude product was separated by silica gel column chromatography [eluent:dichloromethane:methanol] to obtain N,N'-(2,2'-dimethyl-[1,1'-biphenyl]-3,3'-diyl)bis(4-methoxy-5-vinylpicolinamide) (3.63 g, yield: 100%). MS m/z (ESI): 535.4 [M+H]⁺.

Step 6: Synthesis of N,N'-(2,2'-dimethyl-[1,1'-biphenyl]-3,3'-diyl)bis(5-formyl-4-methoxypicolinamide)

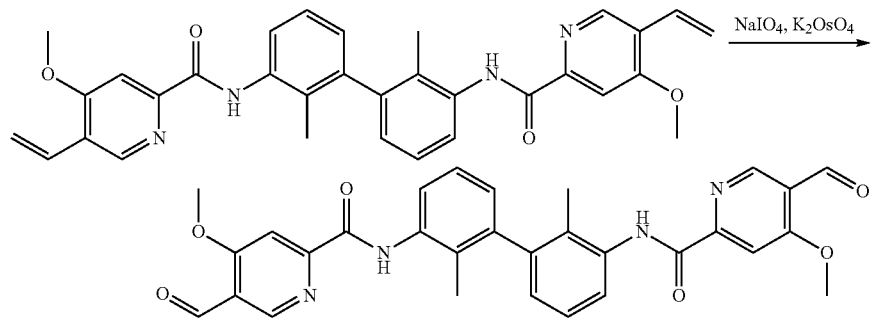

N,N'-(2,2'-dimethyl-[1,1'-biphenyl]-3,3'-diyl)bis(4-methoxy-5-vinylpicolinamide) (3.63 g, 6.8 mmol) was added to a mixture of 1,4-dioxane (60 mL) and water (18 mL), and then sodium periodate (8.71 g, 40.7 mmol) and potassium osmate dihydrate (500 mg, 1.36 mmol) were successively added, and the reaction solution was stirred at room temperature for 0.5 hr. After the reaction was completed, water and dichloromethane were added to extract the reaction solution, and the organic phases were combined and then dried over anhydrous sodium sulfate. The obtained organic phase was filtered and concentrated. The crude product was separated by silica gel column chromatography [eluent:petroleum ether:ethyl acetate] to obtain N,N'-(2,2'-dimethyl-[1,1'-biphenyl]-3,3'-diyl)bis(5-formyl-4-methoxypicolinamide) (1.51 g, yield: 41%). MS m/z (ESI): 539.2 [M+H]⁺.

4. Preparation of N,N'-(2,2'-dimethyl-[1,1'-biphenyl]-3,3'-diyl)bis(4-cyclopropyl-5-formylpicolinamide)

Step 1: Synthesis of ethyl 4-chloro-6-vinylnicotinate

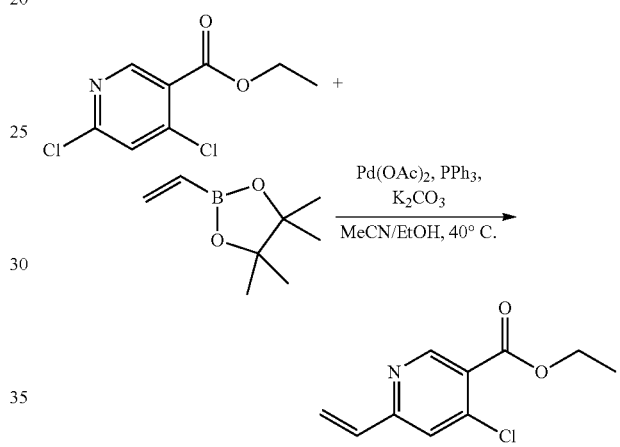

Ethyl 4,6-dichloronicotinate (10 g, 45.45 mmol), 4,4,5,5-tetramethyl-2-vinyl-1,3,2-dioxaborolane (7.7 g, 50 mmol), palladium acetate (0.51 g, 2.27 mmol), triphenylphosphine (1.19 g, 4.55 mmol) and potassium carbonate (12.54 g, 90.9 mmol) were dissolved in a mixed solvent of acetonitrile and ethanol (300 mL, 2:1). The nitrogen was charged to replace by evacuation for protection. The reaction solution was heated to 40° C., and then stirred overnight. After the reaction was completed, the reaction solution was filtered, the filter cake was washed with ethyl acetate, and the filtrate was concentrated. The crude product was separated by silica gel column chromatography (PE/EA=10/1) to obtain ethyl 4-chloro-6-vinylnicotinate (8.64 g, yield: 90%). MS m/z (ESI): 212 [M+H]⁺.

Step 2: Synthesis of ethyl 4-cyclopropyl-6-vinylnicotinate

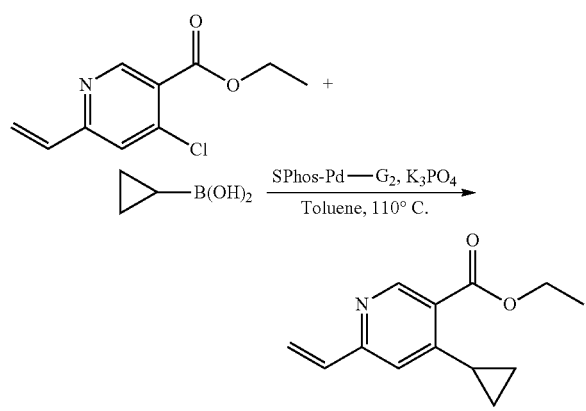

Ethyl 4-chloro-6-vinylnicotinate (5.0 g, 23.7 mmol), cyclopropylboronic acid (6.1 g, 71.1 mmol), SPhos-Pd-G2 (0.85 g, 1.185 mmol) and K₃PO₄ (10 g, 47.4 mmol) were dissolved in toluene (100 mL), and the nitrogen was charged to replace by evacuation for protection. The reaction solution was heated to 110° C., and then stirred overnight. After the reaction was completed, the reaction solution was concentrated. The crude product was separated by silica gel column chromatography (PE/EA=10/1) to obtain ethyl 4-cyclopropyl-6-vinylnicotinate (2.5 g, yield: 48%). MS m/z (ESI): 218 [M+H]⁺.

Step 3: Synthesis of 4-cyclopropyl-5-(ethoxycarbonyl)picolinic Acid

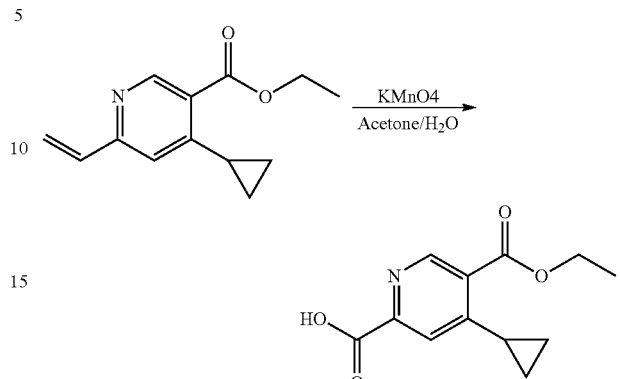

Ethyl 4-cyclopropyl-6-vinylnicotinate (2.5 g, 11.52 mmol) was dissolved in a mixture solvent of acetone and water (60 mL/30 mL), KMnO₄ (5.46 g, 34.56 mmol) was added, the reaction solution was stirred at room temperature for 48 hrs, and LCMS monitored whether the reaction was completed. The reaction solution was filtered, and the filtrate cake was washed with an appropriate amount of acetone. The filtrate was concentrated, and separated by silica gel column chromatography to obtain 4-cyclopropyl-5-(ethoxycarbonyl)picolinic acid (1.86 g, yield: 69%). MS m/z (ESI): 256 [M+H]⁺.

Step 4: Synthesis of diethyl 6,6'-(((2,2'-dimethyl-[1,1'-biphenyl]-3,3'-diyl)bis(azanediyl))bis(carbonyl))bis(4-cyclopropylnicotinate)

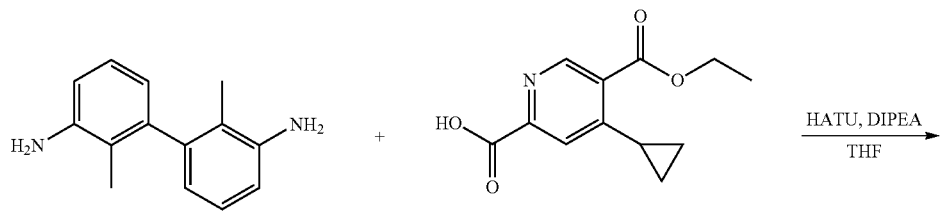

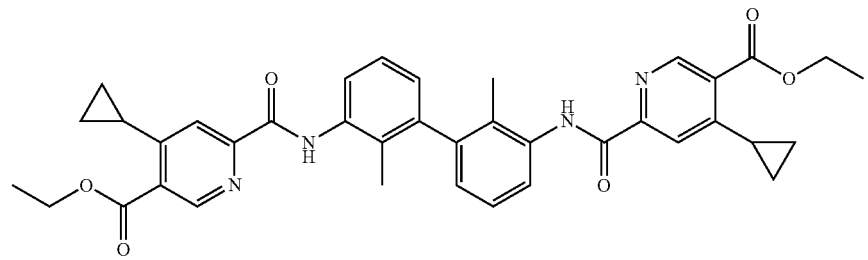

4-cyclopropyl-5-(ethoxycarbonyl)picolinic acid (1.86 g, 7.91 mmol) and 2,2'-dimethyl-[1,1'-biphenyl]-3,3'-diamine (0.84 g, 3.96 mmol) were dissolved in THF (150 mL), HATU (4.51 g, 11.87 mmol) and DIPEA (1.53 g, 11.87 mmol) were added after the mixture was substantially mixed, and the reaction solution was stirred overnight at room temperature. After the reaction was completed, silica gel was directly mixed with the sample, and the mixture was separated by silica gel column chromatography (PE/EA=5/1) to obtain diethyl 6,6'-(((2,2'-dimethyl-[1,1'-biphenyl]-3,3'-diyl)bis(azanediyl))bis(carbonyl))bis(4-cyclopropylnicotinate) (2.1 g, yield: 75%). MS m/z (ESI): 324 [½M+H]⁺; 647 [M+H]⁺.

Step 5: Synthesis of N,N'-(2,2'-dimethyl-[1,1'-biphenyl]-3,3'-diyl)bis(4-cyclopropyl-5-(hydroxymethyl)picolinamide)

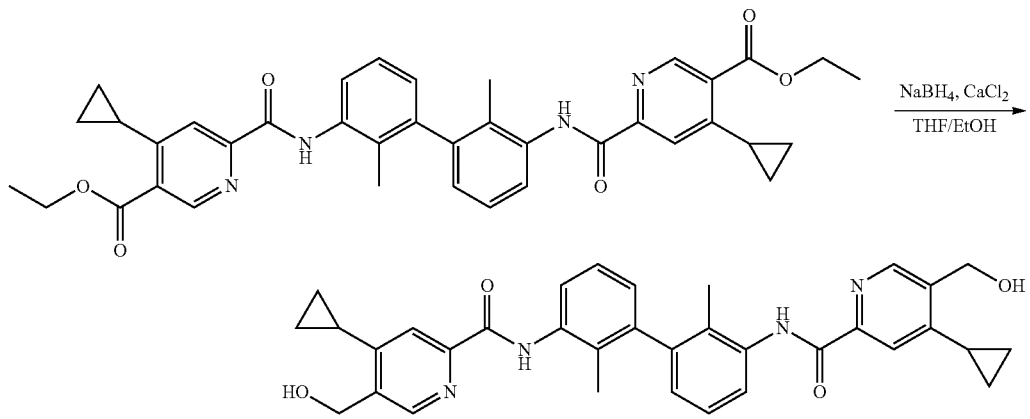

Diethyl 6,6'-(((2,2'-dimethyl-[1,1'-biphenyl]-3,3'-diyl)bis(azanediyl))bis(carbonyl))bis(4-cyclopropylnicotinate) (1.0 g, 1.55 mmol) was dissolved in a mixture solvent of ethanol and tetrahydrofuran (25 mL/50 mL), and then anhydrous CaCl₂ (1.0 g, 9.30 mmol) was added. The solution was stirred for 5 min, and NaBH₄ (0.35 g, 9.30 mmol) was then added. The solution was stirred at room temperature for 4 to 6 hrs until the reaction was completed. HOAc was added for quenching, the reaction solution was stirred for 0.5 hr, filtered, and washed with tetrahydrofuran. The filtrate was concentrated to obtain N,N'-(2,2'-dimethyl-[1,1'-biphenyl]-3,3'-diyl)bis(4-cyclopropyl-5-(hydroxymethyl)picolinamide) (1.2 g), which was directly used in the next step. MS m/z (ESI): 282 [½M+H]⁺; 563 [(M+H]⁺.

Step 6: Synthesis of N,N'-(2,2'-dimethyl-[1,1'-biphenyl]-3,3'-diyl)bis(4-cyclopropyl-5-formylpicolinamide)

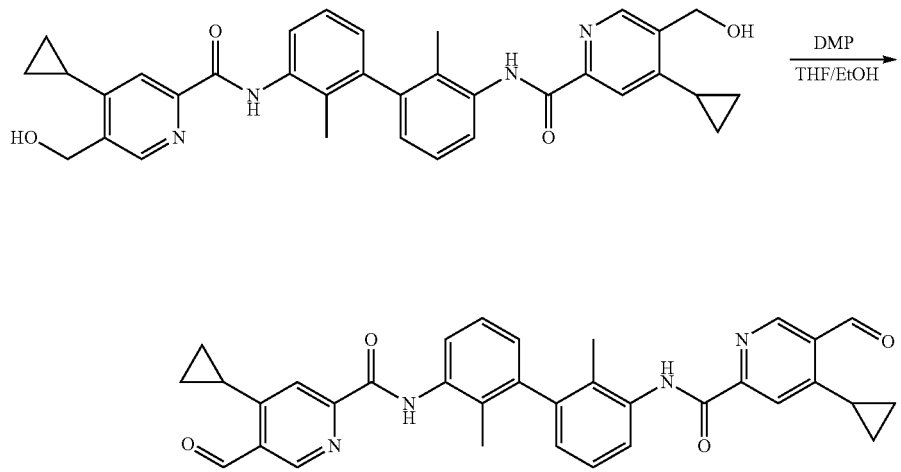

N,N'-(2,2'-dimethyl-[1,1'-biphenyl]-3,3'-diyl)bis(4-cyclopropyl-5-(hydroxymethyl)picolinamide) (1.2 g, 1.55 mmol) was dissolved in a mixture of dichloromethane and tetrahydrofuran, and then Dess-Martin Periodinane (1.97 g, 4.65 mmol) was added. The solution was stirred at room temperature for 2 hrs, added with a saturated sodium bicarbonate aqueous solution (100 mL), and then extracted with dichloromethane, and the organic phase was dried over sodium sulfate. The obtained organic phase was filtrated, concentrated, and separated by silica gel column chromatography (5% MeOH/DCM) to obtain N,N'-(2,2'-dimethyl-[1,1'-biphenyl]-3,3'-diyl)bis(4-cyclopropyl-5-formylpicolinamide) (1.1 g, yield in two steps: quantitive yield). MS m/z (ESI): 280 [½M+H]$^+$; 559 [M+H]$^+$.

5. Preparation of ((2-aminoethyl)imino)dimethyl-$\lambda^6$-sulfanone

Step 1: Synthesis of iminodimethyl-$\lambda^6$-sulfanone

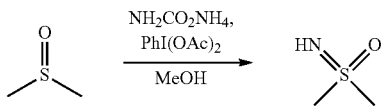

Dimethyl sulfoxide (1.0 g, 12.8 mmol) was added to methanol (50 mL), and Ph(OAc)$_2$ (12.4 g, 38.4 mmol) and ammonium carbamate (4.0 g, 51.2 mmol) were then added. The reaction solution was stirred at room temperature for 1 hr. After the reaction was completed, the reaction solution was concentrated, and separated by silica gel column chromatography (eluent: dichloromethane/methanol) to obtain iminodimethyl-$\lambda^6$-sulfanone (1.01 g, yield: 85%).

Step 2: Synthesis of 2-((dimethyl(oxo)-$\lambda^6$-sulfanylidene)amino)acetonitrile

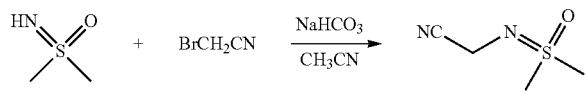

Iminodimethyl-$\lambda^6$-sulfanone (374 mg, 4.02 mmol) was dissolved in acetonitrile (15 mL), bromoacetonitrile (576 mg, 4.82 mmol) and NaHCO$_3$ (506 mg, 6.0 mmol) were then added, and the solution was heated to 88° C. and then reacted for 16 hrs. After the reaction was completed, the reaction solution was filtered, and the filtrate was concentrated, and separated by silica gel column chromatography (eluent: dichloromethane/methanol) to obtain 2-((dimethyl(oxo)-$\lambda^6$-sulfanylidene)amino)acetonitrile (212 mg, yield: 40%). MS m/z (ESI): 133 [M+H]$^+$; 265 [2M+H]$^+$.

Step 3: Synthesis of ((2-aminoethyl)imino)dimethyl-$\lambda^6$-sulfanone

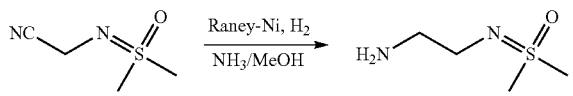

2-((dimethyl(oxo)-$\lambda^6$-sulfanylidene)amino)acetonitrile (257 mg, 1.94 mmol) was dissolved in 2 M solution of ammonia in methanol (15 mL), Raney-Ni (20 mg) was added, and the reaction solution was stirred at room temperature for 16 hrs under a hydrogen atmosphere. After the reaction was completed, the reaction solution was filtered, and the filtrate was concentrated to obtain ((2-aminoethyl)imino)dimethyl-$\lambda^6$-sulfanone (267 mg, yield: 100%). MS m/z (ESI): 137.2 [M+H]$^+$.

6. Preparation of 1-((2-aminoethyl)imino)tetrahydro-1H-1$\lambda^6$-thiophene 1-oxide Step 1: Synthesis of 1-iminotetrahydro-1H-1$\lambda^6$-thiophene 1-oxide

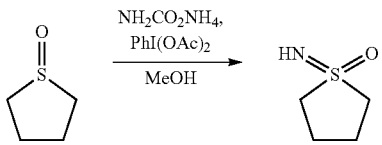 [SMILES: "MeOH" ; O=S1CCCC1 ; N=S1(=O)CCCC1]

Tetrahydrothiophene 1-oxide (500 mg, 4.8 mmol) was added to methanol (20 mL), and then PhI(OAc)$_2$ (4.64 g, 14.4 mmol) and ammonium carbamate (1.5 g, 19.2 mmol) were added, and the reaction solution was stirred at room temperature for 1 hr. After the reaction was completed, the reaction solution was concentrated, and separated by silica gel column chromatography (eluent: dichloromethane/methanol) to obtain 1-iminotetrahydro-1H-1$\lambda^6$-thiophene 1-oxide (385 mg, yield: 67%). MS m/z (ESI): 102.2 [M+H]$^+$.

Step 2: Synthesis of 2-((1-oxidotetrahydro-1$\lambda^6$-thiophen-1-ylidene)amino)acetonitrile

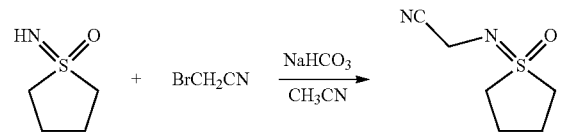

1-iminotetrahydro-1H-1$\lambda^6$-thiophene 1-oxide (385 mg, 3.23 mmol) was dissolved in acetonitrile (15 mL), and then bromoacetonitrile (463 mg, 3.87 mmol) and NaHCO$_3$ (407 mg, 4.84 mmol) were added, and the reaction solution was heated to 88° C. and stirred for 16 hrs. After the reaction was completed, the reaction solution was filtered, and the filtrate was concentrated, and separated by silica gel column chromatography (eluent: dichloromethane/methanol) to obtain 2-((1-oxidotetrahydro-1$\lambda^6$-thiophen-1-ylidene)amino)acetonitrile (281 mg, yield: 55%). MS m/z (ESI): 159 [M+H]$^+$.

Step 3: Synthesis of 1-((2-aminoethyl)imino)tetrahydro-1H-1$\lambda^6$-thiophene 1-oxide

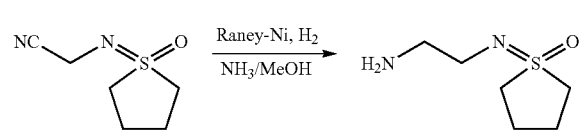

2-((1-oxidotetrahydro-1$\lambda^6$-thiophen-1-ylidene)amino)acetonitrile (281 mg, 1.78 mmol) was dissolved in 2 M solution of ammonia in methanol (15 mL), and then Raney-Ni (20 mg) was added, and the reaction solution was stirred at room temperature for 16 hrs under a hydrogen atmosphere. After the reaction was completed, the reaction solution was filtered, and the filtrate was concentrated to obtain 1-((2-aminoethyl)imino)tetrahydro-1H-1λ⁶-thiophene 1-oxide (248 mg, yield: 86%). MS m/z (ESI): 163.2 [M+H]⁺.

7. Preparation of (2-aminoethyl)(imino)(methyl)-λ⁶-sulfanone

Step 1: Synthesis of tert-butyl (2-(methylsulfinyl)ethyl)carbamate

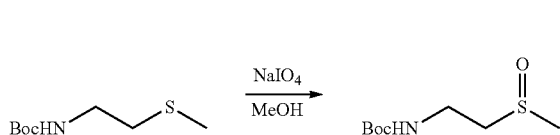

Tert-butyl (2-(methylthio)ethyl)carbamate (1.0 g, 5.23 mmol) was dissolved in a mixture of methanol (20 mL) and water (20 mL), and NaIO₄ (1.12 g, 5.23 mmol) was added under an ice bath. The reaction solution was stirred at room temperature for 16 hrs. After the reaction was completed, water and ethyl acetate were added to extract the reaction solution. The organic phases were combined, successively washed with water and a saturated brine, and then dried over anhydrous sodium sulfate. The obtained organic phase was filtered, concentrated, and separated by silica gel column chromatography (eluent: petroleum ether/ethyl acetate) to obtain tert-butyl (2-(methylsulfinyl)ethyl)carbamate (1.06 g, yield: 98%). MS m/z (ESI): 208.2[M+H]⁺.

Step 2: Synthesis of tert-butyl (2-(S-methylsulfonimidoyl)ethyl)carbamate

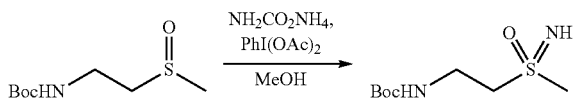

Tert-butyl (2-(methylsulfinyl)ethyl)carbamate (1.06 g, 5.11 mmol) was dissolved in methanol (25 mL), PhI(OAc)₂ (4.94 g, 15.3 mmol) and ammonium carbamate (1.6 g, 20.45 mmol) were then added, and the reaction solution was stirred at room temperature for 1 hr. After the reaction was completed, the reaction solution was concentrated, and separated by silica gel column chromatography (eluent: dichloromethane/methanol) to obtain tert-butyl (2-(S-methylsulfonimidoyl)ethyl)carbamate (827 mg, yield: 73%). MS m/z (ESI): 223.2 [M+H]⁺.

Step 3: Synthesis of (2-aminoethyl)(imino)(methyl)-λ⁶-sulfanone

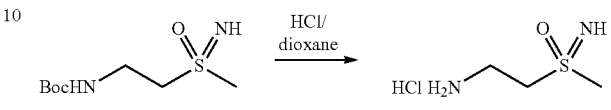

Tert-butyl (2-(S-methylsulfonimidoyl)ethyl)carbamate (370 mg, 1.66 mmol) was dissolved in a 4 M solution of hydrochloric acid in 1,4-dioxane (10 mL), and the reaction solution was stirred at room temperature for 1 hr. After the reaction was completed, the reaction solution was filtered, and the filtrate was concentrated to obtain (2-aminoethyl)(imino)(methyl)-λ⁶-sulfanone (325 mg, yield: 100%). MS m/z (ESI): 105.2 [M-NH]⁺.

PREPARATION OF SPECIFIC EXAMPLES

Example 1: Preparation of N,N'-(2,2'-dimethyl-[1,1'-biphenyl]-3,3'-diyl)bis(5-(((2-hydroxyethyl)amino)methyl)picolinamide)

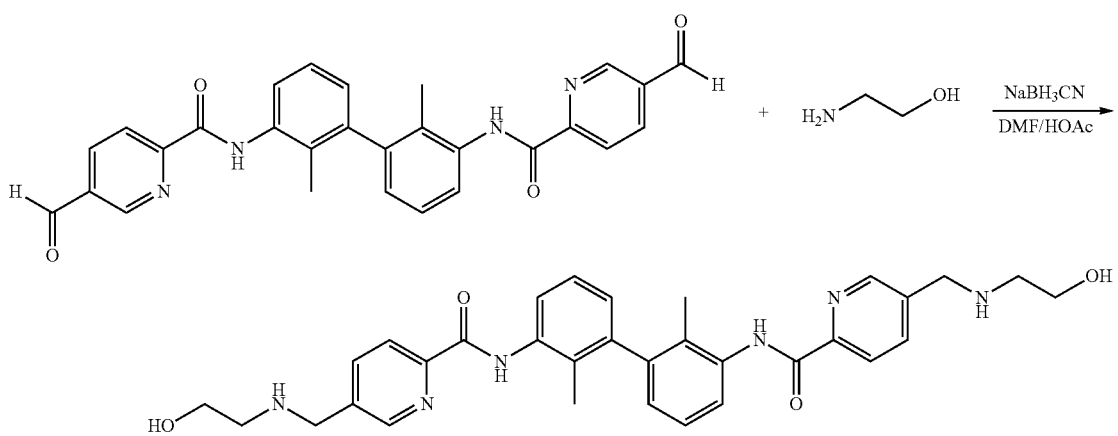

N,N'-(2,2'-dimethyl-[1,1'-biphenyl]-3,3'-diyl)bis(5-formylpicolinamide) (50 mg, 0.104 mmol) was dissolved in DMF (3 mL), and then 2-aminoethan-1-ol (64 mg, 1.045 mmol) and acetic acid (0.5 mL) were added, and the reaction solution was stirred at room temperature for 2 hrs. NaBH₃CN (66 mg, 1.045 mmol) was then added, and the reaction solution was stirred overnight at room temperature. After the reaction was completed, the reaction solution was separated by reversed-phase column chromatography to obtain N,N'-(2,2'-dimethyl-[1,1'-biphenyl]-3,3'-diyl)bis(5-(((2-hydroxyethyl)amino)methyl)picolinamide) (7.7 mg, yield: 13%). MS m/z (ESI): 569 [M+H]⁺.

¹H NMR (400 MHz, DMSO-d₆) δ 10.36 (s, 2H), 8.74 (d, J=2.0 Hz, 2H), 8.26-8.03 (m, 4H), 7.85 (dd, J=8.2, 1.2 Hz, 2H), 7.33 (t, J=7.8 Hz, 2H), 7.00 (dd, J=7.5, 1.3 Hz, 2H), 4.05 (s, 4H), 3.56 (t, J=5.5 Hz, 4H), 2.76 (t, J=5.6 Hz, 4H), 2.02 (s, 6H).

Example 2: Preparation of (2R,2'R)-2,2'-((((((2,2'-dimethyl-[1,1'-biphenyl]-3,3'-diyl)bis (azanediyl))bis (carbonyl))bis(4-methoxypyridine-6,3-diyl))bis (methylene))bis (azanediyl))bis(3-hydroxypropanoic acid)

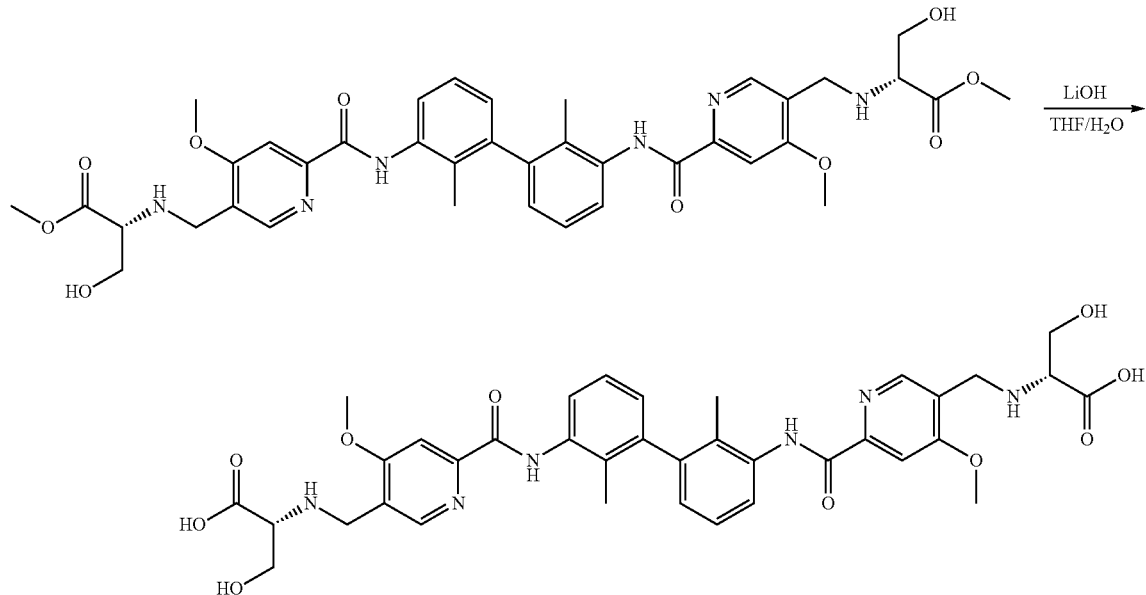

Dimethyl 2,2'-((((((2,2'-dimethyl-[1,1'-biphenyl]-3,3'-diyl)bis(azanediyl))bis(carbonyl))bis(4-methoxypyridine-6,3-diyl))bis(methylene))bis(azanediyl))(2R,2'R)-bis(3-hydroxypropanoate) (54 mg, 0.073 mmol) was dissolved in tetrahydrofuran (1.6 mL) and water (0.4 mL), and then lithium hydroxide (24 mg, 0.58 mmol) was added, and the reaction solution was stirred at room temperature for 1 hr. After the reaction was completed, the reaction solution was concentrated and then acidized with 1N HCl to achieve a pH of 2-3. The solution was directly separated by reverse-phase column chromatography to obtain (2R,2'R)-2,2'-((((((2,2'-dimethyl-[1,1'-biphenyl]-3,3'diyl)bis(azanediyl))bis(carbonyl))bis(4-methoxypyridine-6,3-diyl))bis(methylene))bis(azanediyl))bis(3-hydroxypropanoic acid) (28.7 mg, yield: 56%). MS m/z (ESI): 717.6 [M+H]$^+$; 359.4 [½M+H]$^+$.

$^1$H NMR (400 MHz, DMSO-d$_6$) δ 10.38 (s, 2H), 8.54 (s, 2H), 7.88 (c J=8.0 Hz, 2H), 7.74 (s, 2H), 7.33 (t, J=7.8 Hz, 2H), 6.99 (d, J=7.4 Hz, 2H), 3.99 (s, 6H), 3.97-3.76 (m, 4H), 3.58 (m, 4H), 3.06 (t, J=5.5 Hz, 2H), 2.01 (s, 6H).

The preparation of the compounds of examples 3 to 141 can be obtained by referring to the synthesis method of example 1 or 2:

| Example No. | Structure | Name | MS: m/z [M + 1]+ |
|---|---|---|---|
| 3 | 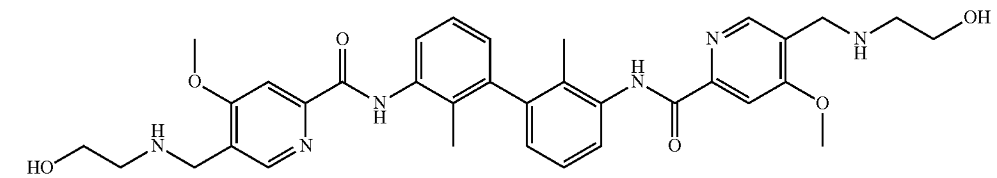 [SMILES: COc1cc(C(=O)Nc2cccc(-c3cccc(NC(=O)c4cc(OC)c(CNCCO)cn4)c3C)c2C)ncc1CNCCO] | N,N'-(2,2'-dimethyl-[1,1'-biphenyl]-3,3'-diyl)bis(5-(((2-hydroxyethyl)amino)methyl)-4-methoxypicolinamide) | 629 |
| 4 | 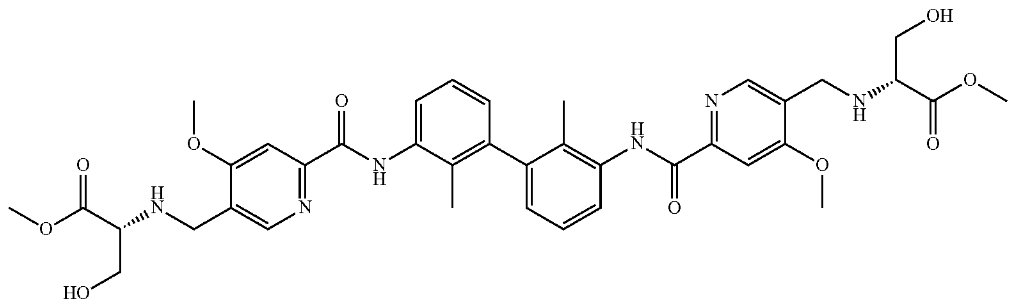 | dimethyl 2,2'-(((((2,2'-dimethyl-[1,1'-biphenyl]-3,3'-diyl)bis(azanediyl)bis(carbonyl))bis(4-methoxypyridine-6,3-diyl))bis(methylene))bis(azanediyl))(2R,2'R)-bis(3-hydroxypropanoate) | 745 |
| 5 | 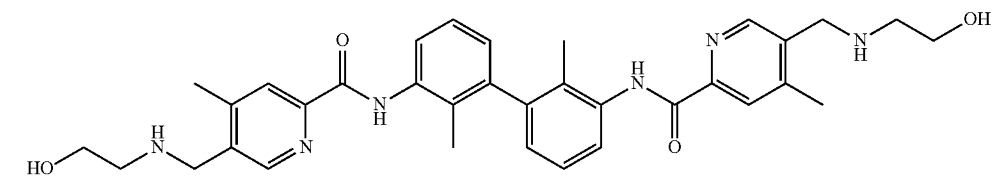 [SMILES: Cc1cc(C(=O)Nc2cccc(-c3cccc(NC(=O)c4cc(C)c(CNCCO)cn4)c3C)c2C)ncc1CNCCO] | N,N'-(2,2'-dimethyl-[1,1'-biphenyl]-3,3'-diyl)bis(5-(((2-hydroxyethyl)amino)methyl)-4-methylpicolinamide) | 597 |
| 6 | 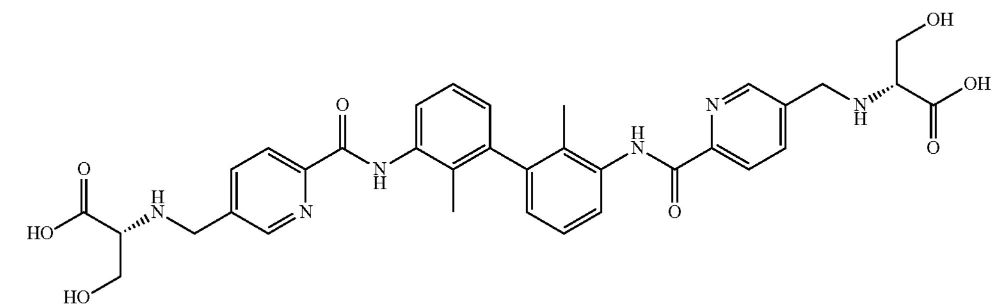 [SMILES: Cc1c(NC(=O)c2ccc(CN[C@H](CO)C(=O)O)cn2)cccc1-c1cccc(NC(=O)c2ccc(CN[C@H](CO)C(=O)O)cn2)c1C] | (2R,2'R)-2,2'-(((((2,2'-dimethyl-[1,1'-biphenyl]-3,3'-diyl)bis(azanediyl)bis(carbonyl))bis(pyridine-6,3-diyl))bis(methylene))bis(azanediyl))bis(3-hydroxypropanoic acid) | 657 |

-continued

| Example No. | Structure | Name | MS: m/z [M + 1]+ |
|---|---|---|---|
| 7 | 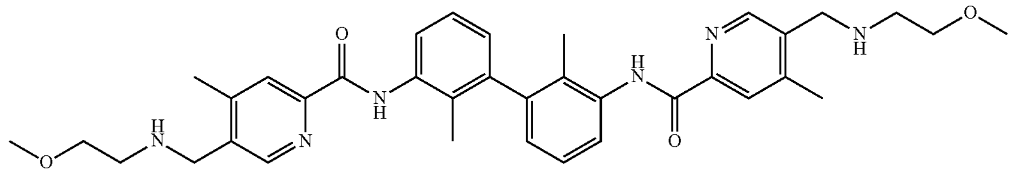 | N,N'-(2,2'-dimethyl-[1,1'-biphenyl]-3,3'-diyl)bis(5-(((2-methoxyethyl)amino)methyl)-4-methylpicolinamide) | 625 |
| 8 | 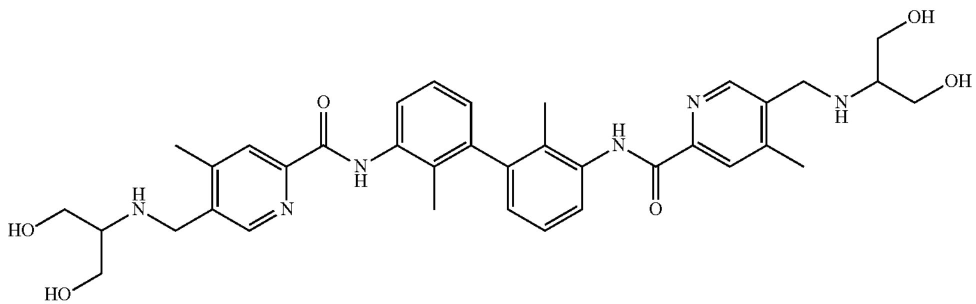 [SMILES: Cc1cc(C(=O)Nc2cccc(-c3cccc(NC(=O)c4cc(C)c(CNC(CO)CO)cn4)c3C)c2C)ncc1CNC(CO)CO] | N,N'-(2,2'-dimethyl-[1,1'-biphenyl]-3,3'-diyl)bis(5-(((1,3-dihydroxypropan-2-yl)amino)methyl)-4-methylpicolinamide) | 657 |
| 9 | 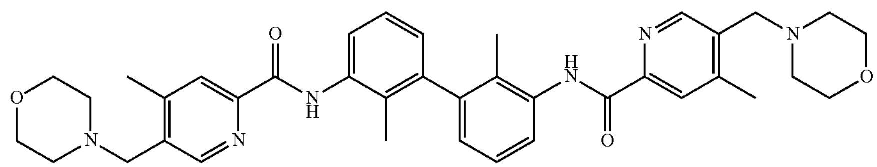 [SMILES: Cc1cc(C(=O)Nc2cccc(-c3cccc(NC(=O)c4cc(C)c(CN5CCOCC5)cn4)c3C)c2C)ncc1CN1CCOCC1] | N,N'-(2,2'-dimethyl-[1,1'-biphenyl]-3,3'-diyl)bis(4-methyl-5-(morpholinomethyl)picolinamide) | 649 |
| 10 | 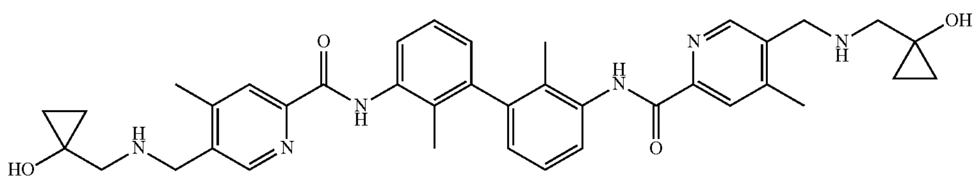 [SMILES: Cc1cc(C(=O)Nc2cccc(-c3cccc(NC(=O)c4cc(C)c(CNCC5(O)CC5)cn4)c3C)c2C)ncc1CNCC1(O)CC1] | N,N'-(2,2'-dimethyl-[1,1'-biphenyl]-3,3'-diyl)bis(5-((((1-hydroxycyclopropyl)methyl)amino)methyl)-4-methylpicolinamide) | 649 |
| 11 | 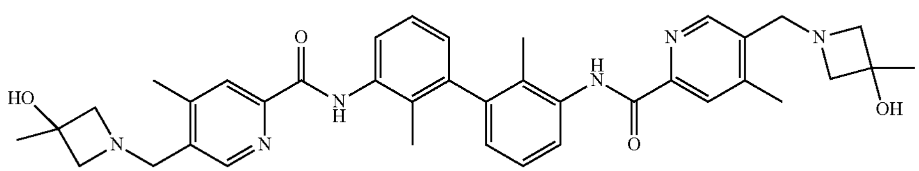 | N,N'-(2,2'-dimethyl-[1,1'-biphenyl]-3,3'-diyl)bis(5-((3-hydroxy-3-methylazetidin-1-yl)methyl)-4-methylpicolinamide) | 649 |

| Example No. | Structure | Name | MS: m/z [M + 1]+ |
|---|---|---|---|
| 12 | 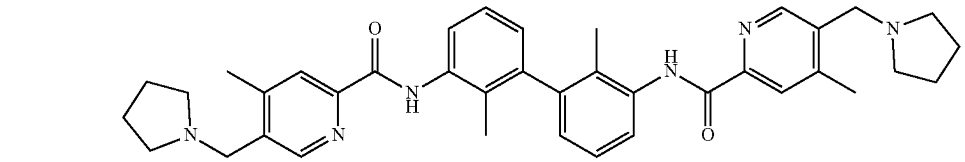 [SMILES: Cc1cc(C(=O)Nc2cccc(-c3cccc(NC(=O)c4cc(C)c(CN5CCCC5)cn4)c3C)c2C)ncc1CN1CCCC1] | N,N'-(2,2'-dimethyl-[1,1'-biphenyl]-3,3'-diyl)bis(4-methyl-5-(pyrrolidin-1-ylmethyl)picolinamide) | 617 |
| 13 | 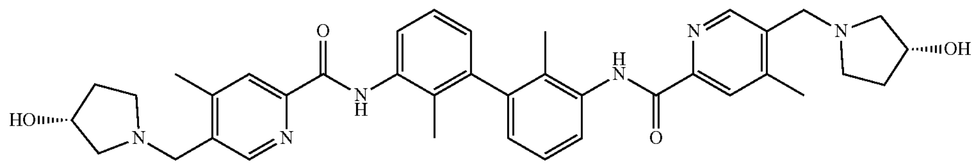 [SMILES: Cc1cc(C(=O)Nc2cccc(-c3cccc(NC(=O)c4cc(C)c(CN5CC[C@@H](O)C5)cn4)c3C)c2C)ncc1CN1CC[C@@H](O)C1] | N,N'-(2,2'-dimethyl-[1,1'-biphenyl]-3,3'-diyl)bis(5-(((R)-3-hydroxypyrrolidin-1-yl)methyl)-4-methylpicolinamide) | 649 |
| 14 | 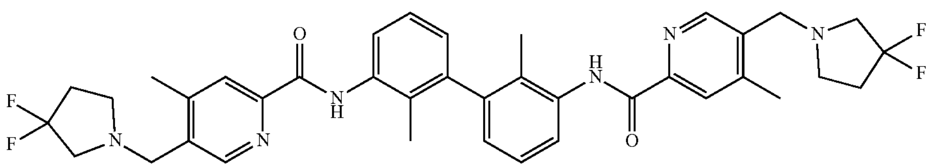 [SMILES: Cc1cc(C(=O)Nc2cccc(-c3cccc(NC(=O)c4cc(C)c(CN5CCC(F)(F)C5)cn4)c3C)c2C)ncc1CN1CCC(F)(F)C1] | N,N'-(2,2'-dimethyl-[1,1'-biphenyl]-3,3'-diyl)bis(5-((3,3-difluoropyrrolidin-1-yl)methyl)-4-methylpicolinamide) | 689 |
| 15 | 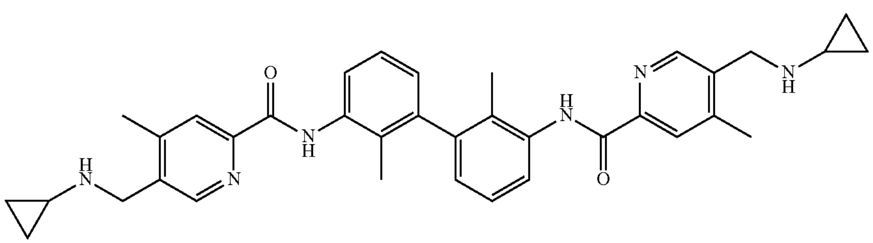 [SMILES: Cc1cc(C(=O)Nc2cccc(-c3cccc(NC(=O)c4cc(C)c(CNC5CC5)cn4)c3C)c2C)ncc1CNC1CC1] | N,N'-(2,2'-dimethyl-[1,1'-biphenyl]-3,3'-diyl)bis(5-(((cyclopropylamino)methyl)-4-methylpicolinamide) | 589 |
| 16 | 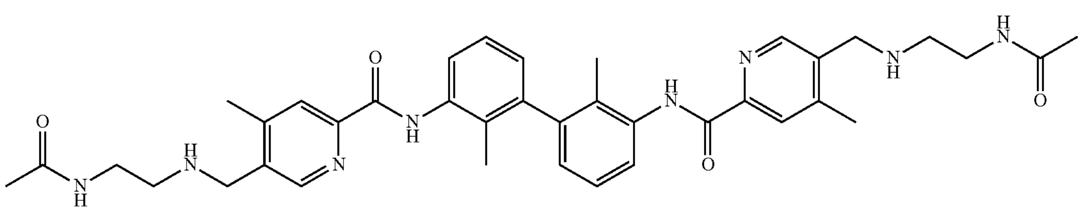 [SMILES: CC(=O)NCCNCc1cnc(C(=O)Nc2cccc(-c3cccc(NC(=O)c4cc(C)c(CNCCNC(C)=O)cn4)c3C)c2C)cc1C] | N,N'-(2,2'-dimethyl-[1,1'-biphenyl]-3,3'-diyl)bis(5-(((2-acetamidoethyl)amino)methyl)-4-methylpicolinamide) | 679 |

-continued

| Example No. | Structure | Name | MS: m/z [M + 1]+ |
|---|---|---|---|
| 17 | 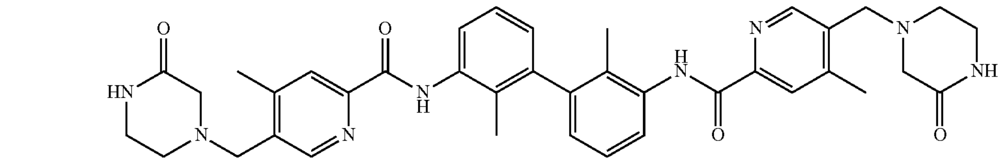 [SMILES: Cc1cc(C(=O)Nc2cccc(-c3cccc(NC(=O)c4cc(C)c(CN5CCNC(=O)C5)cn4)c3C)c2C)ncc1CN1CCNC(=O)C1] | N,N'-(2,2'-dimethyl-[1,1'-biphenyl]-3,3'-diyl)bis(4-methyl-5-((3-oxopiperazin-1-yl)methyl)picolinamide) | 675 |
| 18 | 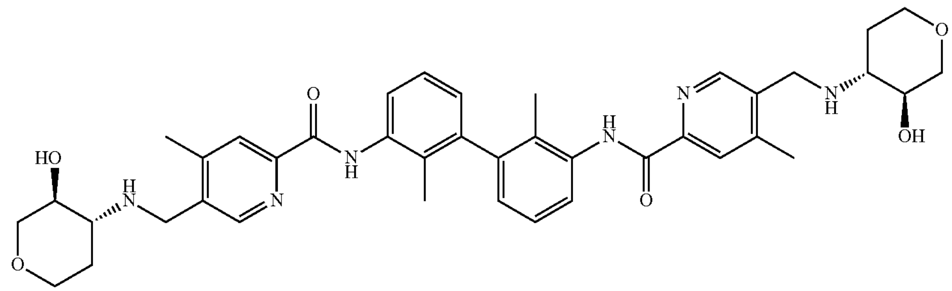 [SMILES: Cc1cc(C(=O)Nc2cccc(-c3cccc(NC(=O)c4cc(C)c(CN[C@@H]5CCOC[C@H]5O)cn4)c3C)c2C)ncc1CN[C@@H]1CCOC[C@H]1O] | N,N'-(2,2'-dimethyl-[1,1'-biphenyl]-3,3'-diyl)bis(5-((((3S,4R)-3-hydroxytetrahydro-2H-pyran-4-yl)amino)methyl)-4-methylpicolinamide) | 709 |
| 19 | 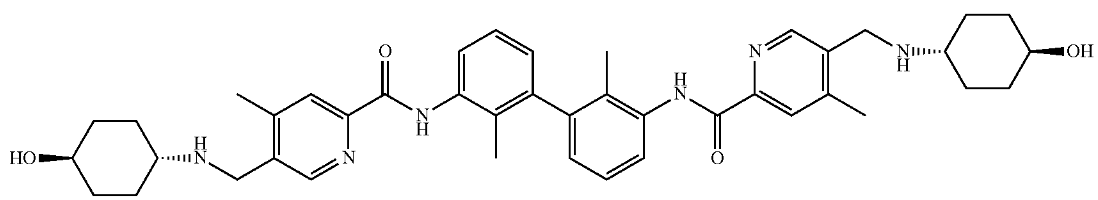 [SMILES: Cc1cc(C(=O)Nc2cccc(-c3cccc(NC(=O)c4cc(C)c(CN[C@H]5CC[C@H](O)CC5)cn4)c3C)c2C)ncc1CN[C@H]1CC[C@H](O)CC1] | N,N'-(2,2'-dimethyl-[1,1'-biphenyl]-3,3'-diyl)bis(5-((((1r,4r)-4-hydroxycyclohexyl)amino)methyl)-4-methylpicolinamide) | 705 |
| 20 | 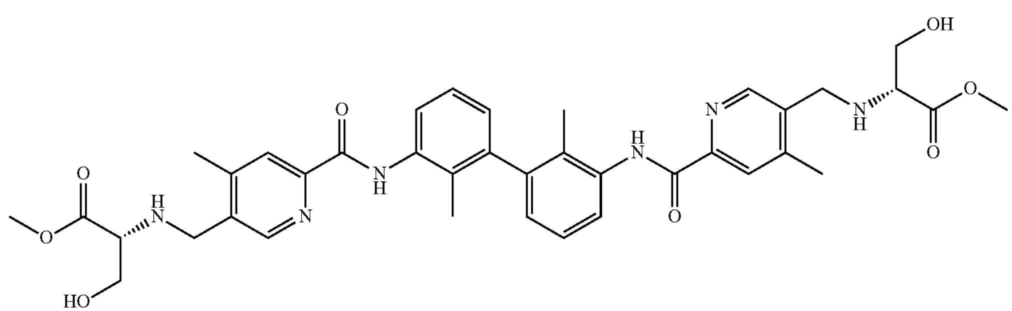 | dimethyl 2,2'-(((((2,2'-dimethyl-[1,1'-biphenyl]-3,3'-diyl)bis(azanediyl))bis(carbonyl))bis(4-methylpyridine-6,3-diyl))bis(methylene))bis(azanediyl))(2R,2'R)-bis(3-hydroxypropanoate) | 713 |

-continued

| Example No. | Structure | Name | MS: m/z [M + 1]+ |
|---|---|---|---|
| 21 | 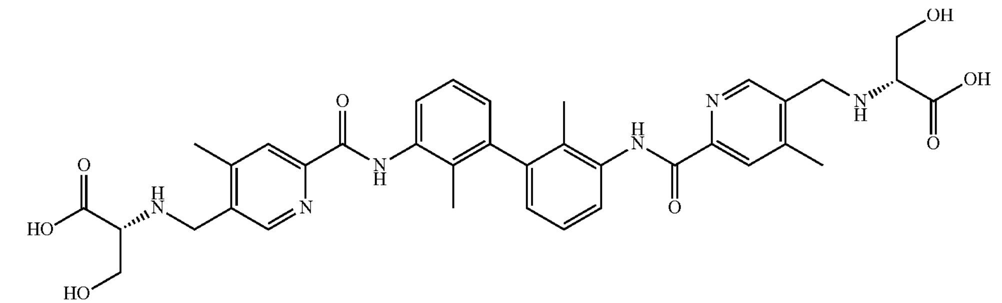 [SMILES: Cc1cc(C(=O)Nc2cccc(-c3cccc(NC(=O)c4cc(C)c(CN[C@H](CO)C(=O)O)cn4)c3C)c2C)ncc1CN[C@H](CO)C(=O)O] | (2R,2'R)-2,2'-(((((2,2'-dimethyl-[1,1'-biphenyl]-3,3'-diyl)bis(azanediyl))bis(carbonyl))bis(4-methylpyridine-6,3-diyl))bis(methylene))bis(azanediyl))bis(3-hydroxypropanoic acid) | 685 |
| 22 | 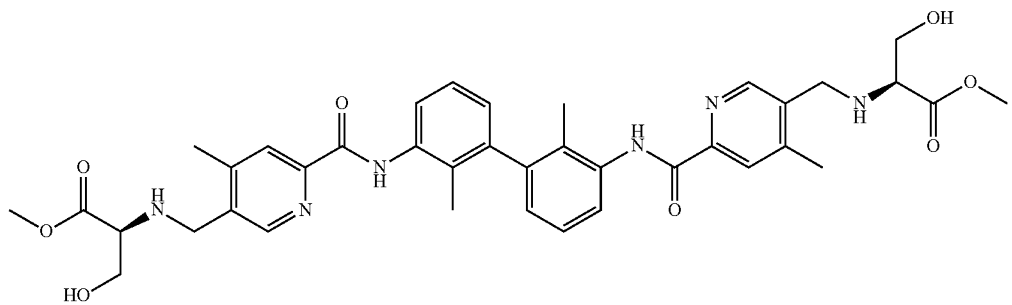 | dimethyl 2,2'-(((((2,2'-dimethyl-[1,1'-biphenyl]-3,3'-diyl)bis(azanediyl))bis(carbonyl))bis(4-methylpyridine-6,3-diyl))bis(methylene))bis(azanediyl))(2S,2'S)-bis(3-hydroxypropanoate) | 713 |
| 23 | 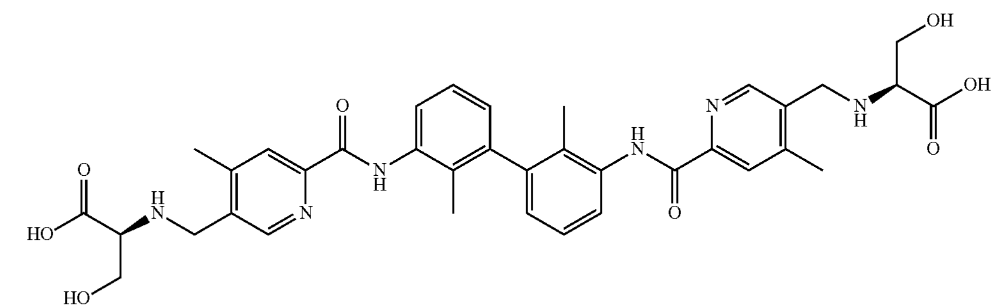 [SMILES: Cc1cc(C(=O)Nc2cccc(-c3cccc(NC(=O)c4cc(C)c(CN[C@@H](CO)C(=O)O)cn4)c3C)c2C)ncc1CN[C@@H](CO)C(=O)O] | (2S,2'S)-2,2'-(((((2,2'-dimethyl-[1,1'-biphenyl]3,3'-diyl)bis(azanediyl))bis(carbonyl))bis(4-methylpyridine-6,3-diyl))bis(methylene))bis(azanediyl))bis(3-hydroxypropanoic acid) | 685 |

| Example No. | Structure | Name | MS: m/z [M + 1]+ |
|---|---|---|---|
| 24 | 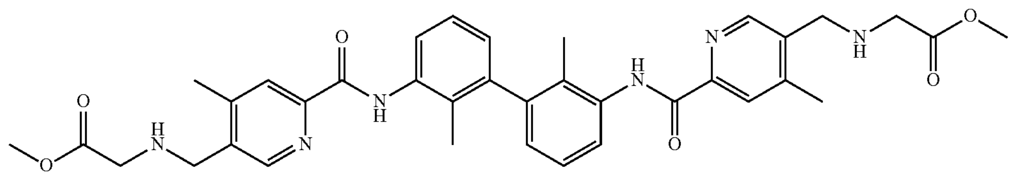 | dimethyl 2,2'-(((((2,2'-dimethyl-[1,1'-biphenyl]-3,3'-diyl)bis(azanediyl))bis(carbonyl))bis(4-methylpyridine-6,3-diyl))bis(methylene))bis(azanediyl))diacetate | 653 |
| 25 | 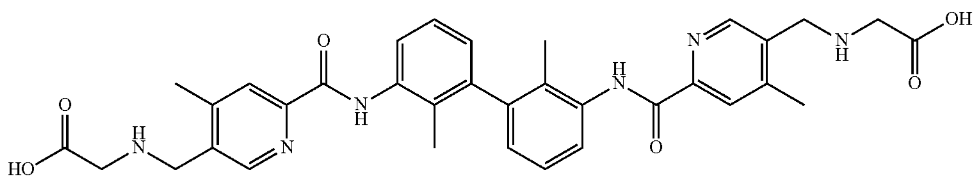 [SMILES: Cc1cc(C(=O)Nc2cccc(-c3cccc(NC(=O)c4cc(C)c(CNCC(=O)O)cn4)c3C)c2C)ncc1CNCC(=O)O] | 2,2'-(((((2,2'-dimethyl-[1,1'-biphenyl]-3,3'-diyl)bis(azanediyl))bis(carbonyl))bis(4-methylpyridine-6,3-diyl))bis(methylene))bis(azanediyl))diacetic acid | 625 |
| 26 | 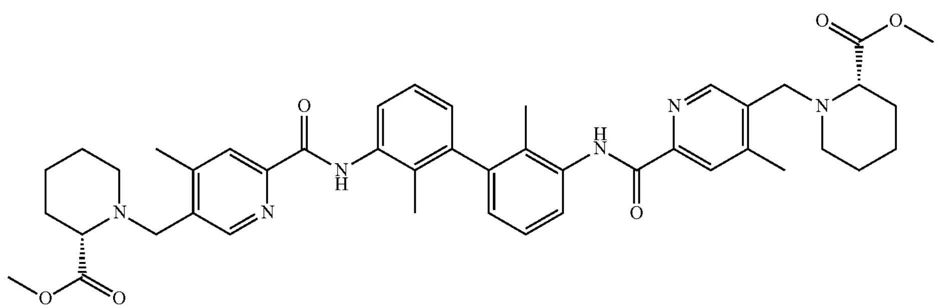 | dimethyl 1,1'-(((((2,2'-dimethyl-[1,1'-biphenyl]-3,3'-diyl)bis(azanediyl))bis(carbonyl))bis(4-methylpyridine-6,3-diyl))bis(methylene))(2S,2'S)-bis(piperidine-2-carboxylate) | 761 |
| 27 | 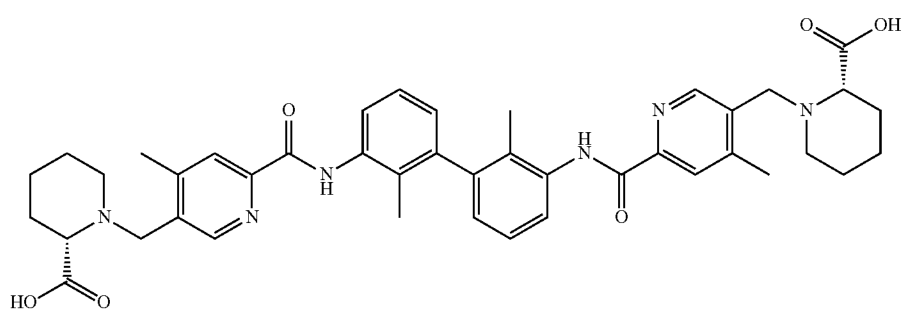 [SMILES: Cc1cc(C(=O)Nc2cccc(-c3cccc(NC(=O)c4cc(C)c(CN5CCCC[C@H]5C(=O)O)cn4)c3C)c2C)ncc1CN1CCCC[C@H]1C(=O)O] | (2S,2'S)-1,1'-(((((2,2'-dimethyl-[1,1'-biphenyl]-3,3'-diyl)bis(azanediyl))bis(carbonyl))bis(4-methylpyridine-6,3-diyl))bis(methylene))bis(piperidine-2-carboxylic acid) | 733 |

| Example No. | Structure | Name | MS: m/z [M + 1]+ |
|---|---|---|---|
| 28 | 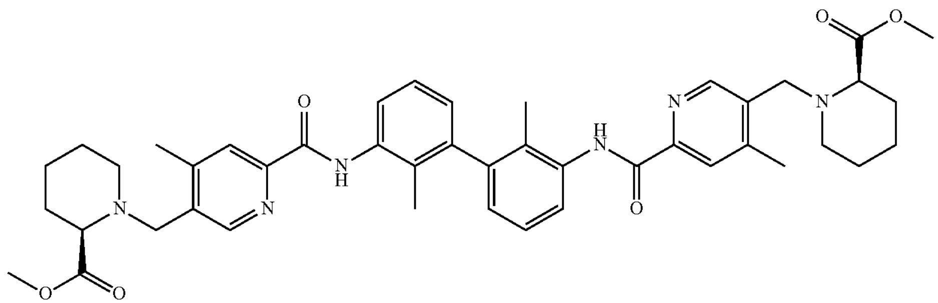 | dimethyl 1,1'-(((((2,2'-dimethyl-[1,1'-biphenyl]-3,3'-diyl)bis(azanediyl))bis(carbonyl))bis(4-methylpyridine-6,3-diyl))bis(methylene))(2R,2'R)-bis(piperidine-2-carboxylate) | 761 |
| 29 | 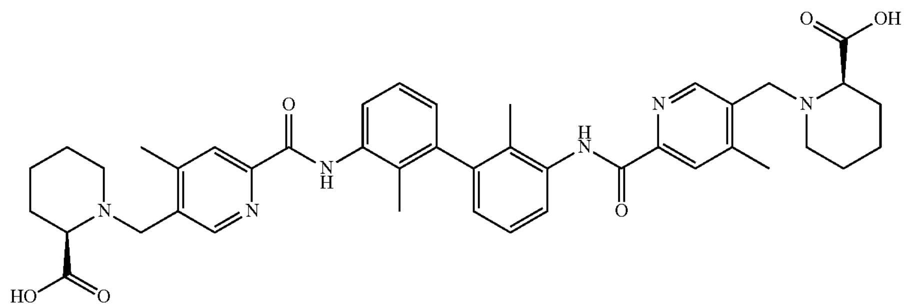 [SMILES: Cc1cc(C(=O)Nc2cccc(-c3cccc(NC(=O)c4cc(C)c(CN5CCCC[C@@H]5C(=O)O)cn4)c3C)c2C)ncc1CN1CCCC[C@@H]1C(=O)O] | (2R,2'R)-1,1'-(((((2,2'-dimethyl-[1,1'-biphenyl]-3,3'-diyl)bis(azanediyl))bis(carbonyl))bis(4-methylpyridine-6,3-diyl))bis(methylene))bis(piperidine-2-carboxylic acid) | 733 |
| 30 | 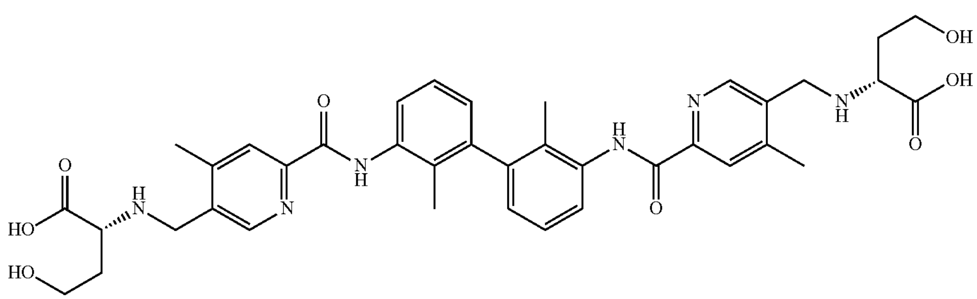 [SMILES: Cc1cc(C(=O)Nc2cccc(-c3cccc(NC(=O)c4cc(C)c(CN[C@H](CCO)C(=O)O)cn4)c3C)c2C)ncc1CN[C@H](CCO)C(=O)O] | (2R,2'R)-2,2'-(((((2,2'-dimethyl-[1,1'-biphenyl]-3,3'-diyl)bis(azanediyl))bis(carbonyl))bis(4-methylpyridine-6,3-diyl))bis(methylene))bis(azanediyl))bis(4-hydroxybuttanoic acid) | 713 |

-continued

| Example No. | Structure | Name | MS: m/z [M + 1]+ |
|---|---|---|---|
| 31 | 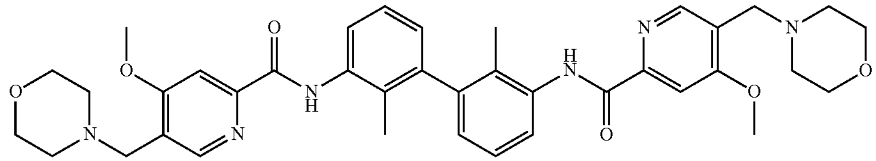 [SMILES: COc1cc(C(=O)Nc2cccc(-c3cccc(NC(=O)c4cc(OC)c(CN5CCOCC5)cn4)c3C)c2C)ncc1CN1CCOCC1] | N,N'-(2,2'-dimethyl-[1,1'-biphenyl]-3,3'-diyl)bis(4-methoxy-5-(morpholinomethyl)picolinamide) | 681 |
| 32 | 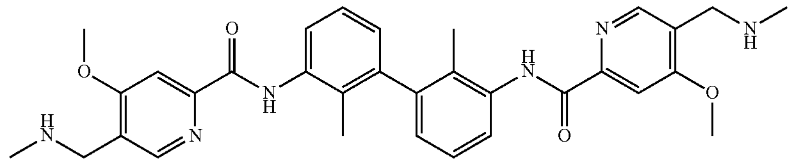 | N,N'-(2,2'-dimethyl-[1,1'-biphenyl]-3,3'-diyl)bis(4-methoxy-5-((methylamino)methyl)picolinamide) | 569 |
| 33 | 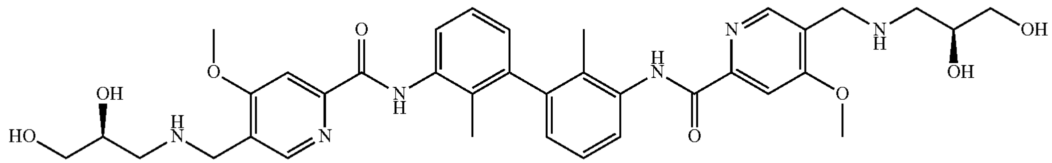 [SMILES: COc1cc(C(=O)Nc2cccc(-c3cccc(NC(=O)c4cc(OC)c(CNC[C@H](O)CO)cn4)c3C)c2C)ncc1CNC[C@H](O)CO] | N,N'-(2,2'-dimethyl-[1,1'-biphenyl]-3,3'-diyl)(5((((S)-2,3-dihydroxypropyl)amino)methyl)-4-methoxypicolinamide) | 689 |
| 34 | 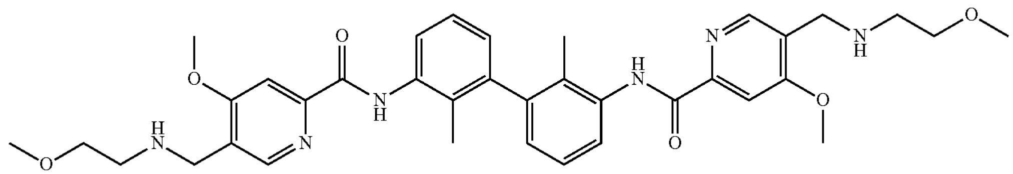 | N,N'-(2,2'-dimethyl-[1,1'-biphenyl]-3,3'-diyl)bis(4-methoxy-5-(((2-methoxyethyl)amino)methyl)picolinamide) | 657 |
| 35 | 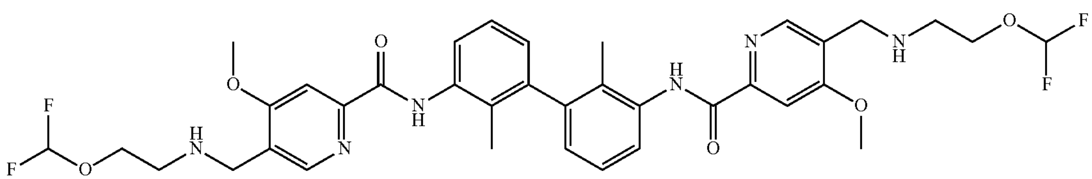 [SMILES: COc1cc(C(=O)Nc2cccc(-c3cccc(NC(=O)c4cc(OC)c(CNCCOC(F)F)cn4)c3C)c2C)ncc1CNCCOC(F)F] | N,N'-(2,2'-dimethyl-[1,1'-biphenyl]-3,3'-diyl)bis(5-(((2-(difluoromethoxy)ethyl)amino)methyl)-4-methoxypicolinamide) | 729 |

| Example No. | Structure | Name | MS: m/z [M + 1]+ |
|---|---|---|---|
| 36 | 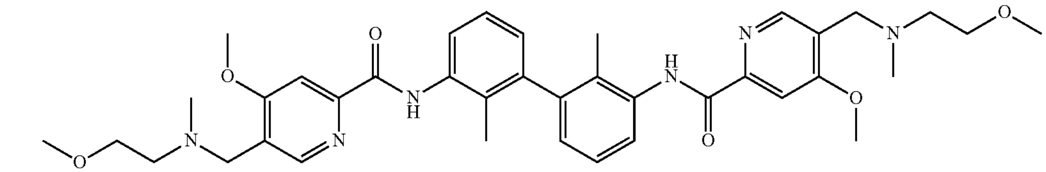 | N,N'-(2,2'-dimethyl-[1,1'-biphenyl]-3,3'-diyl)bis(4-methoxy-5-(((2-methoxyethyl)(methyl)amino)methyl)picolinamide) | 685 |
| 37 | 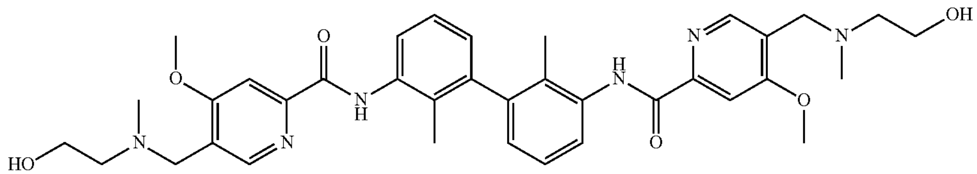 [SMILES: COc1cc(C(=O)Nc2cccc(-c3cccc(NC(=O)c4cc(OC)c(CN(C)CCO)cn4)c3C)c2C)ncc1CN(C)CCO] | N,N'-(2,2'-dimethyl-[1,1'-biphenyl]-3,3'-diyl)bis(5-(((2-hydroxyethyl)(methyl)amino)methyl)-4-methoxypicolinamide) | 657 |
| 38 | 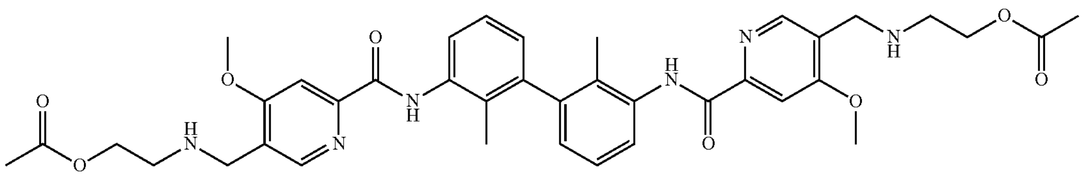 [SMILES: COc1cc(C(=O)Nc2cccc(-c3cccc(NC(=O)c4cc(OC)c(CNCCOC(C)=O)cn4)c3C)c2C)ncc1CNCCOC(C)=O] | (((((2,2'-dimethyl-[1,1'-biphenyl]-3,3'-diyl)bis(azanediyl)bis(carbonyl))bis(4-methoxypyridine-6,3-diyl))bis(methylene))bis(azanediyl))bis(ethane-2,1-diyl) diacetate | 713 |
| 39 | 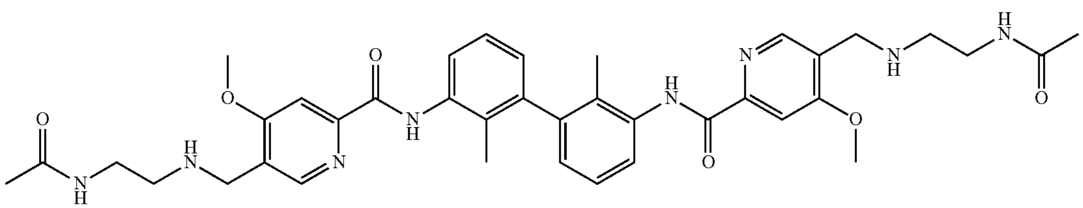 [SMILES: COc1cc(C(=O)Nc2cccc(-c3cccc(NC(=O)c4cc(OC)c(CNCCNC(C)=O)cn4)c3C)c2C)ncc1CNCCNC(C)=O] | N,N'-(2,2'-dimethyl-[1,1'-biphenyl]-3,3'-diyl)bis(5-(((2-acetamidoethyl)amino)methyl)-4-methoxypicolinamide) | 711 |
| 40 | 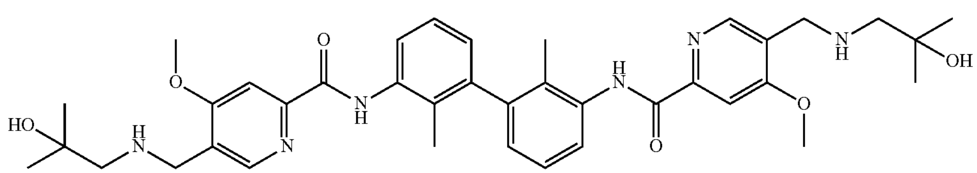 [SMILES: COc1cc(C(=O)Nc2cccc(-c3cccc(NC(=O)c4cc(OC)c(CNCC(C)(C)O)cn4)c3C)c2C)ncc1CNCC(C)(C)O] | N,N'-(2,2'-dimethyl-[1,1'-biphenyl]-3,3'-diyl)bis(5-(((2-hydroxy-2-methylpropyl)amino)methyl)-4-methoxypicolinamide) | 685 |

-continued

| Example No. | Structure | Name | MS: m/z [M + 1]+ |
|---|---|---|---|
| 41 | 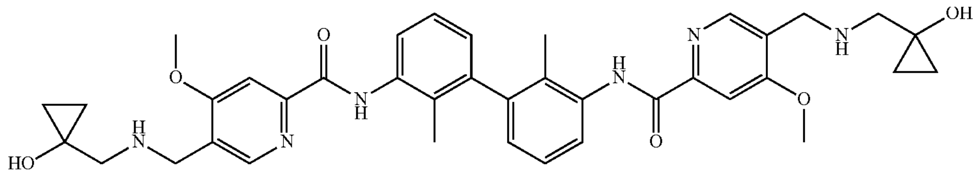 [SMILES: COc1cc(C(=O)Nc2cccc(-c3cccc(NC(=O)c4cc(OC)c(CNCC5(O)CC5)cn4)c3C)c2C)ncc1CNCC1(O)CC1] | N,N'-(2,2'-dimethyl-[1,1'-biphenyl]-3,3'-diyl)bis(5-((((1-hydroxycyclopropyl)methyl)amino)methyl)-4-methoxypicolinamide) | 681 |
| 42 | 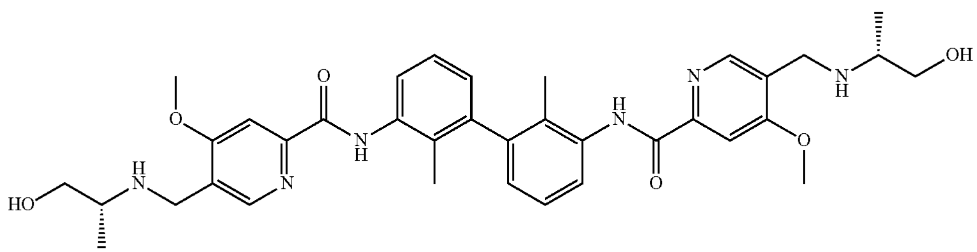 [SMILES: COc1cc(C(=O)Nc2cccc(-c3cccc(NC(=O)c4cc(OC)c(CN[C@H](C)CO)cn4)c3C)c2C)ncc1CN[C@H](C)CO] | N,N'-(2,2'-dimethyl-[1,1'-biphenyl]-3,3'-diyl)bis(5-((((R)-1-hydroxypropan-2-yl)amino)methyl)-4-methoxypicolinamide) | 657 |
| 43 | 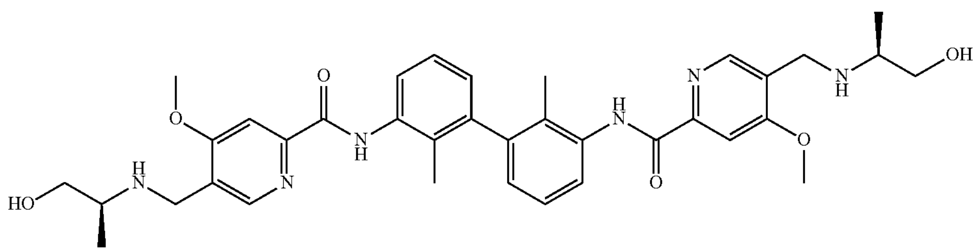 [SMILES: COc1cc(C(=O)Nc2cccc(-c3cccc(NC(=O)c4cc(OC)c(CN[C@@H](C)CO)cn4)c3C)c2C)ncc1CN[C@@H](C)CO] | N,N'-(2,2'-dimethyl-[1,1'-biphenyl]-3,3'-diyl)bis(5-((((S)-1-hydroxypropan-2-yl)amino)methyl)-4-methoxypicolinamide) | 657 |
| 44 | 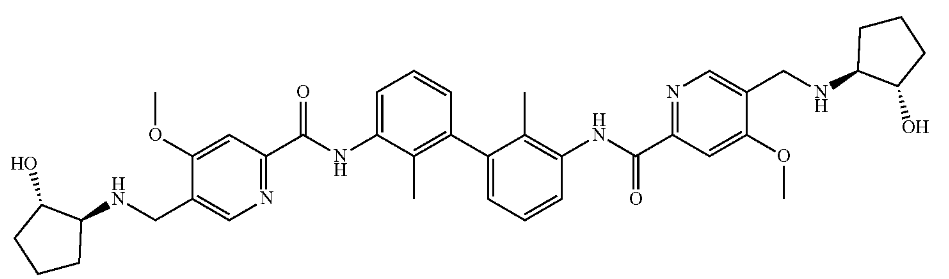 [SMILES: COc1cc(C(=O)Nc2cccc(-c3cccc(NC(=O)c4cc(OC)c(CN[C@H]5CCC[C@@H]5O)cn4)c3C)c2C)ncc1CN[C@H]1CCC[C@@H]1O] | N,N'-(2,2'-dimethyl-[1,1'-biphenyl]-3,3'-diyl)bis(5-((((1S,2S)-2-hydroxycyclopentyl)amino)methyl)-4-methoxypicolinamide) | 709 |

| Example No. | Structure | Name | MS: m/z [M + 1]+ |
|---|---|---|---|
| 45 | 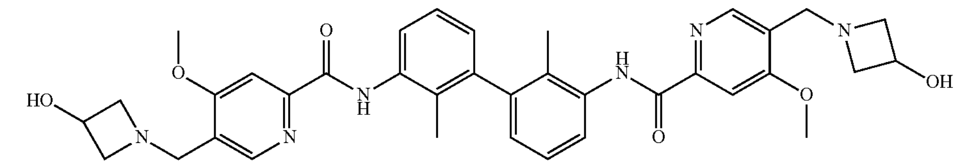 [SMILES: COc1cc(C(=O)Nc2cccc(-c3cccc(NC(=O)c4cc(OC)c(CN5CC(O)C5)cn4)c3C)c2C)ncc1CN1CC(O)C1] | N,N'-(2,2'-dimethyl-[1,1'-biphenyl]-3,3'-diyl)bis(5-((3-hydroxyazetidin-1-yl)methyl)-4-methoxypicolinamide) | 653 |
| 46 | 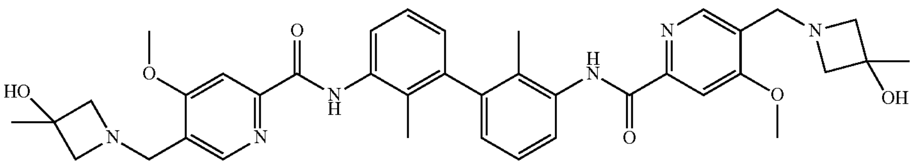 | N,N'-(2,2'-dimethyl-[1,1'-biphenyl]-3,3'-diyl)bis(5-((3-hydroxy-3-methylazetidin-1-yl)methyl)-4-methoxypicolinamide) | 681 |
| 47 | 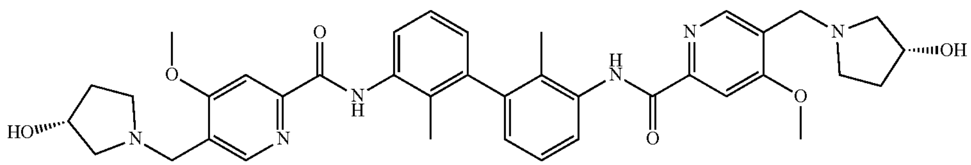 [SMILES: COc1cc(C(=O)Nc2cccc(-c3cccc(NC(=O)c4cc(OC)c(CN5CC[C@@H](O)C5)cn4)c3C)c2C)ncc1CN1CC[C@@H](O)C1] | N,N'-(2,2'-dimethyl-[1,1'-biphenyl]-3,3'-diyl)bis(5-(((R)-3-hydroxypyrrolidin-1-yl)methyl)-4-methoxypicolinamide) | 681 |
| 48 | 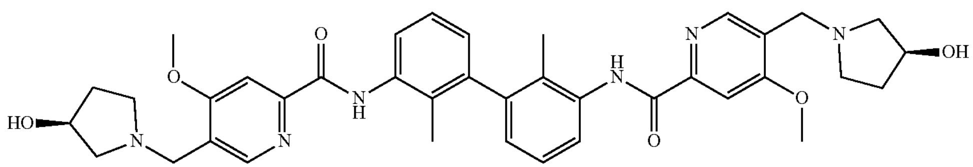 [SMILES: COc1cc(C(=O)Nc2cccc(-c3cccc(NC(=O)c4cc(OC)c(CN5CC[C@H](O)C5)cn4)c3C)c2C)ncc1CN1CC[C@H](O)C1] | N,N'-(2,2'-dimethyl-[1,1'-biphenyl]-3,3'-diyl)bis(5-(((S)-3-hydroxypyrrolidin-1-yl)methyl)-4-methoxypicolinamide) | 681 |
| 49 | 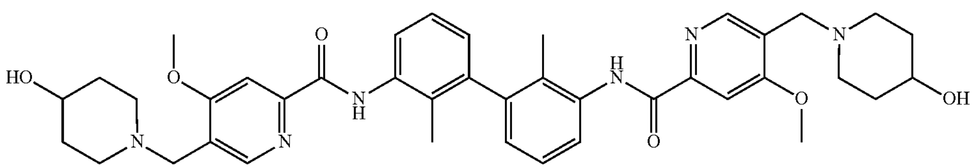 [SMILES: COc1cc(C(=O)Nc2cccc(-c3cccc(NC(=O)c4cc(OC)c(CN5CCC(O)CC5)cn4)c3C)c2C)ncc1CN1CCC(O)CC1] | N,N'-(2,2'-dimethyl-[1,1'-biphenyl]-3,3'-diyl)bis(5-((4-hydroxypiperidin-1-yl)methyl)-4-methoxypicolinamide) | 709 |
| 50 | 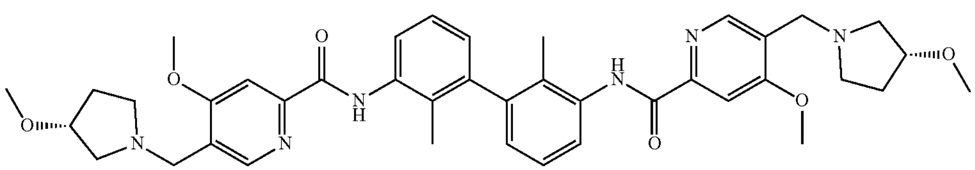 | N,N'-(2,2'-dimethyl-[1,1'-biphenyl]-3,3'-diyl)bis(5-(((R)-3-methoxypyrrolidin-1-yl)methyl)picolinamide) | 709 |

| Example No. | Structure | Name | MS: m/z [M + 1]+ |
|---|---|---|---|
| 51 | 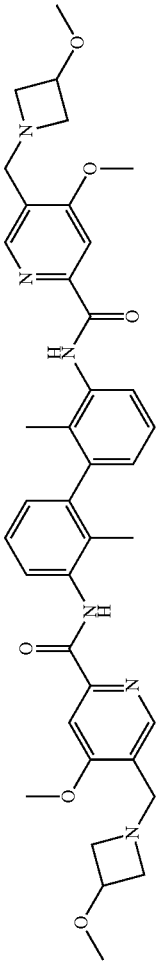 | N,N'-(2,2'-dimethyl-[1,1'-biphenyl]-3,3'-diyl)bis(4-methoxy-5-((3-methoxyazetidin-1-yl)methyl)picolinamide) | 681 |
| 52 | 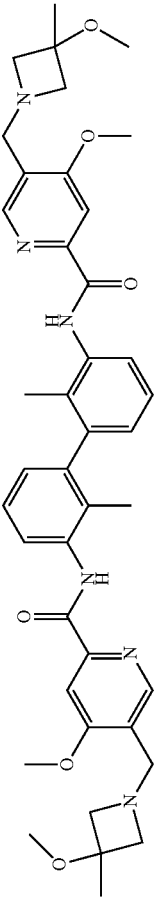 | N,N'-(2,2'-dimethyl-[1,1'-biphenyl]-3,3'-diyl)bis(4-methoxy-5-((3-methoxy-3-methylazetidin-1-yl)methyl)picolinamide) | 709 |
| 53 | 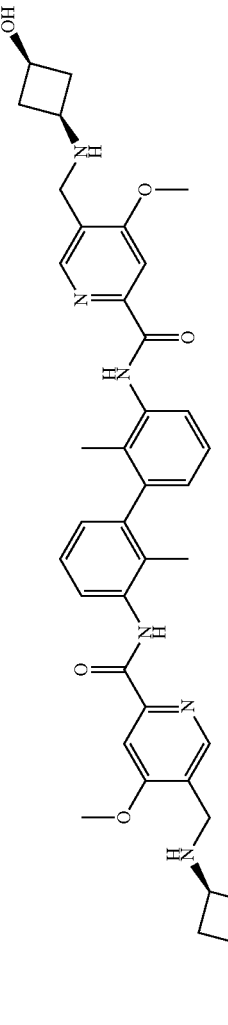 | N,N'-(2,2'-dimethyl-[1,1'-biphenyl]-3,3'-diyl)bis(5-(((1s,3s)-3-hydroxycyclobutyl)amino)methyl)-4-methoxypicolinamide) | 681 |
| 54 | 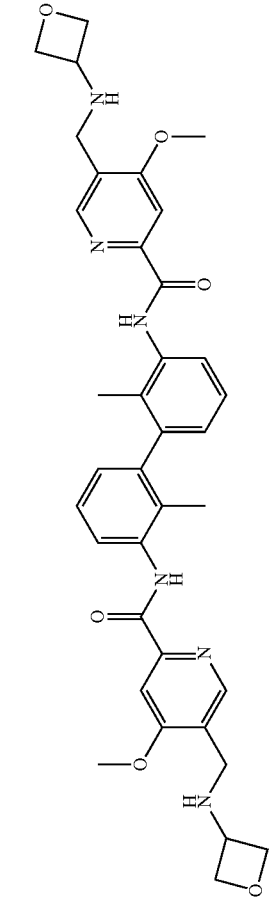 | N,N'-(2,2'-dimethyl-[1,1'-biphenyl]-3,3'-diyl)bis(4-methoxy-5-((oxetan-3-ylamino)methyl)picolinamide) | 653 |

| Example No. | Structure | Name | MS: m/z [M + 1]+ |
|---|---|---|---|
| 55 | 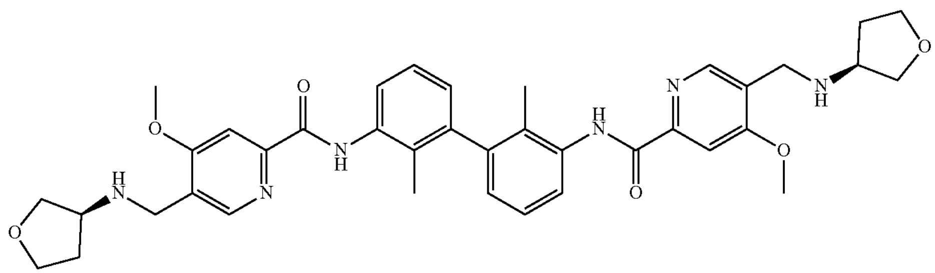 [SMILES: COc1cc(C(=O)Nc2cccc(-c3cccc(NC(=O)c4cc(OC)c(CN[C@H]5CCOC5)cn4)c3C)c2C)ncc1CN[C@H]1CCOC1] | N,N'-(2,2'-dimethyl-[1,1'-biphenyl]-3,3'-diyl)bis(4-methoxy-5-((((S)-tetrahydrofuran-3-yl)amino)methyl)picolinamide) | 681 |
| 56 | 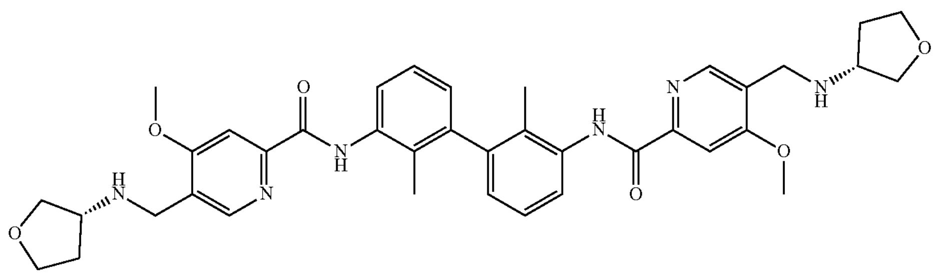 [SMILES: COc1cc(C(=O)Nc2cccc(-c3cccc(NC(=O)c4cc(OC)c(CN[C@@H]5CCOC5)cn4)c3C)c2C)ncc1CN[C@@H]1CCOC1] | N,N'-(2,2'-dimethyl-[1,1'-biphenyl]-3,3'-diyl)bis(4-methoxy-5-((((R)-tetrahydrofuran-3-yl)amino)methyl)picolinamide) | 681 |
| 57 | 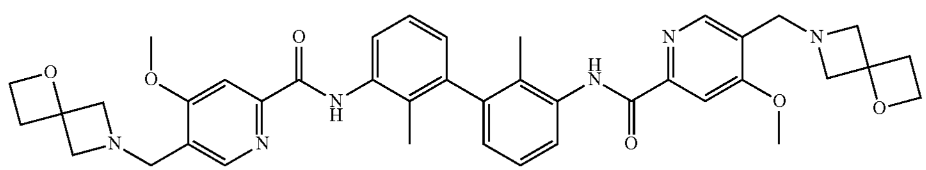 [SMILES: COc1cc(C(=O)Nc2cccc(-c3cccc(NC(=O)c4cc(OC)c(CN5CC6(CCO6)C5)cn4)c3C)c2C)ncc1CN1CC2(CCO2)C1] | N,N'-(2,2'-dimethyl-[1,1'-biphenyl]-3,3'-diyl)bis(5-((1-oxa-6-azaspiro[3.3]heptan-6-yl)methyl)-4-methoxypicolinamide) | 705 |
| 58 | 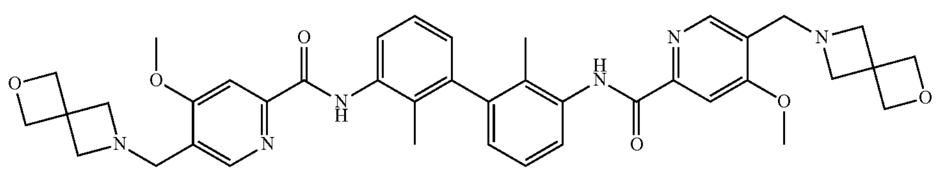 [SMILES: COc1cc(C(=O)Nc2cccc(-c3cccc(NC(=O)c4cc(OC)c(CN5CC6(COC6)C5)cn4)c3C)c2C)ncc1CN1CC2(COC2)C1] | N,N'-(2,2'-dimethyl-[1,1'-biphenyl]-3,3'-diyl)bis(5-((2-oxa-6-azaspiro[3.3]heptan-6-yl)methyl)-4-methoxypicolinamide) | 705 |

| Example No. | Structure | Name | MS: m/z [M + 1]+ |
|---|---|---|---|
| 59 | 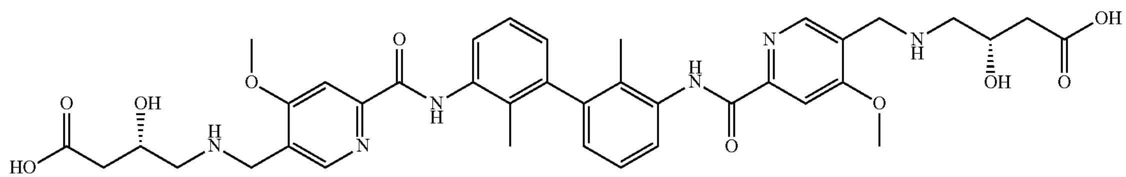 [SMILES: COc1cc(C(=O)Nc2cccc(-c3cccc(NC(=O)c4cc(OC)c(CNC[C@@H](O)CC(=O)O)cn4)c3C)c2C)ncc1CNC[C@@H](O)CC(=O)O] | (3S,3'S)-4,4'-((((((2,2'-dimethyl-[1,1'-biphenyl]-3,3'-diyl)bis(azanediyl))bis(carbonyl))bis(4-methoxypyridine-6,3-diyl))bis(methylene))bis(azanediyl))bis(3-hydroxybutanoic acid) | 745 |
| 60 | 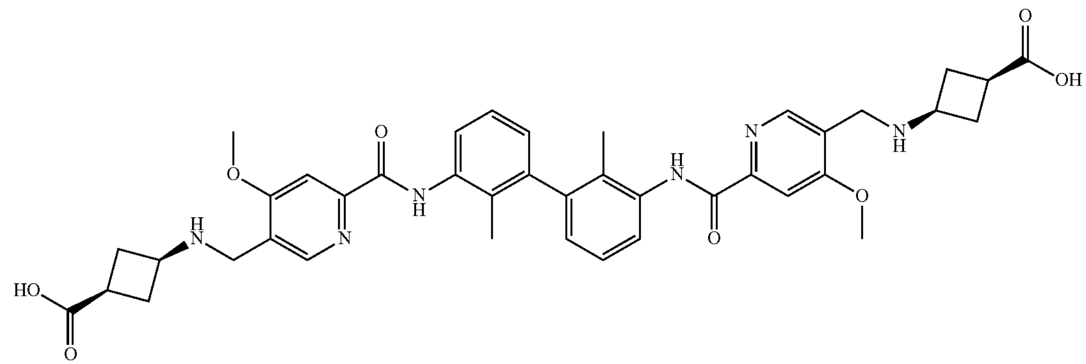 [SMILES: COc1cc(C(=O)Nc2cccc(-c3cccc(NC(=O)c4cc(OC)c(CN[C@H]5C[C@@H](C(=O)O)C5)cn4)c3C)c2C)ncc1CN[C@H]1C[C@@H](C(=O)O)C1] | (1s,1's,3s,3's)-3,3'-((((((2,2'-dimethyl-[1,1'-biphenyl]-3,3'-diyl)bis(azanediyl))bis(carbonyl))bis(4-methoxypyridine-6,3-diyl))bis(methylene))bis(azanediyl))bis(cyclobutane-1-carboxylic acid) | 737 |
| 61 | 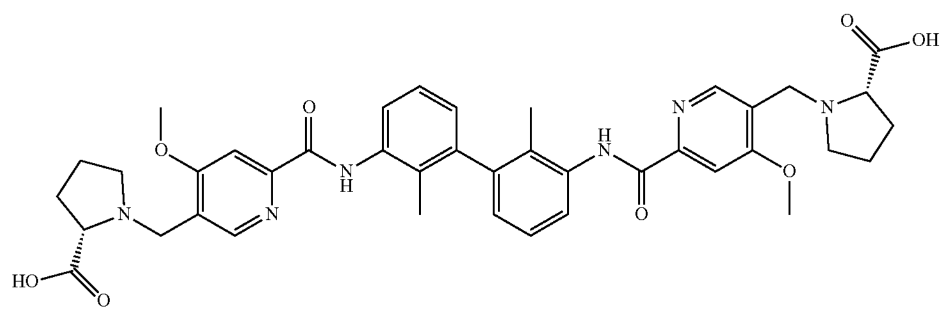 [SMILES: COc1cc(C(=O)Nc2cccc(-c3cccc(NC(=O)c4cc(OC)c(CN5CCC[C@H]5C(=O)O)cn4)c3C)c2C)ncc1CN1CCC[C@H]1C(=O)O] | (2'S)-1,1'-((((((2,2'-dimethyl-[1,1'-biphenyl]-3,3'-diyl)bis(azanediyl))bis(carbonyl))bis(4-methoxypyridine-6,3-diyl))bis(methylene))di-L-proline | 737 |

-continued

| Example No. | Structure | Name | MS: m/z [M + 1]+ |
|---|---|---|---|
| 62 | 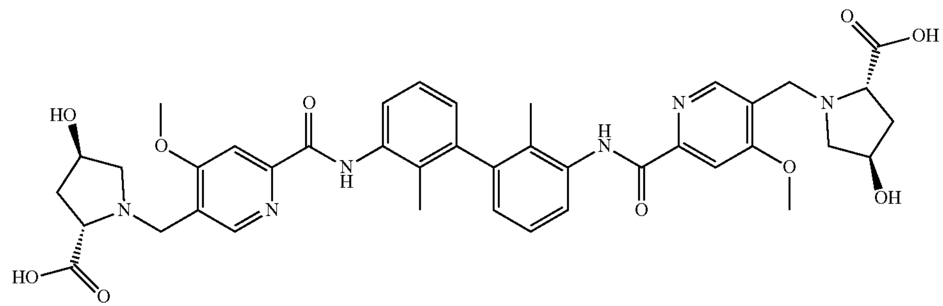 [SMILES: COc1cc(C(=O)Nc2cccc(-c3cccc(NC(=O)c4cc(OC)c(CN5C[C@H](O)C[C@H]5C(=O)O)cn4)c3C)c2C)ncc1CN1C[C@H](O)C[C@H]1C(=O)O] | (2S,2'S,4R,4'R)-1,1'-((((2,2'-dimethyl-[1,1'-biphenyl]-3,3'-diyl)bis(azanediyl))bis(carbonyl))bis(4-methoxypyridine-6,3-diyl))bis(methylene))bis(4-hydroxypyrrolidine-2-carboxylic acid) | 769 |
| 63 | 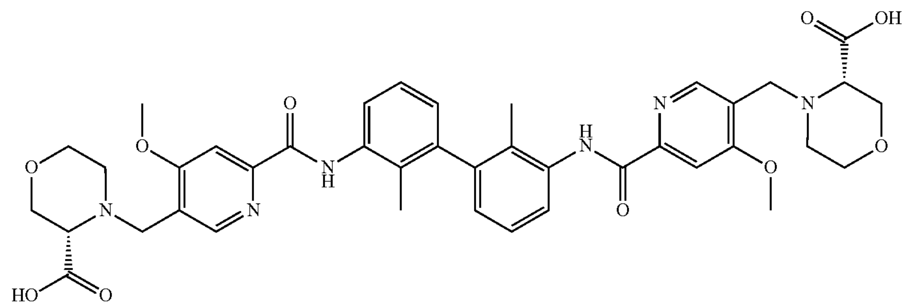 [SMILES: COc1cc(C(=O)Nc2cccc(-c3cccc(NC(=O)c4cc(OC)c(CN5CCOC[C@H]5C(=O)O)cn4)c3C)c2C)ncc1CN1CCOC[C@H]1C(=O)O] | (3S,3'S)-4,4'-(((((2,2'-dimethyl-[1,1'-biphenyl]-3,3'-diyl)bis(azanediyl))bis(carbonyl))bis(4-methoxypyridine-6,3-diyl))bis(methylene))bis(morpholine-3-carboxylic acid) | 769 |
| 64 | 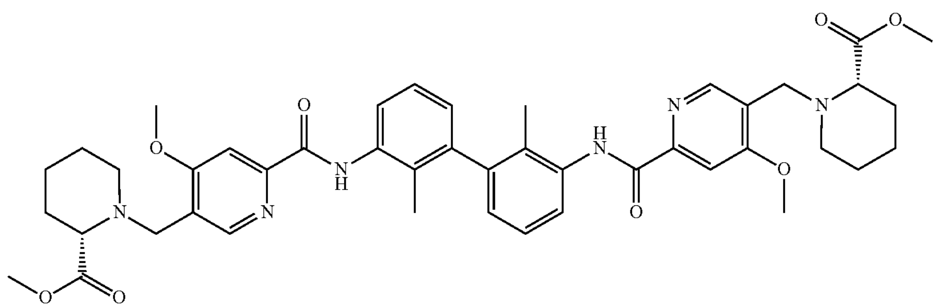 | dimethyl 1,1'-((((2,2'-dimethyl-[1,1'-biphenyl]-3,3'-diyl)bis(azanediyl))bis(carbonyl))bis(4-methoxypyridine-6,3-diyl))bis(methylene))(2S,2'S)-bis(piperidine-2-carboxylate) | 793 |

| Example No. | Structure | Name | MS: m/z [M + 1]+ |
|---|---|---|---|
| 65 | 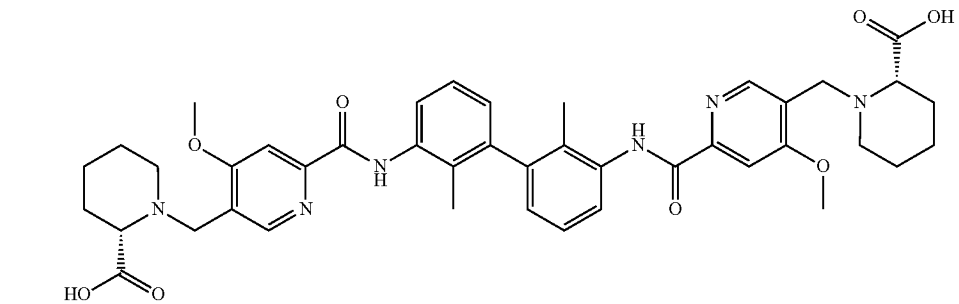 [SMILES: COc1cc(C(=O)Nc2cccc(-c3cccc(NC(=O)c4cc(OC)c(CN5CCCC[C@H]5C(=O)O)cn4)c3C)c2C)ncc1CN1CCCC[C@H]1C(=O)O] | (2S,2S)-1,1'-((((2,2'-dimethyl-[1,1'-biphenyl]-3,3'-diyl)bis(azanediyl))bis(carbonyl))bis(4-methoxypyridine-6,3-diyl))bis(methylene))bis(piperidine-2-carboxylic acid) | 765 |
| 66 | 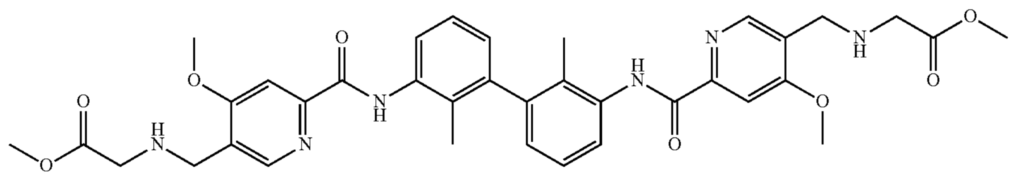 | dimethyl 2,2'-((((((2,2'-dimethyl-[1,1'-biphenyl]-3,3'-diyl)bis(azanediyl))bis(carbonyl))bis(4-methoxypyridine-6,3-diyl))bis(methylene))bis(azanediyl))diacetate | 685 |
| 67 | 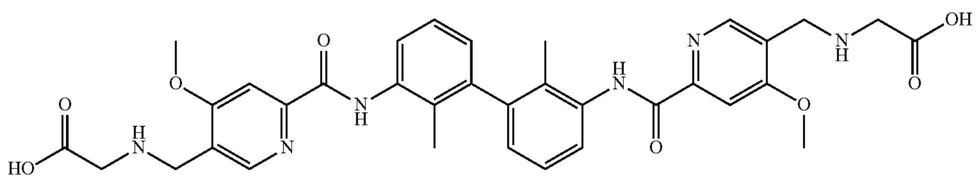 [SMILES: COc1cc(C(=O)Nc2cccc(-c3cccc(NC(=O)c4cc(OC)c(CNCC(=O)O)cn4)c3C)c2C)ncc1CNCC(=O)O] | 2,2'-((((((2,2'-dimethyl-[1,1'-biphenyl]-3,3'-diyl)bis(azanediyl))bis(carbonyl))bis(4-methoxypyridine-6,3-diyl)bis(methylene))bis(azanediyl))diacetic acid | 657 |
| 68 | 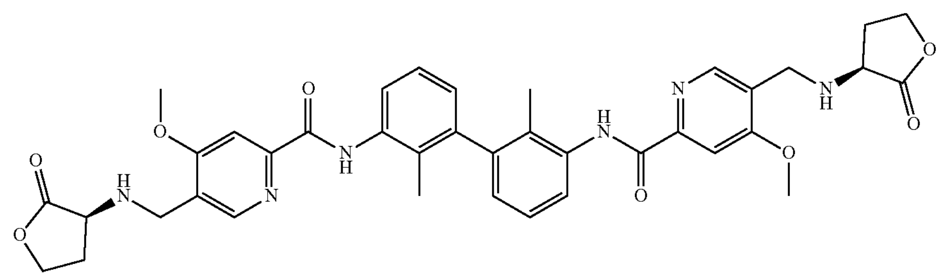 [SMILES: COc1cc(C(=O)Nc2cccc(-c3cccc(NC(=O)c4cc(OC)c(CN[C@H]5CCOC5=O)cn4)c3C)c2C)ncc1CN[C@H]1CCOC1=O] | N,N'-(2,2'-dimethyl-[1,1'-biphenyl]-3,3'-diyl)bis(4-methoxy-5-((((S)-2-oxotetrahydrofuran-3-yl)amino)methyl)picolinamide) | 709 |

| Example No. | Structure | Name | MS: m/z [M + 1]+ |
|---|---|---|---|
| 69 | 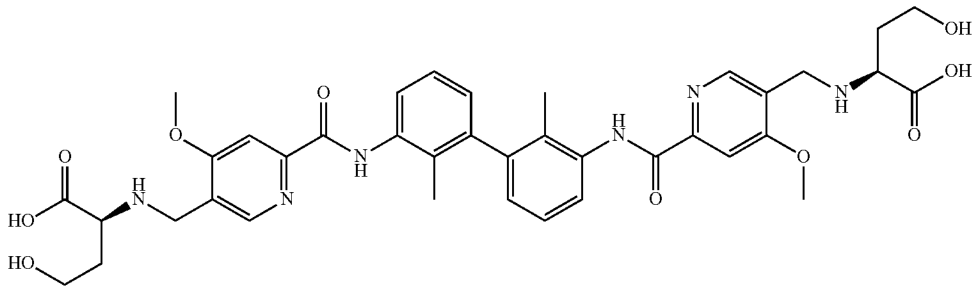 [SMILES: COc1cc(C(=O)Nc2cccc(-c3cccc(NC(=O)c4cc(OC)c(CN[C@@H](CCO)C(=O)O)cn4)c3C)c2C)ncc1CN[C@@H](CCO)C(=O)O] | (2S,2'S)-2,2'-((((((2,2'-dimethyl-[1,1'-biphenyl]-3,3'-diyl)bis(azanediyl))bis(carbonyl))bis(4-methoxypyridine-6,3-diyl))bis(methylene))bis(azanediyl))bis(4-hydroxybutanoic acid) | 745 |
| 70 | 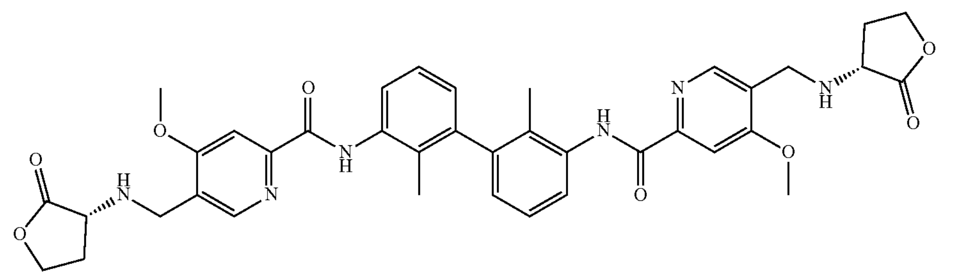 [SMILES: COc1cc(C(=O)Nc2cccc(-c3cccc(NC(=O)c4cc(OC)c(CN[C@@H]5CCOC5=O)cn4)c3C)c2C)ncc1CN[C@@H]1CCOC1=O] | N,N'-(2,2'-dimethyl-[1,1'-biphenyl]-3,3'-diyl)bis(4-methoxy-5-((((R)-2-oxotetrahydrofuran-3-yl)amino)methyl)picolinamide) | 709 |
| 71 | 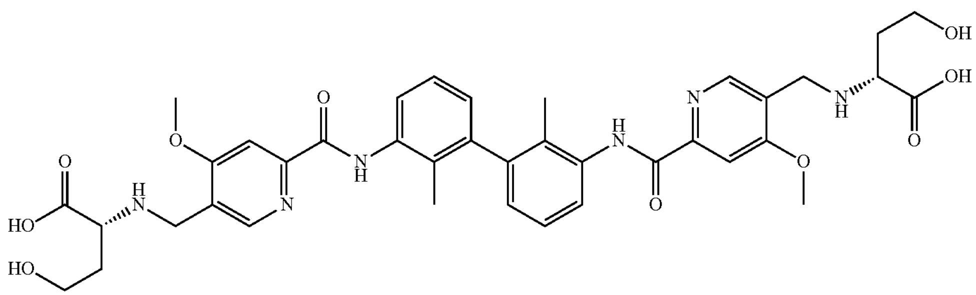 [SMILES: COc1cc(C(=O)Nc2cccc(-c3cccc(NC(=O)c4cc(OC)c(CN[C@H](CCO)C(=O)O)cn4)c3C)c2C)ncc1CN[C@H](CCO)C(=O)O] | (2R,2'R)-2,2'-((((((2,2'-dimethyl-[1,1'-biphenyl]-3,3'-diyl)bis(azanediyl))bis(carbonyl))bis(4-methoxypyridine-6,3-diyl))bis(methylene))bis(azanediyl)bis(4-hydroxybutanoic acid) | 745 |

-continued

| Example No. | Structure | Name | MS: m/z [M + 1]+ |
|---|---|---|---|
| 72 | 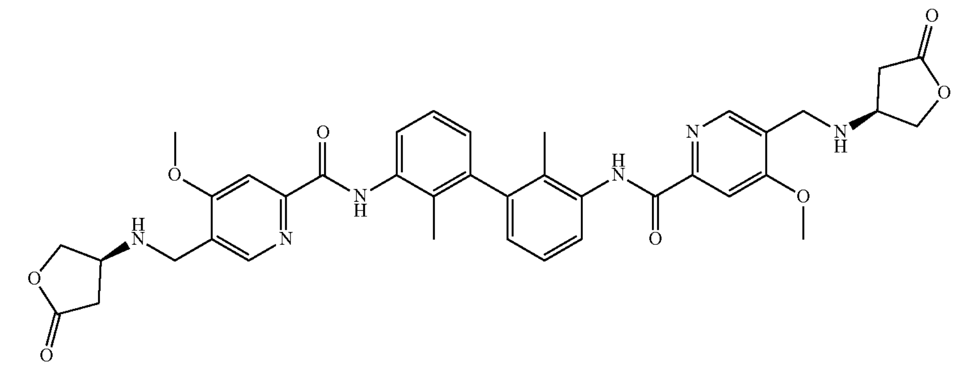 [SMILES: COc1cc(C(=O)Nc2cccc(-c3cccc(NC(=O)c4cc(OC)c(CN[C@@H]5COC(=O)C5)cn4)c3C)c2C)ncc1CN[C@@H]1COC(=O)C1] | N,N'-(2,2'-dimethyl-[1,1'-biphenyl]-3,3'-diyl)bis(4-methoxy-5-((((S)-5-oxotetrahydrofuran-3-yl)amino)methyl)picolinamide) | 709 |
| 73 | 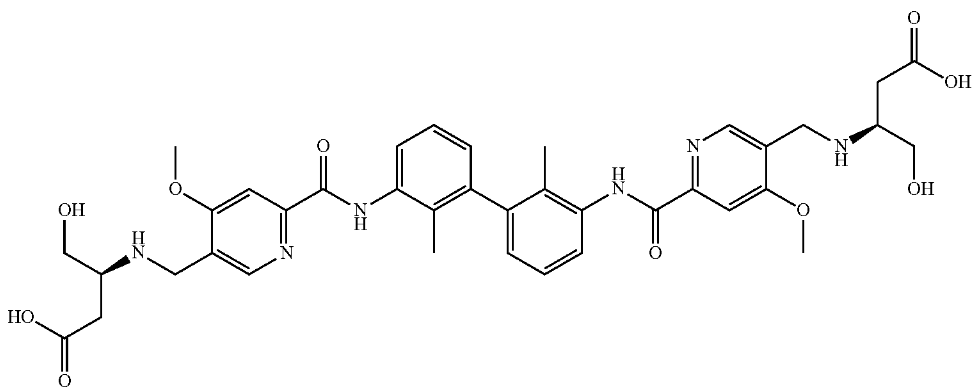 [SMILES: COc1cc(C(=O)Nc2cccc(-c3cccc(NC(=O)c4cc(OC)c(CN[C@H](CO)CC(=O)O)cn4)c3C)c2C)ncc1CN[C@H](CO)CC(=O)O] | (3S,3'S)-3,3'-(((((2,2'-dimethyl-[1,1'-biphenyl]-3,3'-diyl)bis(azanediyl))bis(carbonyl))bis(4-methoxypyridine-6,3-diyl))bis(methylene))bis(azanediyl))bis(4-hydroxybutanoic acid) | 745 |

| Example No. | Structure | Name | MS: m/z [M + 1]+ |
|---|---|---|---|
| 74 | 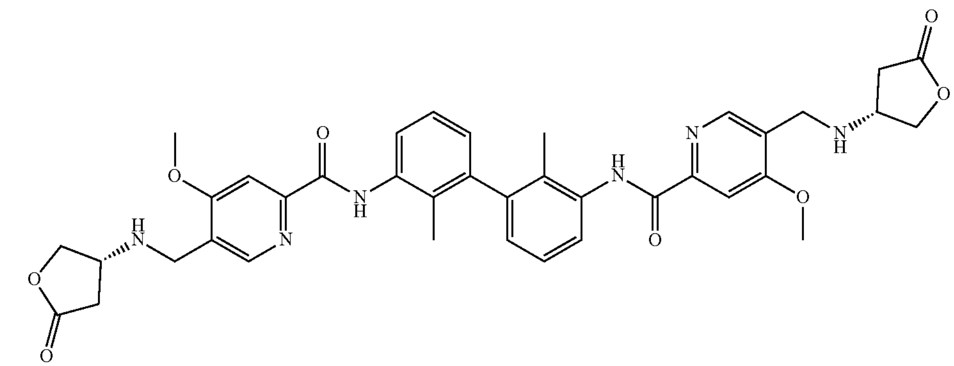 [SMILES: COc1cc(C(=O)Nc2cccc(-c3cccc(NC(=O)c4cc(OC)c(CN[C@H]5COC(=O)C5)cn4)c3C)c2C)ncc1CN[C@H]1COC(=O)C1] | N,N'-2,2'-dimethyl[1,1'-biphenyl]-3,3'-diyl)bis(4-methoxy-5-((((R)-5-oxotetrahydrofuran-3-yl)amino)methyl)picolinamide) | 709 |
| 75 | 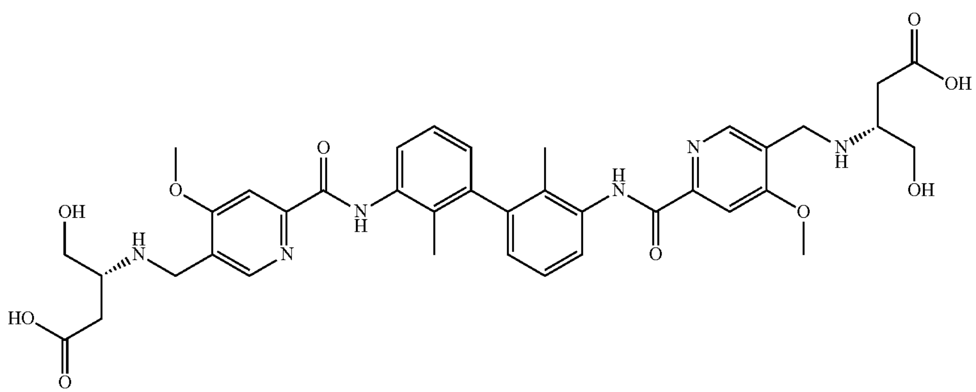 [SMILES: COc1cc(C(=O)Nc2cccc(-c3cccc(NC(=O)c4cc(OC)c(CN[C@@H](CO)CC(=O)O)cn4)c3C)c2C)ncc1CN[C@@H](CO)CC(=O)O] | (3R,3'R)-3,3'-(((((2,2'-dimethyl-[1,1'-biphenyl]-3,3'-diyl)bis(azanediyl))bis(carbonyl))bis(4-methoxypyridine-6,3-diyl))bis(methylene))bis(azanediyl))bis(4-hydroxybutanoic acid) | 745 |

| Example No. | Structure | Name | MS: m/z [M + 1]+ |
|---|---|---|---|
| 76 | 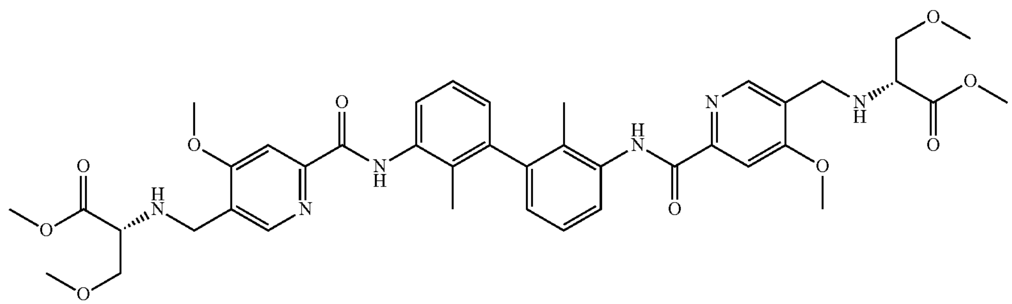 | dimethyl 2,2'-(((((2,2'-dimethyl-[1,1'-biphenyl]-3,3'-diyl)bis(azanediyl))bis(carbonyl))bis(4-methoxypyridine-6,3-diyl))bis(methylene))bis(azanediyl))(2R,2'R)-bis(3-methoxypropanoate) | 773 |
| 77 | 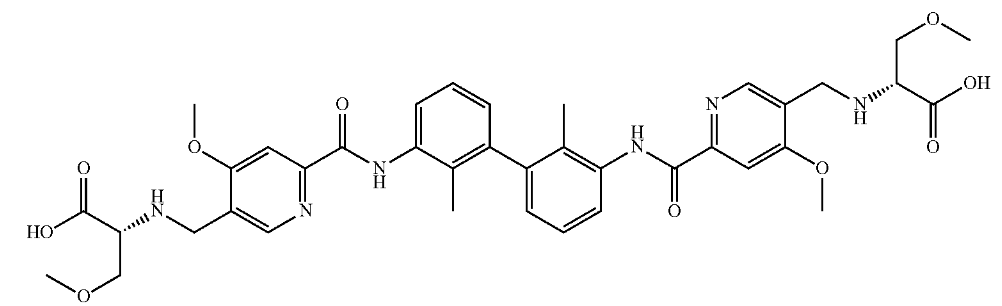 [SMILES: COC[C@@H](NCc1cnc(C(=O)Nc2cccc(-c3cccc(NC(=O)c4cc(OC)c(CN[C@H](COC)C(=O)O)cn4)c3C)c2C)cc1OC)C(=O)O] | (2R,2'R)-2,2'-(((((2,2'-dimethyl-[1,1'-biphenyl]-3,3'-diyl)bis(azanediyl))bis(carbonyl))bis(4-methoxypyridine-6,3-diyl))bis(methylene))bis(azanediyl))bis(3-methoxypropanoic acid) | 745 |
| 78 | 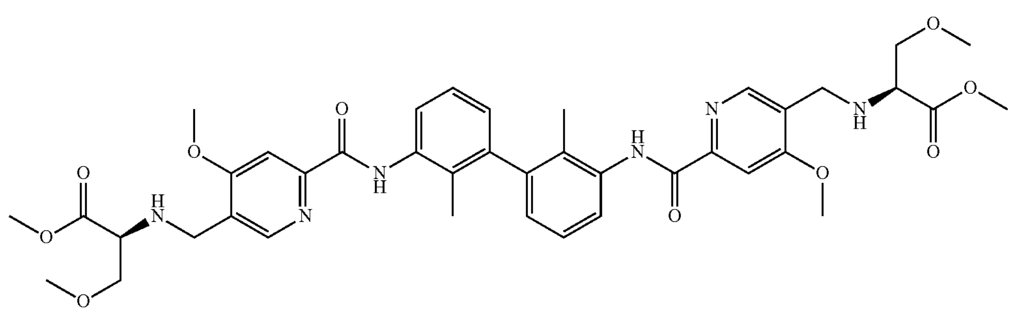 | dimethyl 2,2'-(((((2,2'-dimethyl-[1,1'-biphenyl]-3,3'-diyl)bis(azanediyl))bis(carbonyl))bis(4-methoxypyridine-6,3-diyl))bis(methylene))bis(azanediyl))(2S,2'S)-bis(3-methoxypropanoate) | 773 |

-continued

| Example No. | Structure | Name | MS: m/z [M + 1]+ |
|---|---|---|---|
| 79 | 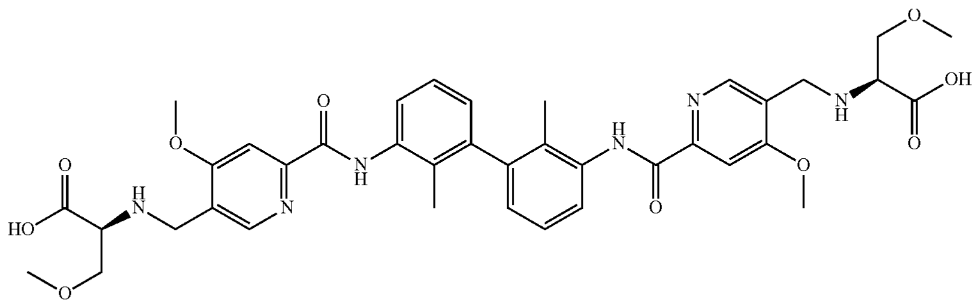 [SMILES: COC[C@H](NCc1cnc(C(=O)Nc2cccc(-c3cccc(NC(=O)c4cc(OC)c(CN[C@@H](COC)C(=O)O)cn4)c3C)c2C)cc1OC)C(=O)O] | (2S,2'S)-2,2'-((((((2,2'-dimethyl-[1,1'-biphenyl]-3,3'-diyl)bis(azanediyl))bis(carbonyl))bis(4-methoxypyridine-6,3-diyl))bis(methylene))bis(azanediyl))bis(3-methoxypropanoic acid) | 745 |
| 80 | 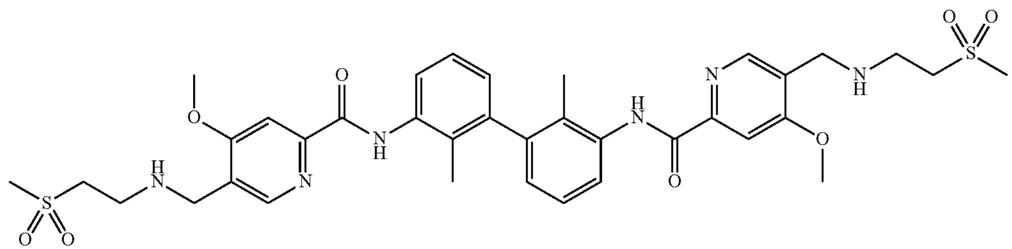 | N,N'-(2,2'-dimethyl-[1,1'-biphenyl]-3,3'-diyl)bis(4-methoxy-5-(((2-(methylsulfonyl)ethyl)amino)methyl)picolinamide) | 753 |
| 81 | 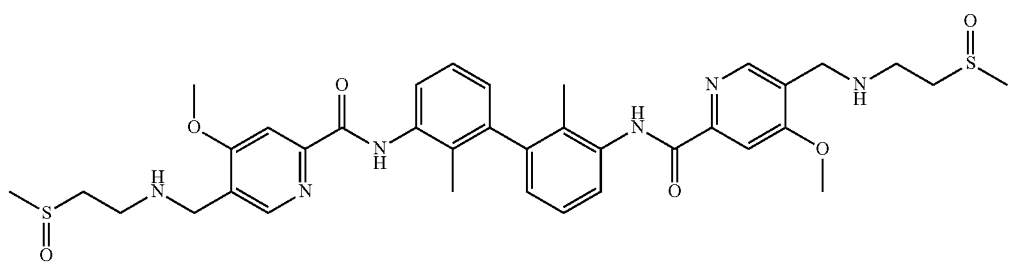 | N,N'-(2,2'-dimethyl-[1,1'-biphenyl]-3,3'-diyl)bis(4-methoxy-5-(((2-(methylsulfinyl)ethyl)amino)methyl)picolinamide) | 721 |
| 82 | 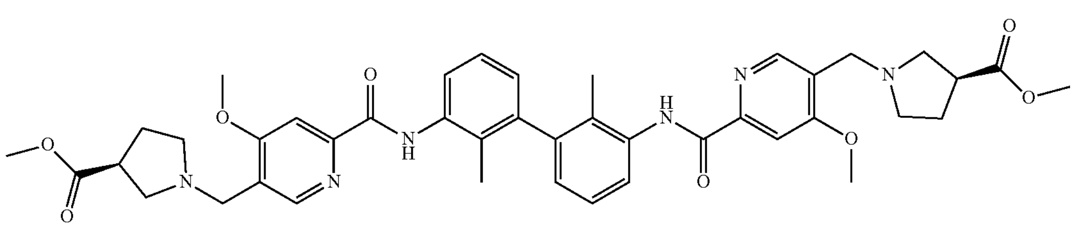 | dimethyl 1,1'-(((((2,2'-dimethyl-[1,1'-biphenyl]-3,3'-diyl)bis(azanediyl))bis(carbonyl))bis(4-methoxypyridine-6,3-diyl))bis(methylene))(3S,3'S)-bis(pyrrolidine-3-carboxylate) | 765 |

-continued

| Example No. | Structure | Name | MS: m/z [M + 1]+ |
|---|---|---|---|
| 83 | 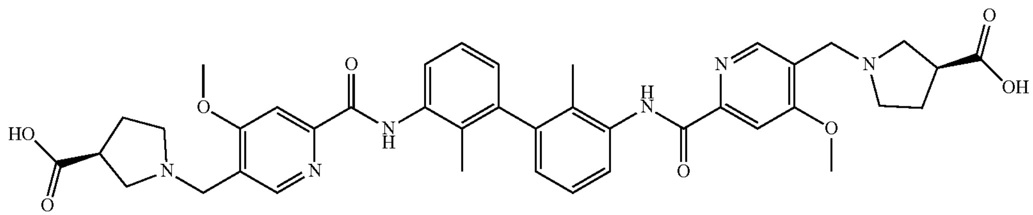 [SMILES: COc1cc(C(=O)Nc2cccc(-c3cccc(NC(=O)c4cc(OC)c(CN5CC[C@H](C(=O)O)C5)cn4)c3C)c2C)ncc1CN1CC[C@H](C(=O)O)C1] | (3S,3'S)-1,1'-((((2,2'-dimethyl-[1,1'-biphenyl]-3,3'-diyl)bis(azanediyl))bis(carbonyl))bis(4-methoxypyridine-6,3-diyl))bis(methylene))bis(pyrrolidine-3-carboxylic acid) | 737 |
| 84 | 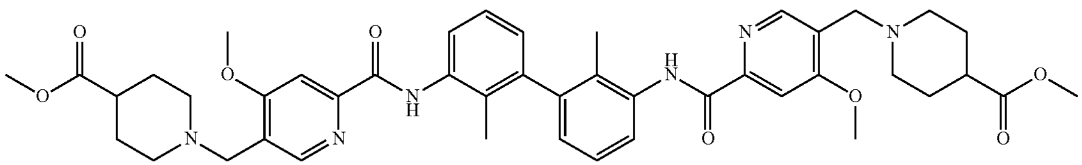 | dimethyl 1,1'-(((((2,2'-dimethyl-[1,1'-biphenyl]-3,3'-diyl)bis(azanediyl))bis(carbonyl))bis(4-methoxypyridine-6,3-diyl))bis(methylene))bis(piperidine-4-carboxylate) | 793 |
| 85 | 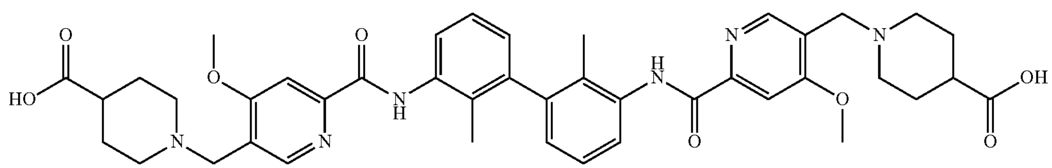 [SMILES: COc1cc(C(=O)Nc2cccc(-c3cccc(NC(=O)c4cc(OC)c(CN5CCC(C(=O)O)CC5)cn4)c3C)c2C)ncc1CN1CCC(C(=O)O)CC1] | 1,1'-(((((2,2'-dimethyl-[1,1'-biphenyl]-3,3'-diyl)bis(azanediyl))bis(carbonyl))bis(4-methoxypyridine-6,3-diyl))bis(methylene))bis(piperidine-4-carboxylic acid) | 765 |
| 86 | 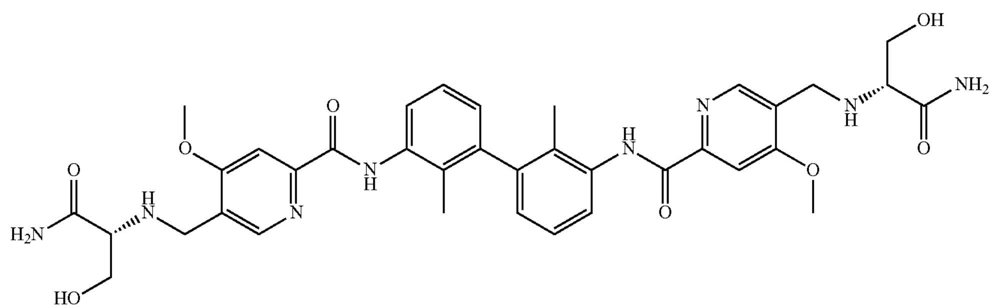 [SMILES: COc1cc(C(=O)Nc2cccc(-c3cccc(NC(=O)c4cc(OC)c(CN[C@H](CO)C(N)=O)cn4)c3C)c2C)ncc1CN[C@H](CO)C(N)=O] | N,N'-(2,2'-dimethyl-[1,1'-biphenyl]-3,3'-diyl)bis(5-((((R)-1-amino-3-hydroxy-1-oxopropan-2-yl)amino)methyl)-4-methoxypicolinamide) | 715 |

-continued

| Example No. | Structure | Name | MS: m/z [M + 1]+ |
|---|---|---|---|
| 87 | 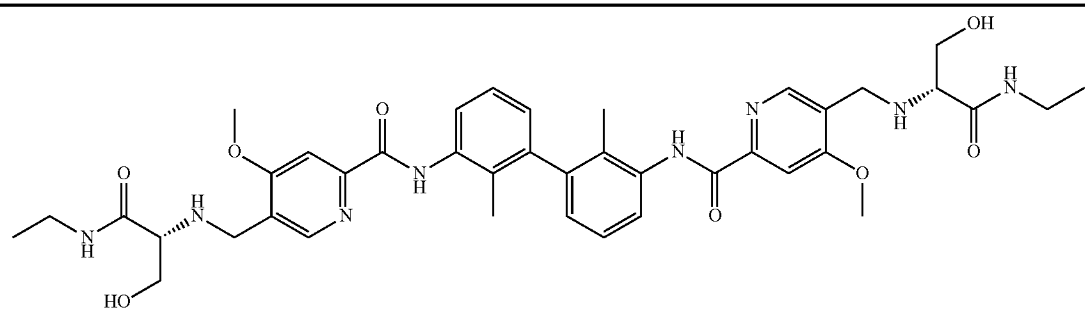 | N,N'-(2,2'-dimethyl-[1,1'-biphenyl]-3,3'-diyl)bis(5-((((R)-1-(ethylamino)-3-hydroxy-1-oxopropan-2-yl)amino)methyl)-4-methoxypicolinamide) | 771 |
| 88 | 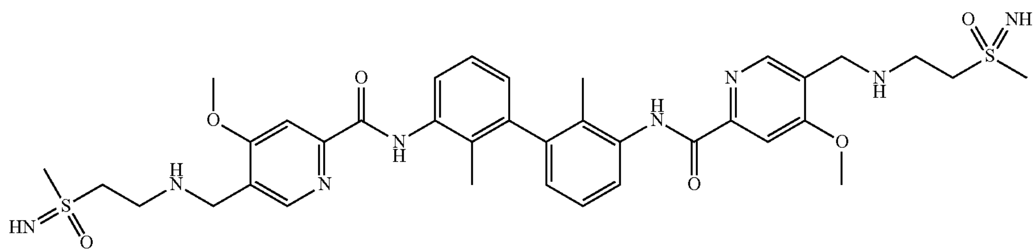 [SMILES: COc1cc(C(=O)Nc2cccc(-c3cccc(NC(=O)c4cc(OC)c(CNCCS(C)(=N)=O)cn4)c3C)c2C)ncc1CNCCS(C)(=N)=O] | N,N'-(2,2'-dimethyl-[1,1'-biphenyl]-3,3'-diyl)bis(4-methoxy-5-((2-(S-methylsulfonimidoyl)ethyl)amino)methyl)picolinamide) | 751 |
| 89 | 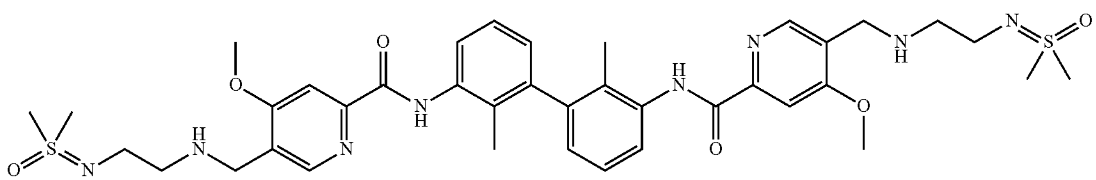 [SMILES: COc1cc(C(=O)Nc2cccc(-c3cccc(NC(=O)c4cc(OC)c(CNCCN=S(C)(C)=O)cn4)c3C)c2C)ncc1CNCCN=S(C)(C)=O] | N,N'-(2,2'-dimethyl-[1,1'-biphenyl]-3,3'-diyl)bis(5-(((2-((dimethyl(oxo)λ⁶-sulfaneylidene)amino)ethyl)amino)methyl)-4-methoxypicolinamide) | 779 |
| 90 | 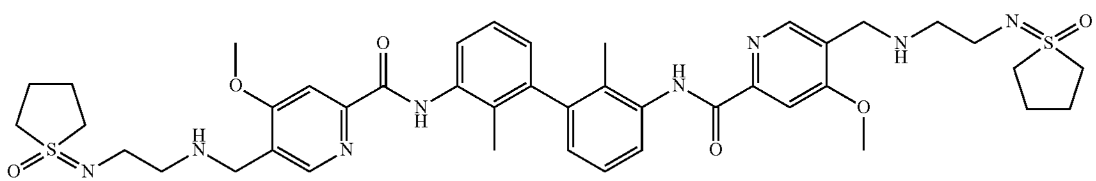 [SMILES: COc1cc(C(=O)Nc2cccc(-c3cccc(NC(=O)c4cc(OC)c(CNCCN=S5(=O)CCCC5)cn4)c3C)c2C)ncc1CNCCN=S1(=O)CCCC1] | N,N'-(2,2'-dimethyl-[1,1'-biphenyl]-3,3'-diyl)bis(4-methoxy-5-(((2-((1-oxidotetrahydro-1λ⁶-thiophen-1-ylidene)amino)ethyl)amino)methyl)picolinamide) | 831 |

| Example No. | Structure | Name | MS: m/z [M + 1]+ |
|---|---|---|---|
| 91 | 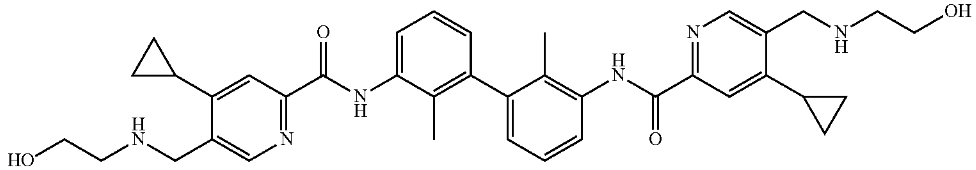 [SMILES: Cc1c(NC(=O)c2cc(C3CC3)c(CNCCO)cn2)cccc1-c1cccc(NC(=O)c2cc(C3CC3)c(CNCCO)cn2)c1C] | N,N'-(2,2'-dimethyl-[1,1'-biphenyl]-3,3'-diyl)bis(4-cyclopropyl-5-(((2-hydroxyethyl)amino)methyl)picolinamide) | 649 |
| 92 | 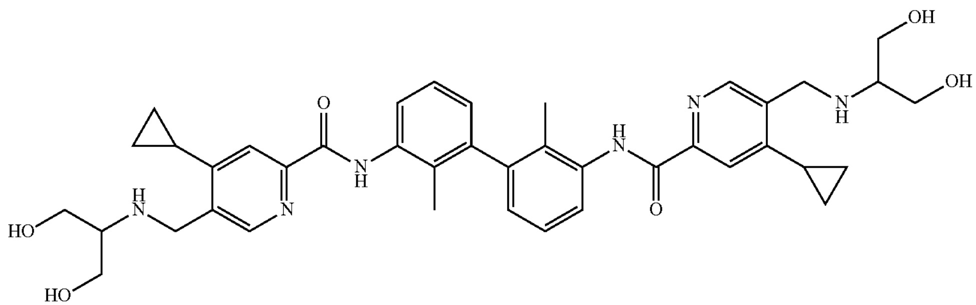 [SMILES: Cc1c(NC(=O)c2cc(C3CC3)c(CNC(CO)CO)cn2)cccc1-c1cccc(NC(=O)c2cc(C3CC3)c(CNC(CO)CO)cn2)c1C] | N,N'-(2,2'-dimethyl-[1,1'-biphenyl]-3,3'-diyl)bis(4-cyclopropyl-5-(((1,3-dihydroxypropan-2-yl)amino)methyl)picolinamide) | 709 |
| 93 | 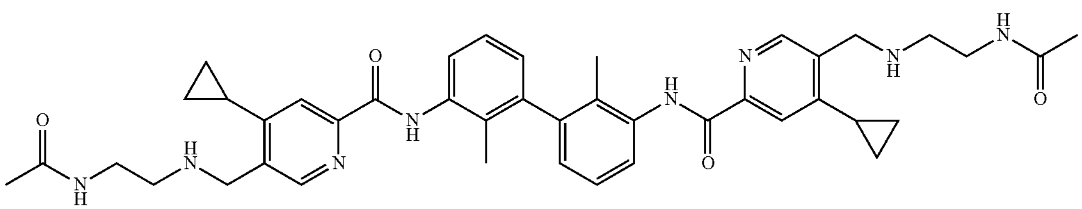 [SMILES: CC(=O)NCCNCc1cnc(C(=O)Nc2cccc(-c3cccc(NC(=O)c4cc(C5CC5)c(CNCCNC(C)=O)cn4)c3C)c2C)cc1C1CC1] | N,N'-(2,2'-dimethyl-[1,1'-biphenyl]-3,3'-diyl)bis(5-(((2-acetamidoethyl)amino)methyl)-4-cyclopropylpicolinamide) | 731 |
| 94 | 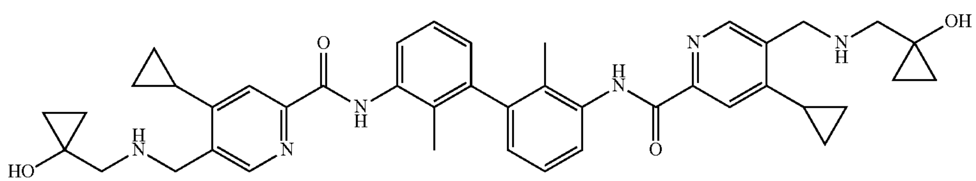 [SMILES: Cc1c(NC(=O)c2cc(C3CC3)c(CNCC3(O)CC3)cn2)cccc1-c1cccc(NC(=O)c2cc(C3CC3)c(CNCC3(O)CC3)cn2)c1C] | N,N'-(2,2'-dimethyl-[1,1'-biphenyl]-3,3'-diyl)bis(4-cyclopropyl-5-(((1-hydroxycyclopropyl)methyl)amino)methyl)picolinamide) | 701 |

| Example No. | Structure | Name | MS: m/z [M + 1]+ |
|---|---|---|---|
| 95 | 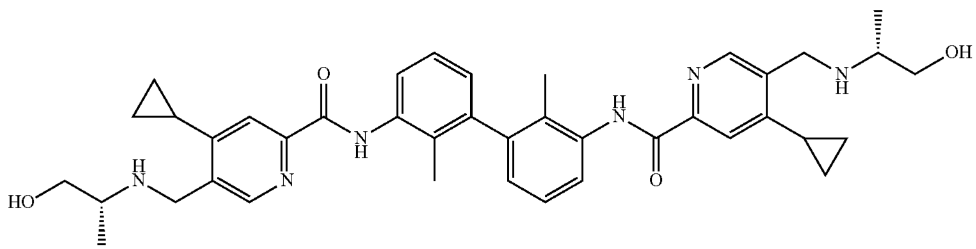 [SMILES: Cc1c(NC(=O)c2cc(C3CC3)c(CN[C@H](C)CO)cn2)cccc1-c1cccc(NC(=O)c2cc(C3CC3)c(CN[C@H](C)CO)cn2)c1C] | N,N'-(2,2'-dimethyl-[1,1'-biphenyl]-3,3'-diyl)bis(4-cyclopropyl-5-((((R)-1-hydroxypropan-2-yl)amino)methyl)picolinamide) | 677 |
| 96 | 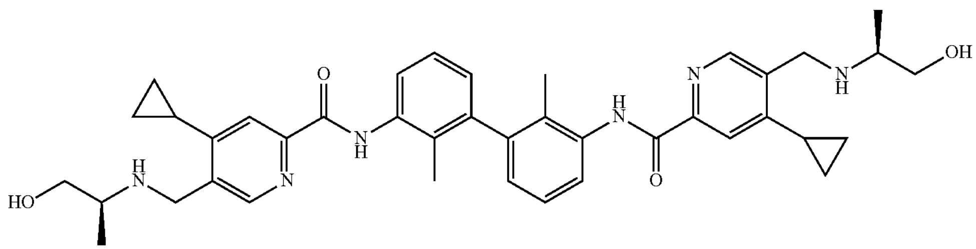 [SMILES: Cc1c(NC(=O)c2cc(C3CC3)c(CN[C@@H](C)CO)cn2)cccc1-c1cccc(NC(=O)c2cc(C3CC3)c(CN[C@@H](C)CO)cn2)c1C] | N,N'-(2,2'-dimethyl-[1,1'-biphenyl]-3,3'-diyl)bis(4-cyclopropyl-5-((((S)-1-hydroxypropan-2-yl)amino)methyl)picolinamide) | 677 |
| 97 | 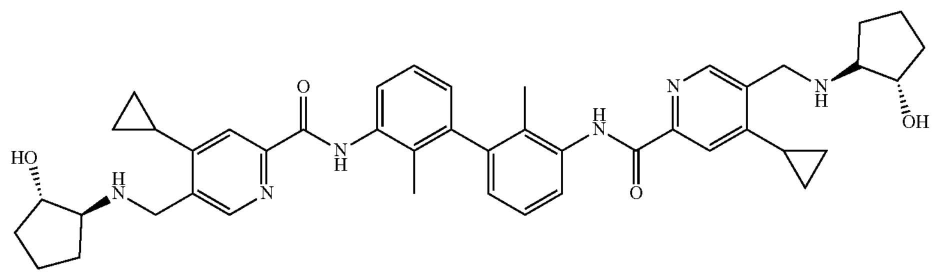 | N,N'-(2,2'-dimethyl-[1,1'-biphenyl]-3,3'-diyl)bis(5-((((1S,2S)-2-hydroxycyclopentyl)amino)methyl)picolinamide) | 729 |
| 98 | 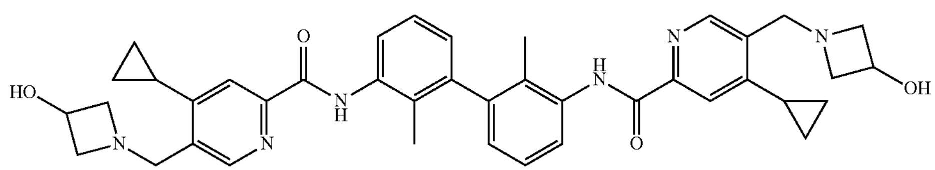 [SMILES: Cc1c(NC(=O)c2cc(C3CC3)c(CN3CC(O)C3)cn2)cccc1-c1cccc(NC(=O)c2cc(C3CC3)c(CN3CC(O)C3)cn2)c1C] | N,N'-(2,2'-dimethyl-[1,1'-biphenyl]-3,3'-diyl)bis(4-cyclopropyl-5-(((3-hydroxyazetidin-1-yl)methyl)picolinamide) | 673 |

-continued

| Example No. | Structure | Name | MS: m/z [M + 1]+ |
|---|---|---|---|
| 99 | 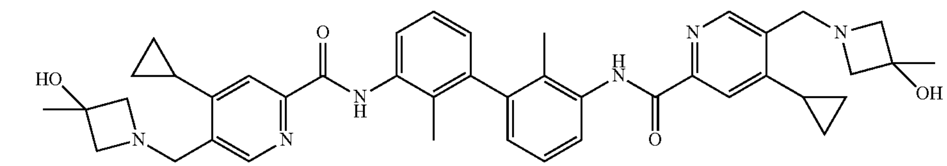 | N,N'-(2,2'-dimethyl-[1,1'-biphenyl]-3,3'-diyl)bis(4-cyclopropyl-5-(((3-hydroxy-3-methylazetidin-1-yl)methyl)picolinamide) | 701 |
| 100 | 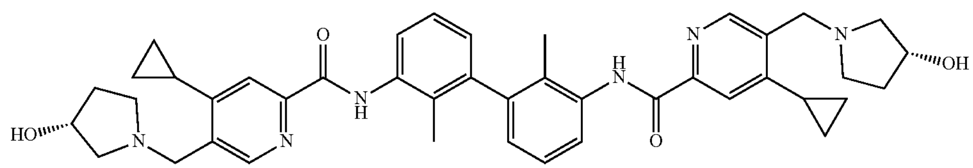 [SMILES: Cc1c(NC(=O)c2cc(C3CC3)c(CN3CC[C@@H](O)C3)cn2)cccc1-c1cccc(NC(=O)c2cc(C3CC3)c(CN3CC[C@@H](O)C3)cn2)c1C] | N,N'-(2,2'-dimethyl-[1,1'-biphenyl]-3,3'-diyl)bis(4-cyclopropyl-5-(((R)-3-hydroxypyrrolidin-1-yl)picolinamide) | 701 |
| 101 | 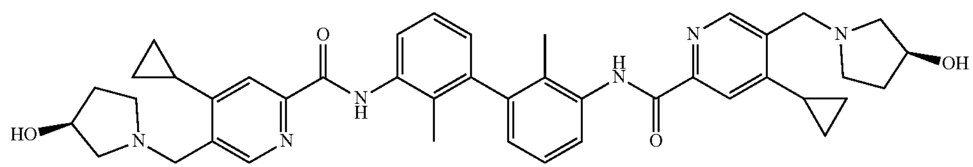 [SMILES: Cc1c(NC(=O)c2cc(C3CC3)c(CN3CC[C@H](O)C3)cn2)cccc1-c1cccc(NC(=O)c2cc(C3CC3)c(CN3CC[C@H](O)C3)cn2)c1C] | N,N'-(2,2'-dimethyl-[1,1'-biphenyl]-3,3'-diyl)bis(4-cyclopropyl-5-(((S)-3-hydroxypyrrolidin-1-yl)methyl)picolinamide) | 701 |
| 102 | 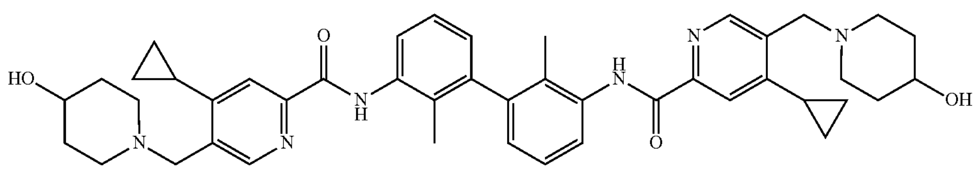 [SMILES: Cc1c(NC(=O)c2cc(C3CC3)c(CN3CCC(O)CC3)cn2)cccc1-c1cccc(NC(=O)c2cc(C3CC3)c(CN3CCC(O)CC3)cn2)c1C] | N,N'-(2,2'-dimethyl-[1,1'-biphenyl]-3,3'-diyl)bis(4-cyclopropyl-5-((4-hydroxypiperidin-1-yl)methyl)picolinamide) | 729 |
| 103 | 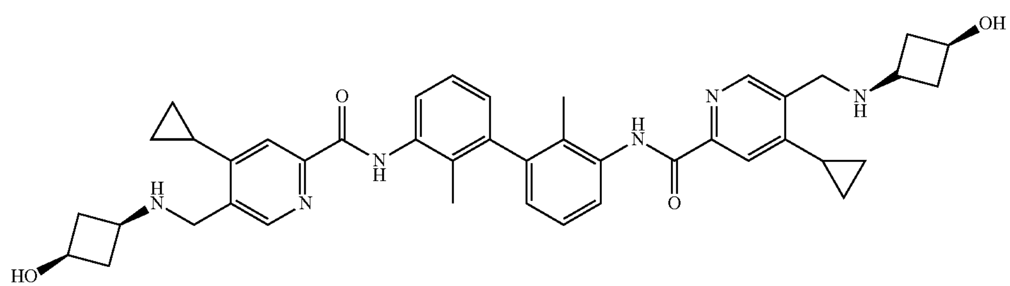 | N,N'-(2,2'-dimethyl-[1,1'-biphenyl]-3,3'-diyl)bis(4-cyclopropyl-5-((((1s,3s)-3-hydroxycyclobutyl)amino)methyl)picolinamide) | 701 |

-continued

| Example No. | Structure | Name | MS: m/z [M + 1]+ |
|---|---|---|---|
| 104 | 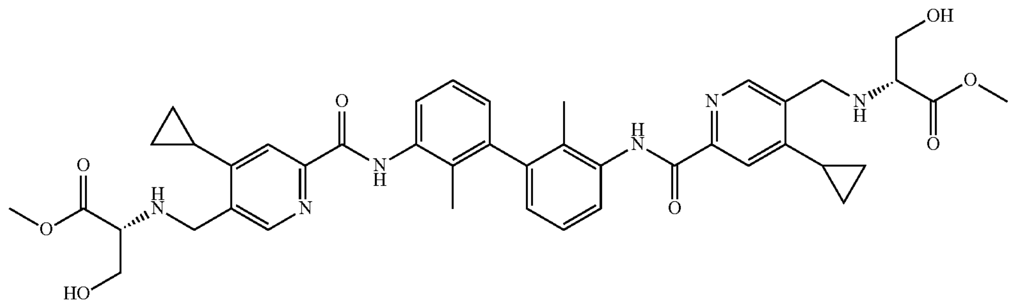 | dimethyl 2,2'-((((((2,2'-dimethyl-[1,1'-biphenyl]-3,3'-diyl)bis(azanediyl))bis(carbonyl)bis(4-cyclopropylpyridine-6,3-diyl))bis(methylene))bis(azanediyl))(2R,2'R)-bis(3-hydroxypropanoate) | 765 |
| 105 | 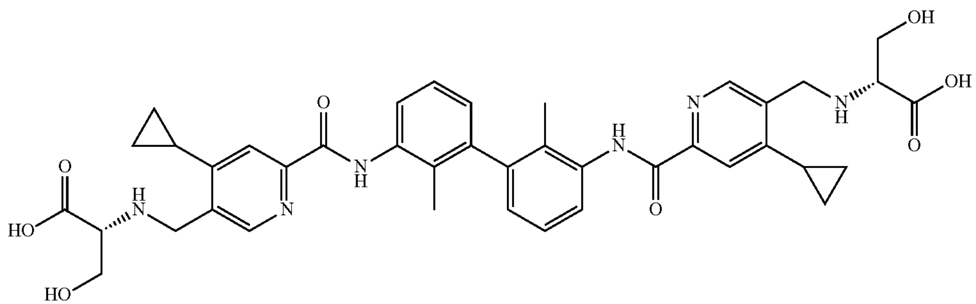 [SMILES: Cc1c(NC(=O)c2cc(C3CC3)c(CN[C@H](CO)C(=O)O)cn2)cccc1-c1cccc(NC(=O)c2cc(C3CC3)c(CN[C@H](CO)C(=O)O)cn2)c1C] | (2R,2'R)-2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))bis(3-hydroxypropanoic acid) | 737 |
| 106 | 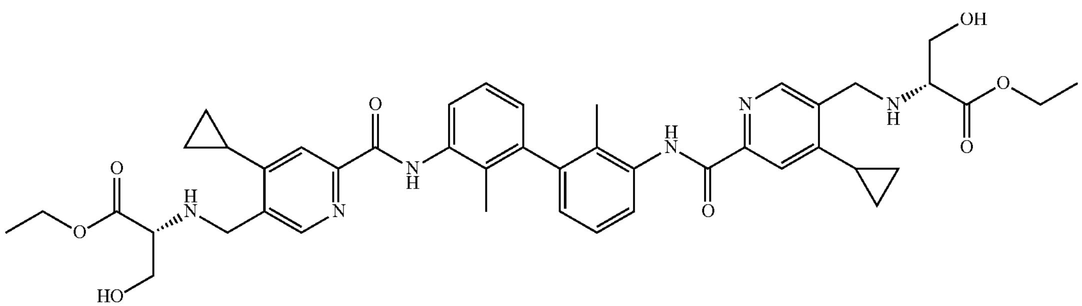 [SMILES: CCOC(=O)[C@@H](CO)NCc1cnc(C(=O)Nc2cccc(-c3cccc(NC(=O)c4cc(C5CC5)c(CN[C@H](CO)C(=O)OCC)cn4)c3C)c2C)cc1C1CC1] | diethyl 2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))(2R,2'R)-bis(3-hydroxypropanoate) | 793 |

| Example No. | Structure | Name | MS: m/z [M + 1]+ |
|---|---|---|---|
| 107 | 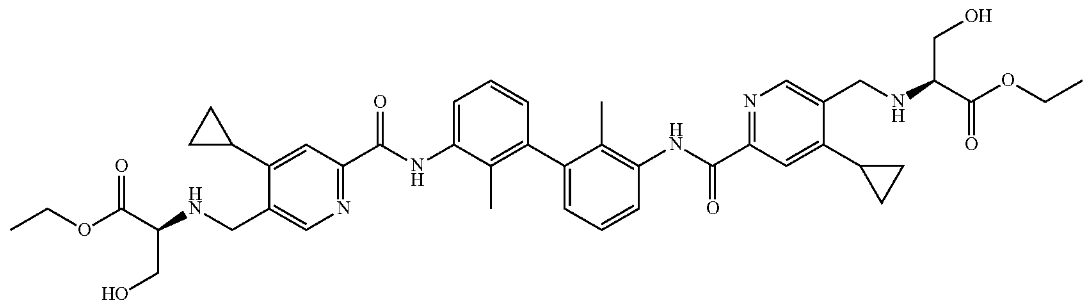 [SMILES: CCOC(=O)[C@H](CO)NCc1cnc(C(=O)Nc2cccc(-c3cccc(NC(=O)c4cc(C5CC5)c(CN[C@@H](CO)C(=O)OCC)cn4)c3C)c2C)cc1C1CC1] | diethyl 2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))(2S,2'S)-bis(3-hydroxypropanoate) | 793 |
| 108 | 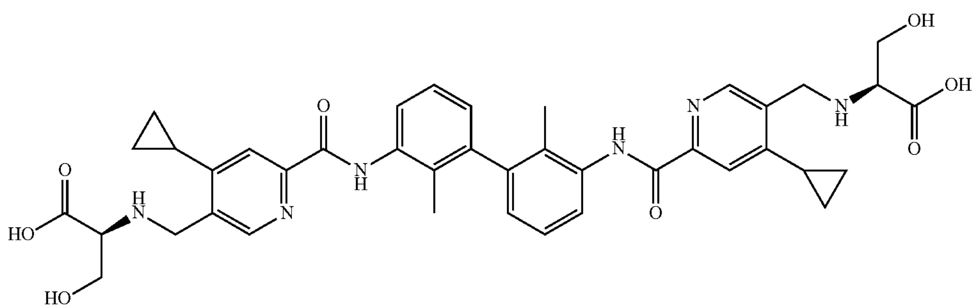 [SMILES: Cc1c(NC(=O)c2cc(C3CC3)c(CN[C@@H](CO)C(=O)O)cn2)cccc1-c1cccc(NC(=O)c2cc(C3CC3)c(CN[C@@H](CO)C(=O)O)cn2)c1C] | (2S,2'S)-2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))bis(3-hydroxypropanoic acid) | 737 |
| 109 | 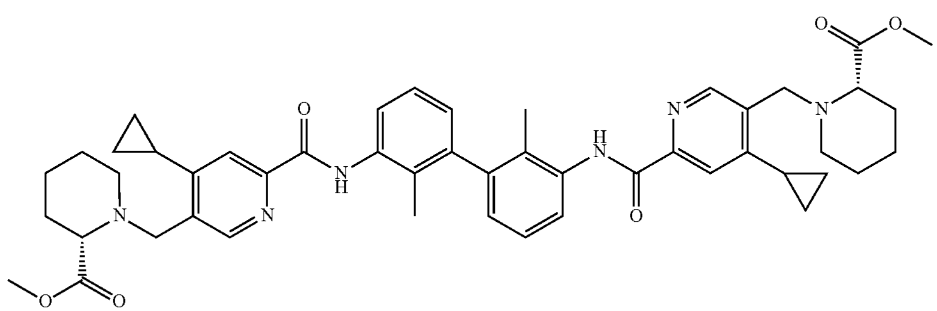 | dimethyl 1,1'-((((((2,2'-dimethyl-[1,1'-biphenyl]-3,3'-diyl)bis(azanediyl))bis(carbonyl))bis(4-cyclopropylpyridine-6,3-diyl))bis(methylene))(2S,2'S)-bis(piperidine-2-carboxylate) | 813 |

| Example No. | Structure | Name | MS: m/z [M + 1]+ |
|---|---|---|---|
| 110 | 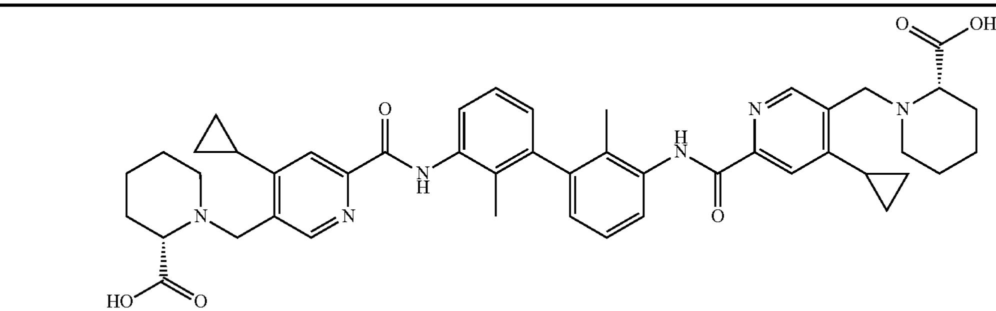 | (2S,2'S)-1,1'-(((((2,2'-dimethyl-[1,1'-biphenyl]-3,3'-diyl)bis(azanediyl))bis(carbonyl))bis(4-cyclopropylpyridine-6,3-diyl))bis(methylene))bis(piperidine-2-carboxylic acid) | 785 |
| 111 | 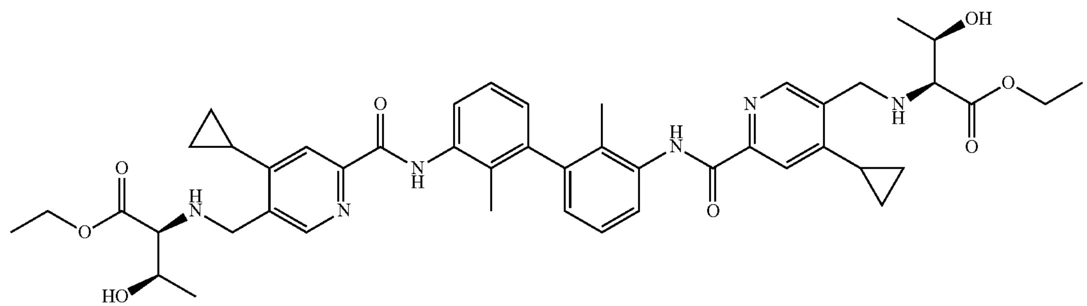 [SMILES: CCOC(=O)[C@@H](NCc1cnc(C(=O)Nc2cccc(-c3cccc(NC(=O)c4cc(C5CC5)c(CN[C@H](C(=O)OCC)[C@@H](C)O)cn4)c3C)c2C)cc1C1CC1)[C@@H](C)O] | diethyl 2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))(2S,2'S,3R,3'R)-bis(3-hydroxybutanoate) | 821 |
| 112 | 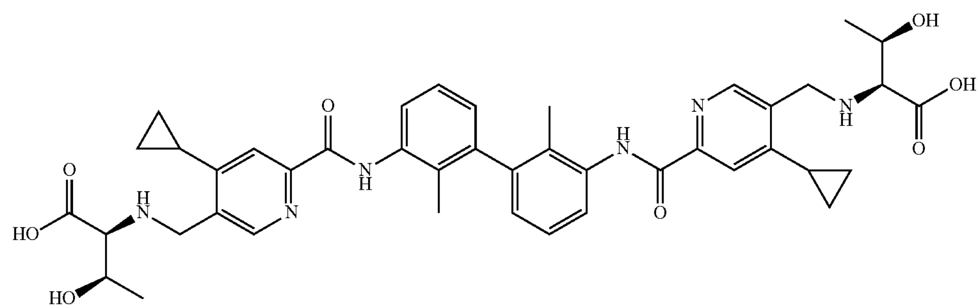 [SMILES: Cc1c(NC(=O)c2cc(C3CC3)c(CN[C@H](C(=O)O)[C@@H](C)O)cn2)cccc1-c1cccc(NC(=O)c2cc(C3CC3)c(CN[C@H](C(=O)O)[C@@H](C)O)cn2)c1C] | (2S,2'S,3R,3'R)-2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))bis(3-hydroxybutanoic acid) | 765 |

| Example No. | Structure | Name | MS: m/z [M + 1]+ |
|---|---|---|---|
| 113 | 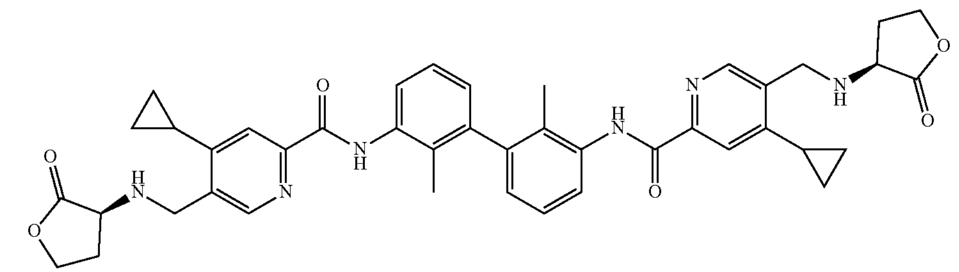 [SMILES: Cc1c(NC(=O)c2cc(C3CC3)c(CN[C@H]3CCOC3=O)cn2)cccc1-c1cccc(NC(=O)c2cc(C3CC3)c(CN[C@H]3CCOC3=O)cn2)c1C] | N,N'-(2,2'-dimethyl-[1,1'-biphenyl]-3,3'-diyl)bis(4-cyclopropyl)-5((((S-2-oxotetrahydrofuran-3-yl)amino)methyl)picolinamide) | 729 |
| 114 | 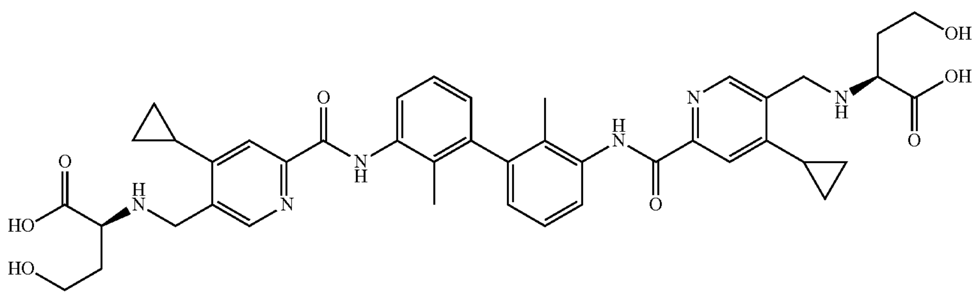 [SMILES: Cc1c(NC(=O)c2cc(C3CC3)c(CN[C@@H](CCO)C(=O)O)cn2)cccc1-c1cccc(NC(=O)c2cc(C3CC3)c(CN[C@@H](CCO)C(=O)O)cn2)c1C] | (2S,2'S)-2,2'-(((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))bis(4-hydroxybutanoic acid) | 765 |
| 115 | 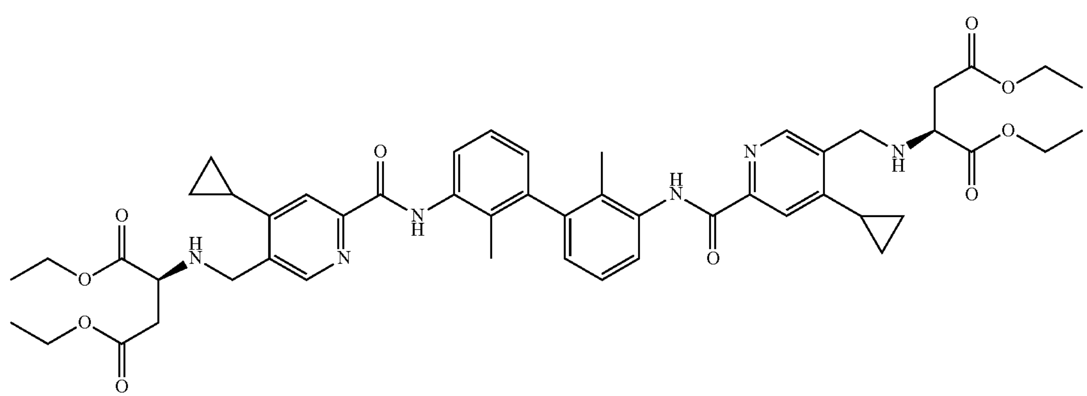 [SMILES: CCOC(=O)C[C@H](NCc1cnc(C(=O)Nc2cccc(-c3cccc(NC(=O)c4cc(C5CC5)c(CN[C@@H](CC(=O)OCC)C(=O)OCC)cn4)c3C)c2C)cc1C1CC1)C(=O)OCC] | tetraethyl 2,2'-(((((2,2'-dimethyl-[1,1'-biphenyl]-3,3'-diyl)bis(azanediyl))bis(carbonyl)bis(4-cyclopropylpyridine-6,3-diyl))bis(methylene))bis(azanediyl))(2S,2'S)-disuccinate | 905 |

| Example No. | Structure | Name | MS: m/z [M + 1]+ |
|---|---|---|---|
| 116 | 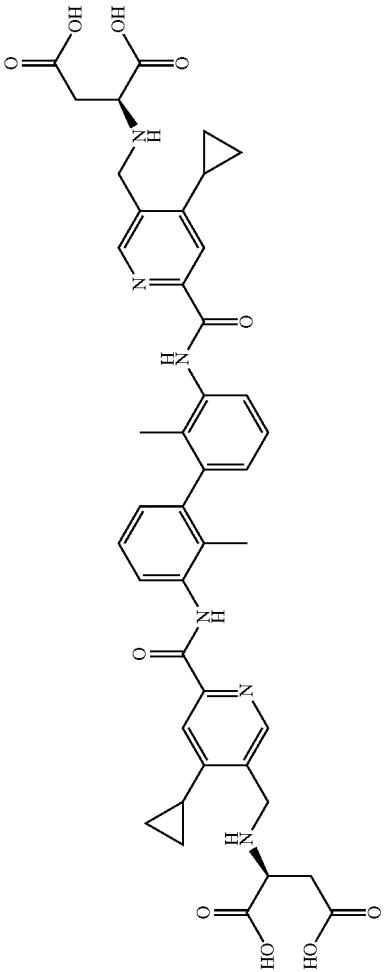 | (2S,2'S)-2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))disuccinic acid | 793 |
| 117 | 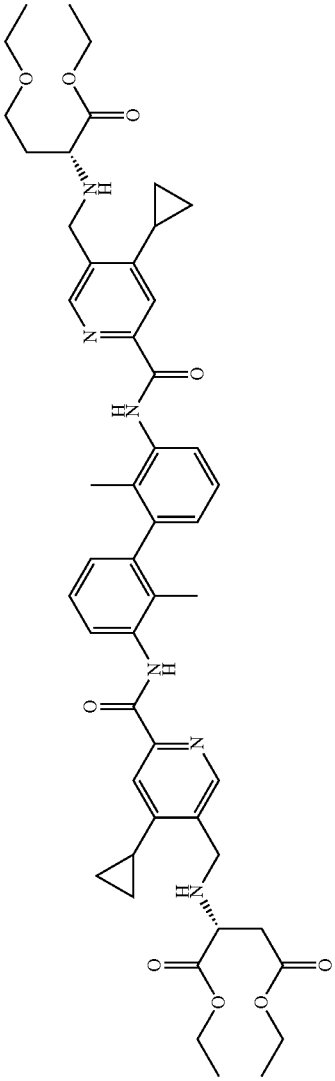 | tetraethyl 2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))(2R,2'R)-disuccinate | 905 |

| Example No. | Structure | Name | MS: m/z [M + 1]+ |
|---|---|---|---|
| 118 | 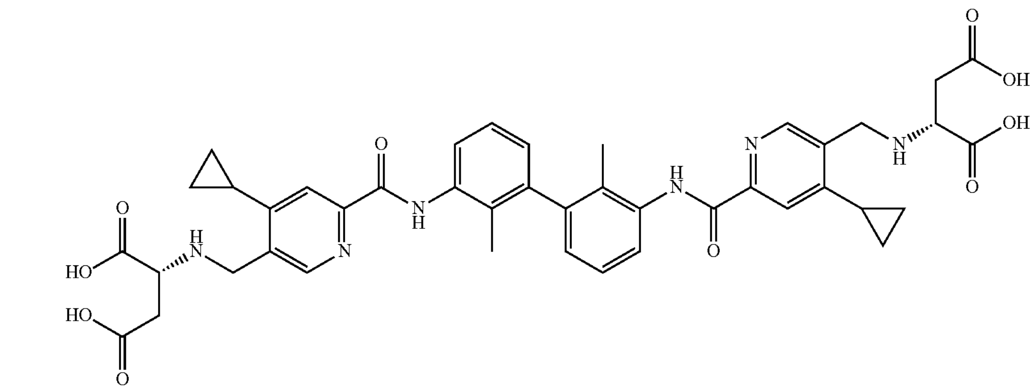 [SMILES: Cc1c(NC(=O)c2cc(C3CC3)c(CN[C@H](CC(=O)O)C(=O)O)cn2)cccc1-c1cccc(NC(=O)c2cc(C3CC3)c(CN[C@H](CC(=O)O)C(=O)O)cn2)c1C] | (2R,2'R)-2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))disuccinic acid | 793 |
| 119 | 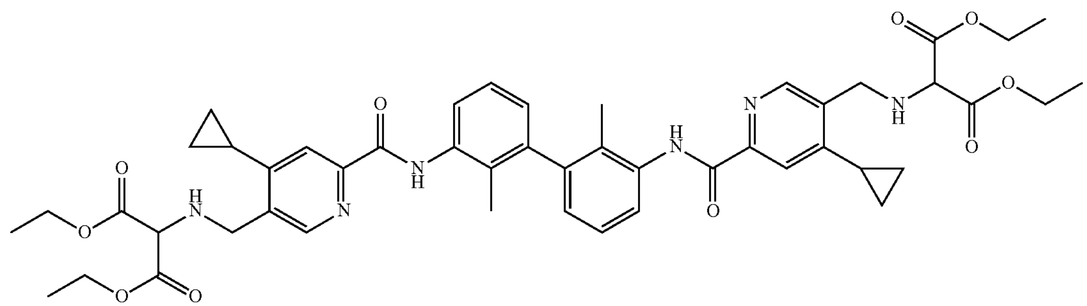 [SMILES: CCOC(=O)C(NCc1cnc(C(=O)Nc2cccc(-c3cccc(NC(=O)c4cc(C5CC5)c(CNC(C(=O)OCC)C(=O)OCC)cn4)c3C)c2C)cc1C1CC1)C(=O)OCC] | tetraethyl 2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))dimalonate | 877 |
| 120 | 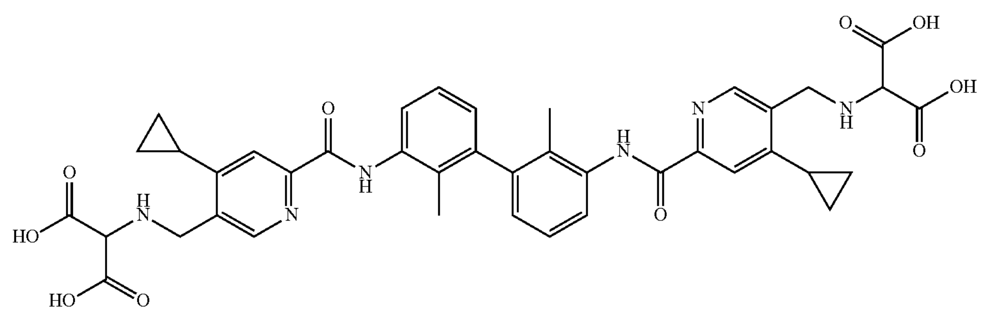 [SMILES: Cc1c(NC(=O)c2cc(C3CC3)c(CNC(C(=O)O)C(=O)O)cn2)cccc1-c1cccc(NC(=O)c2cc(C3CC3)c(CNC(C(=O)O)C(=O)O)cn2)c1C] | 2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))dimalonic acid | 765 |

-continued

| Example No. | Structure | Name | MS: m/z [M + 1]+ |
|---|---|---|---|
| 121 | 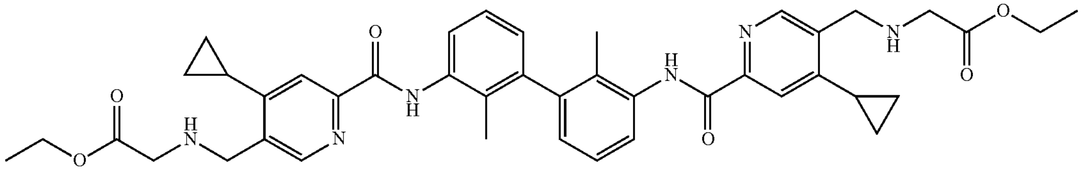 | diethyl 2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))diacetate | 733 |
| 122 | 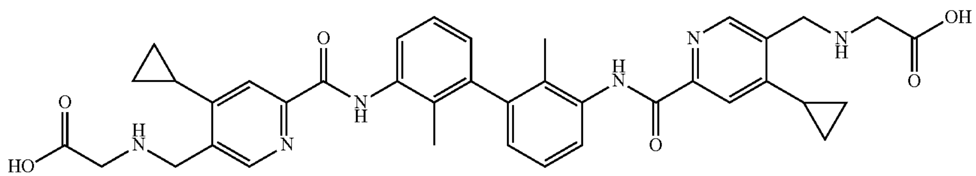 [SMILES: Cc1c(NC(=O)c2cc(C3CC3)c(CNCC(=O)O)cn2)cccc1-c1cccc(NC(=O)c2cc(C3CC3)c(CNCC(=O)O)cn2)c1C] | 2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))diacetic acid | 677 |
| 123 | 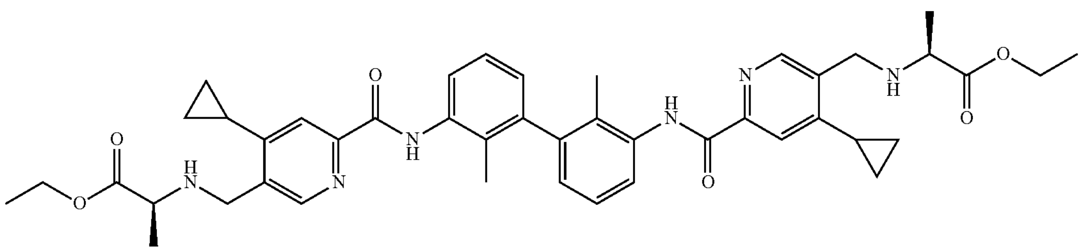 [SMILES: CCOC(=O)[C@H](C)NCc1cnc(C(=O)Nc2cccc(-c3cccc(NC(=O)c4cc(C5CC5)c(CN[C@@H](C)C(=O)OCC)cn4)c3C)c2C)cc1C1CC1] | diethyl 2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))(2S,2S)-dipropionate | 761 |
| 124 | 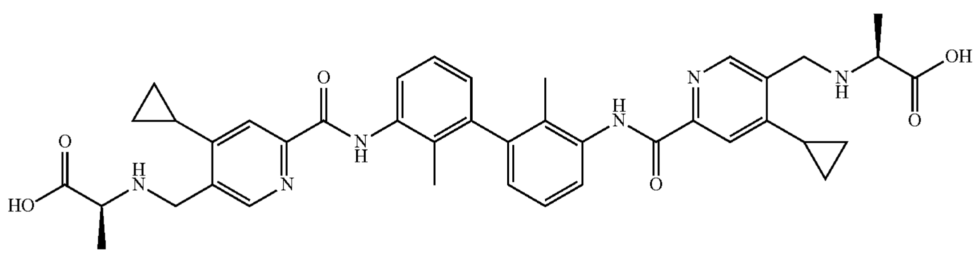 [SMILES: Cc1c(NC(=O)c2cc(C3CC3)c(CN[C@@H](C)C(=O)O)cn2)cccc1-c1cccc(NC(=O)c2cc(C3CC3)c(CN[C@@H](C)C(=O)O)cn2)c1C] | (2S,2S)-2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))dipropionic acid | 705 |

| Example No. | Structure | Name | MS: m/z [M + 1]+ |
|---|---|---|---|
| 125 | 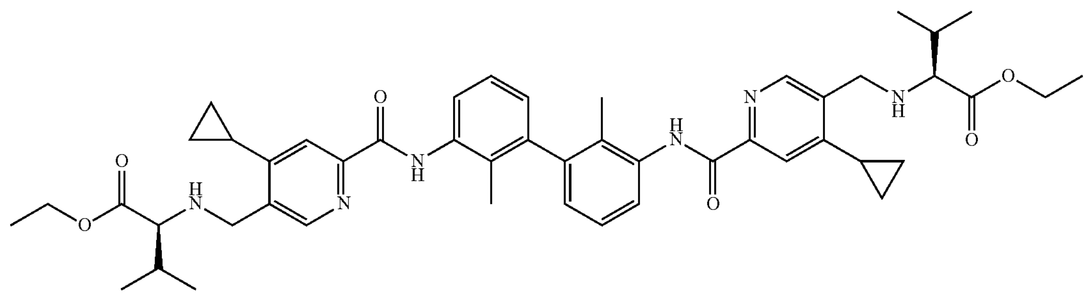 [SMILES: CCOC(=O)[C@@H](NCc1cnc(C(=O)Nc2cccc(-c3cccc(NC(=O)c4cc(C5CC5)c(CN[C@H](C(=O)OCC)C(C)C)cn4)c3C)c2C)cc1C1CC1)C(C)C] | diethyl 2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))(2S,2'S)-bis(3-methylbutanoate) | 817 |
| 126 | 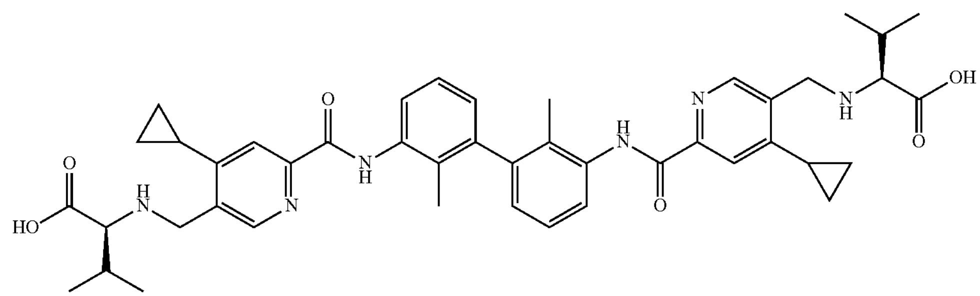 [SMILES: Cc1c(NC(=O)c2cc(C3CC3)c(CN[C@H](C(=O)O)C(C)C)cn2)cccc1-c1cccc(NC(=O)c2cc(C3CC3)c(CN[C@H](C(=O)O)C(C)C)cn2)c1C] | (2S,2'S)-2,2'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))bis(3-methylbutanoic acid) | 761 |
| 127 | 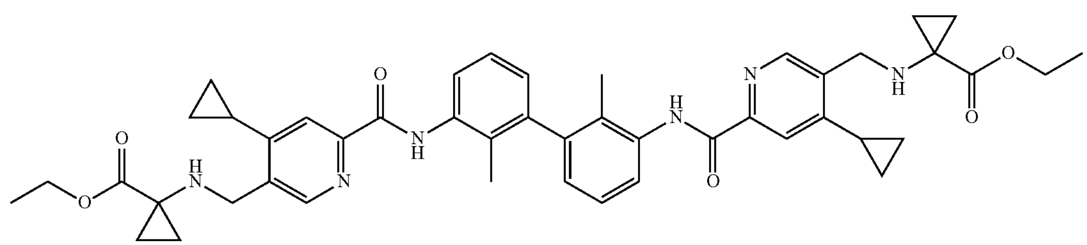 [SMILES: CCOC(=O)C1(NCc2cnc(C(=O)Nc3cccc(-c4cccc(NC(=O)c5cc(C6CC6)c(CNC6(C(=O)OCC)CC6)cn5)c4C)c3C)cc2C2CC2)CC1] | diethyl 1,1'-((((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))bis(cyclopropane-1-carboxylate) | 785 |

| Example No. | Structure | Name | MS: m/z [M + 1]+ |
|---|---|---|---|
| 128 | 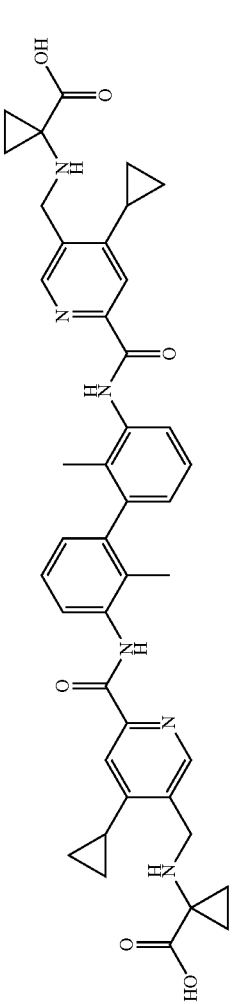 | 1,1'-(((((2,2'-dimethyl-[1,1'-biphenyl]-3,3'-diyl)bis(azanediyl))bis(carbonyl))bis(4-cyclopropyl)pyridine-6,3-diyl)bis(methylene))bis(azanediyl))bis(cyclopropane-1-carboxylic acid) | 729 |
| 129 | 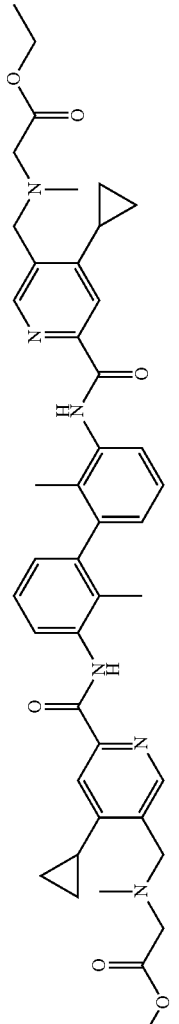 | diethyl 2,2'-(((((2,2'-dimethyl-[1,1'-biphenyl]-3,3'-diyl)bis(azanediyl))bis(carbonyl))bis(4-cyclopropyl)pyridine-6,3-diyl)bis(methylene))bis(methylazanediyl))diacetate | 761 |
| 130 | 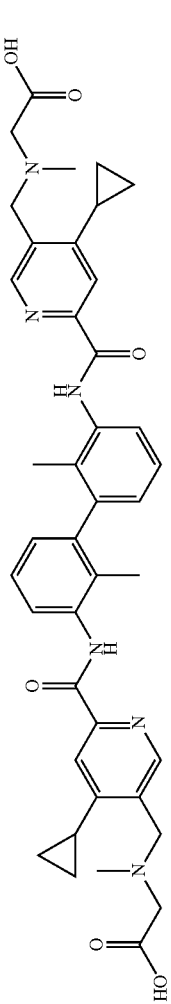 | 2,2'-(((((2,2'-dimethyl-[1,1'-biphenyl]-3,3'-diyl)bis(azanediyl))bis(carbonyl))bis(4-cyclopropylpyridine-6,3-diyl)bis(methylene))bis(methylazanediyl))diacetic acid | 705 |
| 131 | 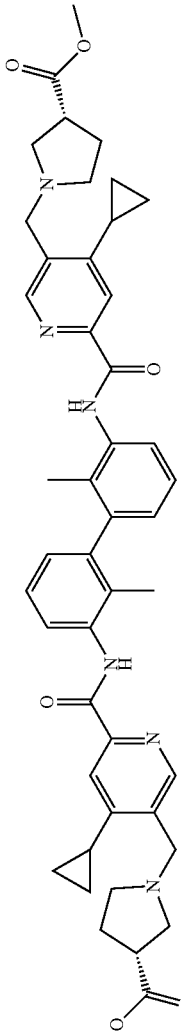 | dimethyl 1,1'-(((((2,2'-dimethyl-[1,1'-biphenyl]-3,3'-diyl)bis(azanediyl))bis(carbonyl))bis(4-cyclopropyl)pyridine-6,3-diyl)bis(methylene))(3R,3'R)-bis(pyrrolidine-3-carboxylate) | 785 |
| 132 | 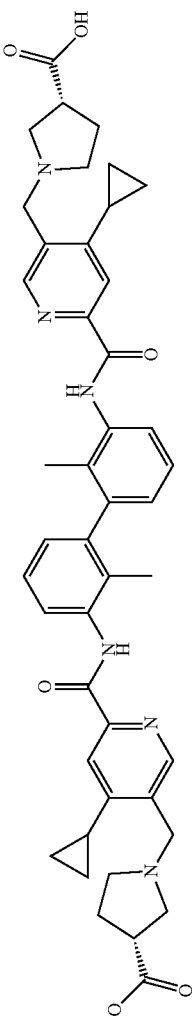 | (3R,3'R)-1,1'-(((((2,2'-dimethyl-[1,1'-biphenyl]-3,3'-diyl)bis(azanediyl))bis(carbonyl))bis(4-cyclopropyl)pyridine-6,3-diyl)bis(methylene))bis(pyrrolidine-3-carboxylic acid) | 757 |

| Example No. | Structure | Name | MS: m/z [M + 1]+ |
|---|---|---|---|
| 133 | 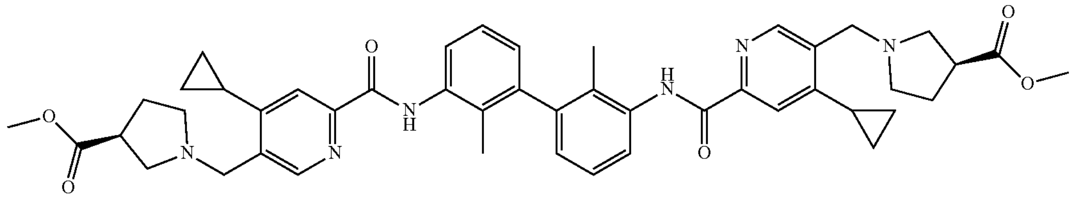 | dimethyl 1,1'-(((((2,2'-dimethyl-[1,1'-biphenyl]-3,3'-diyl)bis(azanediyl))bis(carbonyl))bis(4-cyclopropylpyridine-6,3-diyl))bis(methylene))(3S,3'S)-bis(pyrrolidine-3-carboxylate) | 785 |
| 134 | 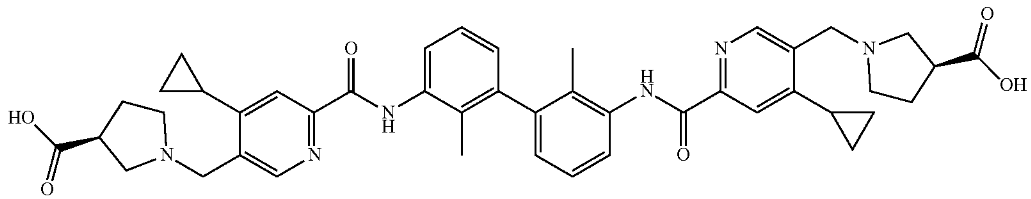 [SMILES: Cc1c(NC(=O)c2cc(C3CC3)c(CN3CC[C@H](C(=O)O)C3)cn2)cccc1-c1cccc(NC(=O)c2cc(C3CC3)c(CN3CC[C@H](C(=O)O)C3)cn2)c1C] | (3S,3'S)-1,1'-(((((2,2'-dimethyl-[1,1'-biphenyl]-3,3'-diyl)bis(azanediyl))bis(carbonyl))bis(4-cyclopropylpyridine-6,3-diyl))bis(methylene))bis(pyrrolidine-3-carboxylic acid) | 757 |
| 135 | 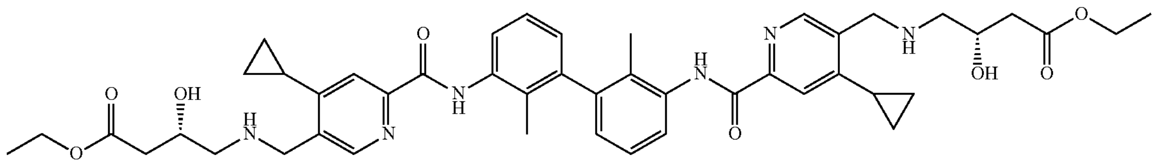 [SMILES: CCOC(=O)C[C@H](O)CNCc1cnc(C(=O)Nc2cccc(-c3cccc(NC(=O)c4cc(C5CC5)c(CNC[C@@H](O)CC(=O)OCC)cn4)c3C)c2C)cc1C1CC1] | diethyl 4,4'-(((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))(3S,3'S)-bis(3-hydroxybutanoate) | 821 |
| 136 | 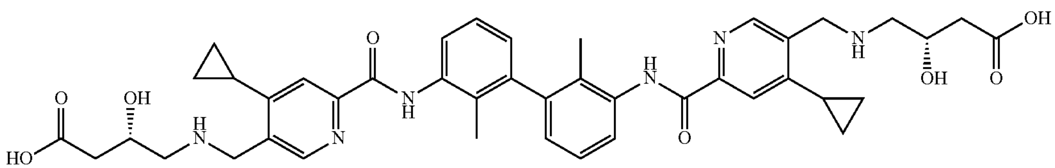 [SMILES: Cc1c(NC(=O)c2cc(C3CC3)c(CNC[C@@H](O)CC(=O)O)cn2)cccc1-c1cccc(NC(=O)c2cc(C3CC3)c(CNC[C@@H](O)CC(=O)O)cn2)c1C] | (3S,3'S)-4,4'-(((((2,2'-dimethyl-[1,1'-biphenyl]-3,3'-diyl)bis(azanediyl))bis(carbonyl))bis(4-cyclopropylpyridine-6,3-diyl))bis(methylene))bis(azanediyl))bis(3-hydroxybutanoic acid) | 765 |
| 137 | 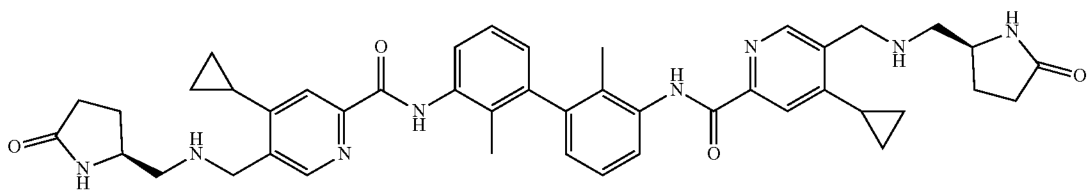 [SMILES: Cc1c(NC(=O)c2cc(C3CC3)c(CNC[C@@H]3CCC(=O)N3)cn2)cccc1-c1cccc(NC(=O)c2cc(C3CC3)c(CNC[C@@H]3CCC(=O)N3)cn2)c1C] | N,N'-(2,2'-dimethyl-[1,1'-biphenyl]-3,3'-diyl)bis(4-cyclopropyl-5-(((((S)-5-oxopyrrolidin-2-yl)methyl)amino)methyl)picolinamide) | 755 |

-continued

| Example No. | Structure | Name | MS: m/z [M + 1]+ |
|---|---|---|---|
| 138 | 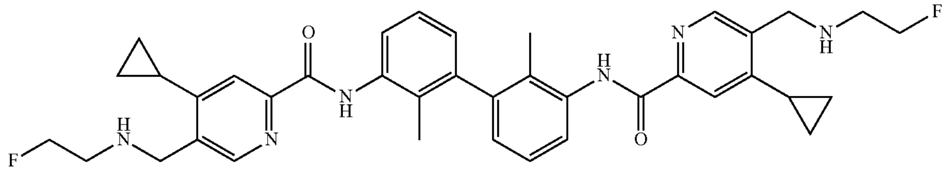 [SMILES: Cc1c(NC(=O)c2cc(C3CC3)c(CNCCF)cn2)cccc1-c1cccc(NC(=O)c2cc(C3CC3)c(CNCCF)cn2)c1C] | N,N'-(2,2'-dimethyl-[1,1'-biphenyl]-3,3'-diyl)bis(4-cyclopropyl-5-(((2-fluoroethyl)amino)methyl)picolinamide) | 653 |
| 139 | 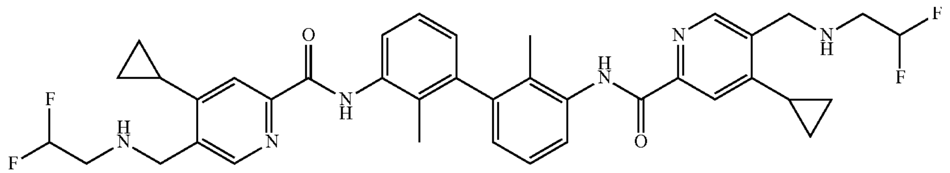 [SMILES: Cc1c(NC(=O)c2cc(C3CC3)c(CNCC(F)F)cn2)cccc1-c1cccc(NC(=O)c2cc(C3CC3)c(CNCC(F)F)cn2)c1C] | N,N'-(2,2'-dimethyl-[1,1'-biphenyl]-3,3'-diyl)bis(4-cyclopropyl-5-(((2,2-difluoroethyl)amino)methyl)picolinamide) | 689 |
| 140 | 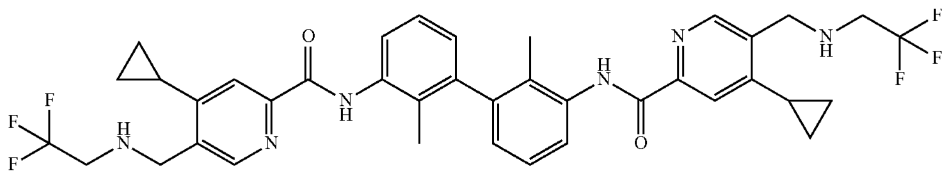 [SMILES: Cc1c(NC(=O)c2cc(C3CC3)c(CNCC(F)(F)F)cn2)cccc1-c1cccc(NC(=O)c2cc(C3CC3)c(CNCC(F)(F)F)cn2)c1C] | N,N'-(2,2'-dimethyl-[1,1'-biphenyl]-3,3'-diyl)bis(4-cyclopropyl-5-(((2,2,2-trifluoroethyl)amino)methyl)picolinamide) | 725 |
| 141 | 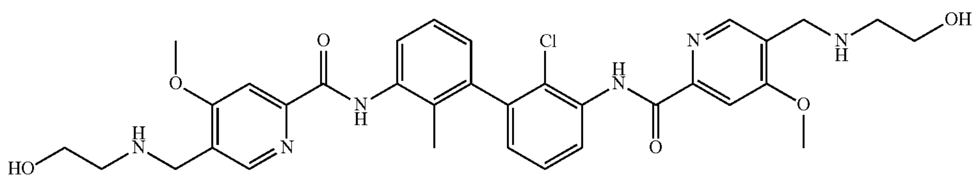 [SMILES: COc1cc(C(=O)Nc2cccc(-c3cccc(NC(=O)c4cc(OC)c(CNCCO)cn4)c3Cl)c2C)ncc1CNCCO] | N,N'-(2-chloro-2'-methyl-[1,1'-biphenyl]-3,3'-diyl)bis(5-(((2-hydroxyethyl)amino)methyl)-4-methoxypicolinamide) | 649 |

¹H NMR data of the compound prepared in the above example are as follows:

| Example No. | ¹H-NMR |
|---|---|
| 3 | ¹H NMR (400 MHz, DMSO-$d_6$) δ 10.39 (s, 2H), 8.54 (s, 2H), 7.90 (d, J = 7.9 Hz, 2H), 7.76 (s, 2H), 7.34 (t, J = 7.8 Hz, 2H), 7.00 (d, J = 7.4 Hz, 2H), 4.00 (s, 6H), 3.85 (s, 4H), 3.51 (t, J = 5.6 Hz, 4H), 2.65 (t, J = 5.6 Hz, 4H), 2.02 (s, 6H). |
| 4 | ¹H NMR (400 MHz, DMSO-$d_6$) δ 10.37 (s, 2H), 8.52 (s, 2H), 7.92 (d, J = 8.1 Hz, H), 7.74 (s, 2H), 7.33 (t, J = 7.8 Hz, 2H), 6.99 (d, J = 7.6 Hz, 2H), 4.87 (brs, 2H), 3.98 (s, 6H), 3.85 (d, J = 14.8 Hz, 2H), 3.72 (d, J = 14.9 Hz, 2H), 3.59 (s, 6H), 3.58 (d, J = 5.8 Hz, 4H), 3.30 (d, J = 5.8 Hz, 2H), 2.02 (s, 6H). |
| 5 | ¹H NMR (400 MHz, DMSO-$d_6$) δ 10.34 (s, 2H), 8.58 (s, 2H), 7.98 (s, 2H), 7.94-7.86 (m, 2H), 7.33 (t, J = 7.9 Hz, 2H), 6.99 (dd, J = 7.6, 1.3 Hz, 2H), 4.54 (t, J = 5.4 Hz, 2H), 3.83 (s, 4H), 3.49 (q, J = 5.6 Hz, 4H), 2.62 (t, J = 5.8 Hz, 4H), 2.45 (s, 6H), 2.02 (s, 6H). |
| 7 | ¹H NMR (400 MHz, DMSO-$d_6$) δ 10.33 (s, 2H), 8.57 (s, 2H), 7.98 (s, 2H), 7.92 (d, J = 7.9 Hz, 2H), 7.33 (t, J = 7.8 Hz, 2H), 6.99 (d, J = 7.5 Hz, 2H), 3.82 (s, 4H), 3.43 (t, J = 5.6 Hz, 4H), 3.25 (s, 6H), 2.71 (t, J = 5.6 Hz, 4H), 2.44 (s, 6H), 2.02 (s, 6H). |
| 8 | ¹H NMR (400 MHz, DMSO-$d_6$) δ 10.23 (s, 2H), 8.52 (s, 2H), 7.88 (s, 2H), 7.83 (d, J = 7.9 Hz, 2H), 7.23 (t, J = 7.8 Hz, 2H), 6.89 (dd, J = 7.6, 1.3 Hz, 2H), 3.80 (s, 4H), 3.54-3.42 (m, 4H), 3.35 (dd, J = 10.8, 5.6 Hz, 2H), 3.29 (dd, J = 10.8, 5.5 Hz, 2H), 2.93 (brs, 2H), 2.48 (p, J = 5.7 Hz, 2H), 2.36 (s, 6H), 1.92 (s, 6H). |
| 10 | ¹H NMR (400 MHz, DMSO-$d_6$) δ 10.33 (s, 2H), 8.61 (s, 2H), 7.98 (s, 2H), 7.92 (d, J = 8.0 Hz, 2H), 7.33 (t, J = 7.8 Hz, 2H), 6.99 (d, J = 7.5 Hz, 2H), 5.19 (s, 2H), 3.88 (s, 4H), 2.66 (s, 4H), 2.45 (s, 6H), 2.02 (s, 6H), 0.60-0.52 (m, 4H), 0.49-0.40 (m, 4H). |
| 11 | ¹H NMR (400 MHz, DMSO-$d_6$) δ 10.31 (s, 2H), 8.49 (s, 2H), 7.99 (s, 2H), 7.92 (d, J = 8.0 Hz, 2H), 7.33 (t, J = 7.8 Hz, 2H), 6.99 (d, J = 7.6 Hz, 2H), 5.21 (s, 2H), 3.70 (s, 4H), 3.21 (d, J = 6.5 Hz, 4H), 2.97 (d, J = 6.5 Hz, 4H), 2.43 (s, 6H), 2.02 (s, 6H), 1.37 (s, 6H). |
| 13 | ¹H NMR (400 MHz, DMSO-$d_6$) δ 10.33 (s, 2H), 8.53 (s, 2H), 8.00 (s, 2H), 7.93 (d, J = 8.0 Hz, 2H), 7.33 (t, J = 7.8 Hz, 2H), 6.99 (d, J = 7.5 Hz, 2H), 4.72 (d, J = 4.4 Hz, 2H), 4.25-4.16 (m, 2H), 3.72 (d, J = 13.6 Hz, 2H), 3.65 (d, J = 13.6 Hz, 2H), 2.70 (dd, J = 9.6, 6.1 Hz, 2H), 2.63 (q, J = 7.7 Hz, 2H), 2.46 (s, 6H), 2.45-2.40 (m, 2H), 2.36 (dd, J = 9.6, 3.6 Hz, 2H), 2.03 (s, 6H), 2.05-1.95 (m, 2H), 1.62-1.51 (m, 2H). |
| 14 | ¹H NMR (400 MHz, DMSO-$d_6$) δ 10.34 (s, 2H), 8.54 (s, 2H), 8.02 (s, 2H), 7.90 (d, J = 8.1 Hz, 2H), 7.33 (t, J = 7.8 Hz, 2H), 6.99 (d, J = 7.6 Hz, 2H), 3.76 (s, 4H), 2.92 (t, J = 13.2 Hz, 4H), 2.74 (t, J = 7.0 Hz, 4H), 2.47 (s, 6H), 2.27 (tt, J = 14.9, 6.9 Hz, 4H), 2.02 (s, 6H). |
| 15 | ¹H NMR (400 MHz, DMSO-$d_6$) δ 10.33 (s, 2H), 8.55 (s, 2H), 7.98 (s, 2H), 7.93 (dd, J = 8.1, 1.2 Hz, 2H), 7.33 (t, J = 7.8 Hz, 2H), 6.99 (dd, J = 7.5, 1.3 Hz, 2H), 3.85 (s, 4H), 2.45 (s, 6H), 2.10 (tt, J = 6.7, 3.6 Hz, 2H), 2.02 (s, 6H), 0.38 (dt, J = 6.1, 3.0 Hz, 4H), 0.31-0.19 (m, 4H). |
| 16 | ¹H NMR (400 MHz, DMSO-$d_6$) δ 10.33 (s, 2H), 8.57 (s, 2H), 7.98 (s, 2H), 7.92 (dd, J = 8.1, 1.2 Hz, 2H), 7.82 (t, J = 5.5 Hz, 2H), 7.33 (t, J = 7.8 Hz, 2H), 6.99 (dd, J = 7.6, 1.3 Hz, 2H), 3.80 (s, 4H), 3.16 (q, J = 6.3 Hz, 4H), 2.59 (t, J = 6.5 Hz, 4H), 2.45 (s, 6H), 2.02 (s, 6H), 1.79 (s, 6H). |
| 17 | ¹H NMR (400 MHz, DMSO-$d_6$) δ 10.35 (s, 2H), 8.54 (s, 2H), 8.03 (s, 2H), 7.90 (dd, J = 8.1, 1.2 Hz, 2H), 7.80 (s, 2H), 7.33 (t, J = 7.8 Hz, 2H), 7.00 (dd, J = 7.6, 1.3 Hz, 2H), 3.67 (s, 4H), 3.14 (t, J = 6.2 Hz, 4H), 2.98 (s, 4H), 2.58 (t, J = 5.5 Hz, 4H), 2.49 (s, 6H), 2.02 (s, 6H). |
| 18 | ¹H NMR (400 MHz, DMSO-$d_6$) δ 10.34 (s, 2H), 8.62 (s, 2H), 7.99 (s, 2H), 7.92 (d, J = 8.0 Hz, 2H), 7.33 (t, J = 7.8 Hz, 2H), 6.99 (dd, J = 7.7, 1.3 Hz, 2H), 3.93 (d, J = 14.0 Hz, 2H), 3.84 (d, J = 14.0 Hz, 2H), 3.76 (ddd, J = 20.6, 9.8, 4.3 Hz, 4H), 3.26 (ddd, J = 11.2, 8.1, 3.2 Hz, 4H), 2.96 (t, J = 10.2 Hz, 2H), 2.46 (s, 6H), 2.02 (s, 6H), 2.00-1.91 (m, 2H), 1.28 (qd, J = 12.6, 4.4 Hz, 2H). |
| 19 | ¹H NMR (400 MHz, DMSO-$d_6$) δ 10.33 (s, 2H), 8.57 (s, 2H), 7.97 (s, 2H), 7.92 (dd, J = 8.1, 1.3 Hz, 2H), 7.32 (t, J = 7.8 Hz, 2H), 6.98 (dd, J = 7.6, 1.4 Hz, 2H), 3.81 (s, 4H), 3.37 (dq, J = 10.0, 4.6 Hz, 2H), 2.44 (s, 6H), 2.42-2.36 (m, 2H), 2.02 (s, 6H), 1.91 (d, J = 11.0 Hz, 4H), 1.80 (d, J = 10.9 Hz, 4H), 1.24-1.01 (m, 8H). |
| 20 | ¹H NMR (400 MHz, DMSO-$d_6$) δ 10.33 (s, 2H), 8.56 (s, 2H), 7.99 (s, 2H), 7.92 (d, J = 8.1 Hz, 2H), 7.33 (t, J = 7.8 Hz, 2H), 6.99 (d, J = 7.5 Hz, 2H), 4.87 (t, J = 5.8 Hz, 2H), 3.91 (d, J = 13.9 Hz, 2H), 3.74 (d, J = 13.9 Hz, 2H), 3.64 (s, 6H), 3.60 (t, J = 5.6 Hz, 4H), 2.45 (s, 6H), 2.02 (s, 6H). |
| 21 | ¹H NMR (400 MHz, DMSO-$d_6$) δ 10.33 (s, 2H), 8.60 (s, 2H), 7.99 (s, 2H), 7.91 (d, J = 8.0 Hz, 2H), 7.32 (t, J = 7.7 Hz, 2H), 6.98 (d, J = 7.6 Hz, 2H), 3.97 (d, J = 13.8 Hz, 2H), 3.82 (d, J = 14.0 Hz, 2H), 3.56 (d, J = 5.3 Hz, 4H), 3.09 (brs, 2H), 2.46 (s, 6H), 2.01 (s, 6H). |
| 22 | ¹H NMR (400 MHz, DMSO-$d_6$) δ 10.33 (s, 2H), 8.56 (s, 2H), 7.98 (s, 2H), 7.91 (d, J = 7.9 Hz, 2H), 7.33 (t, J = 7.8 Hz, 2H), 6.99 (dd, J = 7.6, 1.3 Hz, 2H), 4.88 (t, J = 5.8 Hz, 2H), 3.91 (d, J = 13.9 Hz, 2H), 3.74 (d, J = 13.9 Hz, 2H), 3.64 (s, 6H), 3.61 (t, J = 5.4 Hz, 4H), 2.45 (s, 6H), 2.02 (s, 6H). |
| 23 | ¹H NMR (400 MHz, DMSO-$d_6$) δ 10.34 (s, 2H), 8.61 (s, 2H), 8.00 (s, 2H), 7.90 (d, J = 8.0 Hz, 2H), 7.33 (t, J = 7.8 Hz, 2H), 6.99 (d, J = 7.5 Hz, 2H), 4.01 (d, J = 13.9 Hz, 2H), 3.86 (d, J = 13.8 Hz, 2H), 3.63 (t, J = 4.6 Hz, 2H), 3.21 (t, J = 5.3 Hz, 2H), 2.47 (s, 6H), 2.02 (s, 6H). |

| Example No. | ¹H-NMR |
|---|---|
| 24 | ¹H NMR (400 MHz, DMSO-d$_6$) δ 10.33 (s, 2H), 8.55 (s, 2H), 7.99 (s, 2H), 7.90 (d, J = 8.0 Hz, 2H), 7.33 (t, J = 7.9 Hz, 2H), 6.99 (d, J = 7.5 Hz, 2H), 3.84 (s, 4H), 3.64 (s, 6H), 3.41 (s, 4H), 2.45 (s, 6H), 2.02 (s, 6H). |
| 25 | ¹H NMR (400 MHz, DMSO-d$_6$) δ 10.35 (s, 2H), 8.62 (s, 2H), 8.01 (s, 2H), 7.88 (d, J = 8.0 Hz, 2H), 7.33 (t, J = 7.8 Hz, 2H), 6.99 (d, J = 7.6 Hz, 2H), 3.97 (s, 4H), 3.27 (s, 4H), 2.48 (s, 6H), 2.02 (s, 6H). |
| 27 | ¹H NMR (400 MHz, DMSO-d$_6$) δ 10.34 (s, 2H), 8.54 (s, 2H), 7.99 (s, 2H), 7.91 (d, J = 8.1 Hz, 2H), 7.33 (t, J = 7.8 Hz, 2H), 6.99 (d, J = 7.5 Hz, 2H), 3.89 (d, J = 13.9 Hz, 2H), 3.60 (d, J = 13.8 Hz, 2H), 3.19 (t, J = 4.3 Hz, 2H), 2.89-2.76 (m, 2H), 2.47 (s, 6H), 2.29-2.18 (m, 2H), 2.02 (s, 6H), 1.76 (brs, 4H), 1.44 (brs, 8H). |
| 28 | ¹H NMR (400 MHz, DMSO-d$_6$) δ 10.32 (s, 2H), 8.51 (s, 2H), 7.99 (s, 2H), 7.90 (d, J = 8.1 Hz, 2H), 7.33 (t, J = 7.8 Hz, 2H), 6.99 (d, J = 7.4 Hz, 2H), 3.81 (d, J = 14.0 Hz, 2H), 3.65 (s, 6H), 3.59 (d, J = 14.0 Hz, 2H), 2.84-2.76 (m, 2H), 2.46 (s, 6H), 2.30-2.21 (m, 2H), 2.02 (s, 6H), 2.00-1.94 (m, 2H), 1.82-1.71 (m, 4H), 1.48-1.41 (m, 8H). |
| 29 | ¹H NMR (400 MHz, DMSO-d$_6$) δ 10.32 (s, 2H), 8.54 (s, 2H), 7.97 (s, 2H), 7.92 (d, J = 8.2 Hz, 2H), 7.32 (t, J = 7.8 Hz, 2H), 6.98 (d, J = 6.9 Hz, 2H), 3.91 (d, J = 14.0 Hz, 2H), 3.56 (d, J = 13.9 Hz, 2H), 3.12 (brs, 2H), 2.89-2.78 (m, 2H), 2.47 (s, 6H), 2.26-2.14 (m, 2H), 2.02 (s, 6H), 1.78-1.73 (m, 4H), 1.48-1.40 (m, 8H). |
| 30 | ¹H NMR (400 MHz, DMSO-d$_6$) δ 10.36 (s, 2H), 8.67 (s, 2H), 8.01 (s, 2H), 7.88 (d, J = 8.3 Hz, 2H), 7.33 (t, J = 9.4 Hz, 2H), 6.99 (d, J = 7.2 Hz, 2H), 4.05 (d, J = 15.8 Hz, 2H), 3.92 (d, J = 15.7 Hz, 2H), 3.62-3.49 (m, 4H), 2.50 (s, 6H), 2.02 (s, 6H), 1.85 (brs, 4H). |
| 31 | ¹H NMR (400 MHz, DMSO-d$_6$) δ 10.38 (s, 2H), 8.50 (s, 2H), 7.91 (d, J = 7.8 Hz, 2H), 7.77 (s, 2H), 7.34 (t, J = 7.8 Hz, 2H), 7.00 (dd, J = 7.6, 1.3 Hz, 2H), 3.99 (s, 6H), 3.58 (t, J = 4.6 Hz, 8H), 3.57 (s, 4H), 2.42 (t, J = 4.6 Hz, 8H), 2.02 (s, 6H). |
| 32 | ¹H NMR (400 MHz, DMSO-d$_6$) δ 10.39 (s, 2H), 8.50 (s, 2H), 7.89 (d, J = 8.0 Hz, 2H), 7.75 (s, 2H), 7.33 (t, J = 7.8 Hz, 2H), 7.00 (d, J = 7.5 Hz, 2H), 3.99 (s, 6H), 3.76 (s, 4H), 2.32 (s, 6H), 2.02 (s, 6H). |
| 33 | ¹H NMR (400 MHz, DMSO-d$_6$) δ 10.38 (s, 2H), 8.52 (s, 2H), 7.91 (d, J = 8.1 Hz, 2H), 7.76 (s, 2H), 7.34 (t, J = 7.8 Hz, 2H), 7.00 (d, J = 7.6 Hz, 2H), 4.00 (s, 6H), 3.82 (s, 4H), 3.60-3.55 (m, 2H), 3.35-3.25 (m, 4H), 2.65 (dd, J = 11.9, 4.2 Hz, 2H), 2.50-2.45 (m, 2H), 2.03 (s, 6H). |
| 34 | ¹H NMR (400 MHz, DMSO-d$_6$) δ 10.37 (s, 2H), 8.51 (s, 2H), 7.90 (d, J = 8.1 Hz, 2H), 7.75 (s, 2H), 7.33 (t, J = 7.8 Hz, 2H), 6.99 (d, J = 7.4 Hz, 2H), 3.99 (s, 6H), 3.80 (s, 4H), 3.40 (m, 4H), 3.24 (s, 6H), 2.69 (t, J = 5.6 Hz, 4H), 2.02 (s, 6H). |
| 35 | ¹H NMR (400 MHz, DMSO-d$_6$) δ 10.37 (s, 2H), 8.51 (s, 2H), 7.91 (d, J = 8.1 Hz, 2H), 7.75 (s, 2H), 7.33 (t, J = 7.9 Hz, 2H), 6.99 (d, J = 7.6 Hz, 2H), 6.67 (t, J = 76.4 Hz, 2H), 3.99 (s, 6H), 3.89 (t, J = 5.7 Hz, 4H), 3.79 (s, 4H), 2.75 (t, J = 5.7 Hz, 4H), 2.02 (s, 6H).<br>¹⁹F NMR (376 MHz, DMSO) δ -82.13. |
| 36 | ¹H NMR (400 MHz, DMSO-d$_6$) δ 10.37 (s, 2H), 8.49 (s, 2H), 7.88 (d, J = 8.0 Hz, 2H), 7.74 (s, 2H), 7.33 (t, J = 7.8 Hz, 2H), 6.99 (d, J = 7.6 Hz, 2H), 3.97 (s, 6H), 3.61 (s, 4H), 3.23 (s, 6H), 2.57 (t, J = 6.0 Hz, 4H), 2.22 (s, 6H), 2.01 (s, 6H). |
| 37 | ¹H NMR (400 MHz, DMSO-d$_6$) δ 10.39 (s, 2H), 8.55 (s, 2H), 7.91 (d, J = 8.1 Hz, 2H), 7.76 (s, 2H), 7.34 (t, J = 7.9 Hz, 2H), 7.00 (d, J = 7.6 Hz, 2H), 3.99 (s, 6H), 3.61 (s, 4H), 3.53 (t, J = 6.3 Hz, 4H), 2.48 (t, J = 6.3 Hz, 4H), 2.22 (s, 6H), 2.03 (s, 6H). |
| 38 | ¹H NMR (400 MHz, DMSO-d$_6$) δ 10.38 (s, 2H), 8.52 (s, 2H), 7.91 (d, J = 8.2 Hz, 2H), 7.75 (s, 2H), 7.34 (t, J = 7.8 Hz, 2H), 7.00 (d, J = 7.5 Hz, 2H), 4.07 (t, J = 5.8 Hz, 4H), 3.99 (s, 6H), 3.79 (s, 4H), 2.74 (t, J = 5.8 Hz, 4H), 2.03 (s, 6H), 2.01 (s, 6H). |
| 39 | ¹H NMR (400 MHz, DMSO-d$_6$) δ 10.38 (s, 2H), 8.52 (s, 2H), 7.90 (d, J = 8.2 Hz, 2H), 7.88-7.84 (m, 2H), 7.76 (s, 2H), 7.34 (t, J = 7.8 Hz, 2H), 7.00 (d, J = 7.5 Hz, 2H), 4.00 (s, 6H), 3.83 (s, 4H), 3.17 (q, J = 6.2 Hz, 4H), 2.62 (t, J = 6.4 Hz, 4H), 2.02 (s, 6H), 1.80 (s, 6H). |
| 40 | ¹H NMR (400 MHz, DMSO-d$_6$) δ 10.38 (3, 2H), 8.56 (s, 2H), 7.89 (d, J = 8.0 Hz, 2H), 7.77 (s, 2H), 7.34 (t, J = 7.8 Hz, 2H), 7.00 (d, J = 7.6 Hz, 2H), 4.01 (s, 6H), 3.92 (s, 4H), 2.02 (s, 6H), 1.12 (s, 12H). |
| 41 | ¹H NMR (400 MHz, DMSO-d$_6$) δ 10.39 (s, 2H), 8.57 (s, 2H), 7.91 (d, J = 8.1 Hz, 2H), 7.77 (s, 2H), 7.34 (t, J = 7.8 Hz, 2H), 7.01 (d, J = 7.5 Hz, 2H), 4.01 (s, 6H), 3.91 (s, 4H), 2.69 (s, 4H), 2.03 (s, 6H), 0.62-0.52 (m, 4H), 0.50-0.41 (m, 4H). |
| 42 | ¹H NMR (400 MHz, DMSO-d$_6$) δ 10.37 (s, 2H), 8.54 (s, 2H), 7.90 (d, J = 8.1 Hz, 2H), 7.75 (s, 2H), 7.33 (t, J = 7.8 Hz, 2H), 6.99 (d, J = 7.5 Hz, 2H), 3.99 (s, 6H), 3.88 (d, J = 14.7 Hz, 2H), 3.81 (d, J = 14.7 Hz, 2H), 3.35-3.18 (m, 4H), 2.65 (q, J = 6.1 Hz, 2H), 2.02 (s, 6H), 0.98 (d, J = 6.3 Hz, 6H). |
| 43 | ¹H NMR (400 MHz, DMSO-d$_6$) δ 10.37 (s, 2H), 8.54 (s, 2H), 7.91 (d, J = 8.0 Hz, 2H), 7.75 (s, 2H), 7.34 (t, J = 7.8 Hz, 2H), 7.00 (d, J = 7.5 Hz, 2H), 3.99 (s, 6H), 3.86 (d, J = 14.8 Hz, 2H), 3.79 (d, J = 14.8 Hz, 2H), 3.29 (qd, J = 10.6, 5.8 Hz, 4H), 2.62 (dq, J = 13.0, 6.6 Hz, 2H), 2.03 (s, 6H), 0.97 (d, J = 6.3 Hz, 6H). |
| 44 | ¹H NMR (400 MHz, DMSO-d$_6$) δ 10.37 (s, 2H), 8.52 (s, 2H), 7.93 (d, J = 8.2 Hz, 2H), 7.74 (s, 2H), 7.33 (t, J = 7.8 Hz, 2H), 6.99 (d, J = 7.6 Hz, 2H), 3.99 (s, 6H), 3.79 (brs, 6H), 2.78-2.69 (m, 2H), 2.03 (s, 6H), 1.94-1.72 (m, 4H), 1.66-1.51 (m, 4H), 1.40 (dq, J = 12.7, 6.0 Hz, 2H), 1.30 (dq, J = 13.8, 7.3 Hz, 2H). |

-continued

| Example No. | ¹H-NMR |
|---|---|
| 45 | ¹H NMR (400 MHz, DMSO-d$_6$) δ 10.36 (s, 2H), 8.41 (s, 2H), 7.89 (d, J = 8.1 Hz, 2H), 7.75 (s, 2H), 7.33 (t, J = 7.8 Hz, 2H), 7.00 (d, J = 7.6 Hz, 2H), 4.21 (p, J = 6.2 Hz, 2H), 3.98 (s, 6H), 3.64 (s, 4H), 3.57 (td, J = 6.1, 2.1 Hz, 4H), 2.86 (t, J = 6.9 Hz, 4H), 2.02 (s, 6H). |
| 46 | ¹H NMR (400 MHz, DMSO-d$_6$) δ 10.35 (s, 2H), 8.41 (s, 2H), 7.92 (d, J = 8.1 Hz, 2H), 7.74 (s, 2H), 7.33 (t, J = 7.8 Hz, 2H), 6.99 (d, J = 7.6 Hz, 2H), 3.98 (s, 6H), 3.65 (s, 4H), 3.25 (d, J = 7.3 Hz, 4H), 2.96 (d, J = 6.5 Hz, 4H), 2.02 (s, 6H), 1.37 (s, 6H). |
| 47 | ¹H NMR (400 MHz, DMSO-d$_6$) δ 10.37 (s, 2H), 8.49 (s, 2H), 7.90 (d, J = 8.0 Hz, 2H), 7.75 (s, 2H), 7.33 (t, J = 7.8 Hz, 2H), 6.99 (d, J = 7.6 Hz, 2H), 4.20 (tt, J = 7.1, 3.5 Hz, 2H), 3.98 (s, 6H), 3.72-3.66 (m, 4H), 2.79-2.61 (m, 4H), 2.40 (dd, J = 9.7, 3.5 Hz, 4H), 2.08-1.91 (m, 8H), 1.55 (qd, J = 8.1, 3.7 Hz, 2H). |
| 48 | ¹H NMR (400 MHz, DMSO-d$_6$) δ 10.37 (s, 2H), 8.49 (s, 2H), 7.91 (d, J = 8.1 Hz, 2H), 7.75 (s, 2H), 7.33 (t, J = 7.8 Hz, 2H), 6.99 (d, J = 7.6 Hz, 2H), 4.20 (tt, J = 7.0, 3.5 Hz, 2H), 3.98 (s, 6H), 3.71 (d, J = 14.2 Hz, 2H), 3.65 (d, J = 14.2 Hz, 2H), 2.81-2.60 (m, 4H), 2.41 (dd, J = 9.8, 3.5 Hz, 4H), 2.08-1.91 (m, 8H), 1.60-1.51 (m, 2H). |
| 49 | ¹H NMR (400 MHz, DMSO-d$_6$) δ 10.37 (s, 2H), 8.47 (s, 2H), 7.91 (d, J = 8.1 Hz, 2H), 7.75 (s, 2H), 7.34 (t, J = 7.8 Hz, 2H), 7.00 (d, J = 7.6 Hz, 2H), 3.98 (s, 6H), 3.54 (s, 4H), 2.70 (dd, J = 10.8, 5.5 Hz, 4H), 2.12 (t, J = 10.5 Hz, 4H), 2.03 (s, 6H), 1.80-1.64 (m, 4H), 1.50-1.31 (m, 4H). |
| 50 | ¹H NMR (400 MHz, DMSO-d$_6$) δ 10.37 (s, 2H), 8.47 (s, 2H), 7.90 (d, J = 8.1 Hz, 2H), 7.76 (s, 2H), 7.33 (t, J = 7.8 Hz, 2H), 7.00 (d, J = 7.5 Hz, 2H), 3.99 (s, 6H), 3.94-3.84 (m, 2H), 3.68 (d, J = 14.2 Hz, 2H), 3.64 (d, J = 14.0 Hz, 2H), 3.15 (s, 6H), 2.72 (dd, J = 10.0, 6.2 Hz, 2H), 2.60 (q, J = 7.8 Hz, 2H), 2.49-2.42 (m, 4H) 2.02 (s, 6H), 2.01-1.91 (m, 2H), 1.71-1.60 (m, 2H). |
| 51 | ¹H NMR (400 MHz, DMSO-d$_6$) δ 10.36 (s, 2H), 8.41 (s, 2H), 7.89 (d, J = 8.1 Hz, 2H), 7.74 (s, 2H), 7.33 (t, J = 7.8 Hz, 2H), 7.00 (d, J = 7.6 Hz, 2H), 3.98 (s, 6H), 3.64(s, 4H), 3.53 (dd, J = 7.9, 5.9 Hz, 4H), 3.15 (s, 6H), 2.91 (dd, J = 7.7 5.6 Hz, 4H), 2.02 (s, 6H). |
| 52 | ¹H NMR (400 MHz, DMSO-d$_6$) δ 10.35 (s, 2H), 8.42 (s, 2H), 7.91 (d, J = 8.0 Hz, 2H), 7.74 (s, 2H), 7.33 (t, J = 7.8 Hz, 2H), 6.99 (d, J = 7.6 Hz, 2H), 4.00-3.96 (m, 8H), 3.66 (s, 4H), 3.20-3.15 (m, 4H), 3.10 (s, 6H), 3.08-2.98 (m, 4H), 2.02 (s, 6H), 1.39 (s, 6H). |
| 53 | ¹H NMR (400 MHz, DMSO-d$_6$) δ 10.37 (s, 2H), 8.48 (s, 2H), 7.91 (d, J = 8.3 Hz, 2H), 7.73 (s, 2H), 7.33 (t, J = 7.8 Hz, 2H), 6.99 (d, J = 7.8 Hz, 2H), 3.99 (s, 6H), 3.79-3.64 (m, 6H), 2.43-2.35 (m, 2H), 2.02 (s, 6H), 1.61-1.44 (m, 4H), 1.19-0.95 (m, 4H). |
| 54 | ¹H NMR (400 MHz, DMSO-d$_6$) δ 10.38 (s, 2H), 8.48 (s, 2H), 7.91 (d, J = 8.0 Hz, 2H), 7.74 (s, 2H), 7.34 (t, J = 7.8 Hz, 2H), 7.00 (d, J = 7.5 Hz, 2H), 4.57 (t, J = 6.5 Hz, 4H), 4.28 (t, J = 6.1 Hz, 4H), 4.00 (s, 6H), 3.90 (p, J = 6.6 Hz, 2H), 3.69 (s, 4H), 2.02 (s, 6H). |
| 55 | ¹H NMR (400 MHz, DMSO-d$_6$) δ 10.37 (s, 2H), 8.52 (s, 2H), 7.92 (d, J = 8.1 Hz, 2H), 7.74 (s, 2H), 7.34 (t, J = 7.8 Hz, 2H), 7.00 (d, J = 7.5 Hz, 2H), 3.99 (s, 6H), 3.82-3.59 (m, 10H), 3.46-3.44 (m, 2H), 3.33-3.23 (m, 2H), 2.02 (s, 6H), 2.02-1.88 (m, 2H), 1.76-1.63 (m, 2H). |
| 56 | ¹H NMR (400 MHz, DMSO-d$_6$) δ 10.37 (s, 2H), 8.52 (s, 2H), 7.92 (d, J = 8.0 Hz, 2H), 7.74 (s, 2H), 7.34 (t, J = 7.8 Hz, 2H), 6.99 (d, J = 7.6 Hz, 2H), 3.99 (s, 6H), 3.81-3.61 (m, 10H), 3.46-3.44 (m, 2H), 3.34-3.23 (m, 2H), 2.02 (s, 6H), 2.02-1.88 (m, 2H), 1.77-1.63 (m, 2H). |
| 57 | ¹H NMR (400 MHz, DMSO-d$_6$) δ 10.36 (s, 2H), 8.48 (s, 2H), 7.91 (d, J = 8.0 Hz, 2H), 7.76 (s, 2H), 7.33 (t, J = 7.8 Hz, 2H), 6.99 (d, J = 7.5 Hz, 2H), 4.85 (d, J = 7.2 Hz, 4H), 4.54 (d, J = 7.2 Hz, 4H), 4.00 (s, 6H), 3.86 (s, 4H), 3.06 (t, J = 6.8 Hz, 4H), 2.31 (t, J = 6.8 Hz, 4H), 2.02 (s, 6H). |
| 58 | ¹H NMR (400 MHz, DMSO-d$_6$) δ 10.35 (s, 2H), 8.39 (s, 2H), 7.91 (d, J = 8.0 Hz, 2H), 7.74 (s, 2H), 7.33 (t, J = 7.8 Hz, 2H), 6.99 (d, J = 7.6 Hz, 2H), 4.61 (s, 8H), 3.98 (s, 6H), 3.56 (s, 4H), 2.02 (s, 6H). |
| 59 | ¹H NMR (400 MHz, DMSO-d$_6$) δ 10.38 (s, 2H), 8.52 (s, 2H), 7.90 (d, J = 8.1 Hz, 2H), 7.75 (s, 2H), 7.34 (t, J = 7.8 Hz, 2H), 7.00 (d, J = 7.6 Hz, 2H), 3.99 (s, 6H), 3.96-3.87 (m, 2H), 3.87-3.75 (m, 4H), 2.58-2.51 (m, 4H), 2.40 (dd, J = 15.2, 5.2 Hz, 2H), 2.23 (dd, J = 15.1, 7.3 Hz, 2H), 2.02 (s, 6H). |
| 60 | ¹H NMR (400 MHz, DMSO-d$_6$) δ 10.37 (s, 2H), 8.49 (s, 2H), 7.91 (d, J = 8.0 Hz, 2H), 7.73 (s, 2H), 7.33 (t, J = 7.8 Hz, 2H), 6.99 (d, J = 7.5 Hz, 2H), 3.99 (s, 6H), 3.69 (s, 4H), 3.09 (p, J = 7.7 Hz, 2H), 2.59 (dt, J = 16.9, 8.0 Hz, 2H), 2.34-2.20 (m, 4H), 2.02 (s, 6H), 1.89-1.71 (m, 4H). |
| 61 | ¹H NMR (400 MHz, DMSO-d$_6$) δ 10.38 (s, 2H), 8.57 (s, 2H), 7.91 (d, J = 8.1 Hz, 2H), 7.75 (s, 2H), 7.34 (t, J = 7.9 Hz, 2H), 7.00 (d, J = 7.5 Hz, 2H), 4.07 (d, J = 14.4 Hz, 2H), 3.98 (s, 6H), 3.85 (d, J = 14.5 Hz, 2H), 3.28-3.19 (m, 2H), 3.11-3.02 (m, 2H), 2.02 (s, 6H), 1.95-1.79 (m, 2H), 1.80-1.65 (m, 4H). |
| 62 | ¹H NMR (400 MHz, DMSO-d$_6$) δ 10.38 (s, 2H), 8.55 (s, 2H), 7.93 (d, J = 8.1 Hz, 2H), 7.75 (s, 2H), 7.34 (t, J = 7.8 Hz, 2H), 7.00 (d, J = 7.6 Hz, 2H), 4.21 (brs, 2H), 3.99 (d, J = 14.7 Hz, 2H), 3.98 (s, 6H), 3.83 (d, J = 14.7 Hz, 2H), 3.22 (t, J = 7.5 Hz, 4H), 2.31 (brd, J = 10.1 Hz, 2H), 2.03 (brs, 8H), 1.90-1.88 (m, 2H) |

| Example No. | ¹H-NMR |
|---|---|
| 63 | ¹H NMR (400 MHz, DMSO-d$_6$) δ 10.38 (s, 2H), 8.59 (s, 2H), 7.94 (d, J = 8.1 Hz, 2H), 7.74 (s, 2H), 7.34 (t, J = 7.8 Hz, 2H), 7.00 (d, J = 7.8 Hz, 2H), 3.97 (s, 6H), 3.85-3.70 (m, 4H), 3.65-3.55 (m, 4H), 3.19 (brs, 2H), 2.99 (brs, 2H), 2.32-2.24 (m, 2H), 2.03 (s, 6H). |
| 64 | ¹H NMR (400 MHz, DMSO-d$_6$) δ 10.37 (s, 2H), 8.51 (s, 2H), 7.92 (d, J = 8.1 Hz, 2H), 7.74 (s, 2H), 7.34 (t, J = 7.8 Hz, 2H), 7.00 (d, J = 7.5 Hz, 2H), 3.96 (s, 6H), 3.78-3.58 (m, 10H), 2.91 (dt, J = 11.3, 5.5 Hz, 2H), 2.30 (dt, J = 11.4, 5.4 Hz, 2H), 2.03 (s, 6H), 1.76 (dt, J = 13.0, 6.1 Hz, 4H), 1.55-1.45 (m, 4H), 1.45-1.35 (m, 4H). |
| 65 | ¹H NMR (400 MHz, DMSO-d$_6$) δ 10.37 (s, 2H), 8.58 (s, 2H), 7.94 (d, J = 8.1 Hz, 2H), 7.73 (s, 2H), 7.34 (t, J = 7.8 Hz, 2H), 7.00 (d, J = 7.5 Hz, 2H), 3.97 (s, 6H), 3.83 (d, J = 15.3 Hz, 2H), 3.68 (d, J = 15.3 Hz, 2H), 3.11 (brs, 2H), 2.97-2.89 (m, 2H), 2.23 (brs, 2H), 2.04 (s, 6H), 1.76 (brs, 4H), 1.50 (brs, 6H), 1.36 (brs, 2H). |
| 66 | ¹H NMR (400 MHz, DMSO-d$_6$) δ 10.38 (s, 2H), 8.50 (s, 2H), 7.90 (dd, J = 8.2, 1.3 Hz, 2H), 7.74 (s, 2H), 7.33 (t, J = 7.8 Hz, 2H), 7.00 (dd, J = 7.6, 1.3 Hz, 2H), 3.98 (s, 6H), 3.79 (s, 4H), 3.62 (s, 6H), 3.38 (s, 4H), 2.02 (s, 6H). |
| 67 | ¹H NMR (400 MHz, DMSO-d$_6$) δ 8.55 (s, 2H), 7.87 (d, J = 8.3 Hz, 2H), 7.78 (s, 2H), 7.34 (t, J = 7.9 Hz, 2H), 7.01 (d, J = 7.6 Hz, 2H), 4.01 (s, 10H), 3.19 (s, 4H), 2.02 (s, 6H). |
| 68 | ¹H NMR (400 MHz, DMSO-d$_6$) δ 10.38 (s, 2H), 8.55 (s, 2H), 7.92 (d, J = 8.1 Hz, 2H), 7.76 (s, 2H), 7.34 (t, J = 7.8 Hz, 2H), 7.00 (d, J = 7.6 Hz, 2H), 4.33 (td, J = 8.6, 2.5 Hz, 2H), 4.16 (td, J = 9.2, 6.2 Hz, 2H), 4.01 (s, 6H), 3.98-3.85 (m, 4H), 3.58 (dd, J = 9.9, 8.1 Hz, 2H), 2.49-2.38 (m, 2H), 2.11-1.94 (m, 8H). |
| 69 | ¹H NMR (400 MHz, DMSO-d$_6$) δ 10.38 (s, 2H), 8.54 (s, 2H), 7.88 (d, J = 7.9 Hz, 2H), 7.75 (s, 2H), 7.34 (t, J = 7.9 Hz, 2H), 7.00 (d, J = 7.6 Hz, 2H), 3.99 (s, 6H), 3.99-3.93 (m, 2H), 3.83 (d, J = 15.0 Hz, 2H), 3.23-3.15 (m, 2H), 2.02 (s, 6H), 1.80 (brs, 2H), 1.71 (brs, 2H). |
| 70 | ¹H NMR (400 MHz, DMSO-d$_6$) δ 10.38 (s, 2H), 8.54 (s, 2H), 7.91 (d, J = 8.0 Hz, 2H), 7.75 (s, 2H), 7.33 (t, J = 7.8 Hz, 2H), 7.00 (d, J = 7.5 Hz, 2H), 4.32 (td, J = 8.5, 2.5 Hz, 2H), 4.15 (td, J = 9.3, 6.3 Hz, 2H), 4.00 (s, 6H), 3.98-3.85 (m, 4H), 3.57 (t, J = 9.1 Hz, 2H), 2.48-2.39 (m, 2H), 2.05-2.95 (m, 8H). |
| 71 | ¹H NMR (400 MHz, DMSO-d$_6$) δ 10.38 (s, 2H), 8.54 (s, 2H), 7.89 (d, J = 8.0 Hz, 2H), 7.75 (s, 2H), 7.33 (t, J = 7.8 Hz, 2H), 7.00 (d, J = 7.6 Hz, 2H), 3.99 (s, 6H), 3.93 (d, J = 14.6 Hz, 2H), 3.80 (d, J = 14.8 Hz, 2H), 3.63-3.47 (m, 4H), 3.26-3.22 (m, 2H), 2.02 (s, 6H), 1.90-1.75 (m, 2H), 1.75-1.62 (m, 2H). |
| 72 | ¹H NMR (400 MHz, DMSO-d$_6$) δ 10.38 (s, 2H), 8.51 (s, 2H), 7.92 (d, J = 8.2 Hz, 2H), 7.75 (s, 2H), 7.34 (t, J = 7.8 Hz, 2H), 7.00 (d, J = 7.6 Hz, 2H), 4.29 (dd, J = 9.4, 5.2 Hz, 2H), 4.13 (d, J = 9.2 Hz, 2H), 4.00 (s, 6H), 3.86-3.70 (m, 4H), 3.51-3.48 (m, 2H), 2.72 (dd, J = 17.4, 6.8 Hz, 2H), 2.34 (d, J = 16.9 Hz, 2H), 2.02 (s, 6H). |
| 73 | ¹H NMR (400 MHz, DMSO-d$_6$) δ 10.38 (s, 2H), 8.54 (s, 2H), 7.90 (d, J = 8.0 Hz, 2H), 7.76 (s, 2H), 7.34 (t, J = 7.8 Hz, 2H), 7.00 (d, J = 7.6 Hz, 2H), 3.99 (s, 6H), 3.97-3.78 (m, 4H), 2.94-2.88 (m, 4H), 2.28 (tt, J = 15.8, 8.3 Hz, 4H), 2.02 (s, 6H). |
| 74 | ¹H NMR (400 MHz, DMSO-d$_6$) δ 10.37 (s, 2H), 8.51 (s, 2H), 7.91 (d, J = 8.1 Hz, 2H), 7.75 (s, 2H), 7.34 (t, J = 7.8 Hz, 2H), 7.00 (d, J = 7.6 Hz, 2H), 4.30 (dd, J = 9.4, 5.3 Hz, 2H), 4.13 (dd, J = 9.3, 2.7 Hz, 2H), 4.00 (s, 6H), 3.84-3.69 (m, 4H), 3.55-3.25 (m), 2.72 (dd, J = 17.3, 6.8 Hz, 2H), 2.34 (dd, J = 17.3, 3.0 Hz, 2H), 2.02 (s, 6H). |
| 75 | ¹H NMR (400 MHz, DMSO-d$_6$) δ 10.37 (s, 2H), 8.54 (s, 2H), 7.91 (d, J = 8.0 Hz, 2H), 7.75 (s, 2H), 7.33 (t, J = 7.7 Hz, 2H), 7.00 (d, J = 7.6 Hz, 2H), 3.99 (s, 6H), 3.95-3.81 (m, 4H), 3.49-3.30 (m), 2.89 (brs, 2H), 2.27 (t, J = 7.7 Hz, 4H), 2.02 (s, 6H). |
| 76 | ¹H NMR (400 MHz, DMSO-d$_6$) δ 10.37 (s, 2H), 8.50 (s, 2H), 7.91 (d, J = 8.1 Hz, 2H), 7.73 (s, 2H), 7.33 (t, J = 7.8 Hz, 2H), 7.00 (d, J = 7.5 Hz, 2H), 3.98 (s, 6H), 3.85 (d, J = 14.9 Hz, 2H), 3.73 (d, J = 14.9 Hz, 2H), 3.59 (s, 6H), 3.56-3.50 (m, 4H), 3.49-3.43 (m, 2H), 3.23 (s, 6H), 2.02 (s, 6H). |
| 77 | ¹H NMR (400 MHz, DMSO-d$_6$) δ 10.37 (s, 2H), 8.53 (s, 2H), 7.90 (d, J = 8.1 Hz, 2H), 7.75 (s, 2H), 7.33 (t, J = 7.9 Hz, 2H), 7.00 (d, J = 7.4 Hz, 2H), 3.99 (s, 6H), 3.98-3.80 (m, 4H), 3.56 (t, J = 4.6 Hz, 4H), 2.02 (s, 6H). |
| 78 | ¹H NMR (400 MHz, DMSO-d$_6$) δ 10.37 (s, 2H), 8.50 (s, 2H), 7.91 (d, J = 8.1 Hz, 2H), 7.73 (s, 2H), 7.33 (t, J = 7.8 Hz, 2H), 6.99 (d, J = 7.6 Hz, 2H), 3.98 (s, 6H), 3.85 (d, J = 14.9 Hz, 2H), 3.79-3.63 (m, 4H), 3.59 (s, 6H), 3.59-3.42 (m, 4H), 3.23 (s, 6H), 2.84 (q, J = 7.3 Hz, 2H), 2.02 (s, 6H). |
| 79 | ¹H NMR (400 MHz, DMSO-d$_6$) δ 10.38 (s, 2H), 8.54 (s, 2H), 7.89 (d, J = 7.9 Hz, 2H), 7.75 (s, 2H), 7.33 (t, J = 7.8 Hz, 2H), 7.00 (d, J = 7.7 Hz, 2H), 4.00 (s, 6H), 3.98-3.83 (m, 4H), 3.57 (d, J = 5.1 Hz, 4H), 3.24 (s, 6H), 2.02 (s, 6H). |
| 80 | ¹H NMR (400 MHz, DMSO-d$_6$) δ 10.37 (s, 2H), 8.51 (s, 2H), 7.90 (d, J = 8.0 Hz, 2H), 7.76 (s, 2H), 7.33 (t, J = 7.8 Hz, 2H), 7.00 (d, J = 7.6 Hz, 2H), 3.99 (s, 6H), 3.79 (s, 4H), 3.27 (t, J = 6.6 Hz, 4H), 3.02 (s, 6H), 2.93 (t, J = 6.6 Hz, 4H), 2.02 (s, 6H). |
| 82 | ¹H NMR (400 MHz, DMSO-d$_6$) δ 10.26 (s, 2H), 8.38 (s, 2H), 7.79 (d, J = 8.1 Hz, 2H), 7.65 (s, 2H), 7.23 (t, J = 7.8 Hz, 2H), 6.89 (d, J = 7.5 Hz, 2H), 3.88 (s, 6H), 3.60-3.35 (m), 3.00-2.88 (m, 2H), 2.68-2.56 (m, 4H), 2.47 (t, J = 6.9 Hz, 4H), 1.92 (s, 6H), 1.91-1.76 (m, 4H). |

| Example No. | ¹H-NMR |
|---|---|
| 83 | ¹H NMR (400 MHz, DMSO-d$_6$) δ 10.37 (s, 2H), 8.48 (s, 2H), 7.90 (d, J = 8.0 Hz, 2H), 7.75 (s, 2H), 7.33 (t, J = 7.8 Hz, 2H), 7.00 (d, J = 7.5 Hz, 2H), 3.98 (s, 6H), 3.77-3.63 (m), 2.98-2.79 (m, 2H), 2.79-2.64 (m, 4H), 2.56 (brs, 4H), 2.02 (s, 6H), 1.95 (q, J = 7.8, 7.4 Hz, 4H). |
| 84 | ¹H NMR (400 MHz, DMSO-d$_6$) δ 10.37 (s, 2H), 8.47 (s, 2H), 7.90 (d, J = 8.0 Hz, 2H), 7.76 (s, 2H), 7.34 (t, J = 7.8 Hz, 2H), 7.00 (d, J = 7.5 Hz, 2H), 3.98 (s, 6H), 3.59 (s, 6H), 3.56 (s, 4H), 2.79 (d, J = 11.6 Hz, 4H), 2.38-2.24 (m, 2H), 2.09 (t, J = 11.4 Hz, 4H), 2.03 (s, 6H), 1.85-1.74 (m, 4H), 1.66-1.51 (m, 4H). |
| 86 | ¹H NMR (400 MHz, DMSO-d$_6$) δ 10.38 (s, 2H), 8.56 (s, 2H), 7.92 (d, J = 8.1 Hz, 2H), 7.75 (s, 2H), 7.41-7.28 (m, 4H), 7.11 (d, J = 3.0 Hz, 2H), 7.00 (d, J = 7.5 Hz, 2H), 3.99 (s, 6H), 3.91-3.58 (m), 3.55 (dd, J = 10.7, 4.7 Hz, 2H), 3.44 (dd, J = 10.7, 6.7 Hz, 2H), 3.03 (dd, J = 6.7, 4.7 Hz, 2H), 2.03 (s, 6H). |
| 87 | ¹H NMR (400 MHz, DMSO-d$_6$) δ 10.37 (s, 2H), 8.54 (s, 2H), 7.91 (d, J = 7.9 Hz, 2H), 7.86 (t, J = 5.8 Hz, 2H), 7.75 (s, 2H), 7.34 (t, J = 7.8 Hz, 2H), 7.00 (d, J = 7.5 Hz, 2H), 3.99 (s, 6H), 3.81-3.67 (m, 4H), 3.53 (dd, J = 10.7, 4.9 Hz, 4H), 3.17-2.99 (m, 8H), 2.03 (s, 6H), 1.00 (t, J=7.2 Hz, 6H). |
| 88 | ¹H NMR (400 MHz, DMSO-d$_6$) δ 10.37 (s, 2H), 8.51 (s, 2H), 7.90 (d, J = 8.1 Hz, 2H), 7.75 (s, 2H), 7.33 (t, J = 7.8 Hz, 2H), 7.00 (d, J = 7.6 Hz, 2H), 3.99 (s, 6H), 3.78 (s, 4H), 3.26-3.10 (m, 6H), 2.94 (s, 6H), 2.97-2.90 (m, 2H), 2.02 (s, 6H). |
| 89 | ¹H NMR (400 MHz, DMSO-d$_6$) δ 10.37 (s, 2H), 8.51 (s, 2H), 7.91 (dd, J = 8.0, 1.3 Hz, 2H), 7.75 (s, 2H), 7.34 (t, J = 7.8 Hz, 2H), 7.00 (dd, J = 7.7, 1.3 Hz, 2H), 3.99 (s, 6H), 3.77 (s, 4H), 3.04 (t, J = 6.2 Hz, 4H), 2.98 (s, 12H), 2.59 (t, J = 6.2 Hz, 4H), 2.03 (s, 6H). |
| 90 | ¹H NMR (400 MHz, DMSO-d$_6$) δ 10.37 (s, 2H), 8.52 (s, 2H), 7.89 (d, J = 8.0 Hz, 2H), 7.75 (s, 2H), 7.34 (t, J = 7.8 Hz, 2H), 7.00 (d, J = 7.5 Hz, 2H), 3.99 (s, 6H), 3.83 (s, 4H), 3.13 (dt, J = 13.0, 6.6 Hz, 4H), 3.08 (t, J = 6.1 Hz, 4H), 2.90 (dt, J = 13.2, 6.8 Hz, 4H), 2.66 (t, J = 6.2 Hz, 4H), 2.16-2.05 (m, 4H), 2.02 (s, 6H), 2.05-1.94 (m, 4H). |
| 91 | ¹H NMR (500 MHz, DMSO-d$_6$) δ 10.32 (s, 2H), 8.57 (s, 2H), 7.88 (d, J = 8.0 Hz, 2H), 7.59 (s, 2H), 7.32 (t, J = 7.7 Hz, 2H), 6.98 (d, J = 7.4 Hz, 2H), 3.98 (s, 4H), 3.50 (t, J = 5.7 Hz, 4H), 2.65 (t, J = 5.8 Hz, 4H), 2.28 (td, J = 8.2, 4.2 Hz, 2H), 2.00 (s, 6H), 1.19-1.08 (m, 4H), 0.89-0.80 (m, 4H). |
| 92 | ¹H NMR (500 MHz, DMSO-d$_6$) δ 10.32 (s, 2H), 8.60 (s, 2H), 7.89 (d, J = 8.0 Hz, 2H), 7.60 (s, 2H), 7.32 (t, J = 7.8 Hz, 2H), 6.98 (d, J = 7.5 Hz, 2H), 4.04 (s, 4H), 3.50-3.35 (m, 8H), 2.61 (p, J = 5.7 Hz, 2H), 2.29 (tq, J = 8.8, 4.4, 3.5 Hz, 2H), 2.01 (s, 6H), 1.16-1.10 (m, 4H), 0.86 (q, J = 5.4 Hz, 4H). |
| 93 | ¹H NMR (500 MHz, DMSO-d$_6$) δ 10.32 (s, 2H), 8.56 (s, 2H), 7.89 (dd, J = 8.2, 1.4 Hz, 2H), 7.81 (t, J = 5.6 Hz, 2H), 7.59 (s, 2H), 7.32 (t, J = 7.8 Hz, 2H), 6.98 (dd, J = 7.7, 1.3 Hz, 2H), 3.95 (s, 4H), 3.17 (q, J = 6.2 Hz, 4H), 2.62 (t, J = 6.5 Hz, 4H), 2.28 (ddd, J = 13.7, 8.4, 5.2 Hz, 2H), 2.00 (s, 6H), 1.79 (s, 6H), 1.17-1.07 (m, 4H), 0.89-0.79 (m, 4H). |
| 94 | ¹H NMR (500 MHz, DMSO-d$_6$) δ 10.33 (s, 2H), 8.59 (s, 2H), 7.88 (d, J = 7.8 Hz, 2H), 7.59 (s, 2H), 7.32 (t, J = 7.8 Hz, 2H), 6.98 (d, J = 7.5 Hz, 2H), 4.04 (s, 4H), 2.69 (s, 4H), 2.33-2.27 (m, 2H), 2.00 (s, 6H), 1.16-1.09 (m, 4H), 0.89-0.81 (m, 4H), 0.61-0.52 (m, 4H), 0.49-0.37 (m, 4H). |
| 95 | ¹H NMR (500 MHz, DMSO-d$_6$) δ 10.32 (s, 2H), 8.57 (s, 2H), 7.87 (d, J = 8.0 Hz, 2H), 7.59 (s, 2H), 7.31 (t, J = 7.8 Hz, 2H), 6.97 (d, J = 7.4 Hz, 2H), 4.00 (s, 4H), 3.74 (q, J = 5.9 Hz, 4H), 2.53 (d, J = 4.4 Hz, 2H), 2.27 (td, J = 8.4, 4.3 Hz, 2H), 2.00 (s, 6H), 1.17-1.08 (m, 4H), 1.05 (d, J = 6.1 Hz, 6H), 0.90-0.80 (m, 4H). |
| 96 | ¹H NMR (500 MHz, DMSO-d$_6$) δ 10.33 (s, 2H), 8.58 (s, 2H), 7.88 (d, J = 7.7 Hz, 2H), 7.59 (s, 2H), 7.32 (t, J = 7.8 Hz, 2H), 6.98 (dd, J = 7.6, 1.3 Hz, 2H), 4.03 (d, J = 13.8 Hz, 2H), 3.95 (d, J = 13.8 Hz, 2H), 3.36-3.24 (m, 4H), 2.69 (h, J = 6.2 Hz, 2H), 2.29 (ddd, J = 13.5, 8.4, 5.1 Hz, 2H), 2.00 (s, 6H), 1.17-1.08 (m, 4H), 1.00 (d, J = 6.3 Hz, 6H), 0.91-0.79 (m, 4H). |
| 97 | ¹H NMR (500 MHz, DMSO-d$_6$) δ 10.33 (s, 2H), 8.57 (s, 2H), 7.89 (d, J = 7.9 Hz, 2H), 7.59 (s, 2H), 7.32 (t, J = 7.9 Hz, 2H), 6.98 (d, J = 7.2 Hz, 2H), 3.96 (s, 4H), 3.82 (q, J = 4.9 Hz, 2H), 2.82 (q, J = 5.6 Hz, 2H), 2.28 (td, J = 8.3, 4.1 Hz, 2H), 2.00 (s, 6H), 1.91-1.77 (m, 4H), 1.62-1.52 (m, 4H), 1.46-1.38 (m, 2H), 1.38-1.28 (m, 2H), 1.12 (d, J = 8.3 Hz, 4H), 0.85 (d, J = 5.1 Hz, 4H). |
| 98 | ¹H NMR (500 MHz, DMSO-d$_6$) δ 10.31 (s, 2H), 8.47 (s, 2H), 7.86 (d, J = 7.8 Hz, 2H), 7.57 (s, 2H), 7.31 (t, J = 7.8 Hz, 2H), 6.98 (dd, J = 7.6, 1.3 Hz, 2H), 4.22 (p, J = 6.2 Hz, 2H), 3.82 (s, 4H), 3.54 (td, J = 6.1, 2.1 Hz, 4H), 2.91-2.83 (m, 4H), 2.31-2.21 (m, 2H), 2.00 (s, 6H), 1.17-1.09 (m, 4H), 0.90-0.81 (m, 4H). |
| 99 | ¹H NMR (500 MHz, DMSO-d$_6$) δ 10.30 (s, 2H), 8.48 (s, 2H), 7.88 (dd, J = 8.1, 1.3 Hz, 2H), 7.58 (s, 2H), 7.32 (t, J = 7.8 Hz, 2H), 6.98 (dd, J = 7.6, 1.3 Hz, 2H), 3.85 (s, 4H), 3.27-3.20 (m, 4H), 2.99 (d, J = 6.6 Hz, 4H), 2.31-2.22 (m, 2H), 2.00 (s, 6H), 1.38 (s, 6H), 1.18-1.09 (m, 4H), 0.88-0.81 (m, 4H). |
| 100 | ¹H NMR (500 MHz, DMSO-d$_6$) δ 10.32 (s, 2H), 8.52 (s, 2H), 7.89 (d, J = 8.0 Hz, 2H), 7.59 (s, 2H), 7.32 (t, J = 7.8 Hz, 2H), 6.98 (d, J = 7.6 Hz, 2H), 4.21 (brs, 2H), 3.86 (d, J = 13.5 Hz, 2H), 3.80 (d, J = 13.6 Hz, 2H), 2.75 (dd, J = 9.6, 6.3 Hz, 2H), 2.66 (q, J = 7.6 Hz, 2H), 2.49-2.45 (m, 2H), 2.43-2.30 (m, 4H), 2.01 (s, 6H), 2.05-1.95 (m, 2H), 1.61-1.51 (m, 2H), 1.14 (d, J = 8.2 Hz, 4H), 0.85 (d, J = 5.1 Hz, 4H). |

| Example No. | ¹H-NMR |
|---|---|
| 101 | ¹H NMR (500 MHz, DMSO-d$_6$) δ 10.31 (s, 2H), 8.52 (s, 2H), 7.88 (dd, J = 8.2, 1.2 Hz, 2H), 7.58 (s, 2H), 7.31 (t, J = 7.8 Hz, 2H), 6.97 (dd, J = 7.6, 1.3 Hz, 2H), 4.21 (dp, J = 9.7, 3.5 Hz, 2H), 3.82 (q, J = 13.5 Hz, 4H), 2.75 (dd, J = 9.6, 6.1 Hz, 2H), 2.66 (q, J = 7.8 Hz, 2H), 2.47 (dd, J = 8.4, 5.5 Hz, 2H), 2.39 (dd, J = 9.6, 3.6 Hz, 2H), 2.34 (tt, J = 8.3, 5.2 Hz, 2H), 2.05-1.95 (m, 2H), 2.00 (s, 6H), 1.60-1.51 (m, 2H), 1.17-1.08 (m, 4H), 0.89-0.79 (m, 4H). |
| 102 | ¹H NMR (500 MHz, DMSO-d$_6$) δ 10.32 (s, 2H), 8.48 (s, 2H), 7.87 (d, J = 8.5 Hz, 2H), 7.59 (s, 2H), 7.32 (t, J = 7.8 Hz, 2H), 6.98 (d, J = 7.4 Hz, 2H), 3.68 (s, 4H), 3.48 (brs, 2H), 3.09-3.03 (m, 2H), 2.75-2.67 (m, 4H), 2.38-2.31 (m, 2H), 2.18-2.10 (m, 2H), 2.00 (s, 6H), 1.82-1.75 (m, 2H), 1.74-1.67 (m, 2H), 1.47-1.35 (m, 4H), 1.13 (d, J = 7.8 Hz, 4H), 0.85 (d, J = 6.1 Hz, 4H). |
| 103 | ¹H NMR (500 MHz, DMSO-d$_6$) δ 10.40 (s, 2H), 8.60 (s, 2H), 7.96 (d, J = 8.0 Hz, 2H), 7.65 (s, 2H), 7.39 (t, J = 7.8 Hz, 2H), 7.06 (d, J = 7.5 Hz, 2H), 3.93 (s, 4H), 3.87-3.77 (m, 2H), 2.77 (ddd, J = 15.5, 8.2, 6.3 Hz, 2H), 2.56-2.47 (m, 4H), 2.36 (td, J = 8.4, 4.3 Hz, 2H), 2.08 (s, 6H), 1.64 (qd, J = 8.3, 2.9 Hz, 4H), 1.24-1.16 (m, 4H), 0.96-0.87 (m, 4H). |
| 104 | ¹H NMR (500 MHz, DMSO-d$_6$) δ 10.32 (s, 2H), 8.54 (s, 2H), 7.88 (d, J = 8.1 Hz, 2H), 7.59 (s, 2H), 7.32 (t, J = 7.8 Hz, 2H), 6.98 (dd, J = 7.6, 1.3 Hz, 2H), 4.05 (d, J = 13.8 Hz, 2H), 3.88 (d, J = 13.7 Hz, 2H), 3.64 (s, 6H), 3.62 (d, J = 5.2 Hz, 4H), 3.38-3.35 (m, 2H), 2.29 (ddd, J = 13.6, 8.5, 5.2 Hz, 2H), 2.00 (s, 6H), 1.13 (dd, J = 8.3, 2.1 Hz, 4H), 0.91-0.78 (m, 4H). |
| 105 | ¹H NMR (500 MHz, DMSO-d$_6$) δ 10.31 (s, 2H), 8.58 (s, 2H), 7.89 (d, J = 8.2 Hz, 2H), 7.58 (s, 2H), 7.31 (t, J = 7.7 Hz, 2H), 6.97 (d, J = 7.6 Hz, 2H), 4.10 (d, J = 13.7 Hz, 2H), 3.94 (d, J = 14.0 Hz, 2H), 3.52 (d, J = 5.9 Hz, 4H), 3.04-2.96 (m, 2H), 2.32 (brs, 2H), 2.00 (s, 6H), 1.12 (brs, 4H), 0.85 (brs, 4H). |
| 106 | ¹H NMR (500 MHz, DMSO-d$_6$) δ 10.32 (s, 2H), 8.54 (s, 2H), 7.87 (d, J = 8.1 Hz, 2H), 7.58 (s, 2H), 7.31 (t, J = 7.8 Hz, 2H), 6.98 (dd, J = 7.6, 1.4 Hz, 2H), 4.10 (q, J = 7.1 Hz, 4H), 4.05 (d, J = 13.8 Hz, 2H), 3.89 (d, J = 13.7 Hz, 2H), 3.61 (d, J = 5.2 Hz, 4H), 3.33 (t, J = 5.1 Hz, 2H), 2.34-2.25 (m, 2H), 2.00 (s, 6H), 1.19 (t, J = 7.1 Hz, 6H), 1.12 (dd, J = 8.3, 2.0 Hz, 4H), 0.89-0.79 (m, 4H). |
| 107 | ¹H NMR (500 MHz, DMSO-d$_6$) δ 10.32 (s, 2H), 8.54 (s, 2H), 7.87 (d, J = 8.0 Hz, 2H), 7.59 (s, 2H), 7.32 (t, J = 7.8 Hz, 2H), 6.98 (d, J = 7.5 Hz, 2H), 4.87 (t, J = 5.7 Hz, 2H), 4.10 (q, J = 7.2 Hz, 4H), 4.05 (dd, J = 13.5, 5.0 Hz, 2H), 3.89 (dd, J = 13.7, 6.4 Hz, 2H), 3.61 (t, J = 5.5 Hz, 4H), 2.54 (q, J = 7.1 Hz, 2H), 2.30 (ddd, J = 13.6, 8.5, 5.2 Hz, 2H), 2.00 (s, 6H), 1.20 (t, J = 7.1 Hz, 6H), 1.12 (d, J = 8.7 Hz, 4H), 0.85 (brs, 4H). |
| 108 (TFA salt) | ¹H NMR (500 MHz, DMSO-d$_6$) δ 10.38 (s, 2H), 8.72 (s, 2H), 7.79 (d, J = 7.7 Hz, 2H), 7.64 (s, 2H), 7.33 (t, J = 7.8 Hz, 2H), 7.00 (d, J = 6.9 Hz, 2H), 4.46 (s, 4H), 4.05 (brs, 2H), 4.00-3.94 (m, 2H), 3.91 (dd, J = 11.8, 4.0 Hz, 2H), 2.35 (ddd, J = 13.6, 8.4, 5.1 Hz, 2H), 2.00 (s, 6H), 1.21-1.12 (m, 4H), 0.95-.085 (m, 4H). |
| 109 | ¹H NMR (500 MHz, DMSO-d$_6$) δ 10.32 (s, 2H), 8.49 (s, 2H), 7.87 (d, J = 8.1 Hz, 2H), 7.59 (s, 2H), 7.32 (t, J = 7.8 Hz, 2H), 6.98 (d, J = 7.6 Hz, 2H), 3.95 (d, J = 13.7 Hz, 2H), 3.70 (d, J = 13.9 Hz, 2H), 3.66 (s, 6H), 3.35-3.30 (m, 2H), 2.88-2.77 (m, 2H), 2.45-2.38 (m, 2H), 2.32-2.22 (m, 2H), 2.00 (s, 6H), 1.76 (brs, 4H), 1.45 (brs, 8H), 1.12 (d, J = 8.7 Hz, 4H), 0.94-0.85 (m, 2H), 0.83-0.74 (m, 2H). |
| 110 (TFA salt) | ¹H NMR (500 MHz, DMSO-d$_6$) δ 10.34 (s, 2H), 8.59 (s, 2H), 7.84 (d, J = 8.3 Hz, 2H), 7.61 (s, 2H), 7.32 (t, J = 7.8 Hz, 2H), 7.14 (t, J = 50.0 Hz, 4H), 6.99 (d, J = 7.5 Hz, 2H), 4.40-3.00 (m), 2.46-2.38 (m, 2H), 2.00 (s, 6H), 2.00-1.95 (m, 2H), 1.82-1.70 (m, 2H), 1.64-1.58 (brs, 6H), 1.50-1.42 (brs, 2H), 1.20-1.12 (m, 4H), 1.02-0.92 (brs, 2H), 0.87-0.77 (brs, 2H). |
| 112 (TFA salt) | ¹H NMR (500 MHz, DMSO-d$_6$) δ 10.36 (s, 2H), 8.66 (s, 2H), 7.81 (d, J = 8.0 Hz, 2H), 7.62 (s, 2H), 7.32 (t, J = 7.8 Hz, 2H), 6.99 (d, J = 7.0 Hz, 2H), 4.34 (brs, 2H), 4.03 (brs, 2H), 3.60-3.20 (m), 2.32 (m, 2H), 2.00 (s, 6H), 1.22 (d, J = 6.3 Hz, 6H), 1.15 (d, J = 8.6 Hz, 4H), 0.90 (brs, 4H). |
| 113 | ¹H NMR (500 MHz, DMSO-d$_6$) δ 10.33 (s, 2H), 8.58 (s, 2H), 7.87 (d, J = 7.9 Hz, 2H), 7.60 (s, 2H), 7.32 (t, J = 7.8 Hz, 2H), 6.98 (dd, J = 7.7, 1.3 Hz, 2H), 4.32 (td, J = 8.6, 2.5 Hz, 2H), 4.23-4.11 (m, 4H), 4.06 (d, J = 13.9 Hz, 2H), 3.64 (t, J = 9.1 Hz, 2H), 2.47-2.39 (m, 2H), 2.31 (ddd, J = 13.4, 8.2, 5.1 Hz, 2H), 2.07-2.01 (m, 2H), 2.00 (s, 6H), 1.17-1.08 (m, 4H), 0.90-0.79 (m, 4H). |
| 114 (TFA salt) | ¹H NMR (500 MHz, DMSO-d$_6$) δ 10.36 (s, 2H), 8.62 (s, 2H), 7.82 (d, J = 8.0 Hz, 2H), 7.62 (s, 2H), 7.33 (t, J = 7.8 Hz, 2H), 7.00 (d, J = 7.5 Hz, 2H), 4.47 (d, J = 7.1 Hz, 2H), 4.35-4.20 (m, 4H), 3.65-3.55 (m, 4H), 2.35-2.28 (m, 2H), 2.00 (s, 6H), 1.95-1.80 (m, 4H), 1.16 (d, J = 8.9 Hz, 4H), 0.95-0.84 (m, 4H). |
| 115 | ¹H NMR (500 MHz, DMSO-d$_6$) δ 10.33 (s, 2H), 8.51 (s, 2H), 7.87 (d, J = 8.0 Hz, 2H), 7.59 (s, 2H), 7.32 (t, J = 7.8 Hz, 2H), 6.98 (d, J = 7.5 Hz, 2H), 4.12 (q, J = 7.1 Hz, 4H), 4.09-3.97 (m, 6H), 3.90 (d, J = 13.9 Hz, 2H), 3.61 (q, J = 7.0, 6.4 Hz, 2H), 2.83 (brs, 2H), 2.71 (dd, J = 15.7, 6.3 Hz, 2H), 2.60 (dd, J = 15.7, 7.3 Hz, 2H), 2.26 (td, J = 8.4, 4.3 Hz, 2H), 2.00 (s, 6H), 1.20 (t, J = 7.1 Hz, 6H), 1.14 (t, J = 7.1 Hz, 6H), 1.10 (d, J = 8.5 Hz, 4H), 0.89-0.79 (m, 4H). |
| 116 (TFA salt) | ¹H NMR (500 MHz, DMSO-d$_6$) δ 10.37 (s, 2H), 8.66 (s, 2H), 7.80 (d, J = 8.0 Hz, 2H), 7.64 (s, 2H), 7.33 (t, J = 7.8 Hz, 2H), 7.00 (d, J = 7.5 Hz, 2H), 4.48 (d, J = 10.8 Hz, 2H), 4.40 (m, 2H), 4.15 (brs, 2H), 2.88 (brs, 4H), 2.40-2.27 (m, 2H), 1.99 (s, 6H), 1.17 (d, J = 8.7 Hz, 4H), 0.99-0.81 (m, 4H). |

| Example No. | ¹H-NMR |
|---|---|
| 117 | ¹H NMR (500 MHz, DMSO-$d_6$) δ 10.32 (s, 2H), 8.51 (s, 2H), 7.87 (d, J = 8.0 Hz, 2H), 7.59 (s, 2H), 7.32 (t, J = 7.8 Hz, 2H), 6.98 (dd, J = 7.7, 1.3 Hz, 2H), 4.12 (q, J = 7.1 Hz, 4H), 4.10-3.98 (m, 6H), 3.90 (d, J = 13.9 Hz, 2H), 3.61 (brs, 2H), 2.71 (dd, J = 15.7, 6.3 Hz, 2H), 2.60 (dd, J = 15.7, 7.3 Hz, 2H), 2.27 (ddd, J = 11.0, 8.5, 5.3 Hz, 2H), 2.00 (s, 6H), 1.20 (t, J = 7.1 Hz, 6H), 1.14 (t, J = 7.1 Hz, 6H), 1.15-1.07 (m, 4H), 0.89-0.78 (m, 4H). |
| 118 (TFA salt) | ¹H NMR (500 MHz, DMSO-$d_6$) δ 10.36 (s, 2H), 8.60 (s, 2H), 7.83 (d, J = 8.0 Hz, 2H), 7.61 (s, 2H), 7.32 (t, J = 7.8 Hz, 2H), 6.99 (d, J = 7.4 Hz, 2H), 4.31 (d, J = 13.7 Hz, 2H), 4.17 (d, J = 13.7 Hz, 2H), 3.83 (brs, 2H), 2.77 (dd, J = 16.5, 6.3 Hz, 2H), 2.67 (dd, J = 16.5, 6.3 Hz, 2H), 2.32 (tt, J = 8.4, 4.9 Hz, 2H), 2.00 (s, 6H), 1.19-1.09 (m, 4H), 0.93-0.83 (m, 4H). |
| 119 | ¹H NMR (500 MHz, DMSO-$d_6$) δ 10.33 (s, 2H), 8.53 (s, 2H), 7.86 (d, J = 7.9 Hz, 2H), 7.59 (s, 2H), 7.32 (t, J = 7.8 Hz, 2H), 6.98 (d, J = 7.5 Hz, 2H), 4.22 (d, J = 9.8 Hz, 2H), 4.21-4.07 (m, 8H), 4.03 (d, J = 6.2 Hz, 4H), 3.07 (dt, J = 9.8, 6.3 Hz, 2H), 2.29 (td, J = 8.3, 4.2 Hz, 2H), 2.00 (s, 6H), 1.18 (t, J = 7.1 Hz, 12H), 1.16-1.08 (m, 4H), 0.85 (q, J = 5.1 Hz, 4H). |
| 120 (Li salt) | ¹H NMR (500 MHz, $D_2O$) δ 8.51 (s, 2H), 7.58 (s, 2H), 7.44 (d, J = 7.7 Hz, 2H), 7.39 (t, J = 7.7 Hz, 2H), 7.22 (d, J = 7.6 Hz, 2H), 3.93 (s, 4H), 3.78 (s, 2H), 2.26-2.17 (m, 2H), 1.98 (s, 6H), 1.21 (q, J = 5.9, 5.4 H, 4H), 0.91 (q, J = 5.4 Hz, 4H). |
| 121 (TFA salt) | ¹H NMR (500 MHz, DMSO-$d_6$) δ 10.39 (s, 2H), 8.69 (s, 2H), 7.77 (dd, J = 8.1, 1.3 Hz, 2H), 7.64 (s, 2H), 7.33 (t, J = 7.8 Hz, 2H), 7.01 (dd, J = 7.7, 1.3 Hz, 2H), 4.49 (s, 4H), 4.23 (q, J = 7.1 Hz, 4H), 4.12 (s, 4H), 2.32 (td, J = 8.4, 4.3 Hz, 2H), 1.99 (s, 6H), 1.25 (t, J = 7.1 Hz, 6H), 1.23-1.16 (m, 4H), 0.94 (q, J = 5.1 Hz, 4H). |
| 122 (TFA salt) | ¹H NMR (500 MHz, DMSO-$d_6$) δ 10.39 (s, 2H), 8.70(s, 2H), 7.76 (d, J = 7.9 Hz, 2H), 7.64 (s, 2H), 7.33 (t, J = 7.8 Hz, 2H), 7.01 (d, J = 7.3 Hz, 2H), 4.51 (s, 4H), 4.03 (s, 4H), 2.38-2.28 (m, 2H), 1.99 (s, 6H), 1.23-1.11 (m, 4H), 0.98-0.87 (m, 4H). |
| 123 | ¹H NMR (500 MHz, DMSO-$d_6$) δ 10.31 (s, 2H), 8.53 (s, 2H), 7.88 (d, J = 8.0 Hz, 2H), 7.59 (s, 2H), 7.32 (t, J = 7.8 Hz, 2H), 6.98 (dd, J = 7.7, 1.3 Hz, 2H), 4.10 (q, J = 7.0 Hz, 4H), 3.99 (dd, J = 14.0, 4.9 Hz, 2H), 3.87 (dd, J = 13.8, 5.8 Hz, 2H), 2.65-2.55 (m, 2H), 2.30 (ddd, J = 10.8, 8.5, 5.2 Hz, 2H), 2.00 (s, 6H), 1.24 (d, J = 6.9 Hz, 6H), 1.20 (t, J = 7.1 Hz, 6H), 1.12 (d, J = 8.5 Hz, 4H), 0.91-0.78 (m, 4H). |
| 124 (TFA salt) | ¹H NMR (500 MHz, DMSO-$d_6$) δ 10.38 (s, 2H), 8.71 (s, 2H), 7.78 (d, J = 8.0 Hz, 2H), 7.66 (s, 2H), 7.33 (t, J = 7.8 Hz, 2H), 7.01 (d, J = 7.5 Hz, 2H), 4.52 (s, 4H), 42.4 (q, J = 7.2 Hz, 2H), 2.33 (ddd, J = 13.5, 8.5, 5.4 Hz, 2H), 1.99 (s, 6H), 1.56 (d, J = 7.2 Hz, 6H), 1.23-1.15 (m, 4H), 1.01-0.86 (m, 4H). |
| 125 | ¹H NMR (500 MHz, DMSO-$d_6$) δ 10.33 (s, 2H), 8.51 (s, 2H), 7.86 (dd, J = 8.1, 1.3 Hz, 2H), 7.58 (s, 2H), 7.32 (t, J = 7.8 Hz, 2H), 6.98 (dd, J = 7.8, 1.4 Hz, 2H), 4.19-4.07 (m, 4H), 4.02 (d, J = 13.8 Hz, 2H), 3.80 (d, J = 13.8 Hz, 2H), 2.95 (brs, 2H), 2.30 (td, J = 8.3, 4.2 Hz, 2H), 2.00 (s, 6H), 1.86 (h, J = 6.7 Hz, 2H), 1.21 (t, J = 7.1 Hz, 6H), 1.12 (d, J = 9.0 Hz, 4H), 0.90 (d, J = 6.7 Hz, 6H), 0.87 (d, J = 6.8 Hz, 6H), 0.86-0.82 (m, 4H). |
| 126 (TFA salt) | ¹H NMR (500 MHz, DMSO-$d_6$) δ 10.38 (s, 2H), 8.69 (s, 2H), 7.80 (d, J = 8.1 Hz, 2H), 7.64 (s, 2H), 7.33 (t, J = 7.8 Hz, 2H), 7.00 (d, J = 7.5 Hz, 2H), 4.40 (s, 4H), 2.38-2.24 (m, 4H), 2.00 (s, 6H), 1.17 (d, J = 8.2 Hz, 4H), 1.06 (d, J = 6.9 Hz, 6H), 0.96 (d, J = 6.8 Hz, 6H), 0.96-0.88 (m, 4H). |
| 127 | ¹H NMR (500 MHz, DMSO-$d_6$) δ 10.31 (s, 2H), 8.50 (s, 2H), 7.88 (d, J = 8.0 Hz, 2H), 7.57 (s, 2H), 7.31 (t, J = 7.8 Hz, 2H), 6.97 (d, J = 7.1 Hz, 2H), 4.08 (q, J = 7.1 Hz, 4H), 4.07(s, 4H), 2.37-2.29 (m, 2H), 1.99 (s, 6H), 1.19 (t, J = 7.1 Hz, 6H), 1.18-1.16 (m, 4H), 1.16-1.09 (m, 4H), 0.99 (q, J = 3.8 Hz, 4H), 0.89-0.81 (m, 4H). |
| 128 (TFA salt) | ¹H NMR (500 MHz, DMSO-$d_6$) δ 10.35 (s, 2H), 8.61 (s, 2H), 7.83 (d, J = 8.0 Hz, 2H), 7.61 (s, 2H), 7.32 (t, J = 7.8 Hz, 2H), 6.99 (d, J = 7.3 Hz, 2H), 4.41 (brs, 4H), 2.39-2.30 (m, 2H), 1.99 (s, 6H), 1.43-1.26 (m, 8H), 1.18 (d, J = 7.9 Hz, 4H), 0.91 (brs, 4H). |
| 129 | ¹H NMR (500 MHz, DMSO-$d_6$) δ 10.32 (s, 2H), 8.49 (s, 2H), 7.86 (d, J = 8.0 Hz, 2H), 7.58 (s, 2H), 7.32 (t, J = 7.8 Hz, 2H), 6.98 (dd, J = 7.6, 1.3 Hz, 2H), 4.10 (q, J = 7.1 Hz, 4H), 3.89 (s, 4H), 3.37 (s, 4H), 2.44 (tt, J = 8.4, 5.3 Hz, 2H), 2.31 (s, 6H), 2.00 (s, 6H), 1.20 (t, J = 7.1 Hz, 6H), 1.17-1.11 (m, 4H), 0.89-0.81 (m, 4H). |
| 130 (TFA salt) | ¹H NMR (500 MHz, DMSO-$d_6$) δ 10.38 (s, 2H), 8.68 (s, 2H), 7.79 (d, J = 8.0 Hz, 2H), 7.62 (s, 2H), 7.33 (t, J = 7.8 Hz, 2H), 7.01 (d, J = 7.5 Hz, 2H), 4.50 (s, 4H), 3.99 (s, 4H), 2.73 (s, 6H), 2.43 (ddd, J = 13.4, 8.6, 5.2 Hz, 2H), 2.00 (s, 6H), 1.21 (brd, J = 8.1 Hz, 4H), 0.95 (brd, J = 4.4 Hz, 4H). |
| 131 | ¹H NMR (500 MHz, DMSO-$d_6$) δ 10.32 (s, 2H), 8.52 (s, 2H), 7.88 (d, J = 8.1 Hz, 2H), 7.58 (s, 2H), 7.32 (t, J = 7.9 Hz, 3H), 6.98 (d, J = 7.7 Hz, 2H), 3.87 (d, J = 13.4 Hz, 2H), 3.83 (d, J = 13.4 Hz, 2H), 3.60 (s, 6H), 3.11-3.01 (m, 2H), 2.78 (t, J = 8.7 Hz, 2H), 2.70 (dd, J = 9.2, 6.3 Hz, 2H), 2.58 (t, J = 7.0 Hz, 4H), 2.38-2.29 (m, 2H), 2.06-1.93 (m, 4H), 2.00 (s, 6H), 1.16-1.09 (m, 4H), 0.89-0.82 (m, 4H). |
| 132 | ¹H NMR (500 MHz, DMSO-$d_6$) δ 10.33 (s, 2H), 8.52 (s, 2H), 7.87 (dd, J = 8.0, 3.7 Hz, 2H), 7.58 (s, 2H), 7.32 (t, J = 7.8 Hz, 2H), 6.98 (d, J = 7.5 Hz, 2H), 3.83 (q, J = 13.6 Hz, 4H), 2.95-2.83 (m, 2H), 2.79-2.71 (m, 2H), 2.69 (t, J = 7.7 Hz, 2H), 2.57 (q, J = 7.8 Hz, 4H), 2.39-2.29 (m, 2H), 2.00 (s, 6H), 2.00-1.89 (m, 4H), 1.17-1.09 (m, 4H), 0.90-0.80 (m, 4H). |

| Example No. | $^1$H-NMR |
|---|---|
| 134 (TFA salt) | $^1$H NMR (500 MHz, DMSO-d$_6$) δ 10.39 (s, 2H), 8.75 (s, 2H), 7.77 (d, J = 8.1 Hz, 2H), 7.62 (s, 2H), 7.33 (t, J = 7.8 Hz, 2H), 7.01 (dd, J = 7.6, 1.3 Hz, 2H), 4.76 (brs, 4H), 3.76 (brs, 4H), 3.62-3.40 (m, 6H), 2.43-2.35 (m, 2H), 2.26 (brs, 2H), 1.99 (s, 6H), 1.23 (d, J = 8.3 Hz, 4H), 1.02-0.91 (m, 4H). |
| 136 | $^1$H NMR (500 MHz, DMSO-d$_6$) δ 10.33 (s, 2H), 8.57 (s, 2H), 7.89 (d, J = 8.3 Hz, 2H), 7.59 (s, 2H), 7.32 (t, J = 7.9 Hz, 2H), 6.98 (d, J = 7.7 Hz, 2H), 3.98 (s, 4H), 3.94-3.89 (m, 2H), 2.62-2.53 (m, 2H), 2.34 (dd, J = 14.8, 4.9 Hz, 2H), 2.31-2.23 (m, 2H), 2.23-2.14 (m, 2H), 2.01 (s, 6H), 1.12 (brd, J = 8.6 Hz, 4H), 0.85 (brd, J = 5.2 Hz, 4H). |
| 137 | $^1$H NMR (500 MHz, DMSO-d$_6$) δ 10.32 (s, 2H), 8.57 (s, 2H), 7.88 (d, J = 7.9 Hz, 2H), 7.69 (s, 2H), 7.59 (s, 2H), 7.31 (t, J = 7.8 Hz, 2H), 6.97(d J = 7.5 Hz, 2H), 3.99 (d, J = 14.1 Hz, 2H), 3.95 (d, J = 14.2 Hz, 2H), 3.69-3.59 (m, 2H), 2.58 (d, J = 6.0 Hz, 4H), 2.28 (ddd, J = 13.6, 8.4, 5.2 Hz, 2H), 2.15-2.03 (m, 6H), 2.00 (s, 6H), 1.75-1.63 (m, 2H), 1.17-1.09 (m, 4H), 0.87-0.81 (m, 4H). |
| 138 | $^1$H NMR (500 MHz, DMSO-d$_6$) δ 10.33 (s, 2H), 8.57 (s, 2H), 7.88 (d, J = 8.0 Hz, 2H), 7.59 (s, 2H), 7.32 (t, J = 7.8 Hz, 2H), 6.98 (d, J = 7.3 Hz, 2H), 4.52 (dt, J = 47.7, 5.0 Hz, 4H), 4.00 (s, 4H), 2.87 (dt, J = 27.6, 5.0 Hz, 4H), 2.32-2.25 (m, 2H), 2.00 (s, 6H), 1.18-1.08 (m, 4H), 0.88-0.82 (m, 4H). |
| 139 | $^1$H NMR (500 MHz, DMSO-d$_6$) δ 10.33 (s, 2H), 8.57 (s, 2H), 7.87 (dd, J = 8.1, 1.3 Hz, 2H), 7.60 (s, 2H), 7.32 (t, J = 7.8 Hz, 2H), 6.98 (dd, J = 7.6, 1.3 Hz, 2H), 6.07 (tt, J = 56.3, 4.2 Hz, 2H), 4.03 (s, 4H), 2.96 (td, J = 15.9, 4.3 Hz, 4H), 2.27 (tt, J = 8.3, 5.2 Hz, 2H), 2.00 (s, 6H), 1.16-1.09 (m, 4H), 0.89-0.81 (m, 4H). |
| 140 | $^1$H NMR (500 MHz, DMSO-d$_6$) δ 10.33 (s, 2H), 8.56 (s, 2H), 7.87 (dd, J = 8.1, 1.3 Hz, 2H), 7.61 (s, 2H), 7.32 (t, J = 7.8 Hz, 2H), 6.98 (dd, J = 7.6, 1.3 Hz, 2H), 4.07 (d, J = 6.0 Hz, 4H), 3.05-2.97 (m, 2H), 2.26 (tt, J = 8.4, 5.2 Hz, 2H), 2.00 (s, 6H), 1.17-1.09 (m, 4H), 0.90-0.81 (m, 4H). |
| 141 | $^1$H NMR (400 MHz, DMSO-d$_6$) δ 10.81 (s, 1H), 10.39 (s, 1H), 8.56-8.49 (m, 3H), 7.96 (d, J = 8.0 Hz, 1H), 7.78 (s, 1H), 7.75 (s, 1H), 7.53 (t, J = 7.9 Hz, 1H), 7.36 (t, J = 7.8 Hz, 1H), 7.13 (dd, J = 7.6, 1.6 Hz, 1H), 7.05 (d, J = 7.7 Hz, 1H), 4.48 (s, 2H), 4.01 (s, 3H), 3.99 (s, 3H), 3.78 (s, 4H), 3.47 (d, J = 5.0 Hz, 4H), 2.58 (t, J = 5.7 Hz, 4H), 2.06 (s, 3H). |
| Positive compound | $^1$H NMR (400 MHz, DMSO-d$_6$) δ 10.33 (s, 1H), 8.58 (s, 1H), 7.98 (s, 1H), 7.86 (dd, J = 8.0, 1.3 Hz, 1H), 7.51-7.44 (m, 2H), 7.42-7.36 (m, 1H), 7.36-7.28 (m, 3H), 7.08 (dd, J = 7.6, 1.3 Hz, 1H), 4.51 (t, J = 5.4 Hz, 1H), 3.83 (s, 2H), 3.49 (q, J = 5.7 Hz, 2H), 2.62 (t, J = 5.8 Hz, 2H), 2.45 (s, 3H), 2.18 (s, 3H). |

Biological Test Evaluation

A. PD1-PDL1 HTRF Binding Activity Test

The effect of compounds and positive compounds of the examples of the present invention on the interaction between PD-1 and PD-L1 was determined by the PD-1/PD-L1 binding assay kit from Cisbio (#64ICP01PEG or 64ICP01PEH). The detailed experimental process was as follows:

1. Pre-diluted compound solution, 4 μL of Tag1-PD-L1 and 4 μL of Tag2-PD1 were added to each well of a 384-well plate;

2. After the mixture was incubated at room temperature for 15 min, 5 μL of anti-Tag1-Eu3+ antibody and 5 μL of anti-Tag2-XL665 antibody were then added;

3. After incubated for 2 hrs at room temperature or overnight at 4° C., plates were read on Envision of Pelkin Elmer; and readings at 665 nm and 620 nm were recorded, and the ratio of the two readings was taken as a reading for each well;

4. The reading of each well after compound treatment was compared with the reading of DMSO treated wells to obtain the percent inhibition of the compound; and 5. IC$_{50}$ values of compounds and positive compounds of the examples of the present invention were determined by non-linear regression analysis of percent inhibition at different compound concentrations. The specific experimental results were shown in Table 1.

B. Jurkat Reporter Gene Cellular Assay

The effect of compounds of the examples of the present invention and positive compounds on the interaction between PD-1 and PD-L1 expressed on cell surfaces, and the related influence on T cell functions, were determined by a Jurkat reporter gene cellular assay.

Briefly, the reporter gene plasmid of NF-κB-luc and the plasmid of human PD-1 were transfected into Jurkat cells to establish a stably transfected cell line capable of stably expressing both PD-1 and NF-κB-Luc reporter genes; the expression level of PD-1 on the cell surface was confirmed by flow cytometry: and the expression of the reporter gene was confirmed via the response of the reporter gene stimulated by OKT-3 and Raiji cells.

In addition, the plasmid of human PD-L1 was transfected into Raji cells to obtain a cell line capable of stably expressing PD-L1. Jurkat/NF-κB-luc/PD1 cells and Raji-PD-L1 cells were then cocultured and stimulated with OKT-3. On this basis, the compounds were added, and the enhancement of the signal pathway of T cell activation by the inhibitory effect of the compounds on the interaction between PD-1 and PD-L1 was evaluated by readings of reporter gene responses. The specific experimental process was as follows:

1. 30 μL of compound or antibody solution was added to each well of a white 96-well plate (coming, 3610) at different diluted concentrations, and 10 μL of OKT3 (Biolegend, 317326) was then added (the final concentration of OKT3:1 μg/mL);

2. 20 μL of Raji-PD-L1 cell suspension was added to each well with 5*10$^4$ cells for each well, and was incubated in an incubator for 20 min;

3. 20 μL of Jurkat/NF-κb-luc/PD-1 cell suspension was added to each well with 5*10$^4$ cells for each well, and well mixed, and 6 hrs later, Bright-glo (Promega, E2620) was applied and plates were read on Envision;

4. the reading of each well treated with the compound was compared with the reading of each well treated with DMSO to obtain the activation fold of the compound; and 5. $EC_{50}$ values of compounds and positive compounds of the examples of the present invention were determined by non-linear regression analysis of activation folds at different compound concentrations. The specific experimental results were shown in Table 1:

TABLE 1

Biological Test Results

| Example No. | PD1-PDL1 HTRF Binding Activity $IC_{50}$/nM | Cell Activity $EC_{50}$/nM | Example No. | PD1-PDL1 HTRF Binding Activity $IC_{50}$/nM | Cell Activity $EC_{50}$/nM |
|---|---|---|---|---|---|
| 1 | 0.17 | 137 | 72 | 0.48 | 1563 |
| 2 | 0.18 | 109 | 73 | 0.29 | 812 |
| 3 | 0.20 | 37 | 74 | 0.14 | 303 |
| 4 | 0.064 | 1336 | 75 | 0.36 | 782 |
| 5 | 0.36 | 64 | 76 | 7.80 | 3064 |
| 6 | 0.79 | 658 | 77 | 0.41 | 297 |
| 7 | 0.096 | 139 | 78 | 10.9 | 2913 |
| 8 | 0.41 | 186 | 79 | 0.65 | 171 |
| 9 | 3.8 | >10000 | 80 | 0.082 | 3742 |
| 10 | 0.28 | 50 | 81 | 0.43 | 900 |
| 11 | 0.60 | 134 | 82 | 1.90 | 566 |
| 12 | 1.9 | 594 | 83 | 1.04 | 309 |
| 13 | 0.13 | 109 | 84 | 1.36 | 603 |
| 14 | 227 | NT | 85 | 0.45 | 341 |
| 15 | 0.83 | 511 | 86 | 1.34 | 406 |
| 16 | 0.14 | 310 | 87 | 1.08 | 800 |
| 17 | 1.5 | >10000 | 88 | 0.41 | 182 |
| 18 | 0.34 | 209 | 89 | 0.87 | 427 |
| 19 | 0.15 | 86 | 90 | 0.36 | 131 |
| 20 | 0.36 | 4216 | 91 | 0.16 | 39 |
| 21 | 0.66 | 83 | 92 | 0.87 | 54.7 |
| 22 | 0.28 | 5170 | 93 | 1.49 | 104 |
| 23 | 0.31 | 249 | 94 | 4.75 | 566 |
| 24 | 3.20 | 1047 | 95 | 2.02 | 125 |
| 25 | 0.37 | 124 | 96 | 1.44 | 87 |
| 26 | 65.3 | NT | 97 | 3.38 | 221 |
| 27 | 0.28 | 128 | 98 | 3.78 | 241 |
| 28 | 9.55 | >10000 | 99 | 1.43 | 260 |
| 29 | 0.36 | 1464 | 100 | 1.51 | 121.7 |
| 30 | 1.24 | 448 | 101 | 1.09 | 267 |
| 31 | 1.0 | 2083 | 102 | 3.61 | 194 |
| 32 | 0.27 | 53 | 103 | 4.11 | 206 |
| 33 | 0.65 | 109 | 104 | 1.57 | 296 |
| 34 | 0.21 | 111 | 105 | 0.27 | 14.1 |
| 35 | 1.11 | 257 | 106 | 22.5 | 1263 |
| 36 | 0.74 | 456 | 107 | 15.2 | 752.9 |
| 37 | 0.040 | 118 | 108 (TFA salt) | 0.84 | 42.3 |
| 38 | 0.83 | 6998 | 109 | 375 | >10000 |
| 39 | 0.86 | 225 | 110 (TFA salt) | 0.67 | 51 |
| 40 | 0.29 | 172 | 111 | 79.4 | 5948 |
| 41 | 0.032 | 74 | 112 (TFA salt) | 1.02 | 34.6 |
| 42 | 0.28 | 60 | 113 | 6.77 | 979 |
| 43 | 0.29 | 11 | 114 (TFA salt) | 5.2 | 89 |
| 44 | 0.24 | 55 | 115 | >400 | >10000 |
| 45 | 0.22 | 41 | 116 (TFA salt) | 0.94 | 1340 |
| 46 | 0.25 | 64 | 117 | >400 | >10000 |
| 47 | 0.27 | 46 | 118 (TFA salt) | 1.17 | 1042 |
| 48 | 0.31 | 102 | 119 | >400 | >10000 |
| 49 | 0.33 | 104 | 120 (Li salt) | 1.43 | 1761 |
| 50 | 0.33 | 229 | 121 (TFA salt) | 16.6 | 1341 |
| 51 | 0.22 | 288 | 122 (TFA salt) | 1.14 | 19 |
| 52 | 0.40 | 508 | 123 | 22.0 | 2409 |
| 53 | 0.15 | 52 | 124 (TFA salt) | 1.09 | 14.7 |
| 54 | 0.21 | 4768 | 125 | >2000 | >10000 |
| 55 | 0.40 | 82 | 126 (TFA salt) | 1.11 | 64 |
| 56 | 0.64 | 172 | 127 | 112.7 | >10000 |
| 57 | 0.36 | | 128 (TFA salt) | 1.32 | 77.8 |
| 58 | 0.22 | 625 | 129 | 101.5 | >10000 |
| 59 | 0.31 | 70 | 130 (TFA salt) | 0.99 | 600 |
| 60 | 0.034 | 580 | 131 | 21.8 | 2579 |
| 61 | 0.18 | 319 | 132 | 0.20 | 23.1 |
| 62 | 0.25 | 639 | 133 | 11.8 | 1899 |
| 63 | 0.25 | 4600 | 134 (TFA salt) | 0.82 | 21.0 |
| 64 | 10.7 | 1862 | 136 | 0.32 | 27.4 |
| 65 | 0.12 | 132 | 137 | 2.07 | 108 |
| 66 | 0.64 | 691 | 138 | 5.03 | 581 |
| 67 | 0.51 | 349 | 139 | 119.7 | >10000 |
| 68 | 0.31 | 261 | 140 | 15.1 | 2711 |
| 69 | 0.39 | 105 | 141 | 0.75 | 74 |
| 70 | 0.54 | 2200 | Positive compound | 2.4 | >10000 |
| 71 | 0.33 | 756 | | | |

Notes
1. "NT" is an abbreviation of "Not Tested", and means that an object has not been detected yet.
2. The positive compound is the compound of example 33 of patent WO2017106634, and has a chemical structure shown as follows:

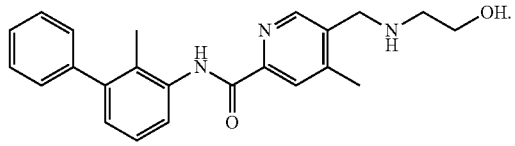 [SMILES: Cc1cc(C(=O)Nc2cccc(-c3ccccc3)c2C)ncc1CNCCO]

The bioactivity data of the compounds of the specific examples indicates that the series of compounds of the present invention have a strong inhibitory effect on the interaction between PD-1 and PD-L1, and moreover, such an inhibitory effect can enhance or recover the activation of T cells at the cellular level.

C. Pharmacokinetic Assay in Mice

1. Purpose of Study

The purpose of this study was to study the pharmacokinetic behaviors of some compounds of the present invention, and administration routes were: per oral administration (PO) to ICR mice:

1). 10 mg/kg: examples 1, 3, 5, 8, 46, 104 and 141.
2). 30 mg/kg: examples 4, 26 and 64.

2. Testing Scheme 2.1 Tested Medicaments

The compounds used in this test came from the compounds of the specific examples of the present invention.

2.2 Tested Animal

ICR mice male N=3 original source: Shanghai Sippr-BK Laboratory Animal Co. Ltd.

2.3 Preparation and Administration of Medicaments

The compounds were weighed, and dissolved in solvent of 0.5% SDS+0.5% CMCNa. The mixture solutions were mixed well by shaking and ultrasonic treatment to obtain colorless clear solutions. The solutions were orally administered to nine mice after an overnight fast. The dosage of administration was 10 mg/kg (or 30 mg/kg).

2.4 Sampling

With about 90 μL/time point, blood was drawn from the submaxillary vein, and heparin sodium was added for anticoagulation. The blood samples were placed onto the ice, and were centrifuged (centrifugation conditions: 8000 r/min, 6 min, 2-8° C.) within 1 hr to obtain plasmas. The time points for blood sampling were at 0 hr, 0.25 hr, 0.5 hr, 1 hr, 2 hrs, 4 hrs, 6 hrs, 8 hrs and 24 hrs after administration. The samples were stored in a refrigerator at −20° C.

40 μL of plasma sample was added to 160 μL of cold acetonitrile containing an internal standard, and the mixture solution was vortexed for 3 min and centrifuged at 11,000 r/min for 5 min. 100 μL of supernate was taken and added to 100 μL of water, and 5 μL of the sample was taken and analyzed by LC/MS/MS. Only the original compounds were analyzed for examples 1, 3, 5, 8, 46 and 141 (for results, see table 2); and both the original compounds and possible products of ester hydrolysis, namely example 2, 27, 65 and 105, were analyzed for examples 4, 26, 64 and 104 (for results, see table 3).

2.5 Test Results

TABLE 2

PK Results for Per Oral Administration (PO) of 10 mg/kg of Compounds to Mice

| Compound No. | $C_{max}$ (ng/mL) | $T_{max}$ (h) | $AUC_{last}$ (hr * ng/mL) | $T_{1/2}$ (h) | MRT (h) |
|---|---|---|---|---|---|
| 1 | * | 1 | + | 2.4 | 3.3 |
| 3 | ** | 0.5 | +++ | 12.9 | 16.7 |
| 5 | ** | 2 | 1685 | 8.3 | 10.2 |
| 8 | 319 | 2 | ++ | 3 | 5.4 |
| 46 | * | 4 | ++ | 10.7 | 15.5 |
| 141 | BQL | NA | NA | NA | NA |

TABLE 3

PK Results for Per Oral Administration (PO) of Compounds to Mice

| Compound No. | Tested Compound | $C_{max}$ (ng/mL) | $T_{max}$ (h) | $AUC_{last}$ (hr * ng/mL) | $T_{1/2}$ (h) | MRT (h) |
|---|---|---|---|---|---|---|
| 4 | 4 | BQL | NA | NA | NA | NA |
|  | 2 | 6480 | 0.5 | 8901 | 1.6 | 1.6 |
| 26 | 26 | *** | 6 | +++ | 3.6 | 7 |
|  | 27 | BQL | NA | NA | NA | NA |
| 64 | 64 | *** | 2 | +++ | 3.7 | 4.6 |
|  | 65 | BQL | NA | NA | NA | NA |
| 104* | 104 | BQL | NA | NA | NA | NA |
|  | 105 | 1813 | 0.5 | 3968 | 20 | 17 |

Notes: The dosage of administration of example 104* is 10 mpk. In Table 2 and Table 3:

1. "BQL" means that it is below the detection limit of the instrument. "NA" means it is ineffective or none.
2. "+++" means $AUC_{last}$ (hr*ng/mL)>2,000; "++" means 500<$AUC_{last}$ (hr*ng/mL)≤2,000; "+" means $AUC_{last}$ (hr*ng/mL)≤500.
3. "*" means $C_{max}$ (ng/mL)>500; "" means 100<$C_{max}$ (ng/mL)≤500;
"*" means $C_{max}$ (ng/mL)≤100.

Example 4 and example 104 were absorbed into the bodies of the mice by oral administration, and rapidly became corresponding acids (example 2 and example 105) via ester hydrolysis. Compared with example 2, the in-vivo metabolism of example 105 significantly slowed down, and the half-life period was prolonged to 20 hrs from 1.6 hrs. The methyl piperidine-2-carboxylate compounds (example 26 and example 64) were orally administered to the mice, and existed almost only as the original forms in their bodies, and no product of ester hydrolysis was detected.

All documents mentioned in the present invention are incorporated by reference, just as each document is cited separately as a reference. In addition, it should be understood that various modifications or changes may be made by those skilled in the art after reading the above teachings of the present invention, and these equivalent forms also fall within the scope defined by the claims appended hereto.

We claim:

1. A compound of formula (III), the stereoisomer, prodrug or pharmaceutically acceptable salt thereof:

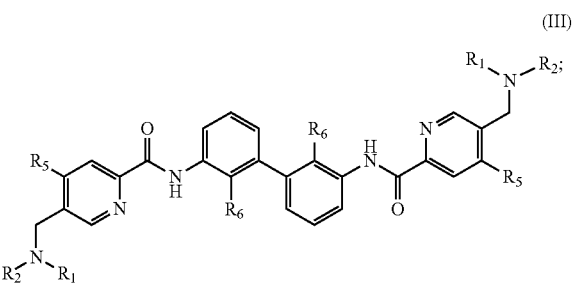

(III)

wherein, $R_6$ is methyl, $R_5$ is selected from the group consisting of hydrogen, deuterium, methyl, ethyl, isopropyl, cyclopropyl, cyclobutyl, and methoxy, $R_1$ and $R_2$ are each independently selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, $C_{3-10}$ cycloalkyl $C_{1-8}$ alkyl, 3-10 membered heterocyclyl, 3-10 membered heterocyclyl $C_{1-8}$ alkyl, $C_{5-10}$ aryl, $C_{5-10}$ aryl $C_{1-8}$ alkyl, and 5-10 membered heteroaryl, or $R_1$ and $R_2$, together with the nitrogen atom directly attached thereto, form 3-10 membered heterocyclyl, above groups are optionally further substituted by one or more substituents selected from the group consisting of deuterium, halogen, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$ alkyl-S(O)(=N—$R_7$)$R_9$, —$C_{0-8}$ alkyl-N=S(O)$R_9R_{10}$, —$C_{0-8}$ alkyl-N=SR$_9R_{10}$, —$C_{0-8}$ alkyl-P(O)(OH)$R_{12}$, —$C_{0-8}$ alkyl-SF$_5$, —$C_{0-8}$ alkyl-O—S(O)$_2R_{12}$, —$C_{0-8}$ alkyl-S(O)$_rR_{12}$, —$C_{0-8}$ alkyl-O—$R_{13}$, —$C_{0-8}$ alkyl-C(O)(O)$_rR_{13}$, —$C_{0-8}$ alkyl-C(O)$R_{14}$, —$C_{0-8}$ alkyl-O—C(O)$R_{14}$, —$C_{0-8}$ alkyl-NR$_{15}R_{16}$, —$C_{0-8}$ alkyl-C(=NR$_{15}$)$R_{14}$, —$C_{0-8}$ alkyl-N(R$_{15}$)—C(=NR$_{16}$)$R_{14}$, —$C_{0-8}$ alkyl-C(O)NR$_{15}R_{16}$ and —$C_{0-8}$ alkyl-N(R$_{15}$)—C(O)$R_{14}$;

$R_7$ is selected from the group consisting of hydrogen, deuterium, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —$C_{0-8}$ alkyl-S(O)$_rR_{12}$, —$C_{0-8}$ alkyl-C(O)OR$_{13}$, —$C_{0-8}$ alkyl-C(O)$R_{14}$, and —$C_{0-8}$ alkyl-C(O)NR$_{15}R_{16}$, above groups are optionally further substituted by one or more substituents selected from the group consisting of deuterium, halogen, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, —$C_{0-8}$ alkyl-S(O)$_rR_{12}$, —$C_{0-8}$ alkyl-O—

R$_{13}$, —C$_{0-8}$ alkyl-C(O)OR$_{13}$, —C$_{0-8}$ alkyl-C(O)R$_{14}$, —C$_{0-8}$ alkyl-O—C(O)R$_{14}$, —C$_{0-8}$ alkyl-NR$_{15}$R$_{16}$, —C$_{0-8}$ alkyl-C(=NR$_{15}$)R$_{14}$, —C$_{0-8}$ alkyl-N(R$_{15}$)—C(=NR$_{16}$)R$_{14}$, —C$_{0-8}$ alkyl-C(O)NR$_{15}$R$_{16}$ and —C$_{0-8}$ alkyl-N(R$_{15}$)—C(O)R$_{14}$;

R$_9$ and R$_{10}$ are each independently selected from the group consisting of hydrogen, deuterium, hydroxy, C$_{1-10}$ alkyl, C$_{2-10}$ alkenyl, C$_{2-10}$ alkynyl, C$_{3-10}$ cycloalkyl, 3-10 membered heterocyclyl, C$_{5-10}$ aryl, and 5-10 membered heteroaryl, or R$_9$ and R$_{10}$, together with the sulfur atom directly attached thereto, form 3-10 membered heterocyclyl, above groups are optionally further substituted by one or more substituents selected from the group consisting of deuterium, halogen, C$_{1-10}$ alkyl, C$_{2-10}$ alkenyl, C$_{2-10}$ alkynyl, C$_{1-10}$ haloalkyl, C$_{1-10}$ deuterioalkyl, C$_{3-10}$ cycloalkyl, 3-10 membered heterocyclyl, C$_{5-10}$ aryl, 5-10 membered heteroaryl, —C$_{0-8}$ alkyl-S(O)$_r$R$_{12}$, —C$_{0-8}$ alkyl-O—R$_{13}$, —C$_{0-8}$ alkyl-C(O)OR$_{13}$, —C$_{0-8}$ alkyl-C(O)R$_{14}$, —C$_{0-8}$ alkyl-O—C(O)R$_{14}$, —C$_{0-8}$ alkyl-NR$_{15}$R$_{16}$, —C$_{0-8}$ alkyl-C(=NR$_{15}$)R$_{14}$, —C$_{0-8}$ alkyl-N(R$_{15}$)—C(=NR$_{16}$)R$_{14}$, —C$_{0-8}$ alkyl-C(O)NR$_{15}$R$_{16}$ and —C$_{0-8}$ alkyl-N(R$_{15}$)—C(O)R$_{14}$;

each R$_{12}$ is independently selected from the group consisting of hydrogen, deuterium, hydroxy, halogen, C$_{1-10}$ alkyl, C$_{1-10}$ alkoxy, C$_{2-10}$ alkenyl, C$_{3-10}$ cycloalkyl, C$_{3-10}$ cycloalkyloxy, 3-10 membered heterocyclyl, 3-10 membered heterocyclyloxy, C$_{5-10}$ aryl, C$_{5-10}$ aryloxy, 5-10 membered heteroaryl, 5-10 membered heteroaryloxy and —NR$_{15}$R$_{16}$, above groups are optionally further substituted by one or more substituents selected from the group consisting of deuterium, halogen, hydroxy, carbonyl, C$_{1-10}$ alkyl, C$_{1-10}$ alkoxy, C$_{3-10}$ cycloalkyl, C$_{3-10}$ cycloalkyloxy, 3-10 membered heterocyclyl, 3-10 membered heterocyclyloxy, C$_{5-10}$ aryl, C$_{5-10}$ aryloxy, 5-10 membered heteroaryl, 5-10 membered heteroaryloxy and —NR$_{15}$R$_{16}$;

each R$_{13}$ is independently selected from the group consisting of hydrogen, deuterium, C$_{1-10}$ alkyl, C$_{2-10}$ alkenyl, C$_{3-10}$ cycloalkyl, 3-10 membered heterocyclyl, C$_{5-10}$ aryl, and 5-10 membered heteroaryl, above groups are optionally further substituted by one or more substituents selected from the group consisting of deuterium, halogen, hydroxy, carbonyl, C$_{1-10}$ alkyl, C$_{1-10}$ alkoxy, C$_{3-10}$ cycloalkyl, C$_{3-10}$ cycloalkyloxy, 3-10 membered heterocyclyl, 3-10 membered heterocyclyloxy, C$_{5-10}$ aryl, C$_{5-10}$ aryloxy, 5-10 membered heteroaryl, 5-10 membered heteroaryloxy and —NR$_{15}$R$_{16}$;

each R$_{14}$ is independently selected from the group consisting of hydrogen, deuterium, hydroxy, C$_{1-10}$ alkyl, C$_{1-10}$ alkoxy, C$_{2-10}$ alkenyl, C$_{2-10}$ alkynyl, C$_{3-10}$ cycloalkyl, C$_{3-10}$ cycloalkyloxy, 3-10 membered heterocyclyl, 3-10 membered heterocyclyloxy, C$_{5-10}$ aryl, C$_{5-10}$ aryloxy, 5-10 membered heteroaryl, 5-10 membered heteroaryloxy, and —NR$_{15}$R$_{16}$, above groups are optionally further substituted by one or more substituents selected from the group consisting of deuterium, halogen, hydroxy, C$_{1-10}$ alkyl, C$_{1-10}$ alkoxy, C$_{3-10}$ cycloalkyl, C$_{3-10}$ cycloalkyloxy, 3-10 membered heterocyclyl, 3-10 membered heterocyclyloxy, C$_{5-10}$ aryl, C$_{5-10}$ aryloxy, 5-10 membered heteroaryl, 5-10 membered heteroaryloxy and —NR$_{15}$R$_{16}$;

R$_{15}$ and R$_{16}$ are each independently selected from the group consisting of hydrogen, deuterium, hydroxy, C$_{1-10}$ alkoxy, C$_{1-10}$ alkyl, C$_{2-10}$ alkenyl, C$_{2-10}$ alkynyl, C$_{3-10}$ cycloalkyl, 3-10 membered heterocyclyl, C$_{5-10}$ aryl, 5-10 membered heteroaryl, sulfinyl, sulfonyl, methanesulfonyl, isopropylsulfonyl, cyclopropylsulfonyl, p-toluenesulfonyl, aminosulfonyl, dimethylaminosulfonyl, amino, monoalkylamino, dialkylamino, and C$_{1-10}$ alkanoyl, above groups are optionally further substituted by one or more substituents selected from the group consisting of deuterium, halogen, hydroxy, C$_{1-10}$ alkyl, C$_{2-10}$ alkenyl, C$_{2-10}$ alkynyl, C$_{1-10}$ haloalkyl, C$_{1-10}$ deuterioalkyl, C$_{1-10}$ alkoxy, C$_{3-10}$ cycloalkyl, C$_{3-10}$ cycloalkyloxy, 3-10 membered heterocyclyl, 3-10 membered heterocyclyloxy, C$_{5-10}$ aryl, C$_{5-10}$ aryloxy, 5-10 membered heteroaryl, 5-10 membered heteroaryloxy, amino, monoalkylamino, dialkylamino and C$_{1-10}$ alkanoyl; or, R$_{15}$ and R$_{16}$, together with the nitrogen atom directly attached thereto, form 4-10 membered heterocyclyl or 4-10 membered heteroaryl, above groups are optionally further substituted by one or more substituents selected from the group consisting of deuterium, halogen, hydroxy, C$_{1-10}$ alkyl, C$_{2-10}$ alkenyl, C$_{2-10}$ alkynyl, C$_{1-10}$ haloalkyl, C$_{1-10}$ deuterioalkyl, C$_{1-10}$ alkoxy, C$_{3-10}$ cycloalkyl, C$_{3-10}$ cycloalkyloxy, 3-10 membered heterocyclyl, 3-10 membered heterocyclyloxy, C$_{5-10}$ aryl, C$_{5-10}$ aryloxy, 5-10 membered heteroaryl, 5-10 membered heteroaryloxy, amino, monoalkylamino, dialkylamino, and C$_{1-10}$ alkanoyl;

and each r is 0, 1 or 2.

2. The compound of formula (III), the stereoisomer, prodrug or pharmaceutically acceptable salt thereof of claim 1, wherein the compound of formula (III) is a compound with the structure shown as formula (IVa), (IVb), (IVc) or (IVd):

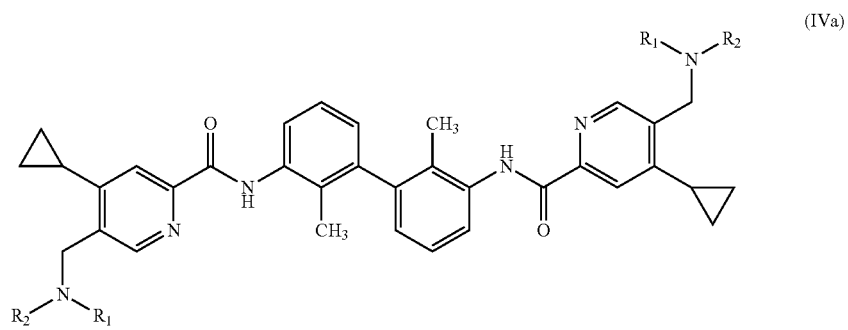

(IVa)

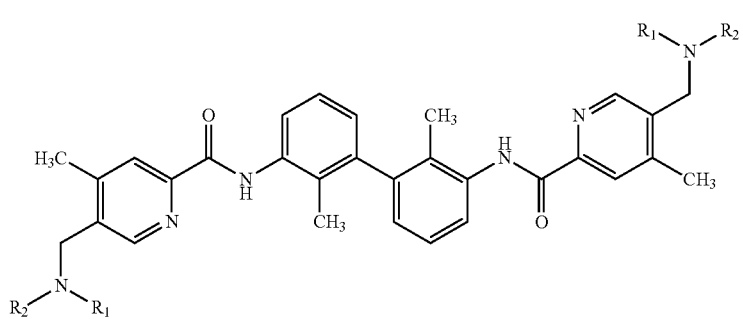

(IVb)

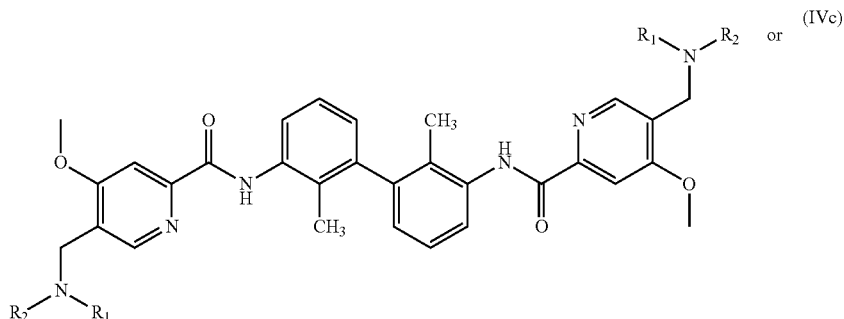

(IVc) or

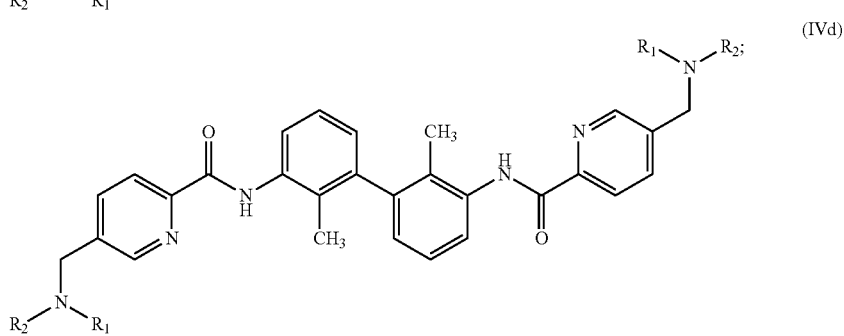

(IVd)

3. The compound of formula (III), the stereoisomer, prodrug or pharmaceutically acceptable salt thereof of claim 1, wherein, $R_1$ and $R_2$ are each independently selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, $C_{3-8}$ cycloalkyl $C_{1-4}$ alkyl, 3-8 membered heterocyclyl, $C_{5-8}$ aryl, and 5-8 membered heteroaryl, or $R_1$ and $R_2$, together with the nitrogen atom directly attached thereto, form 3-8 membered heterocyclyl, the heteroatom in the heterocyclyl is selected from the group consisting of N, O, S and/or Si, above groups are optionally further substituted by one or more substituents selected from the group consisting of deuterium, halogen, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —S(O)(=N—$R_7$)$R_9$, —N=S(O)$R_9R_{10}$, —N=S$R_9R_{10}$, —P(O)(OH)$R_{12}$, —SF$_5$, —O—S(O)$_2R_{12}$, —S(O)$_rR_{12}$, —O—$R_{13}$, —C(O)O$R_{13}$, —C(O)$R_{14}$, —O—C(O)$R_{14}$, —N$R_{15}R_{16}$, —C(=N$R_{15}$)$R_{14}$, —N($R_{15}$)—C(=N$R_{16}$)$R_{14}$, —C(O)N$R_{15}R_{16}$ and —N($R_{15}$)—C(O)$R_{14}$.

4. The compound of formula (III), the stereoisomer, prodrug or pharmaceutically acceptable salt thereof of claim 3, wherein, $R_1$ is hydrogen, deuterium or methyl; $R_2$ is selected from the group consisting of hydrogen, deuterium, hydroxy, $C_{1-4}$ alkyl, $C_{3-8}$ cycloalkyl, $C_{3-8}$ cycloalkyl $C_{1-4}$ alkyl, 3-8 membered heterocyclyl, $C_{5-8}$ aryl, and 5-8 membered heteroaryl, or $R_1$ and $R_2$, together with the nitrogen atom directly attached thereto, form 3-8 membered heterocyclyl, the heteroatom in the heterocyclyl is selected from the group consisting of N, O, S and/or Si, above groups are optionally further substituted by one or more substituents selected from the group consisting of deuterium, halogen, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —S(O)(=N—$R_7$)$R_9$, —N=S(O)$R_9R_{10}$, —N=S$R_9R_{10}$, —P(O)(OH)$R_{12}$, —SF$_5$, —O—S(O)$_2R_{12}$, —S(O)$_rR_{12}$, —O—$R_{13}$, —C(O)O$R_{13}$, —C(O)$R_{14}$, —O—C(O)$R_{14}$, —N$R_{15}R_{16}$, —C(=N$R_{15}$)$R_{14}$, —N($R_{15}$)—C(=N$R_{16}$)$R_{14}$, —C(O)N$R_{15}R_{16}$ and —N($R_{15}$)—C(O)$R_{14}$;

$R_7$ is selected from the group consisting of hydrogen, deuterium, $C_{1-4}$ alkyl, $C_{2-4}$ alkenyl, $C_{3-6}$ cycloalkyl, 3-6 membered heterocyclyl, phenyl, 5-8 membered heteroaryl, methanesulfonyl, and acetyl, above groups are optionally further substituted by one or more substituents selected from the group consisting of deuterium, fluorine, chlorine, hydroxy, methyl, ethyl, trifluoromethyl, difluoromethyl, trideuteriomethyl, dideuteriomethyl, cyclopropyl, phenyl, diazole, triazole, methoxy, ethoxy, carboxyl, methoxycarbonyl, ethoxycarbonyl, acetyl, acetoxy, amino and dimethylamino;

$R_9$ and $R_{10}$ are each independently selected from the group consisting of hydrogen, deuterium, hydroxy, $C_{1-4}$ alkyl, $C_{2-4}$ alkenyl, $C_{3-6}$ cycloalkyl, 3-6 membered heterocyclyl, phenyl, and 5-8 membered heteroaryl, or $R_9$ and $R_{10}$, together with the sulfur atom directly attached thereto, form 3-6 membered heterocyclyl, above groups are optionally further substituted by one or more substituents selected from the group consisting of deuterium, fluorine, chlorine, hydroxy, methyl, ethyl, trifluoromethyl, difluoromethyl, trideuteriomethyl, dideuteriomethyl, cyclopropyl, phenyl, diazole, triazole, methoxy, ethoxy, carboxyl, methoxycarbonyl, ethoxycarbonyl, acetyl, acetoxy, amino and dimethylamino;

each $R_{12}$ is independently selected from the group consisting of hydrogen, deuterium, hydroxy, halogen, $C_{1-4}$ alkyl, $C_{3-6}$ cycloalkyl, 3-6 membered heterocyclyl, phenyl, 5-8 membered heteroaryl, and $—NR_{15}R_{16}$, above groups are optionally further substituted by one or more substituents selected from the group consisting of deuterium, fluorine, chlorine, hydroxy, carbonyl, $C_{1-4}$ alkyl, $C_{1-4}$ alkoxy, $C_{3-6}$ cycloalkyl, $C_{3-6}$ cycloalkyloxy, 3-6 membered heterocyclyl, phenyl, 5-8 membered heteroaryl, amino and dimethylamino;

each $R_{13}$ is independently selected from the group consisting of hydrogen, deuterium, $C_{1-4}$ alkyl, $C_{2-4}$ alkenyl, $C_{3-6}$ cycloalkyl, 3-6 membered heterocyclyl, phenyl, and 5-8 membered heteroaryl, above groups are optionally further substituted by one or more substituents selected from the group consisting of deuterium, halogen, hydroxy, carbonyl, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, phenyl, phenoxy, 5-8 membered heteroaryl, 5-8 membered heteroaryloxy and $—NR_{15}R_{16}$;

each $R_{14}$ is independently selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-6}$ cycloalkyl, $C_{3-6}$ cycloalkyloxy, 3-6 membered heterocyclyl, 3-6 membered heterocyclyloxy, phenyl, phenoxy, 5-8 membered heteroaryl, 5-8 membered heteroaryloxy, and $—NR_{15}R_{16}$, above groups are optionally further substituted by one or more substituents selected from the group consisting of deuterium, halogen, hydroxy, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, phenyl, phenoxy, 5-8 membered heteroaryl, 5-8 membered heteroaryloxy and $—NR_{15}R_{16}$;

each of $R_{15}$ and $R_{16}$ is independently selected from the group consisting of hydrogen, deuterium, hydroxy, $C_{1-4}$ alkoxy, $C_{1-4}$ alkyl, $C_{2-4}$ alkenyl, $C_{2-4}$ alkynyl, $C_{3-6}$ cycloalkyl, 3-6 membered heterocyclyl, phenyl, 5-8 membered heteroaryl, sulfinyl, sulfonyl, methanesulfonyl, isopropylsulfonyl, cyclopropylsulfonyl, p-toluenesulfonyl, aminosulfonyl, dimethylaminosulfonyl, amino, monoalkylamino, dialkylamino, and $C_{1-4}$ alkanoyl, above groups are optionally further substituted by one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, phenyl, phenoxy, 5-8 membered heteroaryl, 5-8 membered heteroaryloxy, amino, monoalkylamino, dialkylamino and $C_{1-4}$ alkanoyl; or, $R_{15}$ and $R_{16}$, together with the nitrogen atom directly attached thereto, form 4-6 membered heterocyclyl or 4-6 membered heteroaryl, above groups are optionally further substituted by one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, phenyl, phenoxy, 5-8 membered heteroaryl, 5-8 membered heteroaryloxy, amino, monoalkylamino, dialkylamino and $C_{1-4}$ alkanoyl.

5. The compound of formula (III), the stereoisomer, prodrug or pharmaceutically acceptable salt thereof of claim 1, wherein the compound is selected from the following compounds:

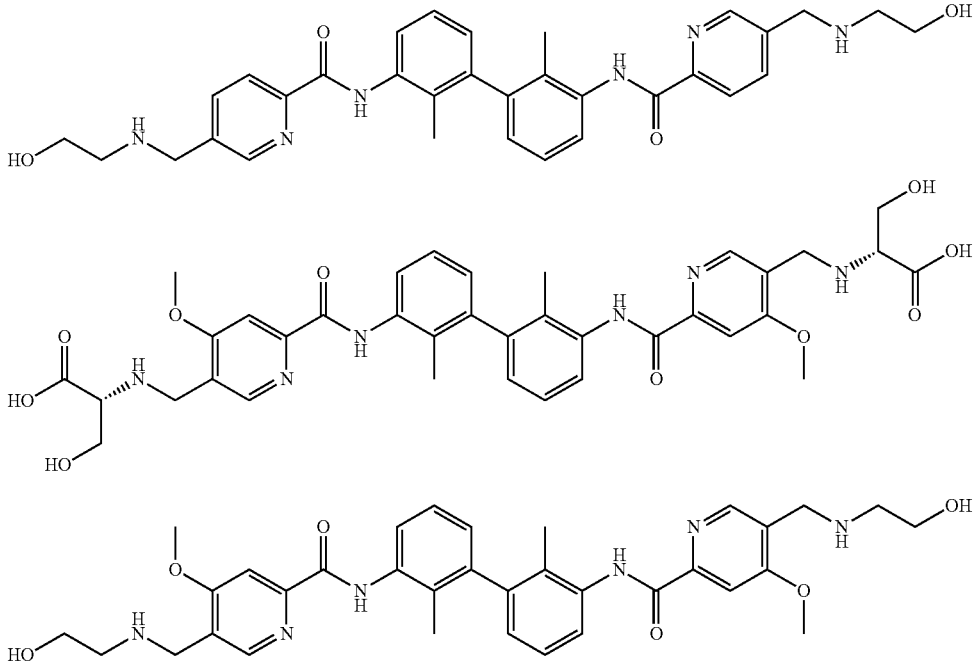

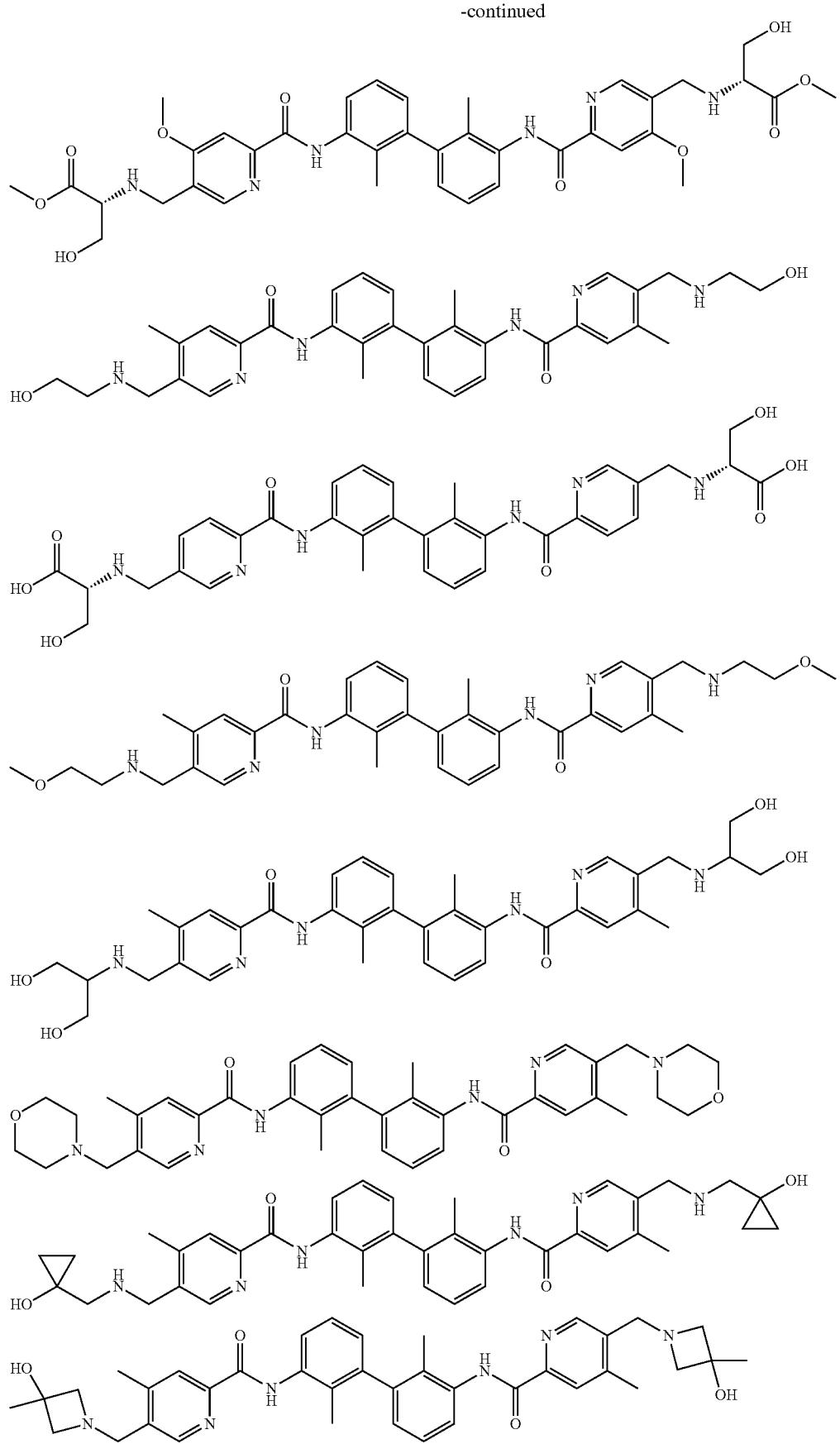

191 192
-continued
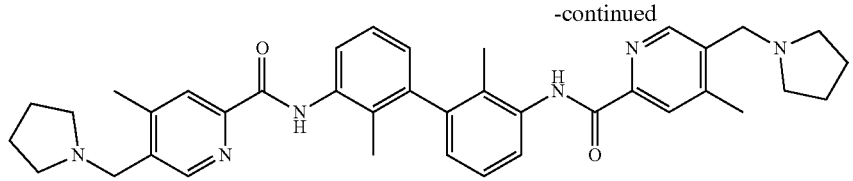
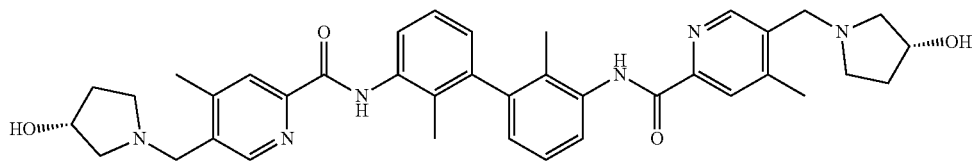
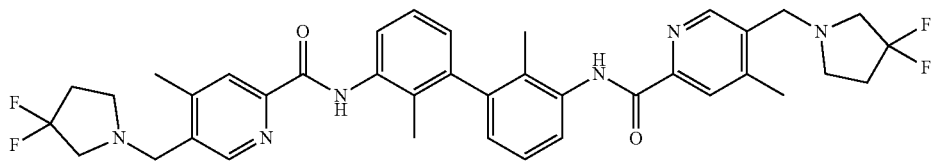
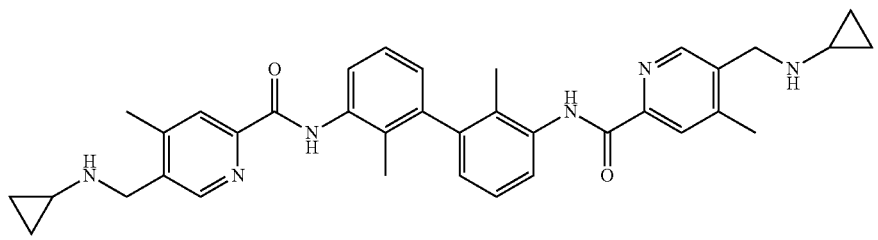
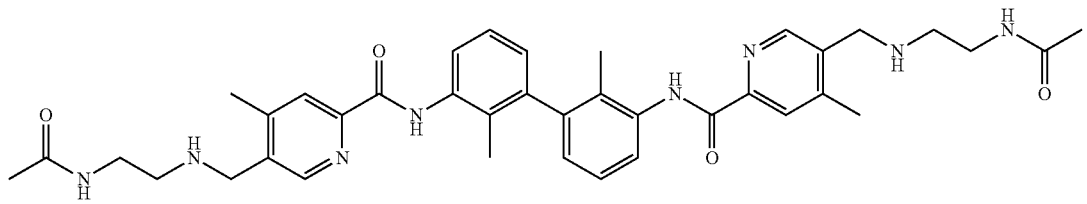
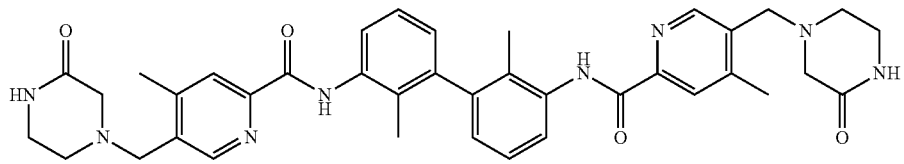
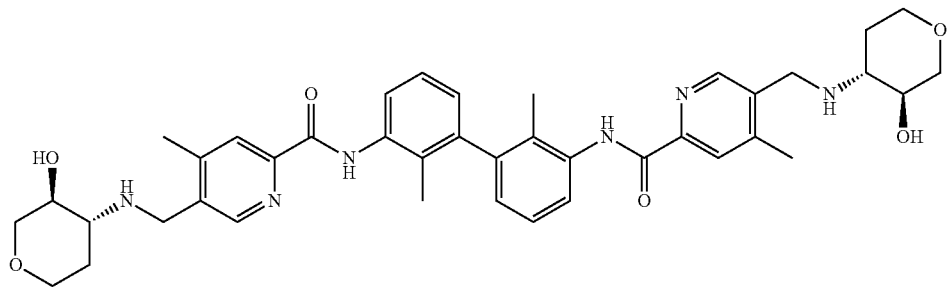
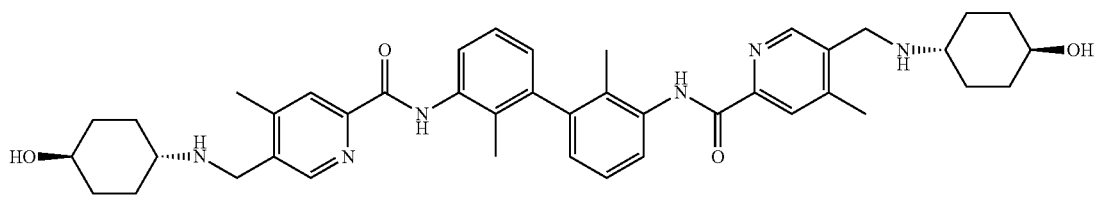

193 194
-continued
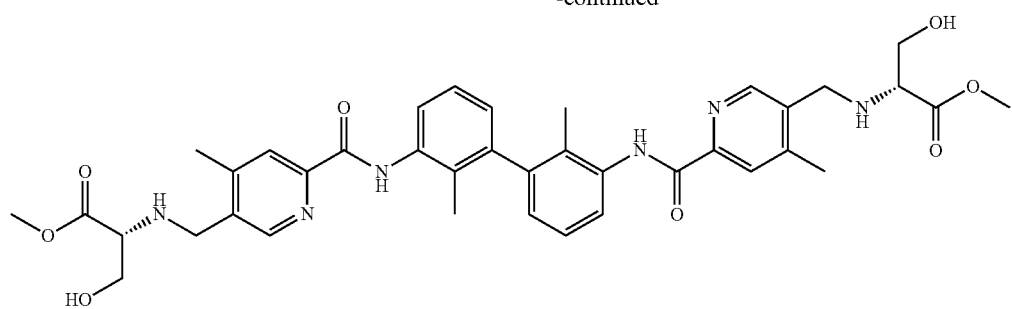
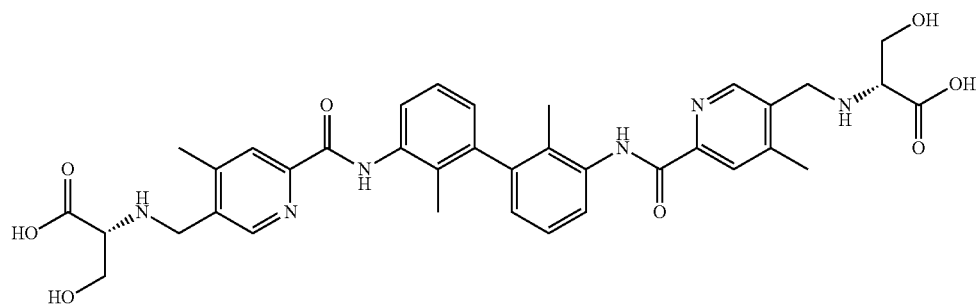
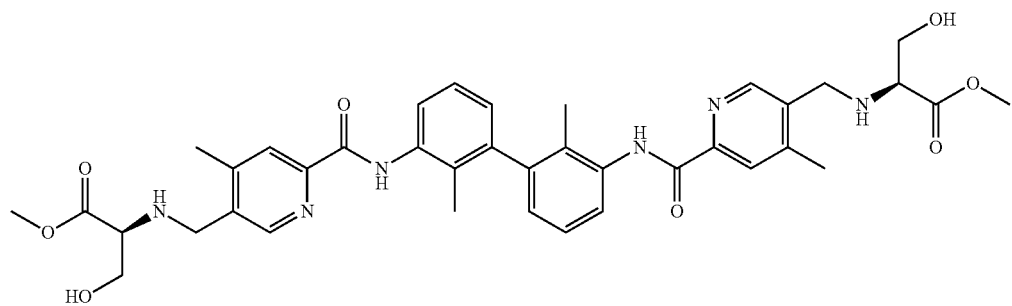
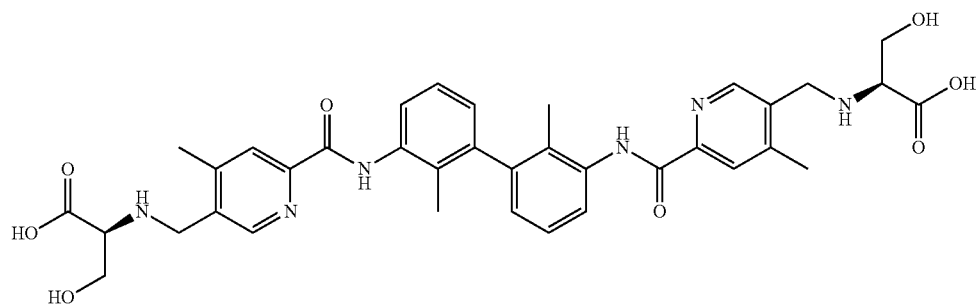
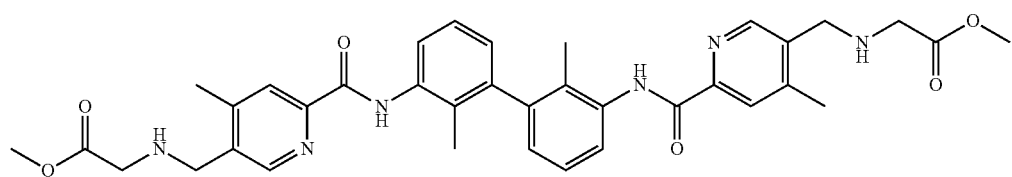
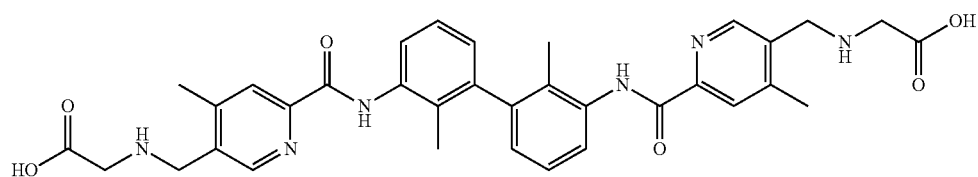

-continued
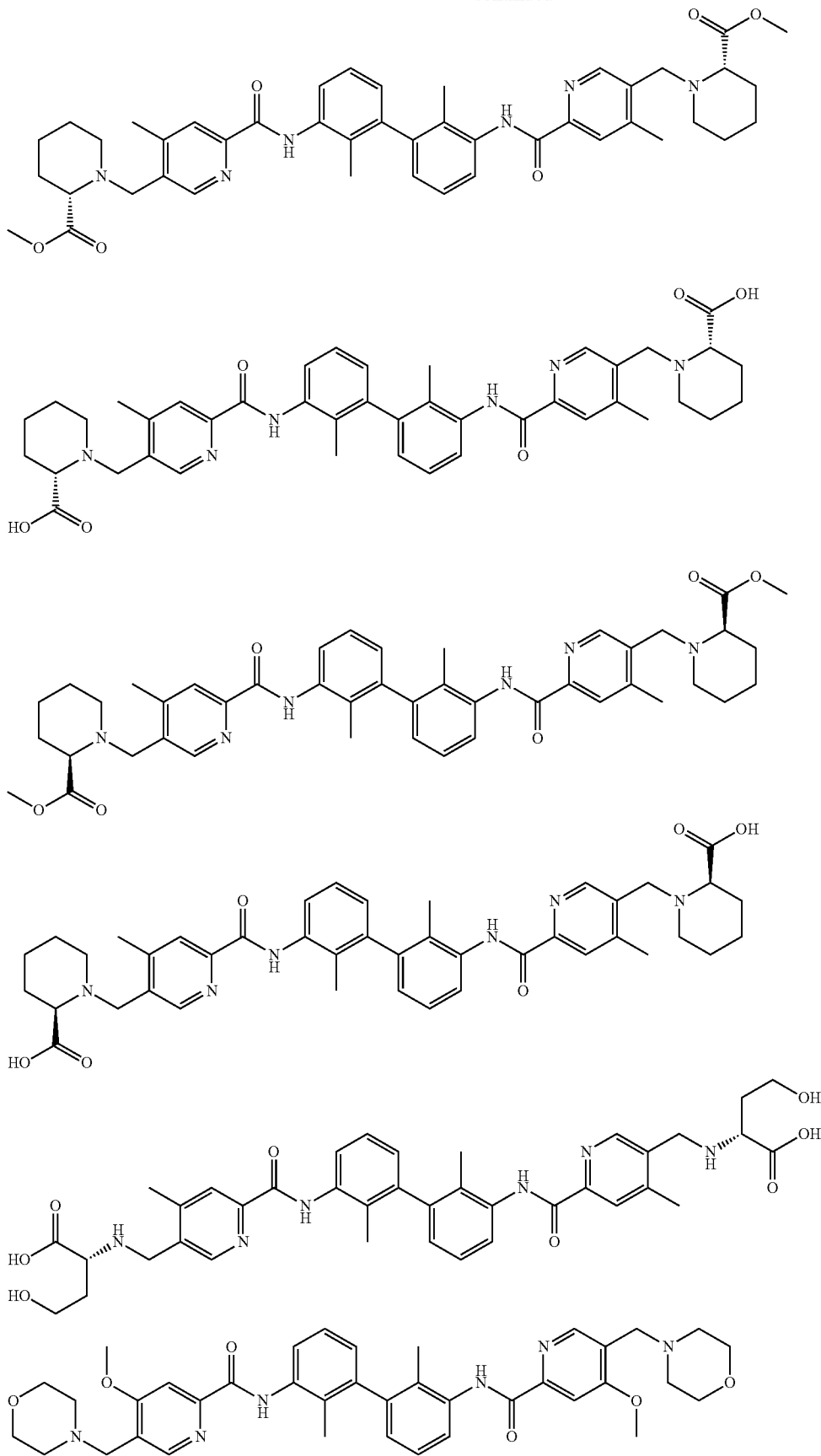

-continued
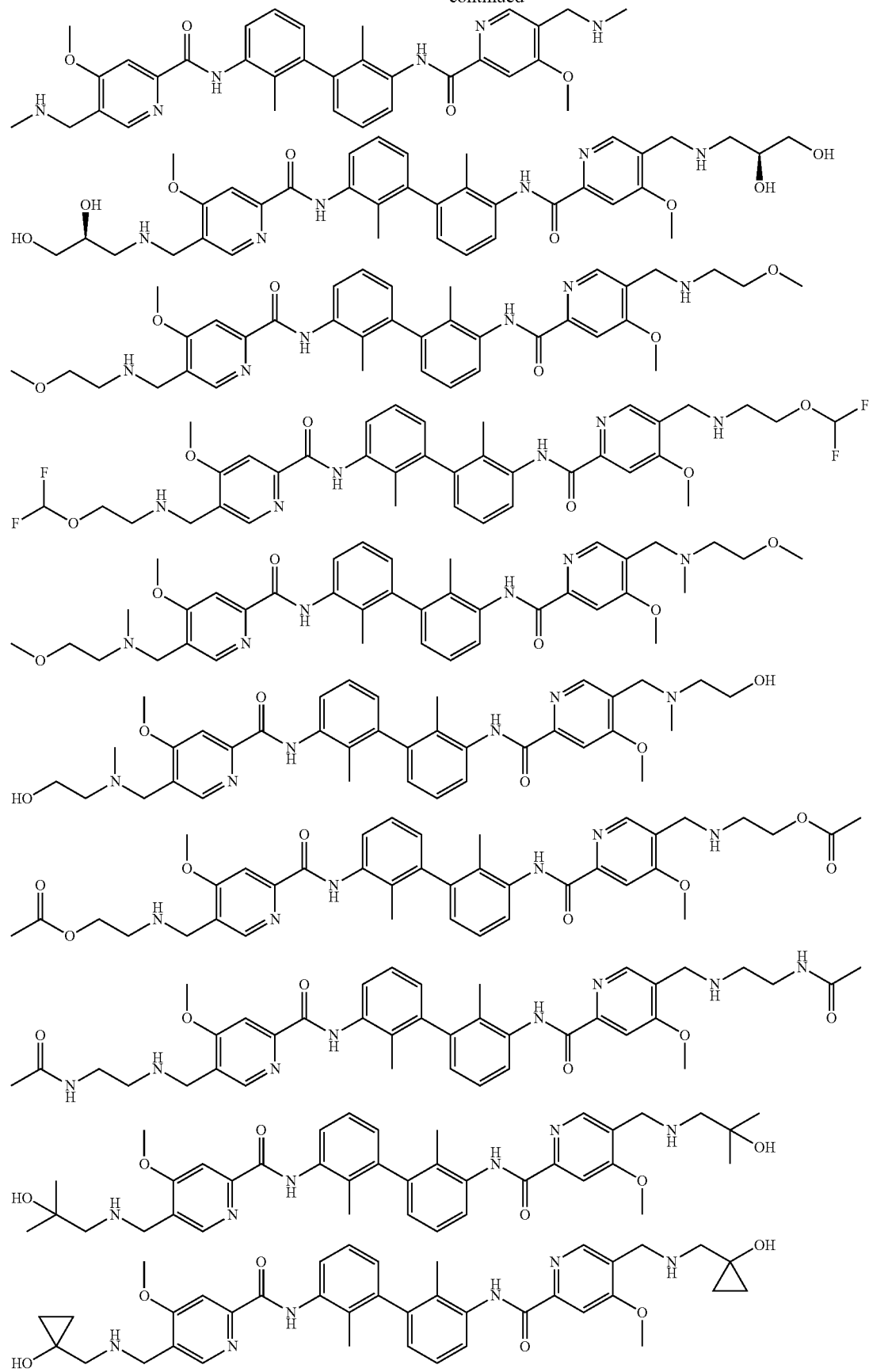

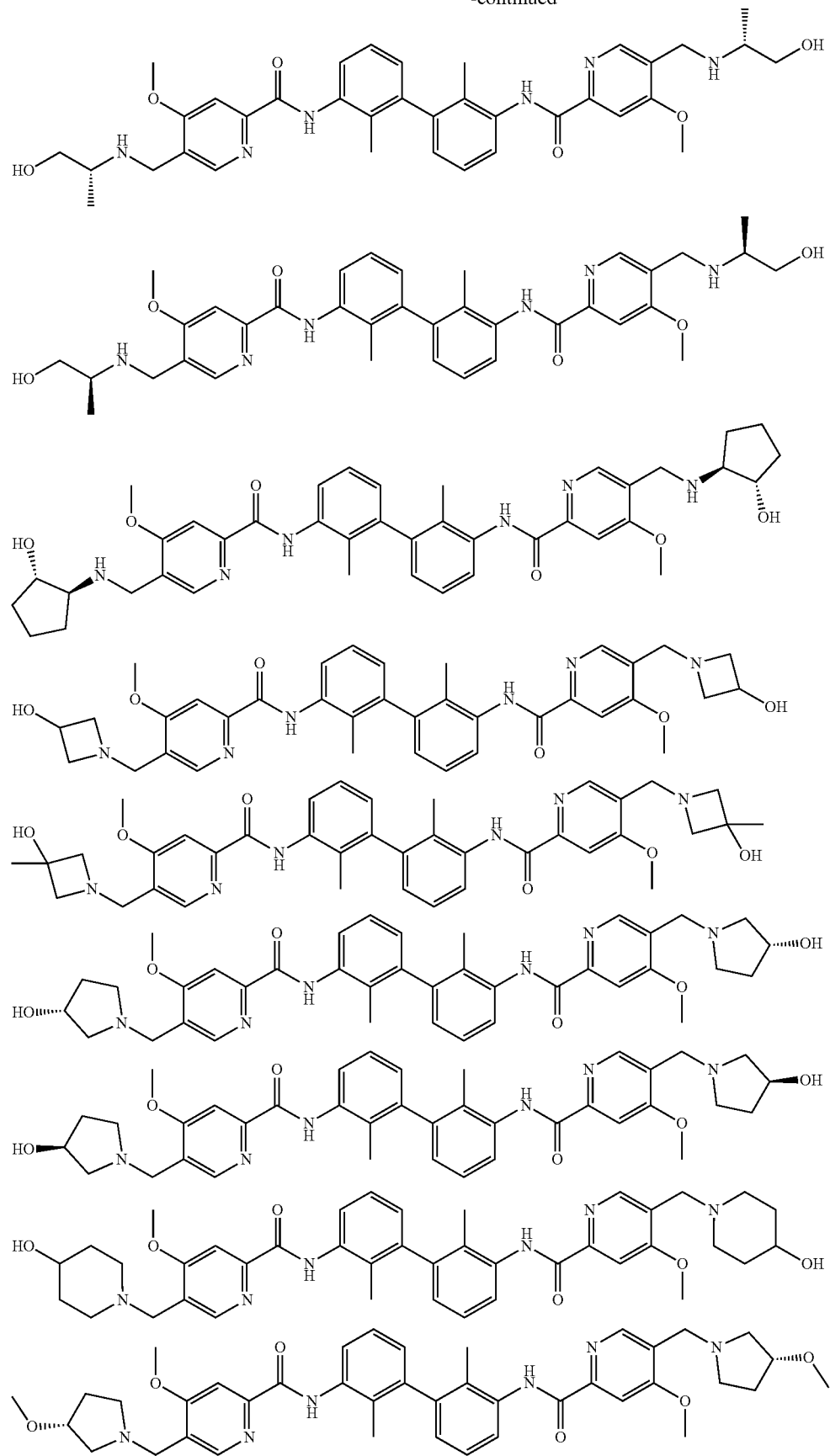

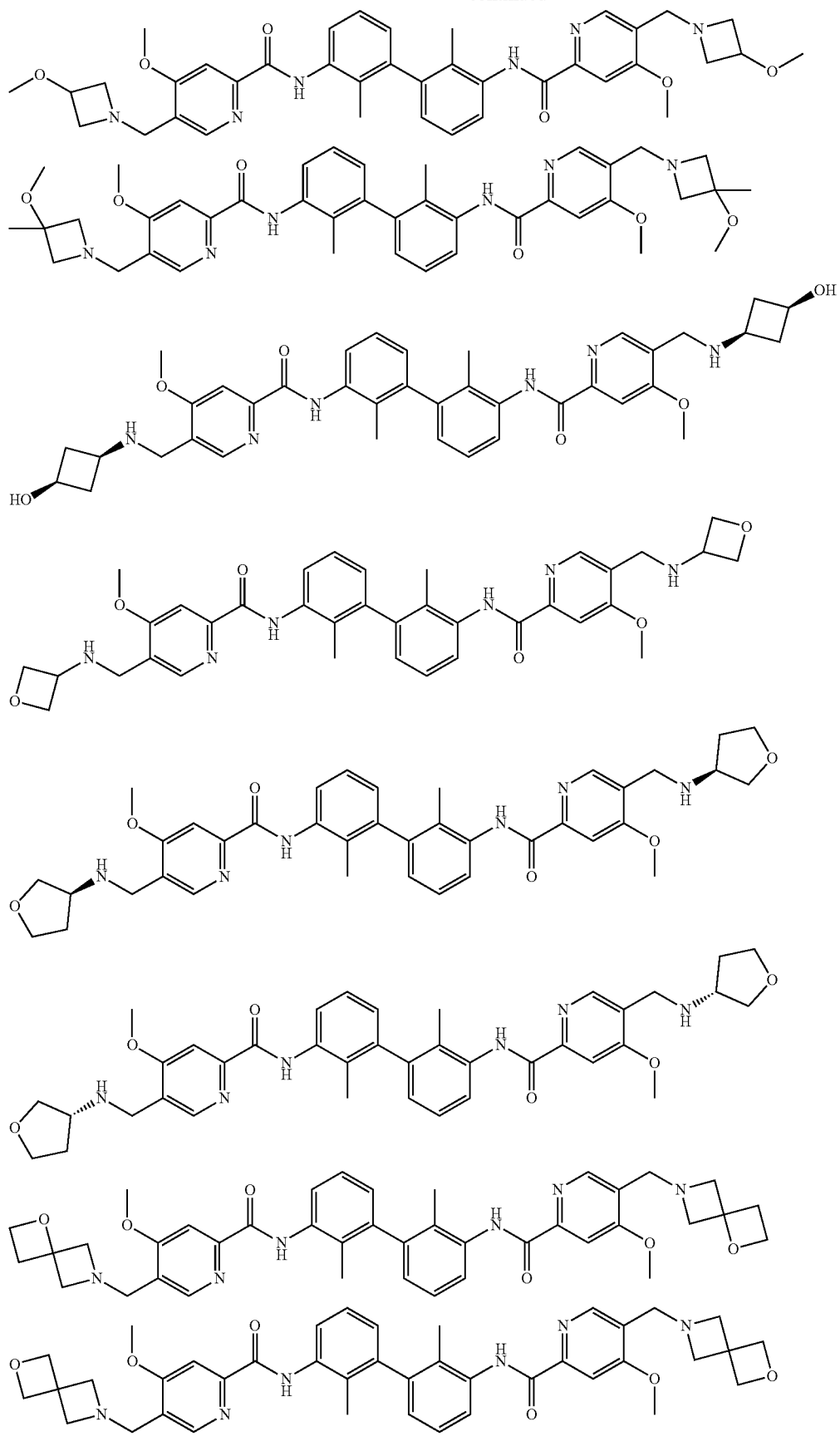

203  204
-continued
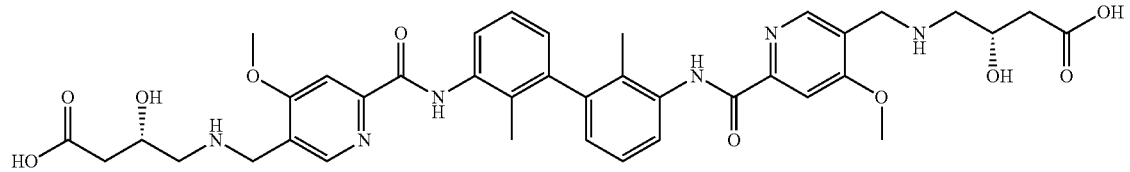
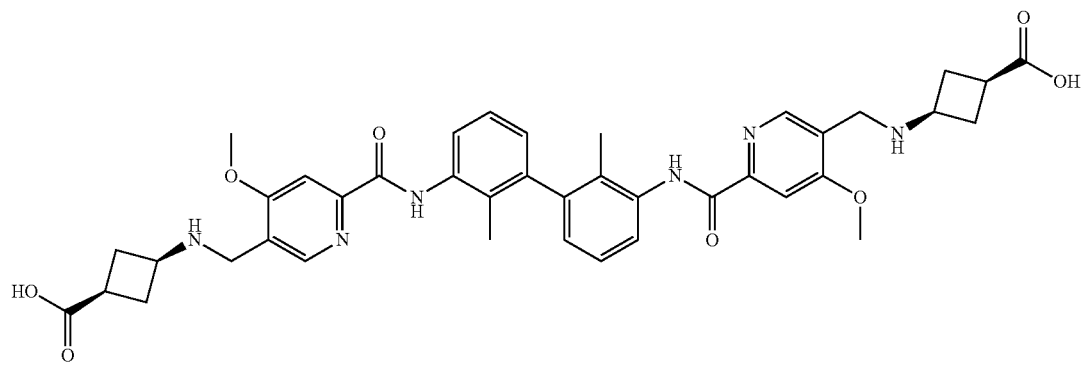
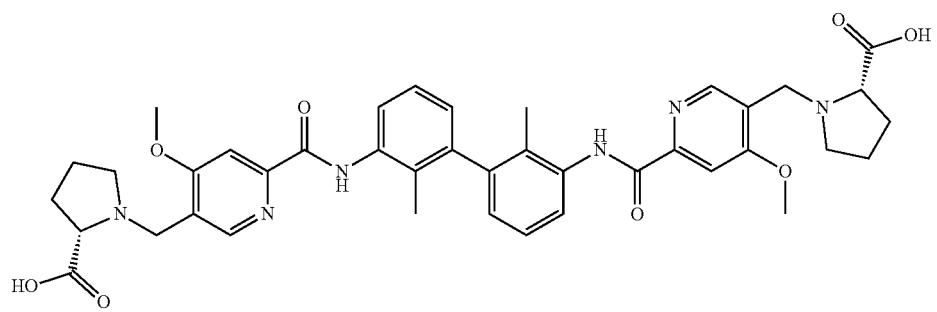
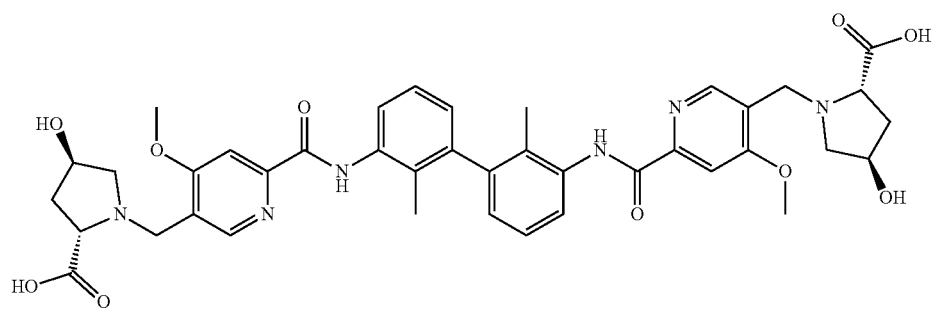
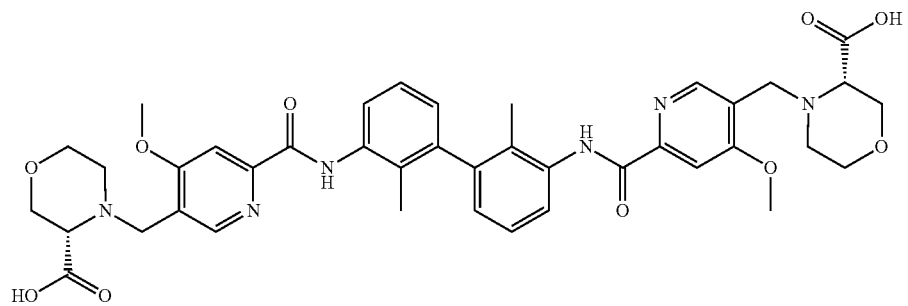

-continued
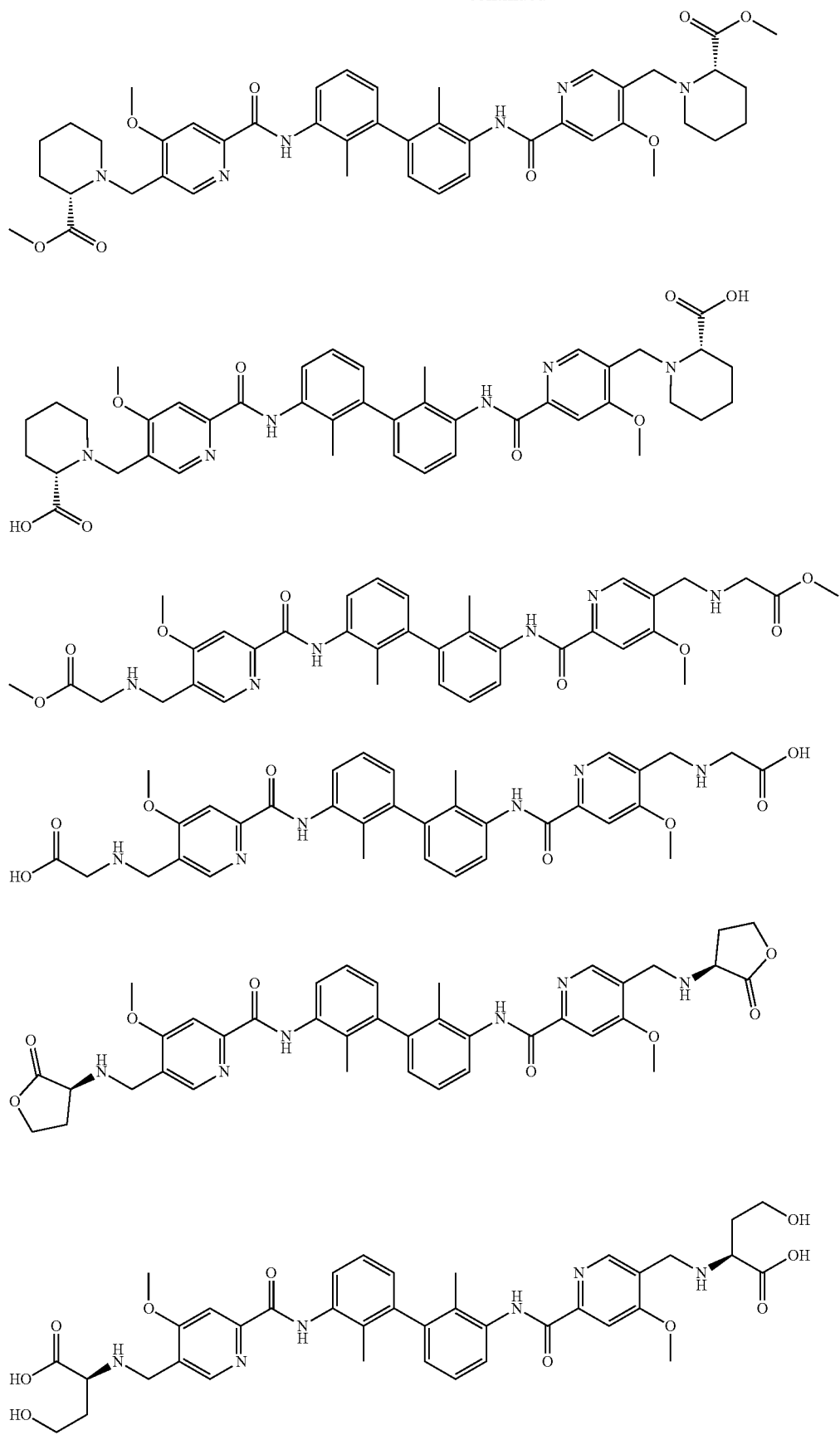

207                                                                           208
-continued
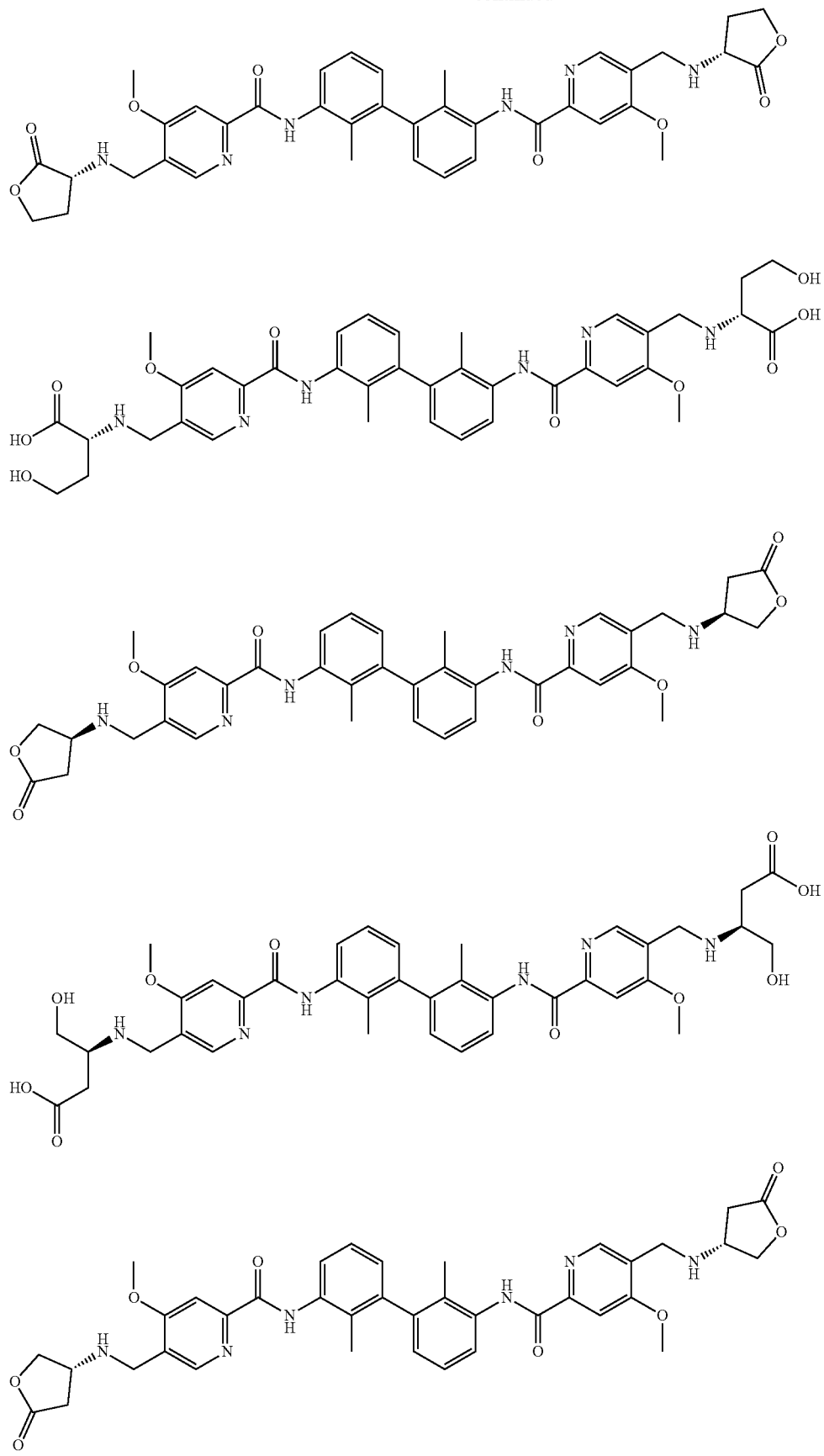

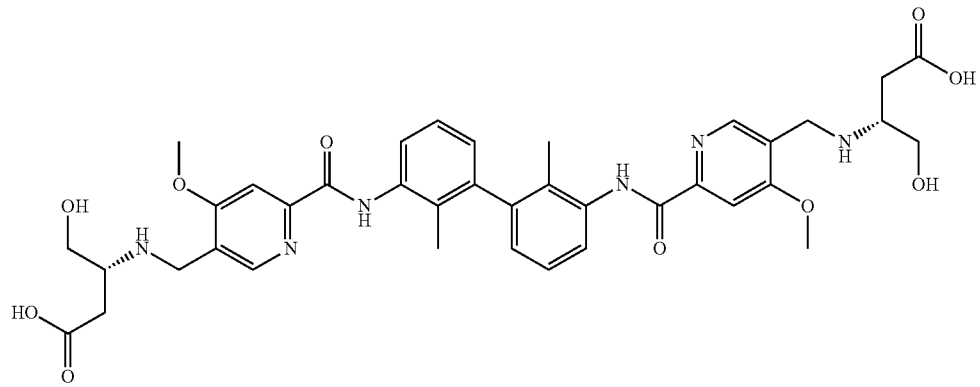
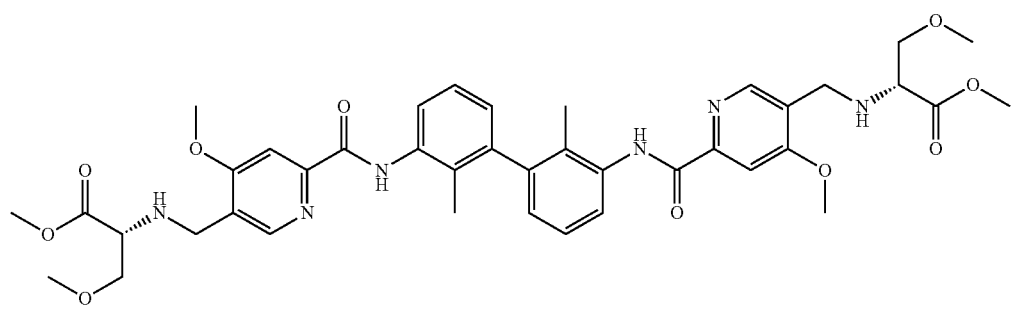
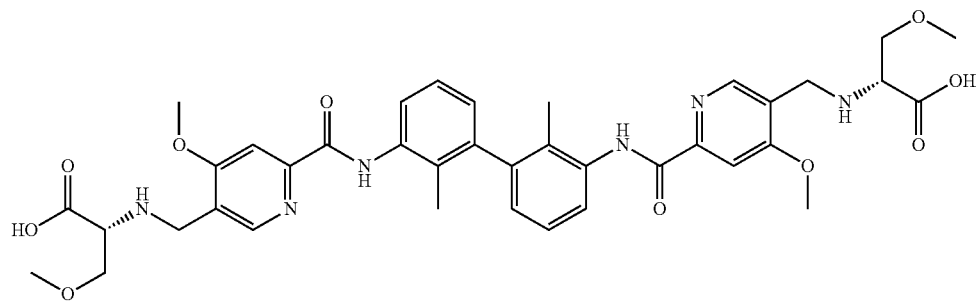
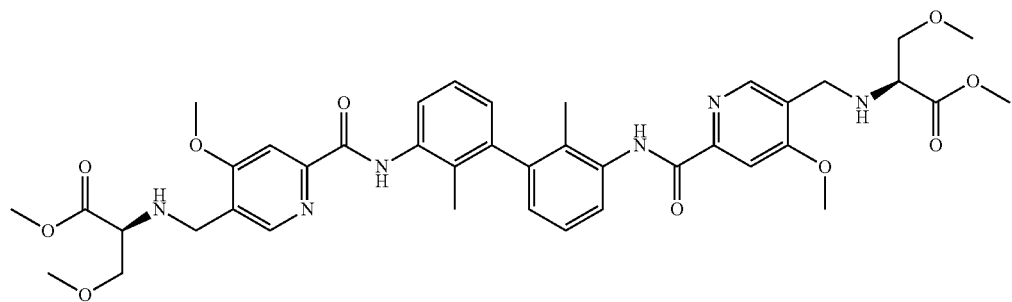
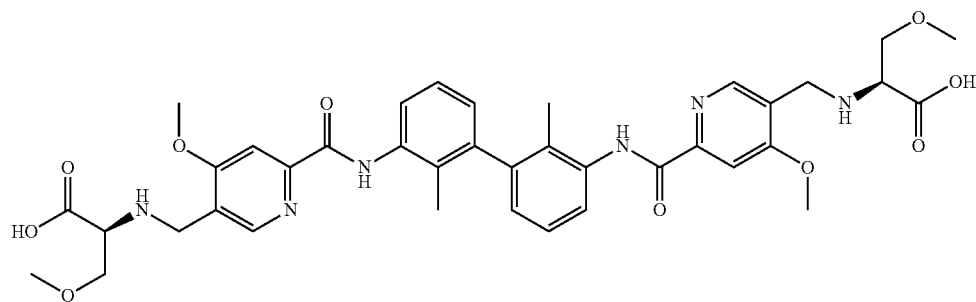

211 212
-continued
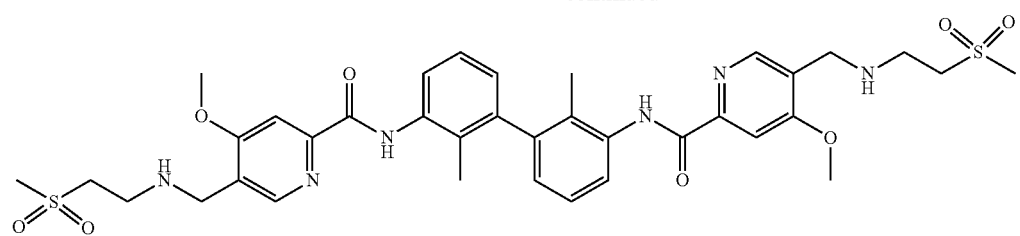
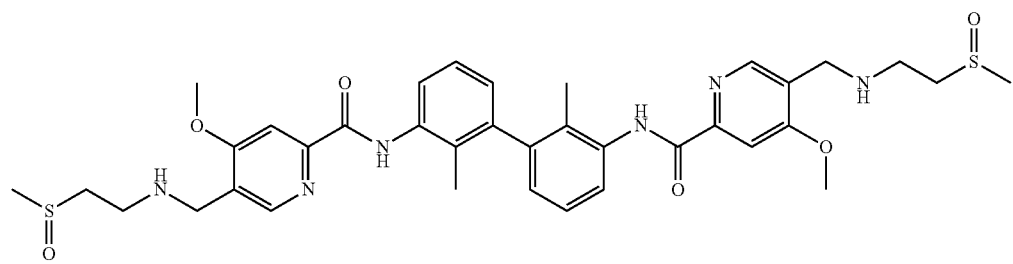
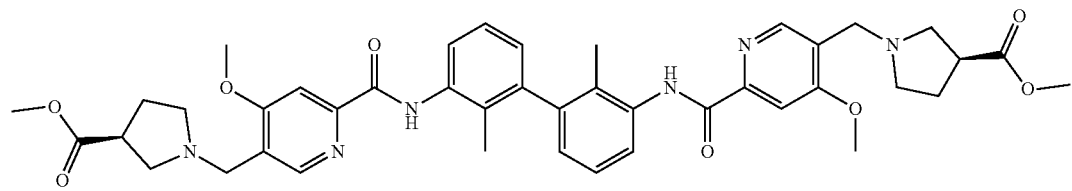
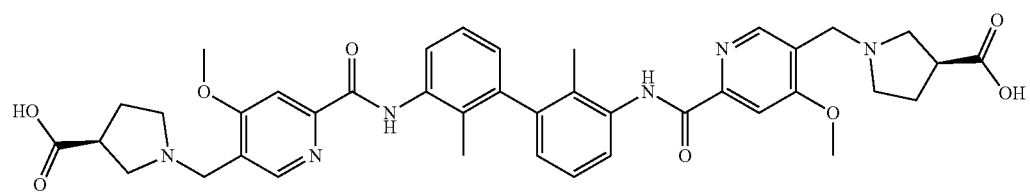
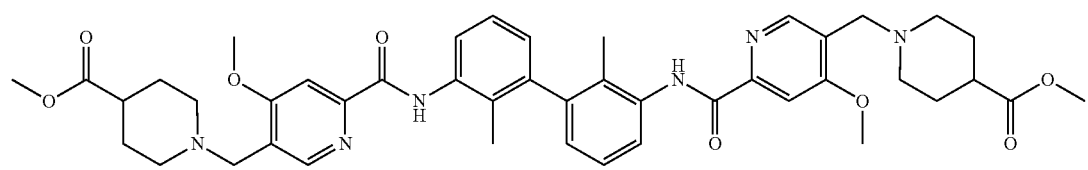
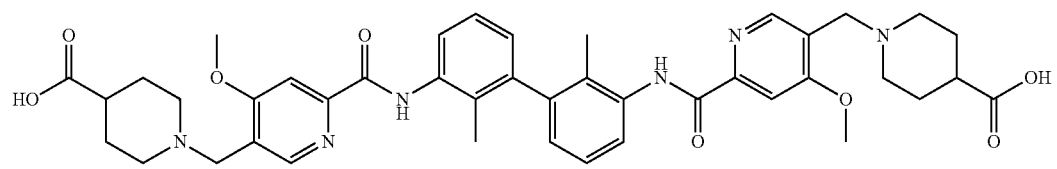
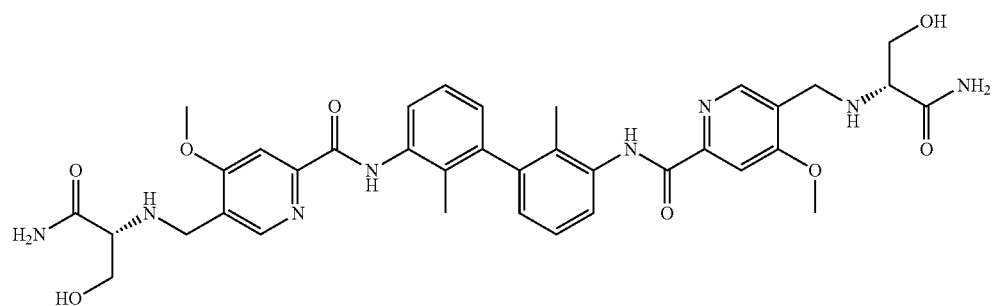

213 214
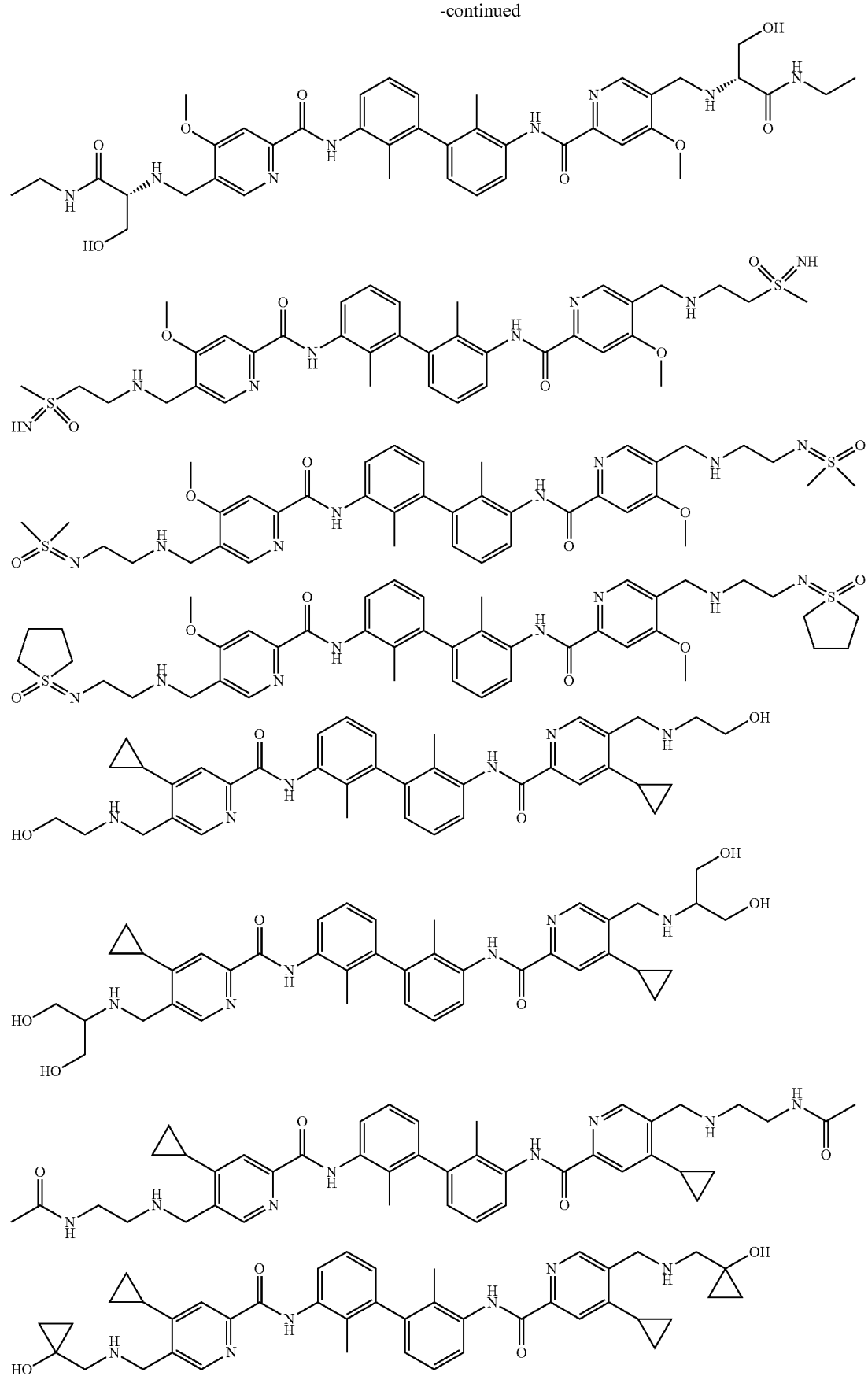

-continued
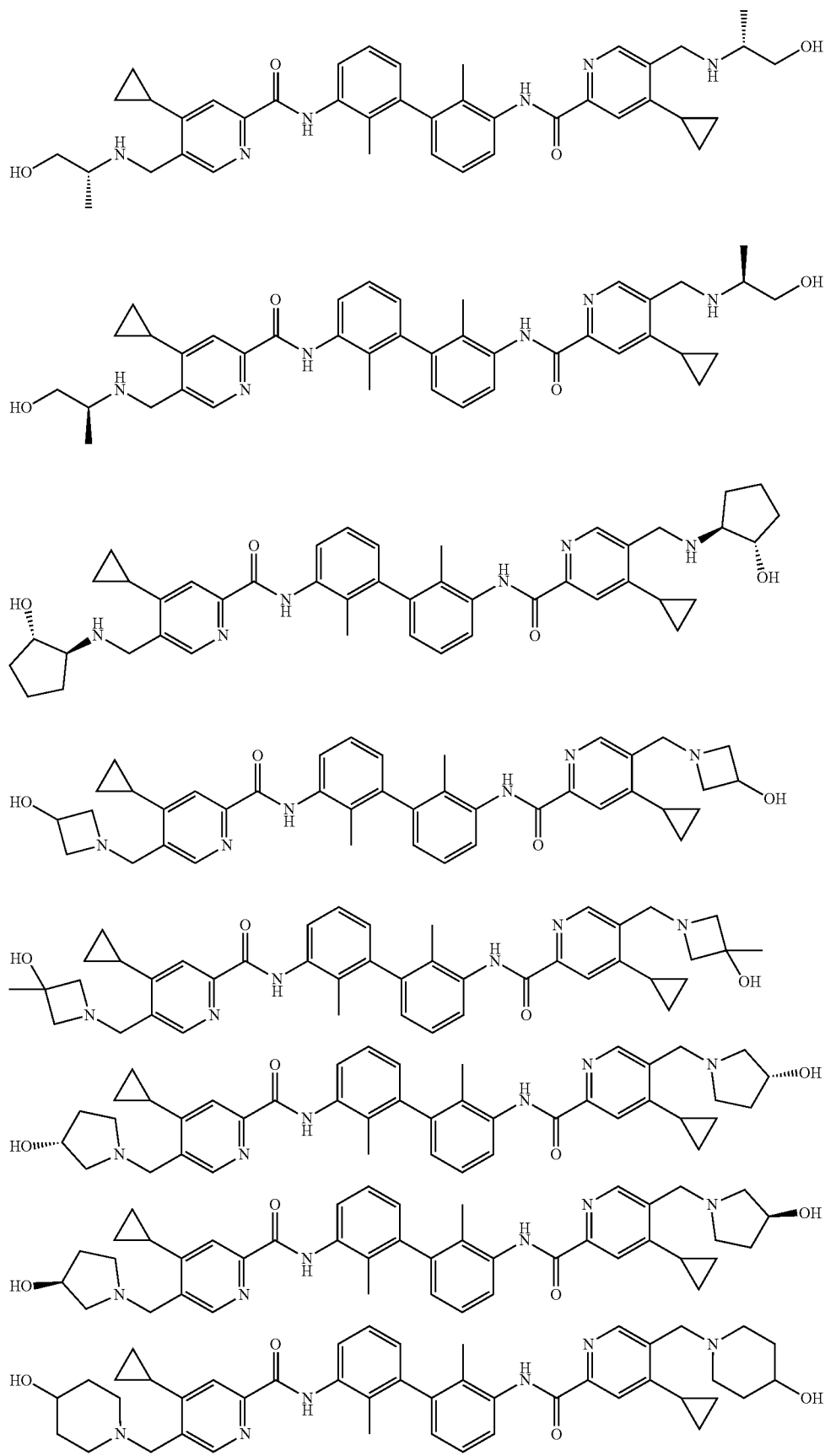

217 218
-continued
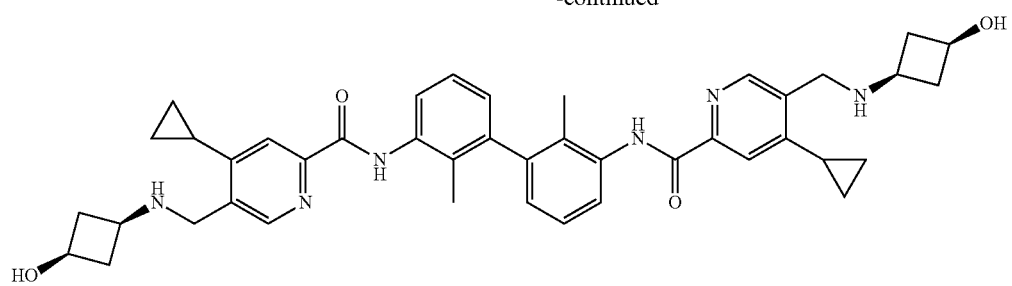
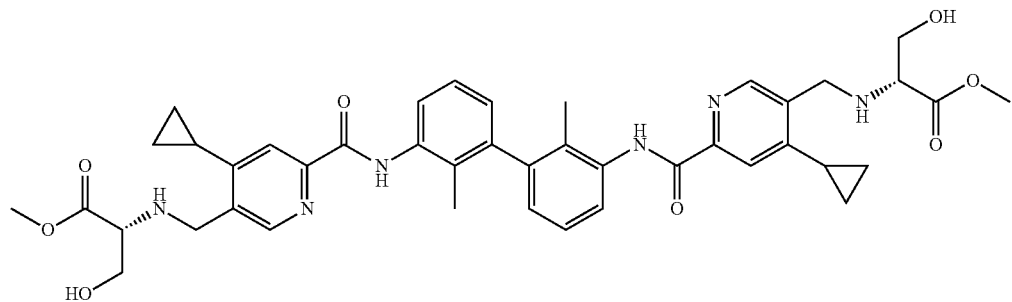
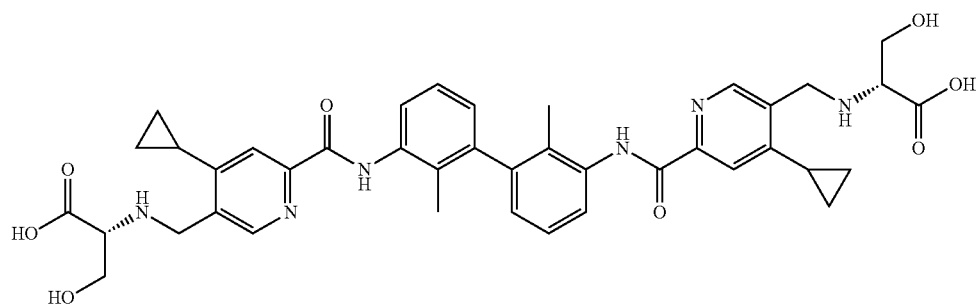
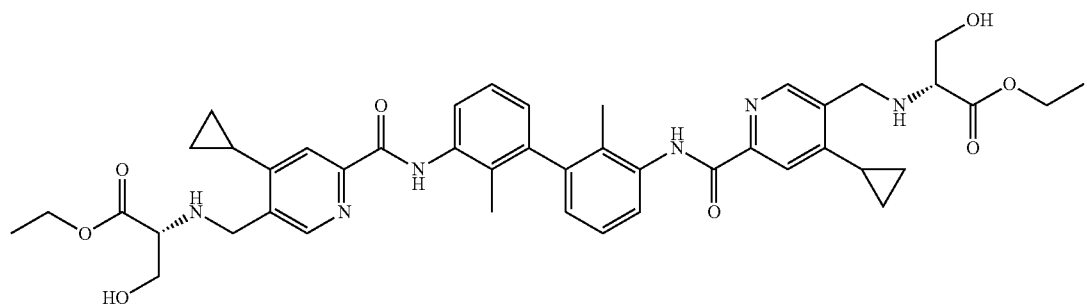
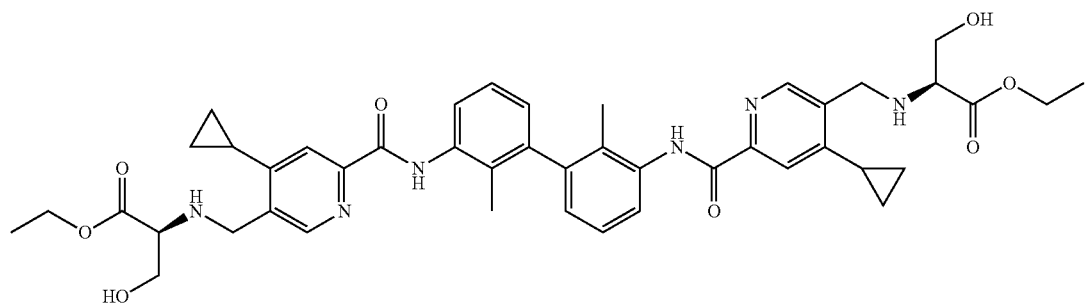

-continued
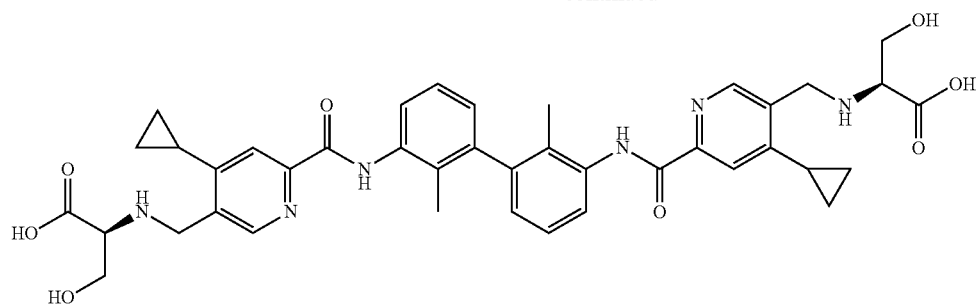
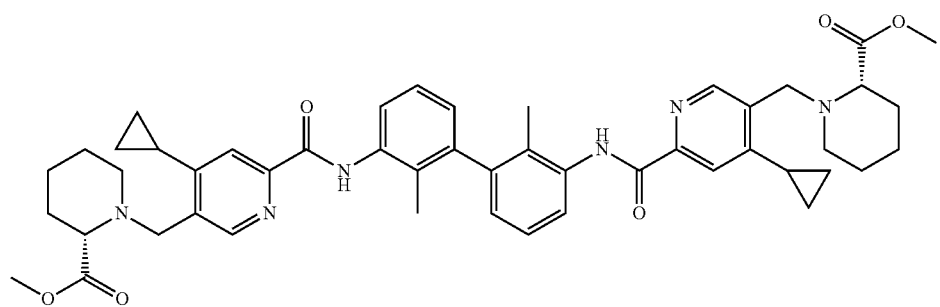
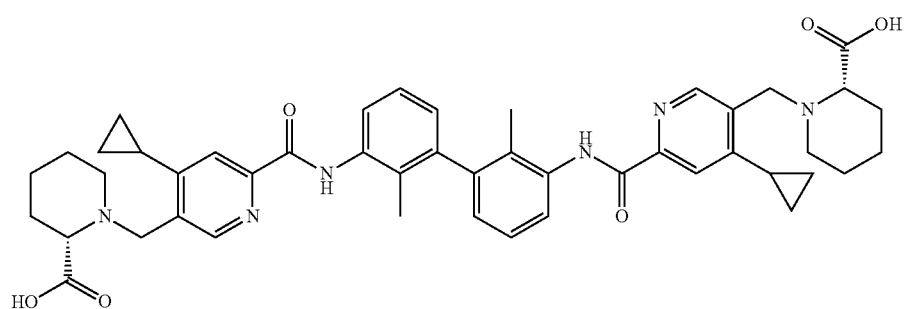
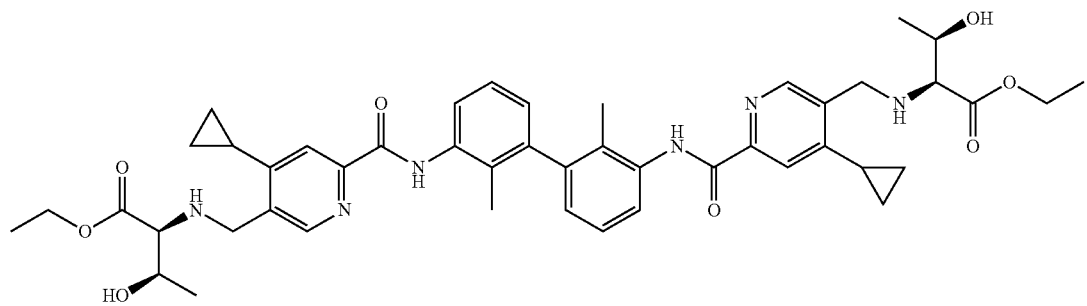
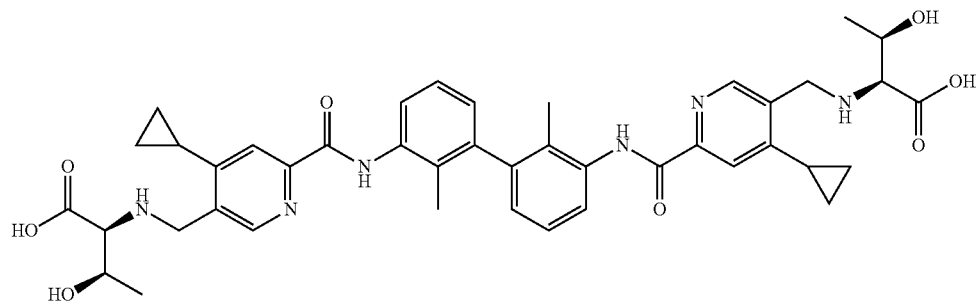

-continued
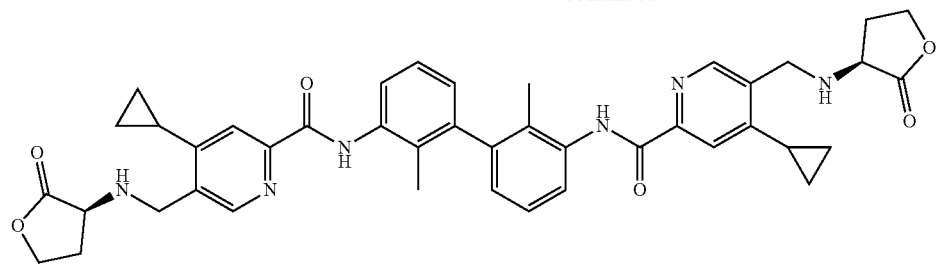
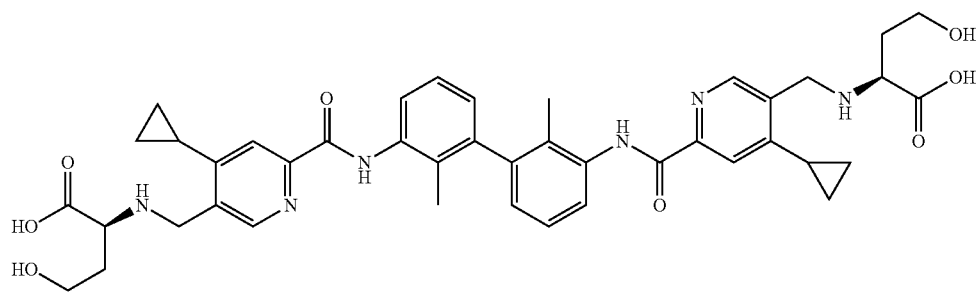
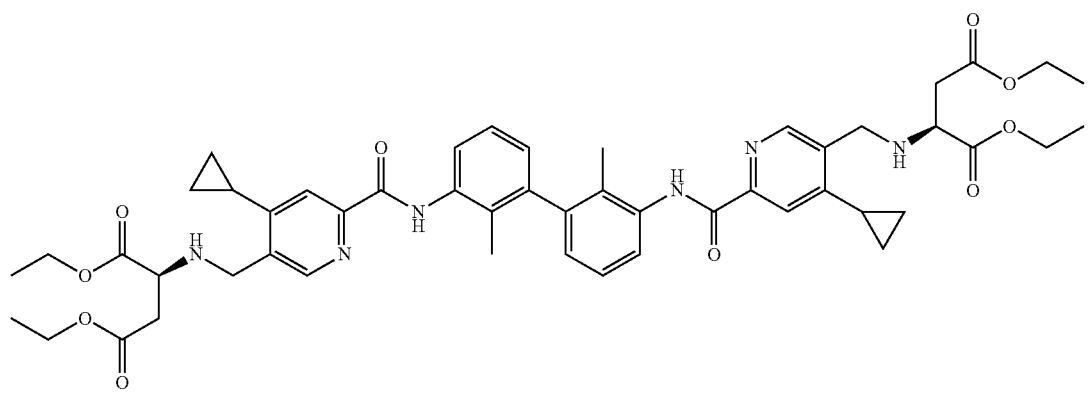
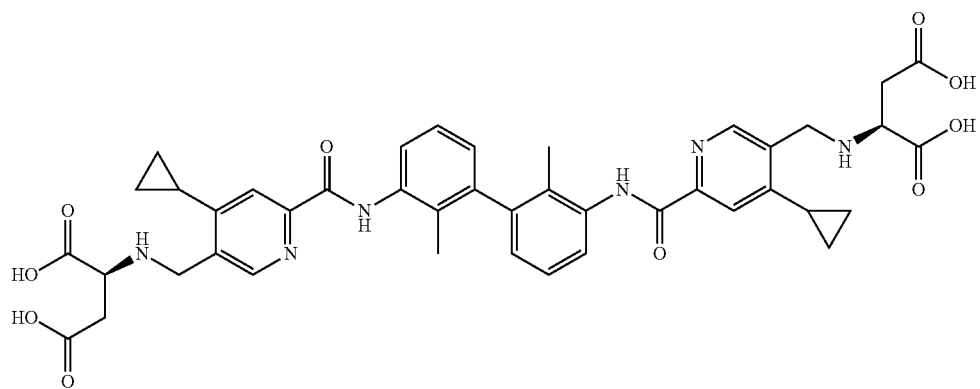
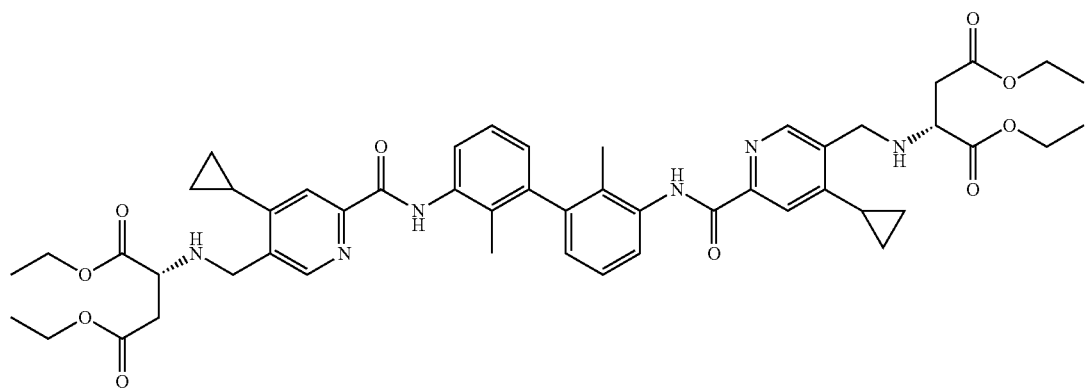

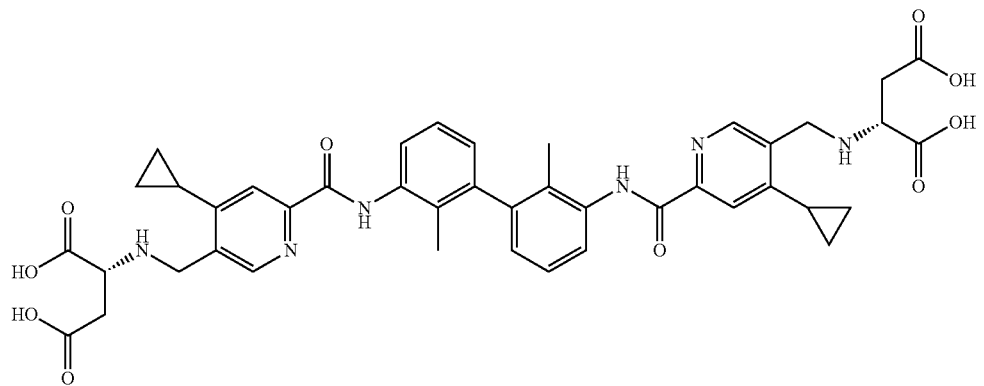
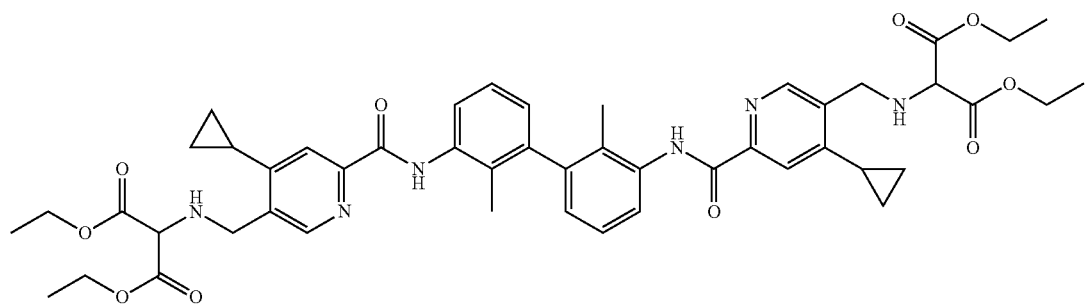
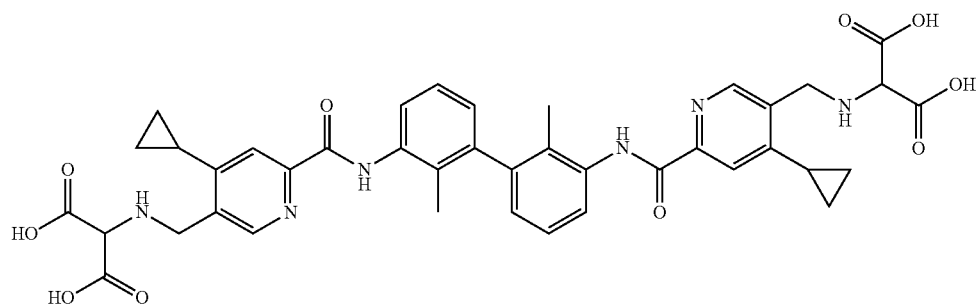
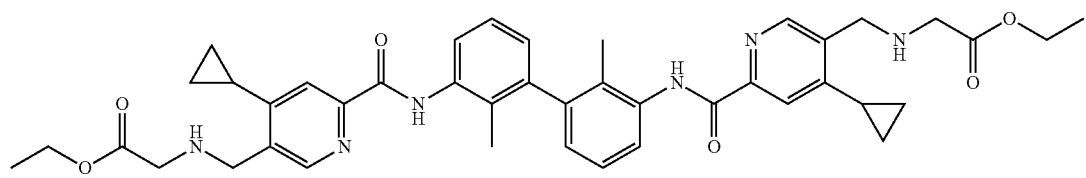
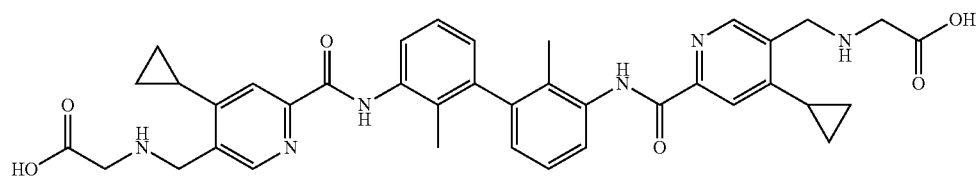
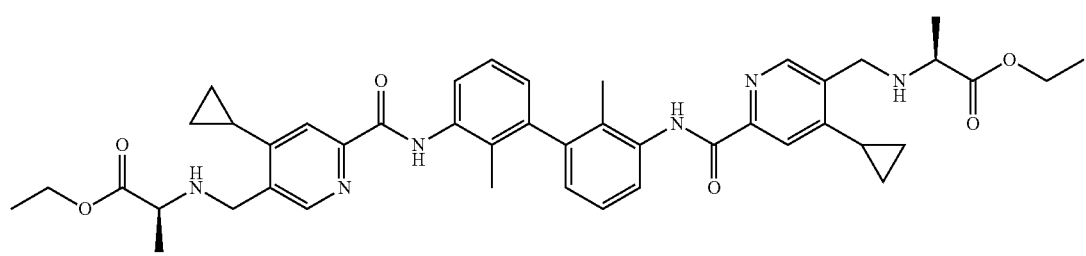

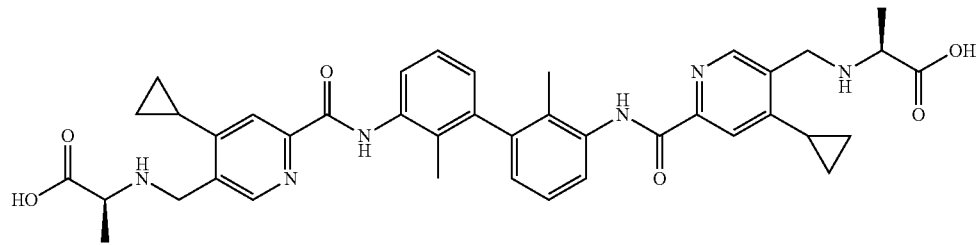
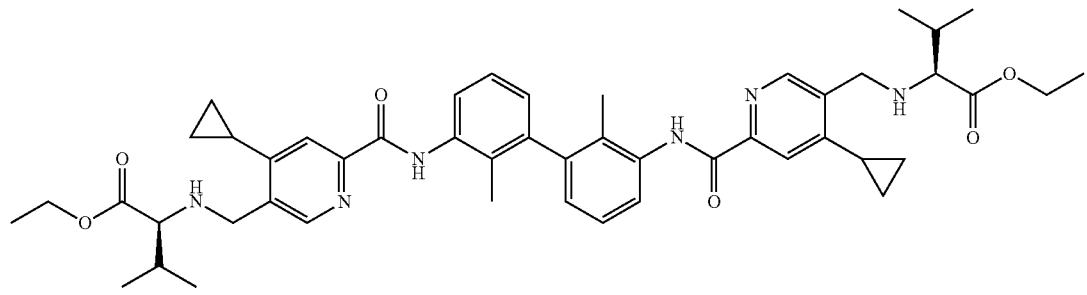
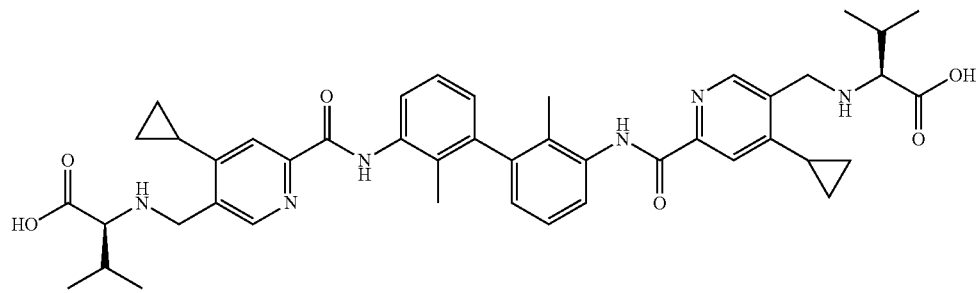
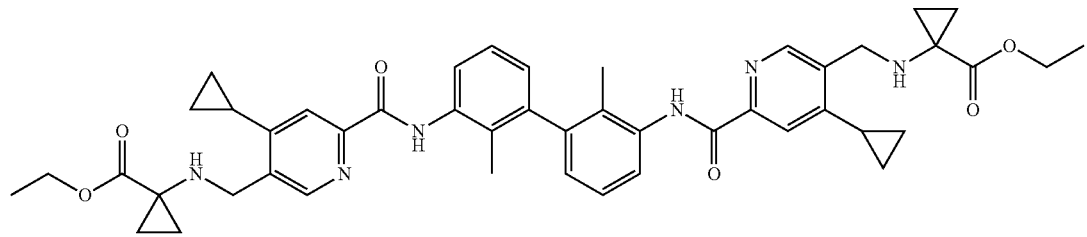
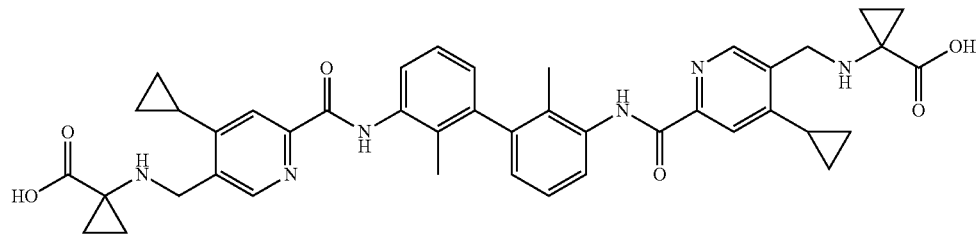
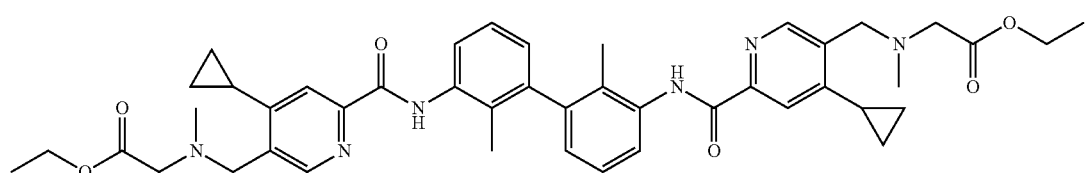
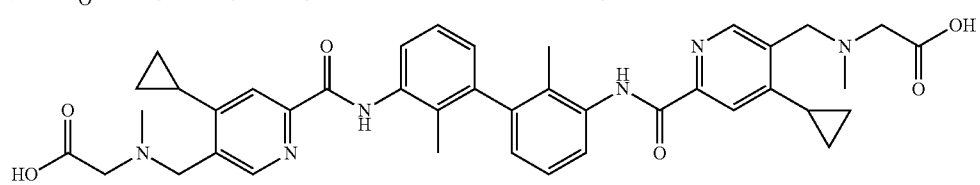

-continued
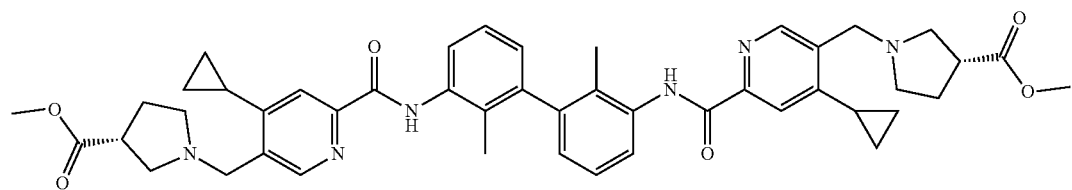
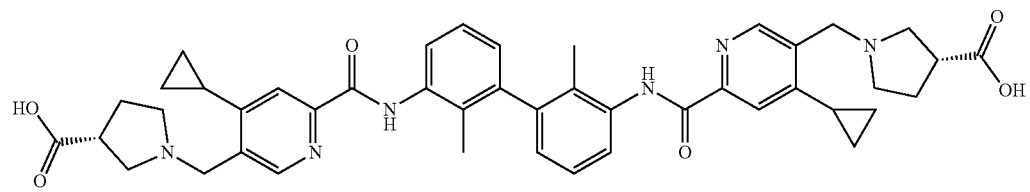
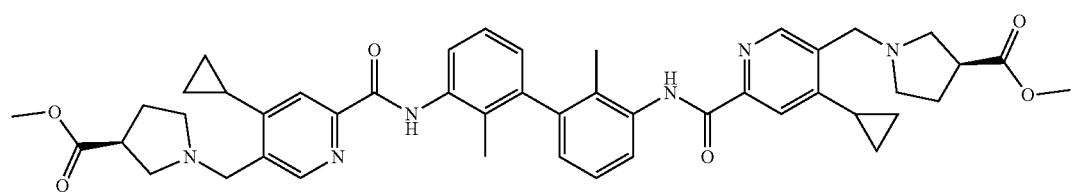
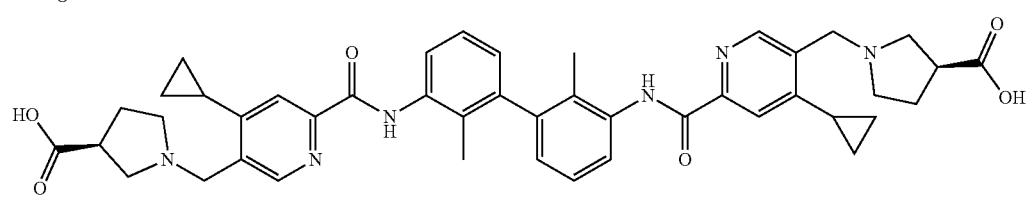
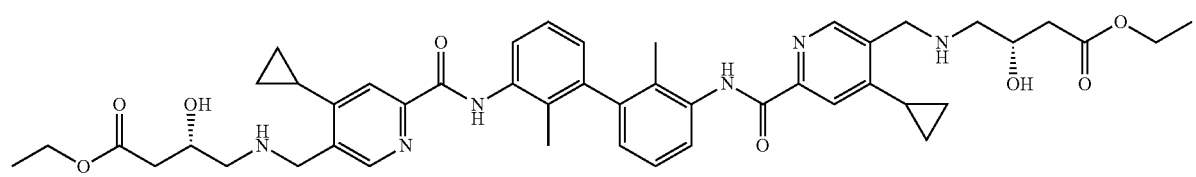
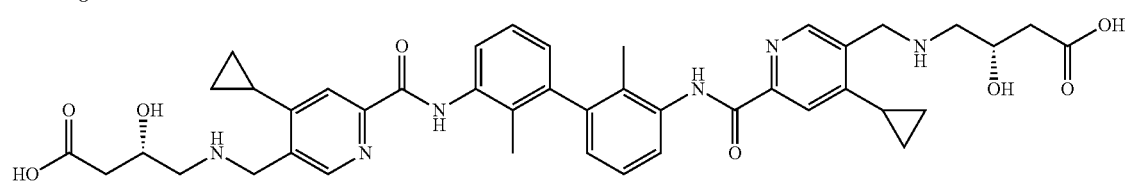
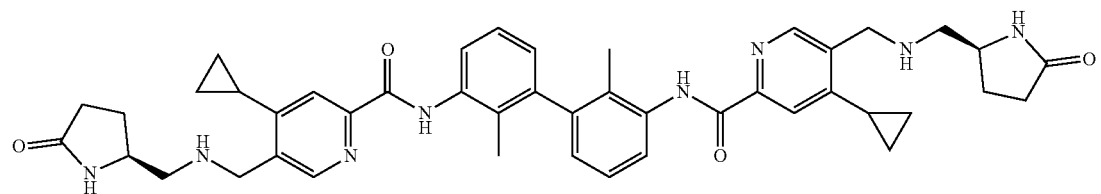
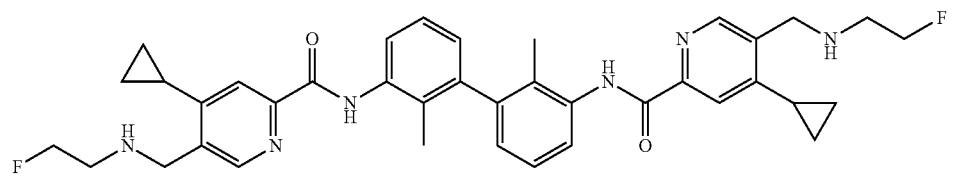
and

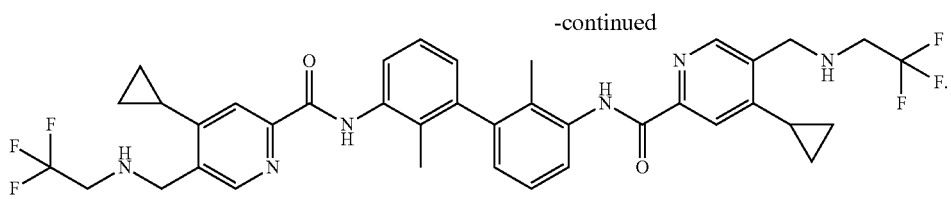

6. A process for preparing the compound of formula (II), the stereoisomer, prodrug or pharmaceutically acceptable salt thereof of claim 1 comprising the following step:

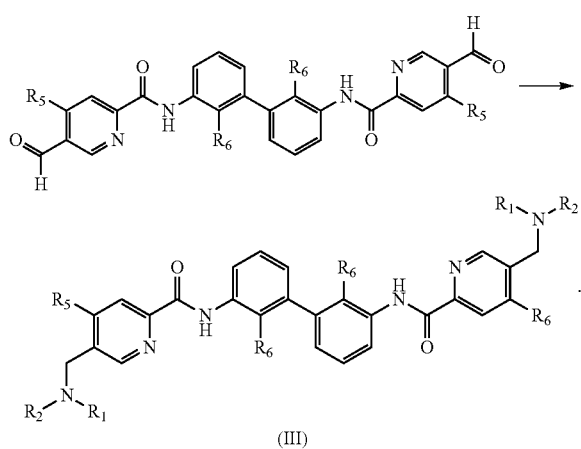

7. A pharmaceutical composition, comprising the compound of formula (III), the stereoisomer, prodrug or pharmaceutically acceptable salt thereof of claim 1 and a pharmaceutically acceptable carrier.

8. A method for preventing and/or treating PD-1/PD-L1 signal pathway-mediated cancer or tumor, immune-related disease and disorder, communicable disease, infectious disease or metabolic disease, comprising administering the compound of formula (III), the stereoisomer, prodrug or pharmaceutically acceptable salt thereof of claim 1 to a patient.

9. A method for enhancing, stimulating, regulating and/or increasing an immune response mediated by the PD-1/PD-L1 signal pathway in a subject in need, comprising administering the compound of formula (III), the stereoisomer, prodrug or pharmaceutically acceptable salt thereof of claim 1 to a patient.

10. A method for inhibiting the growth, proliferation or metastasis of tumor cells, comprising administering the compound of formula (III), the stereoisomer, prodrug or pharmaceutically acceptable salt thereof of claim 1 to a patient.

11. A method for treating PD-1/PD-L1 signal pathway-mediated communicable disease, infectious disease, metabolic disease or disorder, comprising administering the compound of formula (III), the stereoisomer, prodrug or pharmaceutically acceptable salt thereof of claim 1 to a patient.

12. The method of claim 8, wherein the cancer or tumor is selected from lymphoma sarcoma, melanoma, glioblastoma, synovioma, meningioma, biliary tract tumor, thymic tumor, neuroma, seminoma, nephroblastoma, pleomorphic adenoma, hepatocellular papilloma, renal tubule adenoma, cystadenoma, papilloma, adenoma, leiomyoma, rhabdomyoma, hemangioma, lymphangioma, osteoma, chondroma, lipoma, fibroma, central nervous system tumor, rhachiophyma, brain stem glioma, pituitary adenoma, multiple myeloma, ovarian tumor, myelodysplastic syndrome or mesothelioma, prostate cancer, recurrent prostate cancer or prostate cancer having developed resistance to existing medicaments, thyroid cancer, parathyroid cancer, anal cancer, testicular cancer, urethral carcinoma, penile cancer, bladder cancer, ureteral cancer, uterine cancer, ovarian cancer, fallopian tube cancer, endometrial cancer, cervical cancer, vaginal cancer, vulvar cancer, adrenal cancer, Merkel cell carcinoma, embryonal carcinoma, chronic or acute leukemia, bronchial carcinoma, esophageal cancer, nasopharyngeal carcinoma, hepatocellular carcinoma, renal cell carcinoma, small cell lung cancer, basal cell carcinoma, lung cancer, breast cancer, adenocarcinoma, papillary carcinoma, cystadenocarcinoma, squamous non-small cell lung cancer, non-squamous non-small cell lung cancer, rectal cancer, colon cancer, colorectal cancer, gastric cancer, pancreatic cancer, head and neck squamous cell carcinoma, head and neck cancer, gastrointestinal cancer, bone cancer, skin cancer, small intestine cancer, endocrine cancer, renal pelvic carcinoma, epidermoid carcinoma, abdominal wall carcinoma, renal cell carcinoma, transitional cell carcinoma, choriocarcinoma, or metastatic tumor;

the immune-related disease and disorder is selected from rheumatic arthritis, renal failure, lupus erythematosus, asthma, psoriasis, ulcerative colitis, pancreatitis, allergy, fibrosis, anemia, fibromyalgia, Alzheimer's disease, congestive heart failure, stroke, aortic valve stenosis, arteriosclerosis, osteoporosis, Parkinson's disease, infection, Crohn's disease, ulcerative colitis, allergic contact dermatitis and eczema, systemic sclerosis or multiple sclerosis;

the communicable disease or infectious disease is selected from sepsis, liver infection, HIV, hepatitis A, hepatitis B, hepatitis C, hepatitis D, herpes virus, papillomavirus or influenza;

the metabolic disease is selected from diabetes, diabetic ketoacidosis, hyperglycemic hyperosmolar syndrome, hypoglycemia, gout, malnutrition, vitamin A deficiency, scurvy, vitamin D deficiency or osteoporosis.

13. The method of claim 12, wherein the lymphoma is selected from lymphocytic lymphoma, primary central nervous system lymphoma, T cell lymphoma, diffuse large B cell lymphoma, follicle center lymphoma, Hodgkin lymphoma, non-Hodgkin lymphoma or primary mediastinal large B cell lymphoma;

the sarcoma is selected from Kaposi's sarcoma, fibrosarcoma, liposarcoma, chondrosarcoma, osteosarcoma, leiomyosarcoma, rhabdomyosarcoma, soft tissue sarcoma, angiosarcoma or lymphangiosarcoma; and the chronic or acute leukemia is selected from acute myeloid leukemia, chronic myeloid leukemia, acute lymphoblastic leukemia, chronic granulocytic leukemia and chronic lymphoblastic leukemia.

\* \* \* \* \*